(12) United States Patent
Dominianni et al.

(10) Patent No.: US 7,304,062 B2
(45) Date of Patent: Dec. 4, 2007

(54) PEROXISOME PROLIFERATOR ACTIVATED RECEPTOR ALPHA AGONISTS

(75) Inventors: Samuel James Dominianni, Indianapolis, IN (US); Garret Jay Etgen, Carmel, IN (US); Richard Duane Johnston, Greenfield, IN (US); Nathan Bryan Mantlo, Brownsburg, IN (US); Daniel Ray Mayhugh, Carmel, IN (US); Ashraf Saeed, Carmel, IN (US); Richard Craig Thompson, Frankfort, IN (US); Xiaodong Wang, Carmel, IN (US); Christopher Randall Schmid, Indianapolis, IN (US); Yanping Xu, Fishers, IN (US)

(73) Assignee: Eli Lilly and Company, Indianapolis, IN (US)

(*) Notice: Subject to any disclaimer, the term of this patent is extended or adjusted under 35 U.S.C. 154(b) by 269 days.

(21) Appl. No.: 10/415,673

(22) PCT Filed: Nov. 9, 2001

(86) PCT No.: PCT/US01/42928

§ 371 (c)(1),
(2), (4) Date: Sep. 11, 2003

(87) PCT Pub. No.: WO02/38553

PCT Pub. Date: May 16, 2002

(65) Prior Publication Data

US 2004/0102500 A1    May 27, 2004

Related U.S. Application Data

(60) Provisional application No. 60/247,317, filed on Nov. 10, 2000.

(51) Int. Cl.
   A61K 31/5377   (2006.01)
   A61K 31/4709   (2006.01)
   A61K 31/4196   (2006.01)
   C07D 413/06    (2006.01)
   C07D 249/12    (2006.01)
   C07D 215/12    (2006.01)

(52) U.S. Cl. .................. 514/236.2; 514/383; 514/364; 514/378; 514/314; 514/340; 548/263.2; 548/131; 548/249; 544/132; 546/272.4; 546/174

(58) Field of Classification Search ............... 514/383, 514/364, 378, 236.2, 314, 340; 544/132; 546/272.4, 174; 548/263.2, 131, 249
See application file for complete search history.

(56) References Cited

U.S. PATENT DOCUMENTS 5,536,736 A    7/1996   Hamanaka et al.
5,641,796 A *  6/1997   Dominianni et al. ....... 514/374
5,817,677 A    10/1998  Linz et al.

FOREIGN PATENT DOCUMENTS

| EP | 1028111 A1 | 8/2000 |
|---|---|---|
| WO | WO96/13264 | 5/1996 |
| WO | WO96/35680 | 11/1996 |
| WO | WO99/08501 | 2/1999 |
| WO | WO 01/00603 A1 | 1/2001 |
| WO | WO 01/40207 A1 | 6/2001 |
| WO | WO 02/083128 A1 | 10/2002 |

OTHER PUBLICATIONS

Database CAS ONLINE on STN, Chem. Abstr., Accession No. 1966:473439, Kurzer et al., Chemistry & Industry, (1966), (26), 1143 (abstract only).*
Database CAS ONLINE on STN, Chem. Abstr., Accession No. 1943: 16721, Girard, Compt. rend. (1941), 212, 547-9, (abstract only).*
Database CAS ONLINE on STN, Chem. Abstr., Accession No. 1913:5473, Fromm, Ann. (1913), 394, 258-84, (abstract only).*
Database CAS ONLINE on STN, Chem. Abstr., Accession No. 1962:423199, Bellioni, Annali di Chimica, (1962), 52, 187-91, (abstract only).*
Brittain "polymorphism in pharmaceutical solids" marcel Dekker, p. 1, 2, 178-179, 185, 219 and 236 (1999).*
US Pharmacopia #23, national formulary #18, p. 1843-1844 (1995).*
Haluzik et al., Physiol. Res. 55: 115-122, 2006.*
Nissen et al., JAMA, Nov. 23/30, 2005, vol. 294, No. 20, pp. 2582-2586.*
McMahonn et al., Diabetes Care, vol. 28, No. 5, May 2005, pp. 1145-1150.*
Allred et al., Molucular and Cellular Endocrinology 235 (2005) 21-29.*
Science (1999), vol. 286, 531-537.*
Cancer and Metastasis Reviews (1998), 17(1), 91-106.*
Wilson, T.M., et al., "The Structure—Activity Relationship Between Peroxisome Proliferator-Activated Receptor γ Agonism and the Antihyperglycemic Activity of Thiazolidinediones," J. Med. Chem., vol. 39, 665-668, 1996.

* cited by examiner

Primary Examiner—Rebecca Anderson
(74) Attorney, Agent, or Firm—MaCharri Vorndran-Jones

(57) ABSTRACT

The present invention is directed to compounds represented by the following structural formula, and pharmaceutically acceptable salts, solvates and hydrates thereof, R1 is a substituted or unsubstituted group selected from $C_1$-$C_8$ alkyl, aryl-$C_{0-2}$-alkyl, heteroaryl-$C_{0-2}$-alkyl, $C_3$-$C_6$ cycloalkylaryl-$C_{0-2}$-alkyl or phenyl. W is O or S. R2 is H or a substituted or unsubstituted group selected from $C_1$-$C_6$ alkyl, $C_3$-$C_6$ cycloalkyl and heteroaryl. X is a $C_2$-$C_5$ alkylene linker wherein one carbon atom of the linker may be replaced with O, NH or S. Y is C, O, S, NH or a single bond. Furthermore, E is $(CH_2)_n$COOH, wherein n is 0, 1, 2 or 3, or C(R3)(R4)A, wherein A is an acidic functional group such as carboxyl, carboxamide substituted or unsubstituted sulfonamide, or substituted or unsubstituted tetrazole. R3 is H, saturated or unsaturated $C_1$-$C_5$ alkyl, $C_1$-$C_5$ alkoxy. Additionally, R4 is H, halo, a substituted or unsubstituted group selected from $C_1$-$C_5$ alkyl, $C_1$-$C_5$ alkoxy, $C_3$-$C_6$ cycloalkyl, aryl$C_0$-$C_4$alkyl and phenyl, or R3 and R4 are combined to form a $C_3$-$C_4$ cycloalkyl.

37 Claims, No Drawings

PEROXISOME PROLIFERATOR ACTIVATED RECEPTOR ALPHA AGONISTS

This Applicaton claims the benefit of U.S. Provisional Application Ser. No. 60/247,317 filed Nov. 10, 2000, and PCT Application Ser. No. PCT/US01/42928 filed Nov. 9, 2001.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, NUC1, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists which have been shown to increase the sensitivity of insulin sensitive cells. Increasing insulin sensitivity rather than the amount of insulin in the blood reduces the likelihood of hypoglycemic coma. However, TZDs and ISEs typically have little effect in preventing the cardiovascular part of Syndrome X in that their administration usually dose not result in the lowering of triglycerides and LDL-cholesterol while raising HDL-cholesterol. Furthermore, side effects commonly associated with treatment with TZDS include significant weight gain, and, for troglitazone, liver toxicity. Therefore, a need exists for new pharmaceutical agents which affect treat or prevent cardiovascular disease, particularly that associated with Syndrome X, while preventing or minimizing weight gain, and more preferably while improving insulin sensitivity.

SUMMARY OF THE INVENTION

The present invention is directed to compounds represented by the following structural Formula I:

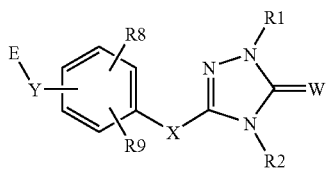

and pharmaceutically acceptable salts, solvates and hydrates thereof, wherein:
(a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, C3-C6 cycloalkylaryl-$C_{0-2}$-alkyl, and —$CH_2$—C(O)—R17-R18, wherein R17 is O or NH and R18 is optionally substituted benzyl;
(b) W is O or S;
(c) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$-alkyl, sulfonamide, amide, OR10 and $C_3$-$C_6$ cycloalkyl;
(d) X is an optionally substituted $C_1$-$C_5$ alkylene linker wherein one carbon atom of the linker may be replaced with O, NH or S;
(e) Y is C, O, S, NH or a single bond; and
(f) E is selected from the group consisting of hydrogen, C(R3)(R4)A, A, substituted or unsubstituted selected from the group consisting of $(CH_2)_n$ COOR19, $C_1$-$C_6$ alkyl, $C_1$-$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  (i) n is 0, 1, 2 or 3,
  (ii) A is an functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
  (iii) R3 is H, saturated or unsaturated $C_1$-$C_5$ alkyl, $C_1$-$C_5$ alkoxy, and
  (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
  (v) R19 is selected from the group consisting of hydrogen, optionally substituted C1-C4alkyl and optionally substituted arylmethyl;
(g) R8 is independently selected from the group consisting of hydrogen, $C_1$-$C_4$ alkyl, $C_1$-$C_4$ alkylenyl, and halo;
(h) R9 is independently selected from the group consisting of hydrogen, $C_1$-$C_4$ alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ allyl, and OR10; and
R10 is independently selected from the group consisting of hydrogen and $C_1$-$C_4$ alkyl.
An additional embodiment is a compound of Structural Formula I' and pharmaceutically acceptable salts, solvates and hydrates thereof:

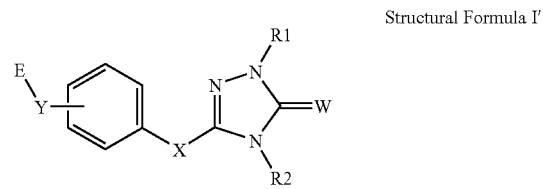

In Structural Formula I', R1 is a substituted or unsubstituted group selected from $C_1$-$C_8$ alkyl, aryl-$CO_{0-2}$alkyl, heteroaryl-$C_{0-2}$-alkyl, C3-C6 cycloalkylaryl-$C_{0-2}$-alkyl or phenyl. W is O or S. R2 is H or a substituted or unsubstituted group selected from $C_1$-$C_6$ alkyl and $C_3$-$C_6$ cycloalkyl. X is a $C_2$-$C_5$ alkylene linker wherein one carbon atom of the linker may be replaced with O, NH or S. Y is C, O, S, NH or a single bond. Furthermore, E is $(CH_2)_n$COOH, wherein n is 0, 1, 2 or 3, or C(R3)(R4)A, wherein A is an acidic functional group such as carboxyl, carboxamide substituted or unsubstituted sulfonamide, or substituted or unsubstituted tetrazole. R3 is H, saturated or unsaturated $C_1$-$C_5$ alkyl, $C_1$-$C_5$ alkoxy. Additionally, R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl.

A further embodiment of the present invention is a compound represented by the following structural formula:

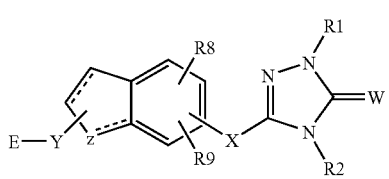

and pharmaceutically acceptable salts, solvates and hydrates thereof, wherein:
- (a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, C3-C6 cycloalkylaryl-$C_{0-2}$-alkyl, and —$CH_2$—C(O)—R17—R18, wherein R17 is O or NH and R18 is optionally substituted benzyl;
- (b) W is O or S;
- (c) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$alkyl, sulfonamide, amide, OR10 and $C_3$-$C_6$ cycloalkyl;
- (d) X is an optionally substituted $C_1$-$C_5$ alkylene linker wherein one carbon atom of the linker may be replaced with O, NH or S;
- (e) Y is C, O, S, NH or a single bond; and
- (f) E is selected from the group consisting of hydrogen, C(R3)(R4)A, A, substituted or unsubstituted selected from the group consisting of $(CH_2)_n$ COOR19, $C_1$-$C_6$ alkyl, $C_1$-$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  - (i) n is 0, 1, 2 or 3,
  - (ii) A is a functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
  - (iii) R3 is H, saturated or unsaturated $C_1$-$C_5$ alkyl, $C_1$-$C_5$ alkoxy, and
  - (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
  - (v) R19 is selected from the group consisting of hydrogen, optionally substituted C1-C4alkyl, and optionally substituted arylmethyl;
- (g) R8 is independently selected from the group consisting of hydrogen, $C_1$-$C_4$ alkyl, $C_1$-$C_4$ alkylenyl, and halo;
- (h) R9 is independently selected from the group consisting of hydrogen, $C_1$-$C_4$ alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ allyl, and OR10;
- (i) R10 is independently selected from the group consisting of hydrogen and $C_1$-$C_4$ alkyl;
- (j) Z is $C_0$-$C_3$ alkylene, O, S, N, O—($C_0$-$C_2$ alkylene), S—($C_0$-$C_2$ alkylene), and N—($C_0$-$C_2$ alkylene); and
- (k) - - - is an optional bond to form a double bond.

Another claimed embodiment of the present invention is a compound of the formula:

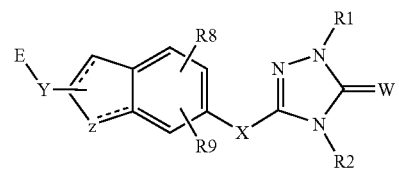

Another embodiment of this invention is compounds of the following formula, which may be preferred:

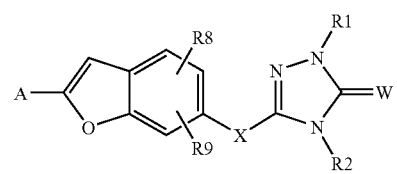

In another embodiment of the present invention, compounds represented the following structure may be preferred:

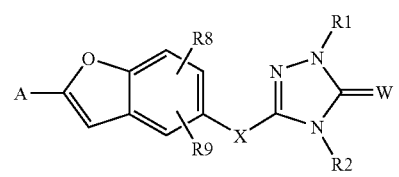

In a further embodiment of this invention, a compound the following structural formula may be preferred:

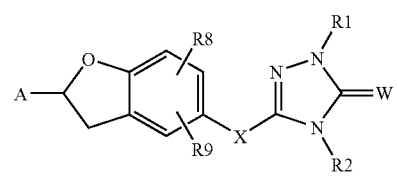

Another compound claimed by this invention that may be preferred is shown by the following structure:

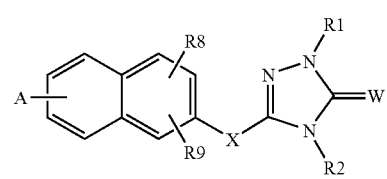

In another feature of this invention, a compound claimed herein is radiolabeled.

The present invention additionally provides a process for preparing a triazolone from an acyl semicarbazide comprising contacting said acyl semicarbazide with an acid. Preferred acids for said process are sulfonic acid and pyridinium hydrochloride. It is a preferred embodiment of this invention when the triazole prepared by said process is a compound of Formula I.

Another embodiment of the present invention is a compound of the formula:

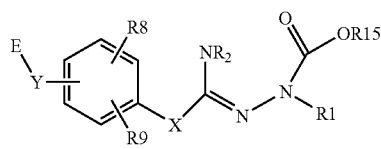

wherein
- (a) R1 is hydrogen or is selected from the group consisting of a substituted or unsubstituted group selected from $C_1$-$C_8$ alkyl, aryl-$C_{0-4}$-alkyl, heteroaryl-$C_{0-4}$-alkyl, and C3-C6 cycloalkylaryl$C_{0-2}$-alkyl;
- (b) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$alkyl, sulfonamide, amide, OR10 and $C_3$-$C_6$ cycloalkyl;
- (c) X is an optionally substituted $C_1$-$C_5$ alkylene linker wherein one carbon atom of the linker may be replaced with O, NH or S;
- (d) Y is C, O, S, NH or a single bond; and
- (e) E is selected from the group consisting of hydrogen, $(CH_2)_n$ COOR19, C(R3)(R4)A, substituted or unsubstituted selected from the group consisting of $C_1$-$C_6$ alkyl, $C_1$-$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  - (i) n is 0, 1, 2 or 3,
  - (ii) A is a functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
  - (iii) R3 is H, saturated or unsaturated $C_1$-$C_5$ alkyl, $C_1$-$C_5$ alkoxy, and
  - (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
  - (v) R19 is selected from the group consisting of hydrogen, optionally substituted C1-C4alkyl and optionally substituted arylmethyl;
- (f) R8 is independently selected from the group consisting of hydrogen, $C_1$-$C_4$ alkyl, $C_1$-$C_4$ alkylenyl, and halo;
- (g) R9 is independently selected from the group consisting of hydrogen, $C_1$-$C_4$ alkyl, $C_1$-C4 alkylenyl, halo, substituted or unsubstituted aryl, substituted or unsubstituted aryl-$C_1$-$C_4$ alkyl, substituted or unsubstituted heteroaryl, $C_1$-$C_6$ allyl, and OR10 ; and
- (h) R10 is independently selected from the group consisting of hydrogen and $C_1$-$C_4$ alkyl; and
- (i) R15 is selected from the group consisting of hydrogen and an optionally substituted substituent selected from the group consisting of $C_1$-$C_4$ alkyl, aryl, and benzyl. Such compounds are particularly useful as intermediates for the preparation of compounds claimed herein.

Another embodiment of the present invention is a compound of the formula:

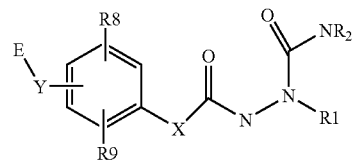

wherein
- (a) R1 is hydrogen or is selected from the group consisting of a substituted or unsubstituted group selected from $C_1$-$C_8$ alkyl, aryl-$C_{0-4}$-alkyl, heteroaryl-$C_{0-4}$-alkyl, and C3-C6 cycloalkylaryl-$C_{0-2}$-alkyl;
- (b) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$alkyl, sulfonamide, amide, OR10 and $C_3$-$C_6$ cycloalkyl;
- (c) X is an optionally substituted $C_1$-$C_5$ alkylene linker wherein one carbon atom of the linker may be replaced with O, NH or S;
- (d) Y is C, O, S, NH or a single bond; and
- (e) E is selected from the group consisting of hydrogen, substituted or unsubstituted selected from the group consisting of $(CH_2)_n$ COOR19, C(R3) (R4)A, $C_1$-$C_6$ alkyl, $C_1$-$C_6$ allyl, aryl-$C_{0-4}$alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  - (i) n is 0, 1, 2 or 3,
  - (ii) A is an acidic functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
  - (iii) R3 is H, saturated or unsaturated $C_1$-$C_5$ alkyl, $C_1$-$C_5$ alkoxy, and
  - (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
  - (v) R19 is selected from the group consisting of hydrogen, optionally substituted C1-C4alkyl and optionally substituted arylmethyl;
- (f) R8 is independently selected from the group consisting of hydrogen, $C_1$-$C_4$ alkyl, $C_1$-$C_4$ alkylenyl, and halo;
- (g) R9 is independently selected from the group consisting of hydrogen, $C_1$-C4 alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ allyl, and OR10; and
- (h) R10 is independently selected from the group consisting of hydrogen and $C_1$-$C_4$ alkyl. Such compounds are particularly useful as intermediates for the preparation of compounds of Formula I.

Another embodiment of the invention claimed herei is a compound of the formula:

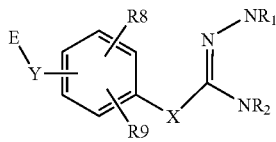

wherein
(a) R1 is hydrogen or is selected from the group consisting of a substituted or unsubstituted group selected from $C_1$-$C_8$ alkyl, aryl-$C_{0-4}$-alkyl, heteroaryl-$C_{0-4}$-alkyl, and C3-C6 cycloalkylaryl-$C_{0-2}$-alkyl;
(b) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$alkyl, sulfonamide, amide, OR10 and $C_3$-$C_6$ cycloalkyl;
(c) X is an optionally substituted $C_1$-$C_5$ alkylene linker wherein one carbon atom of the linker may be replaced with O, NH or S;
(d) Y is C, O, S, NH or a single bond; and
(e) E is selected from the group consisting of hydrogen, substituted or unsubstituted selected from the group consisting of $(CH_2)_n$ COOR19, C(R3) (R4)A, $C_1$-$C_6$ alkyl, $C_1$-$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino$C_{1-4}$alkyl, and wherein
  (i) n is 0, 1, 2 or 3,
  (ii) A is an acidic functional group selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
  (iii) R3 is H, saturated or unsaturated $C_1$-$C_5$ alkyl, $C_1$-$C_5$ alkoxy, and
  (iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
  (v) R19 is selected from the group consisting of hydrogen, optionally substituted C1-C4alkyl and optionally substituted arylmethyl;
(f) R8 is independently selected from the group consisting of hydrogen, $C_1$-$C_4$ alkyl, $C_1$-$C_4$ alkylenyl, and halo;
(g) R9 is independently selected from the group consisting of hydrogen, $C_1$-$C_4$ alkyl, $C_1$-$C_4$ alkylenyl, halo, substituted or unsubstituted aryl, substituted or unsubstituted aryl-$C_1$-$C_4$ alkyl, substituted or unsubstituted heteroaryl, $C_1$-$C_6$ allyl, and OR10; and
(h) R10 is independently selected from the group consisting of hydrogen and $C_1$-$C_4$ alkyl. Such compounds are especially useful as intermediates for the manufacture of compounds of Formula I.

For compounds having Structural Formula I, it is preferred that E is C(R3)(R4)A. It is more preferred that A is a carboxyl group. It is even more preferred that E is C(R3)(R4)COOH and $R_3$ is H or $CH_3$.

The present invention further provides a crystalline Propanoic Acid, 2-[4-[3-[2,5-dihydro-1-[(4-methylphenyl)methyl]-5-oxo-1H-1,2,4-triazol-3-yl]propyl]phenoxy]-2-methyl-compound of Formula I or a pharmaceutically acceptable salt, solvate, hydrate or prodrug thereof.

In one embodiment, the present invention also relates to pharmaceutical compositions which comprising at least one compound of the present invention, or a pharmaceutically acceptable salt, solvate, hydrate or prodrug thereof, and a pharmaceutically acceptable carrier.

In another embodiment, the present invention relates to a method of modulating a PPAR alpha receptor by contacting the receptor with at least one compound represented by Structural Formula I, and pharmaceutically acceptable salts, solvates and hydrates thereof In a further embodiment, the present invention relates to a method of making a compound represented by Structural Formula I.

The compounds of the present invention and pharmaceutically acceptable salts, solvates and hydrates thereof are believed to be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. In addition, the compounds exhibit fewer side effects than compounds currently used to treat these conditions. Further, compounds of this invention can be useful for lowering fibringoen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, alkyl groups include straight chained or branched hydrocarbons, which are completely saturated.

As used herein, alkylene linker is an optionally unsaturated $C_1$-$C_5$ straight or branched chain hydrocarbon group.

Cycloalkyl groups, as used herein, include cyclic hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl).

Heterocyclic group, as used herein, is a ring system having at least one heteroatom such as nitrogen, sulfur or oxygen. Heterocyclic groups include benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl and thienyl.

Examples of R1, R5, E, R4, R19 and R9 suitable substituents when said R1, E, R4, R5, R19 or R9 are one or more independently selected from the group consisting of $C_1$-$C_8$alkyl, aryl, $(CH_2)_n$COOR19, $C_1$-$C_6$ allyl, thio-$C_1$-$C_4$alkyl, thioaryl, $C_1$-$C_4$alkoxyaryl, $C_1$-$C_4$alkoxy $C_1$-$C_4$alkyl, aminoaryl and amino$C_1$-$C_4$alkyl, aryl-$C_{0-4}$ alkyl, heteroaryl$C_{0-4}$alkyl, heterocyclic, —$CH_2$—C(O)—R17—R18, ($C_3$-$C_6$)cycloalkylaryl-$C_{0-2}$-alkyl and cycloalkyl, then suitable substituted groups include, for example, C1-C5 alkyl, C1-C5 alkoxy, C1-C5 haloalkyl, C1-C5 haloalkoxy, nitro, cyano, CHO, hydroxyl, C1-C4 alkanoic acid phenyl, aryloxy, SO2R7, SR7, benzyloxy, alkylcarboxamido or COOH. R7 is an alkyl or a haloalkyl. When R1, R5, E, R4, R19 or R9 is substituted, it is preferred that there are from 1-3 substitutions on said R1, R5, E, R4, R19 or R9 group.

Examples of suitable substituents for an "optionally substituted $C_2$-$C_5$ alkylene linker", include one or more independently selected from the group consisting of $C_1$-$C_6$alkyl, oxo, substituted or unsubstituted aryl$C_0$-$C_3$alkyl, $C_1$-$C_3$alkoxy, hydroxy, $C_3$-$C_6$cycloalkyl and halo. When the alkylene linker is substituted, it is preferred that there are from one to three independent substitutions.

Examples of suitable substituents for a substituted $C_1$-$C_3$ alkylene, include one or more independently selected from $C_1$-$C_6$alkyl, oxo, aryl $C_0$-$C_3$alkyl, $C_1$-$C_3$alkoxy, hydroxy, and halo. When the alkylene is substituted it is preferred that there are from 1-3 independent substitutions.

Suitable substituents for substituted R2 groups wherein R2 is $C_1$-$C_6$alkyl, $C_1$-$C_6$allyl, aryl$C_0$-$C_4$alkyl, aryl$C_0$-$C_4$alkyl, sulfonamide, amide, OR10, or $C_3$-$C_6$cycloalkyl, include for example, one or more independently selected from the group consisting of OH, alkoxy, haloalkyl, amino, COOH, heteroaryl-O—, heteroaryl-C(O)—, alkyl-O—, alkyl-C(O)—, C3-C6 cycloalkyl, aryl-O—, aryl-C(O)—, heteroaryl, aryl, heterocycloalkyl, heterocycloalkyl-O—, and heterocycloalkylC(O)—. When R2 is substituted it is preferred that there are from 1-3 independent substitutions on the R2 group.

Examples of suitable substituents for A groups, wherein the A is a sulfonamide, include one or more independently selected from C1-C4 alkyl, C1-C4 haloalkyl, substituted or unsubstituted heteroaryl, or substituted or unsubstituted aryl. When the A group is substituted, it is preferred that there are from 1-3 independent substitutions on the A group.

Examples of suitable substituents for A groups, wherein A is acylsulfonamide and tetrazole include, for example, one or more independently selected from C1-C4 alkyl, C1-C4 haloalkyl, substituted or unsubstituted heteroaryl, or substituted or unsubstituted aryl.

Suitable substitutents for R4 wherein R4 is $C_1$-$C_5$ alkyl, $C_1$-$C_5$alkoxy, $C_1$-$C_6$cycloalkyl, aryl$C_0$-$C_4$alkyl or phenyl, include, for example phenyl, C1-C4 alkoxy, hydroxy and alkoxy. When R4 is substituted, it is preferred that there are from 1-4 independent substitutions on the R4 group.

Preferably, for the compounds of the present invention, represented by Structural Formula I, and with their respective pharmaceutical compositions, W is an oxygen.

More preferably, the compounds of the present invention, and with their respective pharmaceutical compositions, have a structure represented by Structural Formula II:

Structural Formula II

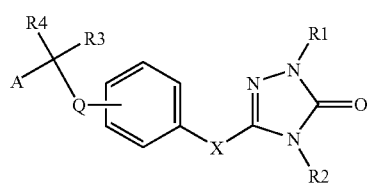

In Structural Formula II, R1, R2, X, R3, R4 and A are as defined for Structural Formula I. Q is C, O or S.

For compounds having Structural Formula I, it is preferred that $R_3$ is H or $CH_3$.

Compounds that may be especially preferred are Compounds of Formula III, and with their respective pharmaceutical compositions. Such compounds have a structure represented by Structural Formula III:

Structural Formula III

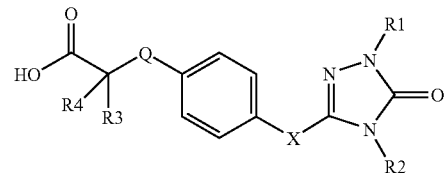

In Structural Formula III, R1, R2, X, Q, R3 and R4 are as defined for Structural Formulas I and II.

A further prefered embodiment is the compounds of the present invention having Formula IV, and their respective pharmaceutical compositions, have a structure represented by Structural Formula IV.

Structural Formula IV

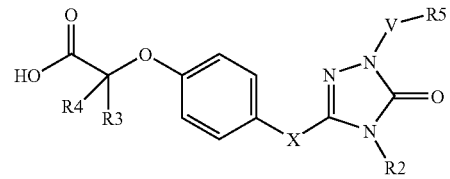

In Structural Formula IV, R2, X, R3 and R4 are as defined for Structural Formulas I and II. V is a bond, C1-C3 alkylene which is unsubstituted or substituted with oxo or alkyl) group. R5 is substituted or unsubstituted group selected from aryl, heteroaryl and cycloalkyl groups.

Another prefered embodiment is the compounds of the present invention, and with their respective pharmaceutical compositions, having a structure represented by Structural Formula V.

Structural Formula V

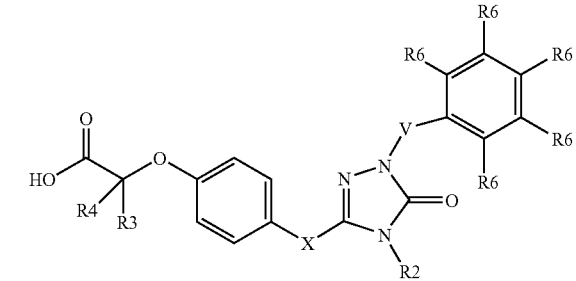

In Structural Formula V, R2, X, R3, R4 and V are as defined for Structural Formulas I, II and IV. R6 is H, OH, $C_1$-C5 alkyl, alkoxy, halo, haloalkyl, haloalkoxy, nitro, phenyl, aryloxy, SO2R7, SR7, cyano, benzyloxy, phenoxy, alkylcarboxamido or COOH. R7 is an alkyl or a haloalkyl.

For, the compounds of the present invention, and their respective pharmaceutical compositions, having a structure represented by Structural Formula V, it is preferred that V is methylene. It is more preferred that V is methylene and X is propylene. It is even further preferred that V is methylene, X is propylene, R3 is methyl, and R4 is methyl.

Another prefered embodiment is the compounds of the present invention, and with their respective pharmaceutical compositions, have a structure represented by Structural Formula VI.

Structural Formula VI

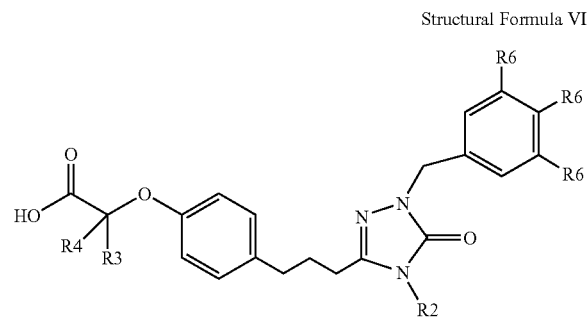

In Structural Formula VI, R2, R3, R4 and R6, are as defined for Structural Formulas I, II, IV and V. For the compounds of Structural Formula VI, it is preferred that, independently, each R6 group is H or methyl.

The present invention further provides a desired crystalline Propanoic Acid, 2-[4-[3-[2,5-dihydro-1-[(4methylphenyl)methyl]-5-oxo-1H-1,2,4-triazol-3-yl]propyl]phenoxy]-2-methyl- having an X-ray diffraction pattern which comprises at least one of the following peaks: 13.2+/−0.2, 15.9+/−0.2, 20.7+/−0.2, and 24.1+/−0.2 in 2θ when obtained from a copper radiation source.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may also exist in the form of solvates, for example hydrates, and the present invention includes each solvate and mixtures thereof.

"Pharmaceutically-acceptable salt" refers to salts of the compounds of the Structural Formula I which are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium and magnesium; and ammonium or substituted ammonium salts. Examples of substituted ammonium salts include, for instance, those with lower alkylamines such as trimethylamine, triethylamine; hydroxyalkylamines such as 2-hydroxyethylamine, bis-(2hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydroabietylamine, glucamine, N-methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

These salts may be prepared by methods known to those skilled in the art.

Certain compounds of Structural Formula I and their salts may-also exist in the form of solvates, for example hydrates, and the present invention includes each solvate and mixtures thereof.

Poorly crystalline and/or amorphous materials are typically less desirable than highly crystalline materials for formulation processing. Amorphous compounds are chemically and physically less stable as they tend to adsorb significant amounts of water. The adsorption of water by an amorphous material in a gelatin capsule, for example, may cause the capsule to shrink or buckle as moisture is transferred from the capsule to the amorphous component. In addition, amorphous compounds have a tendency to precipitate out of solutions containing them. If an amorphous drug substance precipitates from a delivery solution, the dissolution and bioavailability properties of the drug may be negatively affected.

In addition, it is generally not desirable to formulate pharmaceuticals containing substantial amounts of organic solvent (e.g., ethyl acetate) due to potential solvent toxicity to the recipient thereof and changes in potency of the pharmaceutical as a function of the solvent. In addition, from a manufacturing perspective, it is also generally less desirable to prepare non-crystalline materials whenever said preparation involves a collection of the final product via filtration. Such filtrations are often more difficult to perform when the material collected is non-crystalline. Moreover, it is also generally less desirable, from a manufacturing perspective, to formulate pharmaceuticals containing substantial amounts of water (hydrates) because the level of hydration will typically be some function of the relative humidity at which the pharmaceutical is produced and stored. In other words, potency variability is typically more problematic with a hydrate relative to its anhydrous form. The present invention provides a desired crystalline form.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of Formula I in a medium such as methanol with an acid or base esterification catalyst (e.g., NaOH, $H_2SO_4$). Ethyl ester prodrugs are prepared in similar fashion using ethanol in place of methanol.

Morpholinylethyl ester prodrugs may be prepared by reaction of the sodium salt of a compound of Structural Formula I (in a medium such as dimethylformamide) 4-(2-chloroethyl)morphine hydrochloride (available from Aldrich Chemical Co., Milwaukee, Wis. USA, Item No. C4,220-3).

Characterization of Propanoic Acid, 2-[4-[3-[2,5-dihydro-1[(4-methylphenyl)methyl]-5-oxo-1H-1,2,4-triazol-3-yl]propyl]phenoxy]-2-methyl-crystalline form Differential scanning calorimetry/thermogravimetric analysis (DSC/TGA), moisture sorption/desorption, and X-ray powder diffraction (XRD) methods were used to characterize Propanoic Acid, 2-[4-[3-[2,5-dihydro-1-[(4methylphenyl)methyl]-5-oxo-1H-1,2,4-triazol-3-yl]propyl] phenoxy]-2-methyl-. TGA is a measure of the thermally induced weight loss of the material as a function of temperature. It is most commonly used to study desolvation processes and quantatively determine the total volatile content of a solid. DSC is a technique that is often used to screen compounds for polymorphism because the temperatures(s) at which a physical change in a material occurs is usually characteristic of that material. Moisture sorption isotherms provide evaluation of the degree of hydroscopicity associated with a given material and characterization of non-hydrates and hydrates. Lastly, XRD is a technique that detects long-range order in a crystalline material.

The thermodynamically favorable crystalline Propanoic Acid, 2-[4-[3-[2,5-dihydro-1-[(4-methylphenyl)methyl]-5-oxo-1H-1,2,4-triazol-3-yl]propyl]phenoxy]-2-methyl-polymorph was characterized using a Siemens D5000 diffractometer equipped with a CuKα radiation source ($\lambda$=1.54056 Angstroms) and a solid state detector.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that, for any given crystal form, the angular peak positions may vary slightly. For example, peak positions can shift due to a variation in the temperature at which a sample is analyzed, sample displacement, or the presence or absence of an internal standard. In the present case, a peak position variability of ±0.2 in 2θ will take into account these potential variations without hindering the unequivocal identification of the desired crystalline form.

A well known and accepted method for searching crystal forms in the literature is the "Fink" method. The Fink method uses the four most intense lines for the initial search followed by the next four most intense lines. In accord with the Fink method, based on peak intensities as well as peak position, the desired crystalline form of Propanoic Acid, 2-[4-[3-[2,5-dihydro-1-[(4-methylphenyl)methyl]-5-oxo-1H-1,2,4-triazol-3-yl]propyl]phenoxy]-2-methyl- may be identified by the presence of peaks at 13.2+/−0.2, 15.9+/−0.2, 20.7+/−0.2, and 24.1+/−0.2 in 2θ; when the pattern is obtained from a copper radiation source. The presence of desired Propanoic Acid, 2-[4-[3-[2,5-dihydro-1-[(4-methylphenyl)methyl]-5-oxo-1H-1,2,4-triazol-3-yl]propyl]phenoxy]-2-methyl- crystalline form may be further verified by peaks at 7.9+/−0.2, 17.37+/−0.2, and 19.57+/−0.2 in 2θ; when the pattern is obtained from a copper radiation source.

The term, "active ingredient" means the compounds generically described by Structural Formula I as well as the salts, solvates, and prodrugs of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

"Preventing" refers to reducing the likelihood that the recipient will incur or develop any of the pathological conditions described herein.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, hydrate or prodrug thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR alpha receptor or to prevent or mediate a disease or condition. Conditions prevented or treated by PPARα receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixirs, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks's solution, Ringer's solution, or physiological saline buffer, ethanol, polyol (e.g. glycerol, propylene glycol and liquid polyethylene glycol), propylene glycol and liquid polyethylene glycol), suitable mixtures thereof, and. vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
| --- | --- |
| Starch | 59 mg |

-continued

| | |
|---|---|
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| | |
|---|---|
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active Ingredient | 100 mg |
| Isotonic saline | 1,000 ml |

The solution of the above materials generally is administered intravenously to a subject at a rate of 1 ml per minute.

In yet another embodiment of the compounds of the present invention, the compound is radiolabelled, such as with carbon-14, or tritiated. Said radiolabelled or tritiated compounds are useful as reference standards for in vitro assays to identify new PPARα agonists.

SYNTHESIS

Compounds of the present invention have been formed as specifically described in the examples. Further, many compounds were prepared as more generally as shown in the following schematic. Alternative synthesis methods may also be effective and known to the skilled artisan. Certain compounds of this invention were prepared as shown in scheme 1. Intermediates 1, 2 were obtained from commercially available p-bromo salicyl aldehyde and alpha-bromo esters. Intermediates A and B were obtained following the reaction sequence shown in scheme 2. The final compounds were obtained through a palladium catalized coupling reaction between 1 and 2 with A or B, followed by basic hydrolysis of the ester to the acid.

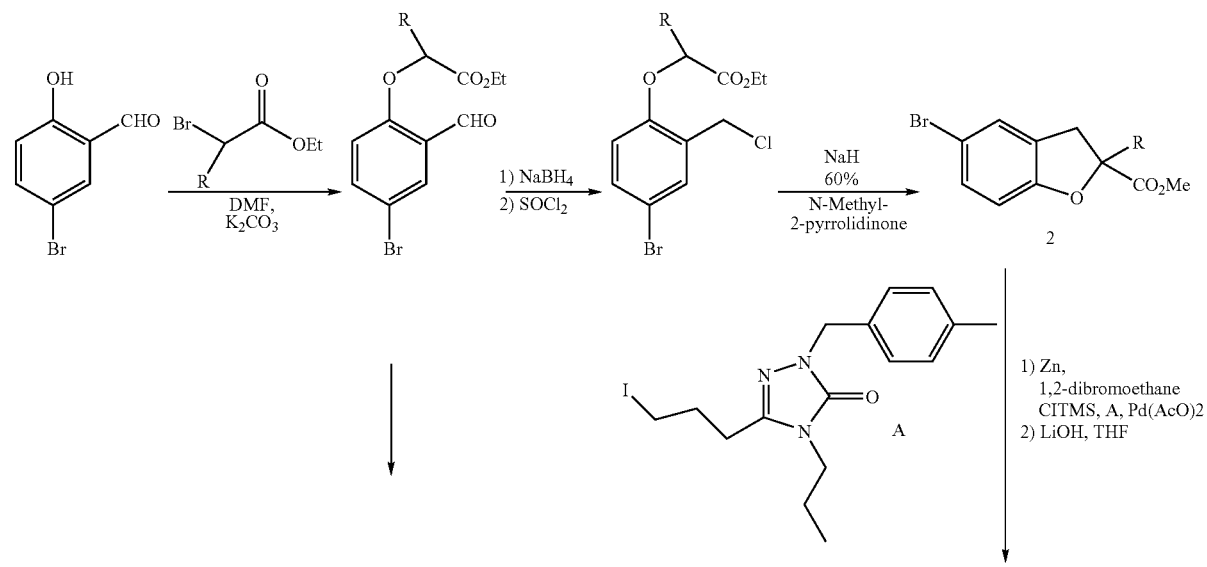

-continued
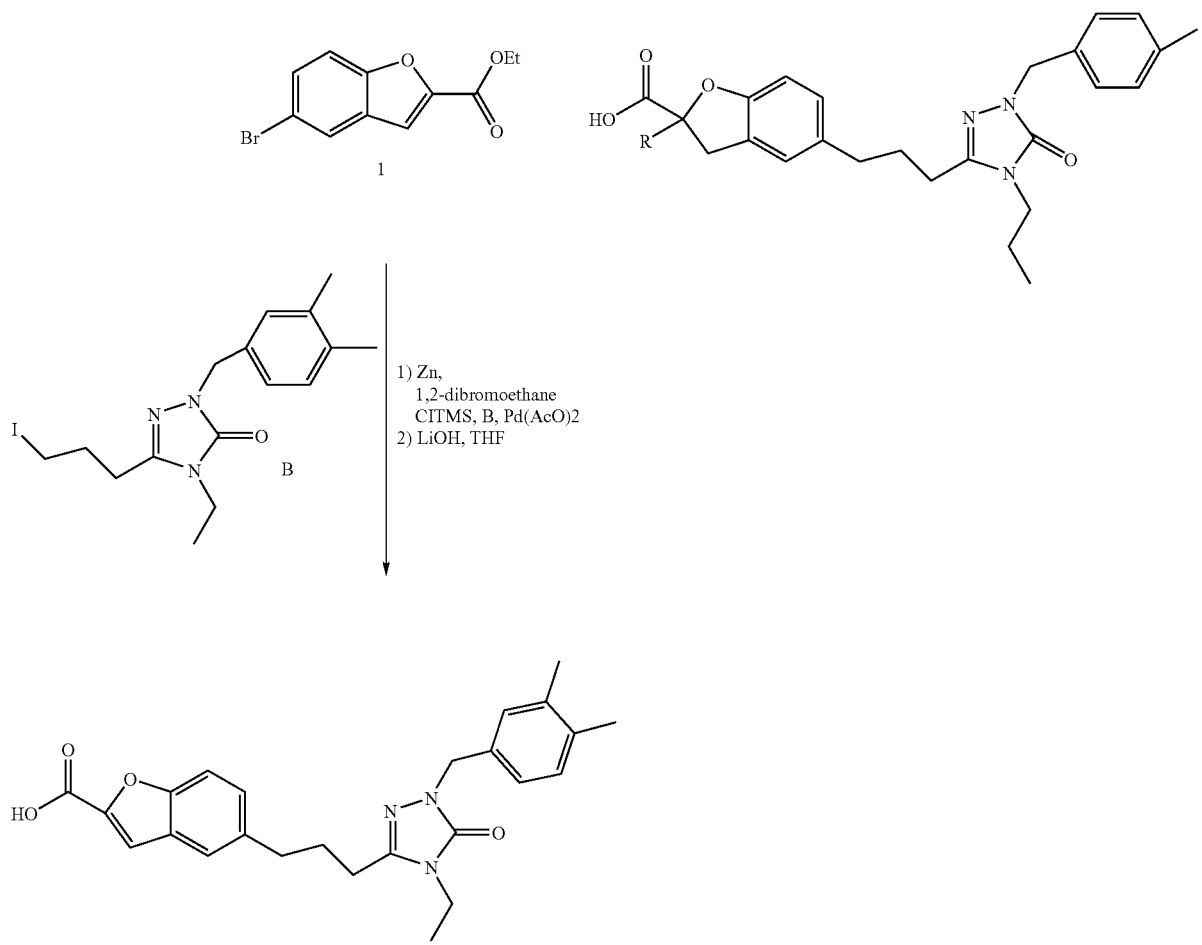
Scheme 2
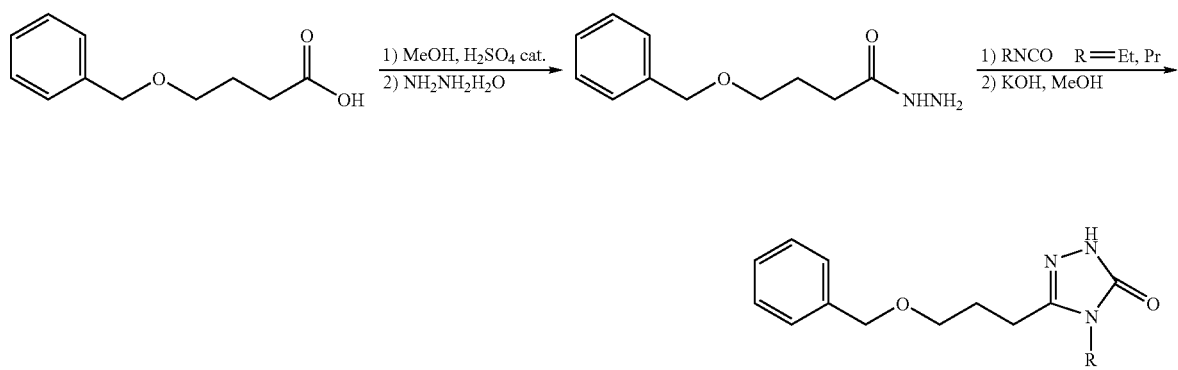
Ar = p-Tol, 3,4-dimethylphenyl
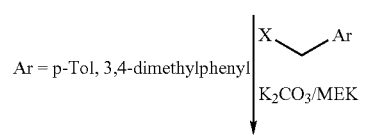

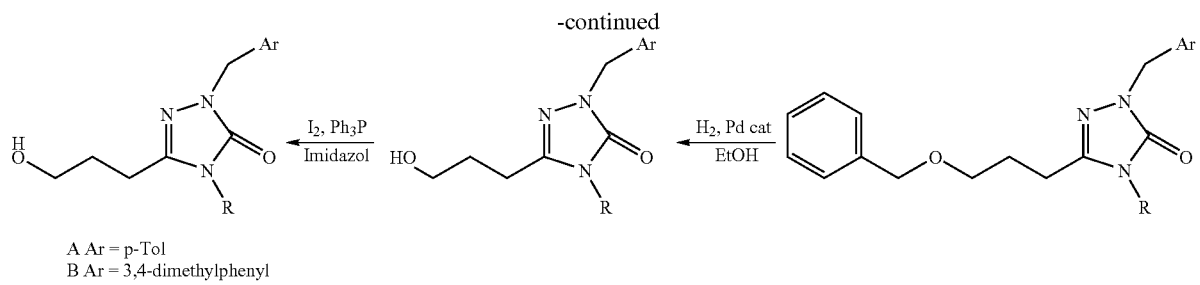

A Ar = p-Tol
B Ar = 3,4-dimethylphenyl

The Examples provided herein are illustrative of the invention claimed herein and are not intended to limit the scope of the claimed invention in any way.

EXEMPLIFICATION

Instrumental Analysis

Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Exemplified Compounds

Example 1

Compound 1(1)

Compound 1, shown below, was prepared according to the Steps outlined below:

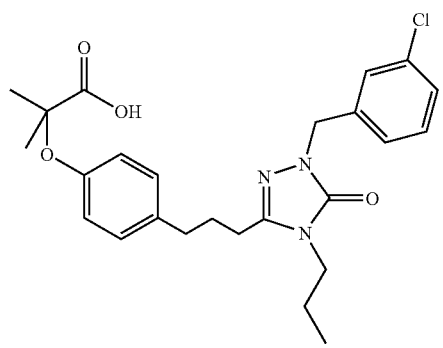

Step A: Preparation of

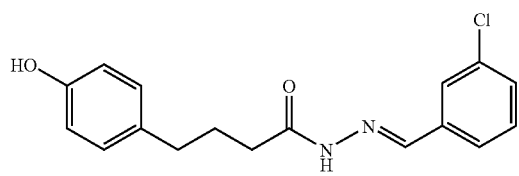

To a suspension of 4-(4-hydroxyphenyl)butyrylhydrazide (0.5 g, 2.58 mmol) in isopropanol (5 mL) was added 3-chloro-benzaldehyde (Aldrich, 420 mg, 3 mmol), followed by p-toluenesulphonic acid (25 mg). The reaction mixture was stirred at room temperature for 20 h. A solid separated, which was filtered, washed with isopropanol (0.25 mL), and dried to give the product as a solid. MS: m/z (M$^+$+1): 317

Additional compounds, shown below, were prepared by substituting the appropriate benzaldehyde for 3-chloro-benzaldehyde.

| R | MS: m/z (M$^+$ + 1) |
|---|---|
| 3-Methylphenyl | 297 |
| Phenyl | 283 |
| 2,4-Difluorophenyl | 319 |
| 2-Methylphenyl | 297 |
| 3-Methoxyphenyl | 313 |

Step B: Preparation of

To a solution of the Step A product (650 mg, 2.05 mmol, Example 1) in a mixture of 5 mL of isopropanol, tetrahydrofuran, and acetic acid (1:1:0.3) was added sodium cyanoborohydride (1.25 g, 20 mmol). The reaction mixture was stirred at room temperature for 30 h. Reaction mixture was diluted with ethyl acetate (50 mL) and washed with water 2×75 mL). The organic phase was dried (Na$_2$SO$_4$) and concentrated to dryness to give the product as syrup. MS: m/z (M$^+$+1): 319

Additional compounds, shown below, were also prepared.

| R | MS: m/z (M⁺ + 1) |
|---|---|
| 3-Methylphenyl | 299 |
| Phenyl | 285 |
| 2,4-Difluorophenyl | 321 |
| 2-Methylphenyl | 299 |
| 3-Methoxyphenyl | 315 |

Step C: Preparation of

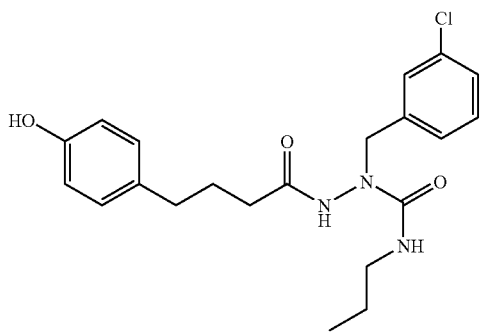

To a solution of the Step B product (400 mg, 1.26 mmol) in anhydrous THF (5 mL) was added n-propylisocyanate (213 mg, 2.52 mmol). The reaction mixture was stirred for 16 h. Methanol (1 mL) was added to the reaction mixture and the stirring was continued for an additional 30 min. The solvent was removed on a rotary evaporator to give the product as an oily residue. MS: m/z (M⁺+1): 404

Additional compounds, shown below, were also prepared.

| R | MS: m/z (M⁺ + 1) |
|---|---|
| 3-Methylphenyl | 384 |
| Phenyl | 370 |
| 2,4-Difluorophenyl | 406 |
| 2-Methylphenyl | 384 |
| 3-Methoxyphenyl | 400 |

Step D: Preparation of 2-(3-chlorobenzyl)-5-(3-(4-hydroxyphenyl)propyl)-4-n-propyltriazolin-3H-3-one

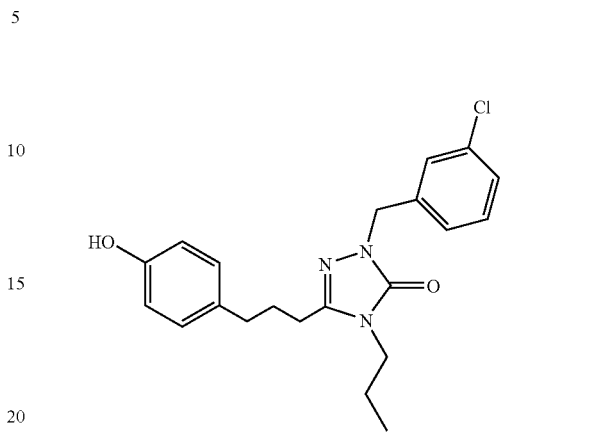

The Step C product, [1-(4-(4-hydroxyphenyl))butyryl-2-(3-chlorobenzyl)-4-n-propylcarbazate], (200 mg) was dissolved in methanol (20 mL). To this solution was added solid potassium hydroxide (0.50 g) and the reaction mixture was heated at reflux for 24 h with stirring. The reaction mixture was concentrated to a small volume (5 mL) and diluted with water (50 mL) and the aqueous layer was then acidified with 5N hydrochloric acid (pH~2). The aqueous layer was extracted with ethyl acetate (2×50 ml), the organic layer was dried (Na₂SO₄), and the solvent was removed on a rotary evaporator to give the product as an oily residue. MS: m/z (M⁺+1): 386

Additional compounds, shown below, were also prepared.

| R | MS: m/z (M⁺ + 1) |
|---|---|
| 3-Methylphenyl | 366 |
| Phenyl | 352 |
| 2,4-Difluorophenyl | 388 |
| 2-Methylphenyl | 366 |
| 3-Methoxyphenyl | 382 |

Step E: Preparation of

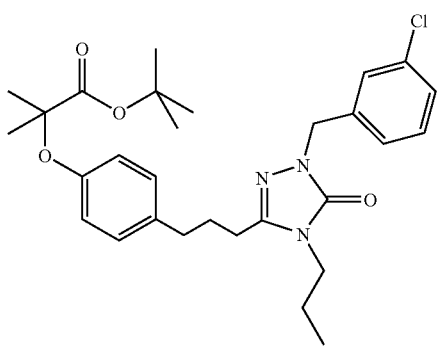

To a solution of the Step D product [2-(3-chlorobenzyl)-5-(3-(4-hydroxyphenyl)propyl)-4-n-propyltriazolin-3H-3-one] (0.17 g, 0.45 mmol) in anhydrous DMF (5 mL) was added tertbutyl bromoisobutyrate (0.70 gm, 3.14 mmol) followed by anhydrous $K_2CO_3$ (1.0 gm, powdered). The reaction mixture was stirred at 50° C. for 64 h. The reaction mixture was diluted with water (30 mL) and extracted with ethyl acetate (2×25 mL). The ethyl acetate layer was dried ($Na_2SO_4$) and concentrated on a rotary evaporaor to give an oily residue which was further purified on a silica gel column (1 cm×7 in.) eluting with ethyl acetate-hexane mixture (20-30% v/v) to give the product as an oil. MS: m/z ($M^+$+1): 530

Additional compounds, shown below, were also prepared.

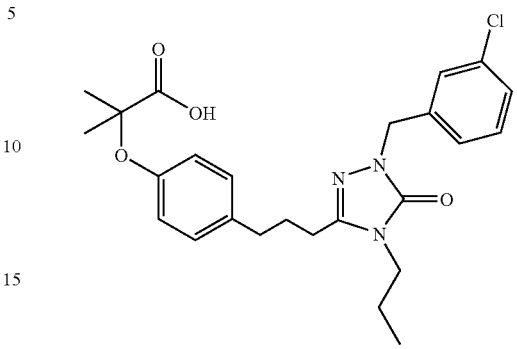

| R | MS: m/z ($M^+$ + 1) |
|---|---|
| 3-Methylphenyl | 466 |
| Phenyl | 452 |
| 2,4-Difluorophenyl | 530 |
| 2-Methylphenyl | 466 |
| 3-Methoxyphenyl | |

Step F: Preparation of

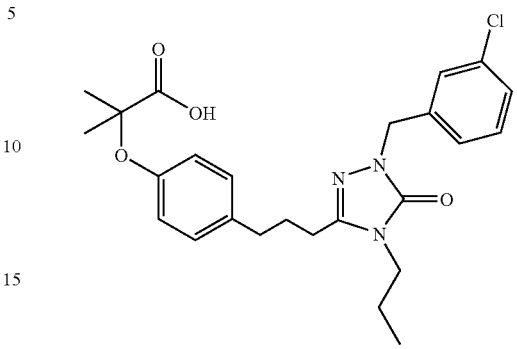

The Step E product (180 mg) was treated a mixture of triflouroacetic acid and dichloromethane (10 mL, 50% v/v) with stirring for 3 h. The solvent was removed on a rotary evaporator and the residue dried under high vacuum to give the title compound as an oil. MS: m/z ($M^+$+1): 472.9

Additional compounds, shown below, were also prepared.

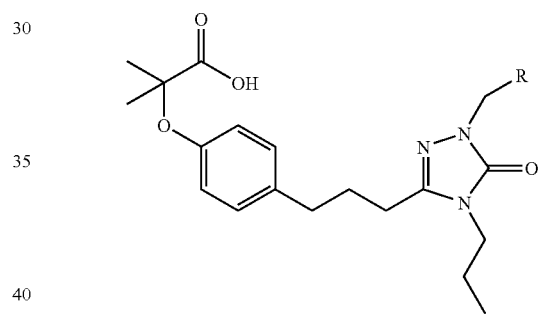

| Example Number | R | MS: m/z ($M^+$ + 1) |
|---|---|---|
| 1(2) | 3-Methylphenyl | 452 |
| 1(3) | Phenyl | 438 |
| 1(4) | 2,4-Difluorophenyl | 473 |
| 1(5) | 2-Methylphenyl | 452 |
| 1(6) | 3-Methoxyphenyl | 468 |

Example 2

Compound 2(1)

The compound shown below was prepared as follows:

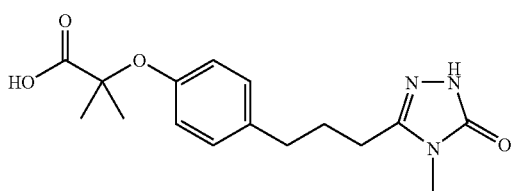

Step A: Preparation of

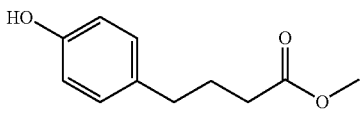

To a cooled (0° C.) solution of boron tribromide (50 g, 200 mmol) in $CH_2Cl_2$ (50 mL) was added a solution of methyl 4-(4-methoxyphenyl)butyrate (15.5 g, 74.4 mmol) in $CH_2Cl_2$ (100 mL) dropwise over one hour. After stirring for an additional hour at 0° C., the reaction mixture was treated with 1:1 $CH_3OH:CH_2Cl_2$ (120 mL) with cooling and stirred overnight at ambient temperature. Concentration of the mixture gave an oil which was partitioned between ethyl acetate (150 mL) and water (150 mL). The aqueous layer was extracted with ethyl acetate (2×50 mL), and the combined organic extracts washed with water (50 mL), brine (50 mL), dried ($Na_2SO_4$), then concentrated to give the desired phenol as an oil. $C_{11}H_{14}O_3$ (MW=194.23); MS: m/z ($M^+$+1)=195

Step B: Preparation of

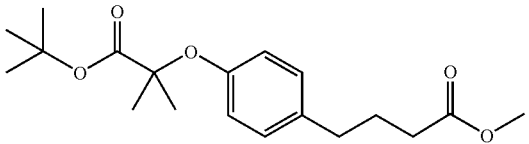

The phenol from Step A (18.6 g, 96 mmol) was dissolved in DMF (300 mL) and treated with t-butyl 2-bromoisobutyrate (50 mL, 288 mmol), powdered $K_2CO_3$ (53.0 g, 384 mmol) and $MgSO_4$ (1.6 g, 96 mmol), and the resulting mixture heated at 75° C. overnight. After cooling to ambient temperature, the reaction mixture was decanted into 1N aqueous HCl (300 ml) and extracted with diethyl ether (3×150 ml). The remaining solids from the decantation were washed several times with diethyl ether. The diethyl ether extracts and washes were combined and washed with 1N aqueous HCl (150 ml), dried ($Na_2SO_4$), and concentrated to a dark oil. Purification by flash chromatography (gradient elution, hexanes to 95:5 hexanes:ethyl acetate) gave the desired ether as an oil. $C_{19}H_{28}O_5$ (MW=336.43); MS: m/z ($M^+$+1)=337

Step C: Preparation of

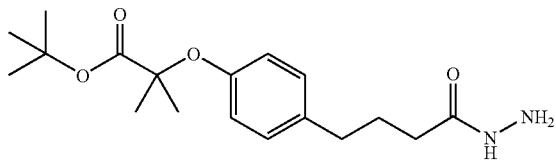

A solution of the ether from Step B (21.8 g, 64 mmol) in methanol (250 mL) was treated with hydrazine hydrate (32.0 g, 650 mmol) and the mixture stirred overnight at ambient temperature. The reaction mixture was concentrated and the residue partitioned between ethyl acetate (250 mL) and water (100 mL). The aqueous layer was extracted with ethyl acetate (2×100 mL), and the combined organic extracts washed with brine (100 mL), dried ($Na_2SO_4$), and concentrated to give the desired acylhydrazide as an oil. $C_{18}H_{28}N_2O_4$ (MW=336.43); MS: m/z ($M^+$+1)=337

Step D: Preparation of

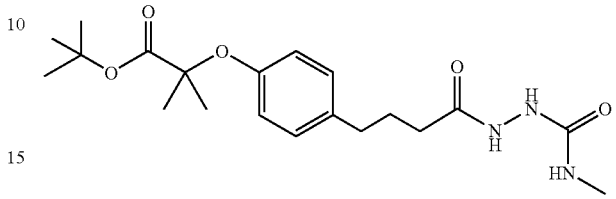

To a solution of the acylhydrazide from Step C (6.6 g, 19.6 mmol) in anhydrous THF (150 mL) was added methyl isocyanate (1.51 mL, 25.5 mmol) in one portion. The reaction mixture was stirred overnight at ambient temperature, then concentrated to give the desired acylsemicarbazate as an oil. $C_{20}H_{31}N_3O_5$ (MW=393.49); MS: m/z ($M^+$+1)=394

The compounds shown below were also prepared by substituting an appropriate alkylisocyanate or arylisocyanate for methylisocyanate.

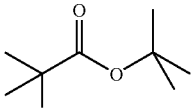

| R | MS: m/z ($M^+$ + 1) |
|---|---|
| Ethyl | 408 |
| n-Propyl | 422 |
| n-Butyl | 436 |
| n-Pentyl | 450 |
| n-Hexyl | 464 |
| 2,4-Dimethoxybenzyl | 530 |
| 2,4,6-Trimethoxybenzyl | 664 |
| Allyl | |

Step E: Preparation of

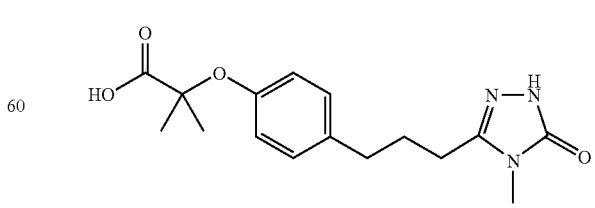

To a solution of the acylsemicarbazide from Step D in methanol (175 mL) was added solid potassium hydroxide (13 g, 231 mmol) and the reaction mixture heated at reflux for 48 hours. After cooling to ambient temperature, the reaction mixture was diluted with water (50 mLl) and methylene chloride (200 mL), then acidified to pH 2 with 5N hydrochloric acid. The aqueous layer was extracted with methylene chloride (2×40 mL). The combined organic extracts were washed with water (75 mL), brine (75 mL), dried (Na$_2$SO$_4$), and concentrated to give the desired triazolinone as an oil. C$_{16}$H$_{21}$N$_3$O$_4$ (MW=319.36); MS: m/z (M$^+$+1)=320

The compounds listed below were also prepared by this cyclization procedure.

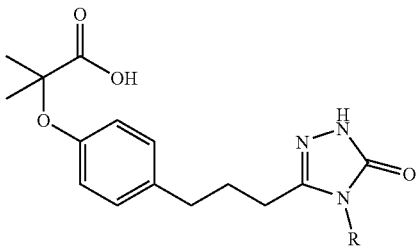

| R | MS: m/z (M + 1) |
| --- | --- |
| Ethyl | 334 |
| n-Propyl | 348 |
| n-Butyl | 362 |
| n-Pentyl | 376 |
| n-Hexyl | 390 |
| 2,4-Dimethoxybenzyl | 456 |
| 2,4,6-Trimethoxybenzyl | 590 |
| Allyl | |

Step F: Preparation of

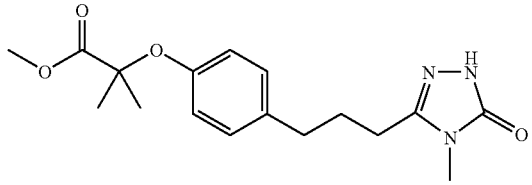

To a solution of the triazolinone from Step E in methanol (150 mL) was added concentrated sulfuric acid (1 mL) and the reaction mixture stirred at room temperature for 18 hours. After concentration to remove methanol, the oil was dissolved in ethyl acetate (125 mL), washed with water (50 ml), saturated aqueous NaHCO$_3$ (50 ml), and (brine 50 ml). The organic layer was dried (Na$_2$SO$_4$) and concentrated to give the methyl ester as a solid. C$_{17}$H$_{23}$N$_3$O$_4$ (MW=333.39); MS: m/z (M$^+$+1)=334

The compounds listed below were also prepared by Fisher esterification of the appropriate carboxylic acids above.

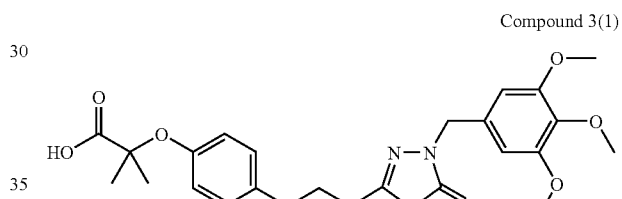

| Example Number | R | MS: m/z (M$^+$ + 1) |
| --- | --- | --- |
| 2 (2) | Ethyl | 348 |
| 2 (3) | n-Propyl | 362 |
| 2 (4) | n-Butyl | 376 |
| 2 (5) | n-Pentyl | 390 |
| 2 (6) | n-Hexyl | 404 |
| 2 (7) | 2,4-Dimethoxybenzyl | 470 |
| 2 (8) | 2,4,6-Trimethoxybenzyl | 604 |
| 2 (9) | Allyl | |

Example 3

Compound 3(1)

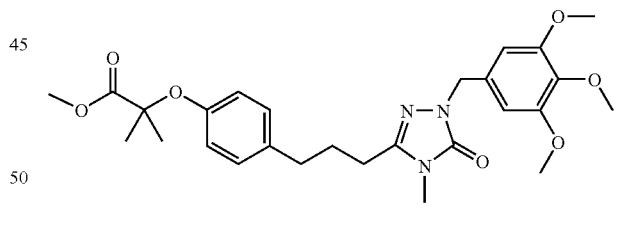

Step A: Preparation of

To a solution of the methyl ester, specifically Compound 2(1) (100 mg, 0.29 mmol) in DMF (2 mL), was added 3,4,5-trimethoxybenzyl chloride (129 mg, 0.6 mmol) and powdered potassium carbonate (350 mg, 2.53 mmol) and the resulting mixture heated at 45° C. for 24 hours. After cooling to ambient temperature, the reaction mixture was diluted with water (10 mL) and extracted with ethyl acetate (3×3 mL). The combined organic extracts were concentrated to an oil which was purified by flash chromatography (gradient elution, 1:4 ethyl acetate:hexanes to 4:1 ethyl acetate:hexanes) to give the desired product as an oil. C$_{27}$H$_{35}$N$_3$O$_7$ (MW=513.60); MS: m/z (M$^+$+1)=514

The compounds listed below were also prepared by alkylation of N-methyltriazolinone using appropriate alkylhalides in the place of 3,4,5-trimethoxybenzyl chloride.

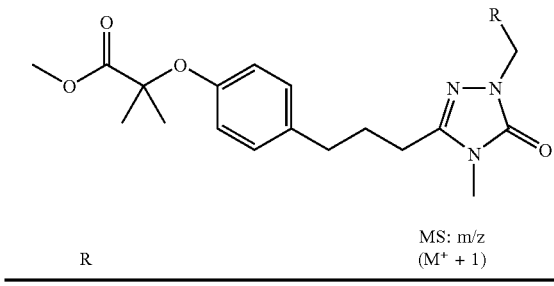

| R | MS: m/z (M+ + 1) |
|---|---|
| 3,5-Dimethoxyphenyl | 484 |
| 4-Biphenyl | 500 |
| 3-Chlorophenyl | 458 |
| 3-Chloro-4-methylphenyl | 472 |
| Bis-trifluoromethylphenyl | 560 |
| 3,4-Diflourophenyl | 460 |
| 3-Phenoxyphenyl | 516 |
| 4-Isopropylphenyl | 468 |
| 3-triflouromethoxyphenyl | 508 |
| 4-Methoxyphenyl | 454 |
| 4-Trifluoromethoxyphenyl | 508 |
| 4-Methylsulphonylphenyl | 502 |
| 3-(triflouromethylthio)phenyl | 524 |
| 4-Ethylphenyl | 452 |
| 3,4-Dimethylphenyl | 452 |
| 4-tert-Butylphenyl | 480 |
| 2-Naphthyl | 474 |
| 3-Methylphenyl | 438 |
| Phenmethyl | 438 |
| 3-(5-Chloro)benzothiophene | 515 |
| 4-Methylphenyl | 438 |
| 3,5-Difluorophenyl | 460 |
| 3-Trifluorophenyl | 492 |
| 3,4-Dichlorophenyl | 493 |
| Phenyl | 424 |
| 3,5-Dimethylphenyl | 452 |
| 4-Chlorophenyl | 458 |

Step B: Preparation of

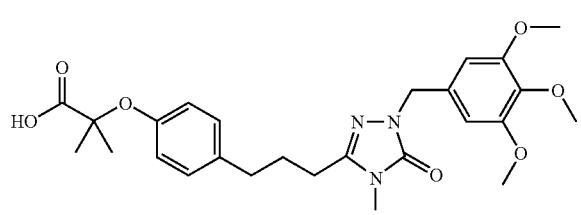

A solution of the methyl ester from Step A (125 mg, 0.24 mmol) in methanol (3 mL) was treated with 5N aqueous NaOH (0.30 mL) and the mixture stirred overnight at ambient temperature. After concentration to dryness, the residue was dissolved in water (5 mL), the solution acidified to pH 3 with concentrated hydrochloric acid, then extracted into methylene chloride (3×2 mL). The combined organic extracts were dried by eluting through a cartridge packed with diatomaceous earth, then concentrated to provide the carboxylic acid as a waxy solid. $C_{26}H_{33}N_3O_7$ (MW=499.57); MS: m/z (M++1)=500

The compounds listed below were also prepared by hydrolysis of appropriate methyl ester listed above.

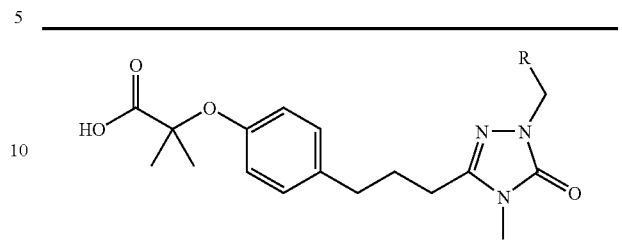

| Example Number | R | MS: m/z (M+ + 1) |
|---|---|---|
| 3 (2) | 3,5-Dimethoxyphenyl | 470 |
| 3 (3) | 4-Biphenyl | 486 |
| 3 (4) | 3-Chlorophenyl | 444 |
| 3 (5) | 3-Chloro-4-methylphenyl | 458 |
| 3 (6) | 2,4-Diflouromethylphenyl | 546 |
| 3 (7) | 3,4-Difluorophenyl | 446 |
| 3 (8) | 3-Phenoxyphenyl | 502 |
| 3 (9) | 4-Isopropylphenyl | 452 |
| 3 (10) | 3-triflouromethoxyphenyl | 494 |
| 3 (11) | 4-Methoxyphenyl | 440 |
| 3 (12) | 4-Trifluoromethoxy | 494 |
| 3 (13) | 4-Methylsulphonylphenyl | 488 |
| 3 (14) | 3-(triflouromethylthio)phenyl | 510 |
| 3 (15) | 4-Ethylphenyl | 438 |
| 3 (16) | 3,4-Dimethylphenyl | 438 |
| 3 (17) | 4-tert-Butylphenyl | 466 |
| 3 (18) | 2-Naphthyl | 460 |
| 3 (19) | 3-Methylphenyl | 424 |
| 3 (20) | Phenmethyl | 424 |
| 3 (21) | 3-(5-Chloro)benzothiophene | 501 |
| 3 (22) | 4-Methylphenyl | 424 |
| 3 (23) | 3,5-Difluorophenyl | 446 |
| 3 (24) | 3-Trifluorophenyl | 478 |
| 3 (25) | 3,4-Dichlorophenyl | 479 |
| 3 (26) | Phenyl | 410 |
| 3 (27) | 3,5-Dimethylphenyl | 438 |
| 3 (28) | 4-Chlorophenyl | 444 |

Example 4

Compound 4(1)

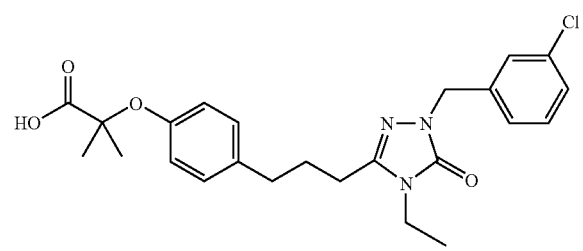

Step A: Preparation of

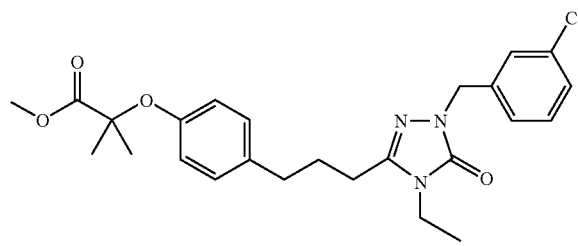

To a solution of Compound 2(2) (100 mg, 0.28 mmol) in DMF (2 mL), was added m-chlorobenzyl bromide (119 mg, 0.58 mmol) and powdered potassium carbonate (350 mg, 2.53 mmol) and the resulting mixture heated at 45° C. for 24 hours. After cooling to ambient temperature, the reaction mixture was diluted with water (10 mL) and extracted with ethyl acetate (3×3 mL). The combined organic extracts were concentrated to an oil which was purified by flash chromatography (gradient elution, 1:4 ethyl acetate:hexanes to 4:1 ethyl acetate:hexanes) to give the desired product as an oil. $C_{25}H_{30}ClN_3O_4$ (MW=471.99); MS: m/z (M$^+$+1)=473.

The compounds listed below were also prepared by alkylation of Compound 2(2) using the appropriate alkyl-halide in the place of m-chlorobenzyl bromide.

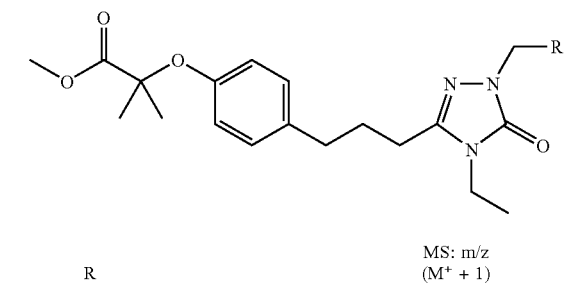

| R | MS: m/z (M$^+$ + 1) |
|---|---|
| n-propyl | |
| 3-chlorophenyl | 472 |
| 3-methylphenyl | 452 |
| phenyl | 438 |
| 2,4-difluorophenyl | |
| 3-trifluoromethylphenyl | 506 |
| 4-methylphenyl | 452 |
| 2-methylphenyl | |
| 3-nitrophenyl | |
| 4-carboxyphenyl | |
| 2-phenylethyl | |
| 3,5-difluorophenyl | 474 |
| 2-pyridyl | |
| 4-pyridyl | |
| 3-pyridyl | |
| 2-quinolinoyl | 489 |
| 6-(4-methoxy-2-trifluoromethyl) quinolinoyl | |
| 3-(5-chloro)benzo[b]thienyl | |
| 4-tert-butylphenyl | 494 |
| β-naphthyl | 488 |
| α-methylbenzyl | |
| 3,5-dimethylphenyl | |
| 2,6-dichlorophenyl | |
| 3-cyanophenyl | 463 |
| 5-(6-chloro)piperonyl | |
| 4-cyanophenyl | 463 |
| 5-piperonyl | 482 |
| 3-trifluoromethoxyphenyl | 522 |
| bis-2,4-trifluoromethylphenyl | |
| Cyclohexyl | |
| 4-ethylphenyl | |
| 3,4-dimethylphenyl | 466 |
| 4-trifluoromethylthiophenyl | |
| 4-isopropylphenyl | 480 |
| 4-methoxyphenyl | 466 |
| 4-trifluoromethoxyphenyl | 522 |
| 3,4-dichlorophenyl | 507 |
| 4-chlorophenyl | |
| 3,4-difluorophenyl | 474 |
| 4-methylsulfonylphenyl | |
| 2-methoxyphenyl | |
| 3,5-dimethoxyphenyl | 498 |
| 3,4,5-trimethoxyphenyl | 528 |
| 4-tert-pentylphenyl | |
| 2-(6-methyl)naphthyl | 502 |
| 2-naphthoyl | 516 |
| 5-(tert-butyl)1,2,4-oxadiazol-3-yl | 486 |
| 3-methyl-4-methoxyphenyl | 482 |
| 4-benzyloxyphenyl | 544 |
| 3-chloro-4-methylphenyl | 487 |
| 3-phenoxyphenyl | 530 |
| 4-acetamidophenyl | 495 |
| 4-trifluoromethylphenyl | 506 |
| p-biphenyl | 514 |
| 3,5-dimethylisoxazol-4-yl | 457 |

Step B: Preparation of

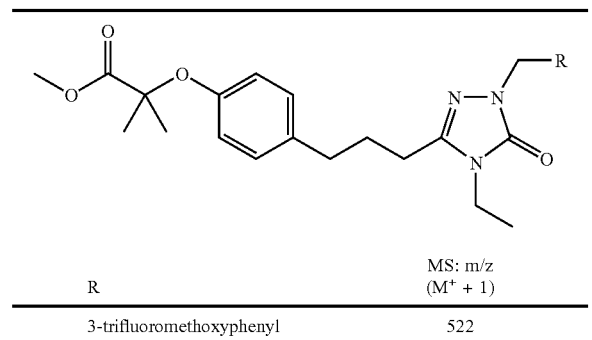

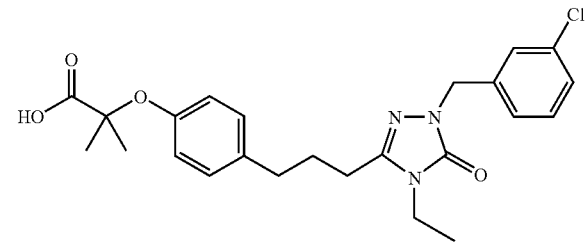

A solution of the product (125 mg, 0.24 mmol) from Step A in methanol (3 mL) was treated with 5N aqueous NaOH (0.30 mL) and the mixture stirred overnight at ambient temperature. After concentration to dryness, the residue was dissolved in water (5 mL), the solution acidified to pH 3 with concentrated hydrochloric acid, then extracted into methylene chloride (3×2 mL). The combined organic extracts were dried by eluting through a cartridge packed with diatomaceous earth, then concentrated to provide the carboxylic acid as a waxy solid. $C_{26}H_{33}N_3O_7$ (MW=457.96); MS: m/z (M$^+$+1)=458.

The compounds listed below were also prepared by hydrolysis of appropriate methyl ester listed above.

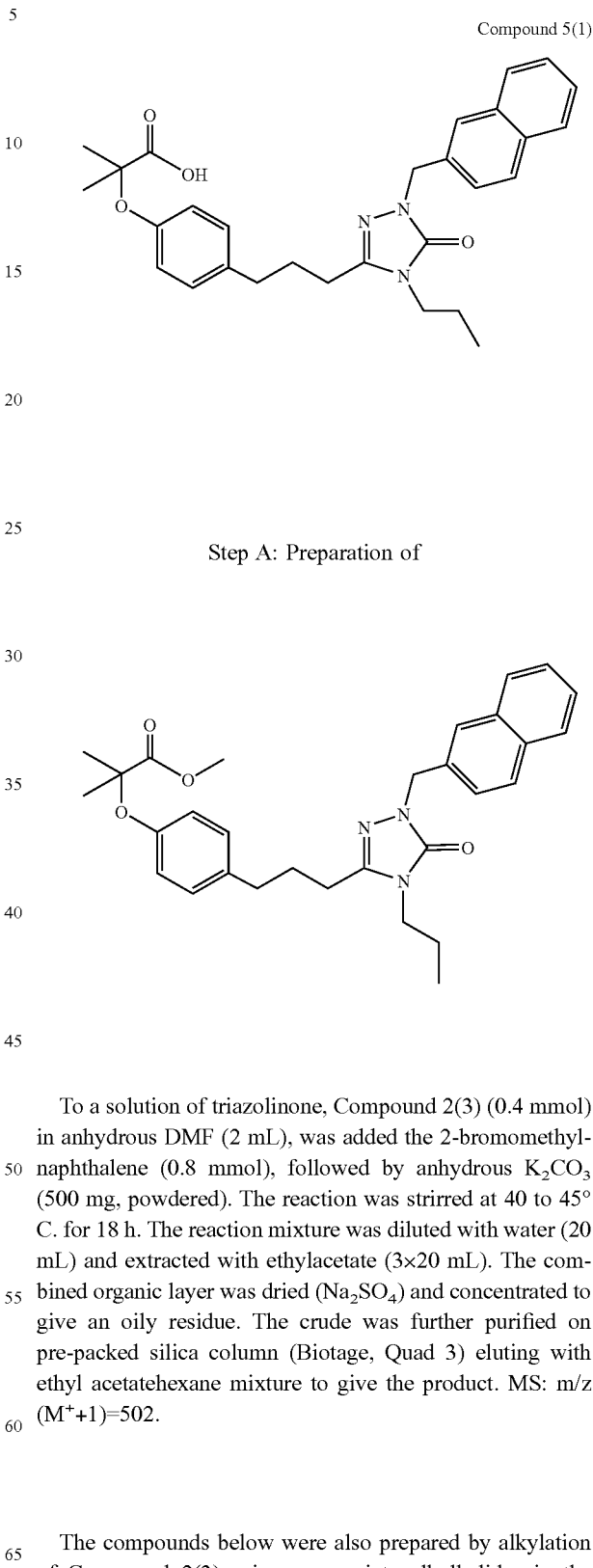

| Example Number | R | MS: m/z (M+ + 1) |
|---|---|---|
| 4 (2) | n-propyl | |
| 4 (3) | 3-methylphenyl | 438 |
| 4 (4) | phenyl | 424 |
| 4 (5) | 2,4-difluorophenyl | |
| 4 (6) | 3-trifluoromethylphenyl | 492 |
| 4 (7) | 4-methylphenyl | 438 |
| 4 (8) | 2-methylphenyl | |
| 4 (9) | 3-nitrophenyl | |
| 4 (10) | 4-carboxyphenyl | |
| 4 (11) | 2-phenylethyl | |
| 4 (12) | 3,5-difluorophenyl | 460 |
| 4 (13) | 2-pyridyl | |
| 4 (14) | 4-pyridyl | |
| 4 (15) | 3-pyridyl | |
| 4 (16) | 2-quinolinoyl | 475 |
| 4 (17) | 6-(4-methoxy-2-trifluoromethyl)quinolinoyl | |
| 4 (18) | 3-(5-chloro)benzo[b]thiophenyl | 515 |
| 4 (19) | 4-tert-butylphenyl | 480 |
| 4 (20) | β-naphthyl | 474 |
| 4 (21) | α-methylbenzyl | |
| 4 (22) | 3,5-dimethylphenyl | |
| 4 (23) | 2,6-dichlorophenyl | |
| 4 (24) | 3-cyanophenyl | 449 |
| 4 (25) | 5-(6-chloro)piperonyl | |
| 4 (26) | 4-cyanophenyl | 449 |
| 4 (27) | 5-piperonyl | 468 |
| 4 (28) | 3-trifluoromethoxyphenyl | 508 |
| 4 (29) | bis-2,4-trifluoromethylphenyl | |
| 4 (30) | Cyclohexyl | |
| 4 (31) | 4-ethylphenyl | |
| 4 (32) | 3,4-dimethylphenyl | 452 |
| 4 (33) | 4-trifluoromethylthiophenyl | |
| 4 (34) | 4-isopropylphenyl | 466 |
| 4 (35) | 4-methoxyphenyl | 454 |
| 4 (36) | 4-trifluoromethoxyphenyl | 508 |
| 4 (37) | 3,4-dichlorophenyl | 493 |
| 4 (38) | 4-chlorophenyl | |
| 4 (39) | 3,4-difluorophenyl | 460 |
| 4 (40) | 4-methylsulfonylphenyl | |
| 4 (41) | 2-methoxyphenyl | |
| 4 (42) | 3,5-dimethoxyphenyl | 484 |
| 4 (43) | 3,4,5-trimethoxyphenyl | 514 |
| 4 (44) | 4-tert-pentylphenyl | |
| 4 (45) | 2-(6-methyl)naphthyl | 488 |
| 4 (46) | 2-naphthoyl | 502 |
| 4 (47) | 5-(tert-butyl)1,2,4-oxadiazol-3-yl | 472 |
| 4 (48) | 3-methyl-4-methoxyphenyl | 468 |
| 4 (49) | 4-benzyloxyphenyl | 530 |
| 4 (50) | 3-chloro-4-methylphenyl | 473 |
| 4 (51) | 3-phenoxyphenyl | 516 |
| 4 (52) | 4-acetamidophenyl | 481 |
| 4 (53) | 4-trifluoromethylphenyl | 492 |
| 4 (54) | p-biphenyl | 500 |
| 4 (55) | 3,5-dimethylisoxazol-4-yl | 443 |

Example 5

Compound 5(1)

Step A: Preparation of

To a solution of triazolinone, Compound 2(3) (0.4 mmol) in anhydrous DMF (2 mL), was added the 2-bromomethyl-naphthalene (0.8 mmol), followed by anhydrous $K_2CO_3$ (500 mg, powdered). The reaction was stirred at 40 to 45° C. for 18 h. The reaction mixture was diluted with water (20 mL) and extracted with ethylacetate (3×20 mL). The combined organic layer was dried ($Na_2SO_4$) and concentrated to give an oily residue. The crude was further purified on pre-packed silica column (Biotage, Quad 3) eluting with ethyl acetatehexane mixture to give the product. MS: m/z (M++1)=502.

The compounds below were also prepared by alkylation of Compound 2(3) using appropriate alkylhalides in the place of 2-bromomethylnaphthalene.

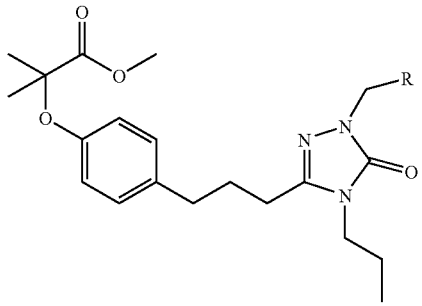

| R | MS: m/z (M+ + 1) |
|---|---|
| n-ethyl | 404 |
| 3-chlorophenyl | 486 |
| 3-methylphenyl | 466 |
| Phenyl | 452 |
| 2,4-difluorophenyl | 488 |
| 3-trifluoromethylphenyl | 520 |
| 4-methylphenyl | 466 |
| 2-methylphenyl | 466 |
| 3-nitrophenyl | 497 |
| 4-carboxyphenyl | 496 |
| 2-phenylmethyl | 466 |
| 3,5-difluorophenyl | 488 |
| 2-pyridyl | 443 |
| 4-pyridyl | 443 |
| 3-pyridyl | 443 |
| 2-quinolinoyl | 503 |
| 6-(4-methoxy-2-trifluoromethyl)quinolinoyl | 601 |
| 3-(5-chloro)benzo[b]thienyl | 543 |
| 4-tert-butylphenyl | 508 |
| β-naphthyl | 502 |
| α-methylbenzyl | 466 |
| 3,5-dimethylphenyl | 480 |
| 2,6-dichlorophenyl | 521 |
| 3-cyanophenyl | 477 |
| 5-(6-chloro)piperonyl | 531 |
| 4-cyanophenyl | 477 |
| 5-piperonyl | 496 |
| 3-trifluoromethoxyphenyl | 536 |
| Bis-2,4-trifluoromethylphenyl | 588 |
| Cyclohexyl | 458 |
| 4-ethylphenyl | 480 |
| 3,4-dimethylphenyl | 480 |
| 4-trifluoromethylthiophenyl | 552 |
| 4-isopropylphenyl | 494 |
| 4-methoxyphenyl | 482 |
| 4-trifluoromethoxyphenyl | 536 |
| 3,4-dichlorophenyl | 521 |
| 4-chlorophenyl | 486 |
| 3,4-difluorophenyl | 488 |
| 4-methylsulfonylphenyl | 530 |
| 2-methoxyphenyl | 482 |
| 3,5-dimethoxyphenyl | 512 |
| 3,4,5-trimethoxyphenyl | 542 |
| 4-tert-pentylphenyl | 522 |
| 2-(6-methyl)naphthyl | 516 |
| 2-naphthoyl | 530 |
| 5-(tert-butyl)1,2,4-oxadiazol-3-yl | 500 |

Step B: Preparation of

Compound 5(1)

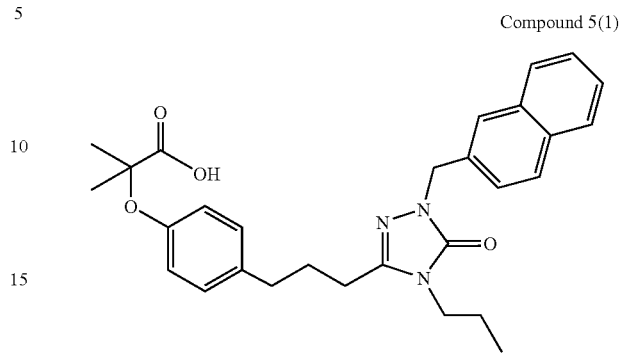

To a solution of the methyl ester of Step A (150 mg) in methanol (2 mL) was added 1N aqueous KOH solution (2 mL). The reaction mixture was stirred at room temp for 4 h. Methanol was removed on a rotary evaporator and the aqueous layer diluted with water (1 mL). This was then acidified with 5 N aqueous HCl (pH~2). The aqueous layer was extracted with dichloromethane (3×20 mL), dried ($Na_2SO_4$) and concentrated to dryness to give the product as a foam. MS: m/z (M++1)=488.

The compounds below were also prepared by hydrolysis of the appropriate methyl ester.

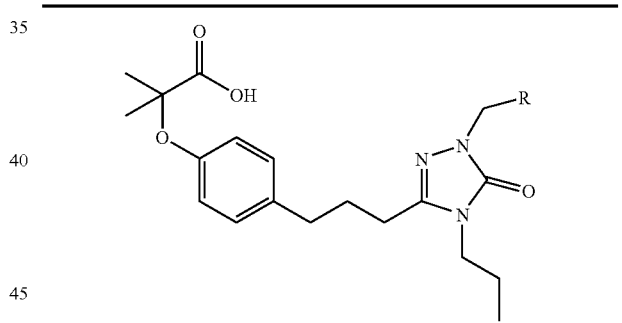

| Example Number | R | MS: m/z (M+ + 1) |
|---|---|---|
| 5 (2) | n-Ethyl | 390 |
| 5 (3) | 3-chlorophenyl | 472 |
| 5 (4) | 3-methylphenyl | 452 |
| 5 (5) | Phenyl | 438 |
| 5 (6) | 2,4-difluorophenyl | 474 |
| 5 (7) | 3-trifluoromethylphenyl | 506 |
| 5 (8) | 4-methylphenyl | 452 |
| 5 (9) | 2-methylphenyl | 452 |
| 5 (10) | 3-nitrophenyl | 483 |
| 5 (11) | 4-carboxyphenyl | 482 |
| 5 (12) | phenylmethyl | 452 |
| 5 (13) | 3,5-difluorophenyl | 474 |
| 5 (14) | 2-pyridyl | 439 |
| 5 (15) | 4-pyridyl | 439 |
| 5 (16) | 3-pyridyl | 439 |
| 5 (17) | 2-quinolinoyl | 489 |
| 5 (18) | 6-(4-methoxy-2-trifluoromethyl)quinolinoyl | 587 |
| 5 (19) | 3-(5-chloro)benzo[b]thienyl | 529 |

-continued

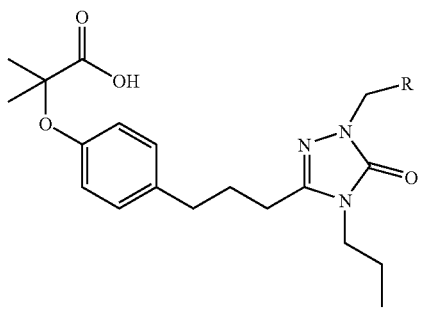

| Example Number | R | MS: m/z (M+ + 1) |
|---|---|---|
| 5 (20) | 4-tert-butylphenyl | 494 |
| 5 (21) | a-methylbenzyl | 452 |
| 5 (22) | 3,5-dimethylphenyl | 466 |
| 5 (23) | 2,6-dichlorophenyl | 507 |
| 5 (24) | 3-cyanophenyl | 463 |
| 5 (25) | 5-(6-chloro)piperonyl | 517 |
| 5 (26) | 4-cyanophenyl | 463 |
| 5 (27) | 5-piperonyl | 482 |
| 5 (28) | 3-trifluoromethoxyphenyl | 522 |
| 5 (29) | Bis-2,4-trifluoromethylphenyl | 574 |
| 5 (30) | Cyclohexyl | 444 |
| 5 (31) | 4-ethylphenyl | 466 |
| 5 (32) | 3,4-dimethylphenyl | 466 |
| 5 (33) | 4-trifluoromethylthiophenyl | 538 |
| 5 (34) | 4-isopropylphenyl | 480 |
| 5 (35) | 4-methoxyphenyl | 468 |
| 5 (36) | 4-trifluoromethoxyphenyl | 522 |
| 5 (37) | 3,4-dichlorophenyl | 507 |
| 5 (38) | 4-chlorophenyl | 472 |
| 5 (39) | 3,4-difluorophenyl | 474 |
| 5 (40) | 4-methylsulfonylphenyl | 516 |
| 5 (41) | 2-methoxyphenyl | 468 |
| 5 (42) | 3,5-dimethoxyphenyl | 498 |
| 5 (43) | 3,4,5-trimethoxyphenyl | 528 |
| | 4-tert-pentylphenyl | 508 |
| 5 (45) | 2-(6-methyl)naphthyl | 502 |
| 5 (46) | 2-naphthoyl | 516 |
| 5 (47) | 5-(tert-butyl)1,2,4-oxadiazol-3-yl | 486 |

Example 6

Compound 6(1)

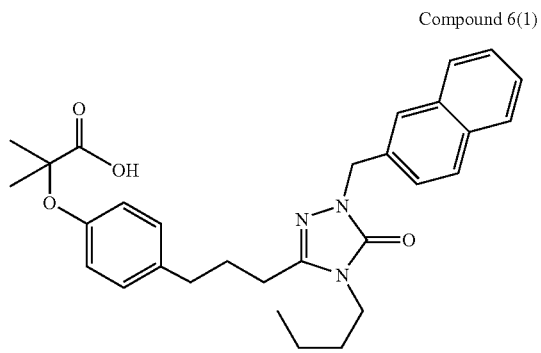

Step A: Preparation of

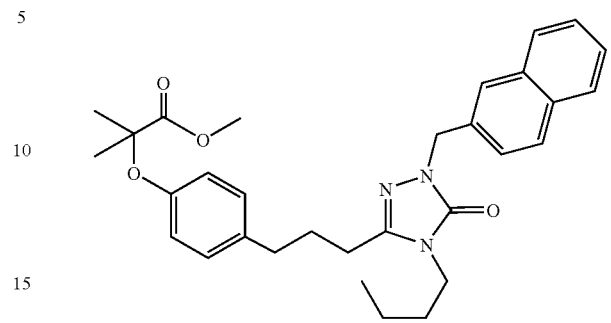

To a solution of 4-butyltriazolinone derivative, Compound 2(4) (188 mg, 0.4 mmol) in anhydrous DMF (3 mL), was added the 2-bromethylnaphthalene (265 mg, 1.2 mmol), followed by anhydrous K$_2$CO$_3$ (500 mg, powdered). The reaction was stirred at 40 to 45° C. for 18 h. The reaction mixture was diluted with water (20 mL) and extracted with ethylacetate (3×20 mL). The combined organic layers were concentrated to give an oily residue. The crude was purified on pre-packed silica column (Biotag, Quad 3) eluting with ethyl acetate-hexane mixture to give the product. MS: m/z (M$^+$+1)=516.

The compounds below were also prepared by alkylation of the 4-butyltriazolinone derivative using the appropriate alkylhalide in place of 2-bromethylnaphthalene.

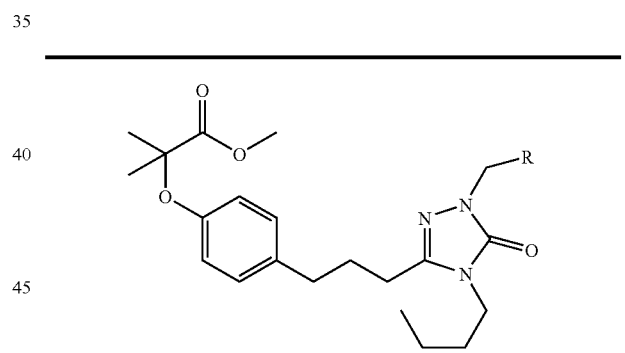

| R | MS: m/z (M+ + 1) |
|---|---|
| 3-Trifluoromethylphenyl | 534 |
| 3-Cyanophenyl | 491 |
| 3,5-Bistrifluoromethylphenyl | 502 |
| Phenyl | 466 |
| 4-Cyanophenyl | 491 |
| 3,5-Dimethylphenyl | 494 |
| 4-tert-Butylphenyl | 522 |
| 4-Methylphenyl | 480 |
| 2-Biphenyl | 542 |
| 3,5-Diflourophenyl | 502 |
| Piperonyl | 510 |
| Phenylmethyl | 480 |

Step B: Preparation of

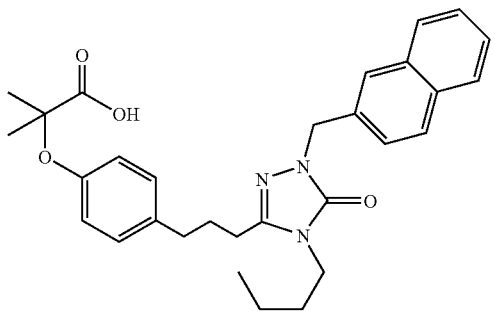

To a solution of ester from Step A (150 mg) in 2 mL of methanol was added 2N aqueous NaOH solution (2 mL). The reaction mixture was stirred at room temperature for 2 h. Methanol was removed on the rotary evaporator. The reaction mixture was acidified with 5N aqueous HCl (pH~3) and extracted with dichloromethane (2×25 mL). The organic layer was dried over $Na_2SO_4$ and concentrated to dryness to give the product as an oily residue. MS: m/z ($M^+$+1)=502.

The compounds below were also prepared by hydrolysis of appropriate methyl ester.

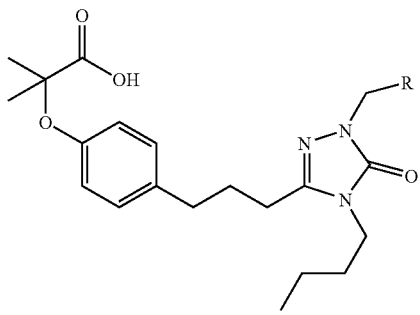

| Example Number | R | MS: m/z ($M^+$ + 1) |
|---|---|---|
| 6 (2) | 3-Trifluoromethylphenyl | 520 |
| 6 (3) | 3-Cyanophenyl | 477 |
| 6 (4) | 3,5-Bistrifluoromethylphenyl | 588 |
| 6 (5) | Phenyl | 452 |
| 6 (6) | 4-Cyanophenyl | 477 |
| 6 (7) | 3,5-Dimethylphenyl | 480 |
| 6 (8) | 4-tert-Butylphenyl | 508 |
| 6 (9) | 4-Methylphenyl | 466 |
| 6 (10) | 2-Biphenyl | 528 |
| 6 (11) | 3,5-Diflourophenyl | 488 |
| 6 (12) | Piperonyl | 496 |
| 6 (13) | Phenylmethyl | 466 |

Example 7

Compound 7(1)

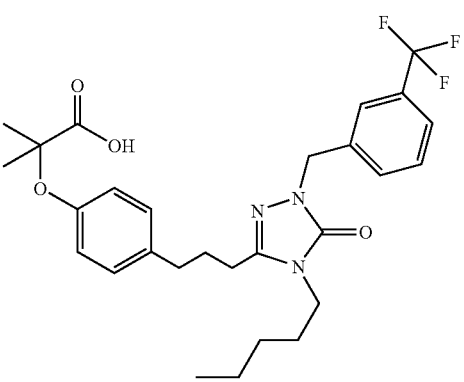

Step A: Preparation of

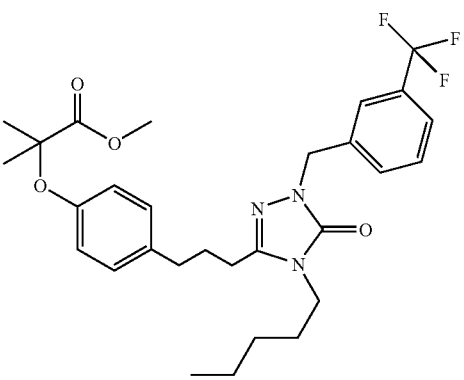

To a solution of the 4-n-pentyltriazolinone derivative, Compound 2(5) (150 mg, 0.39 mmol) in anhydrous DMF (3 mL), was added the 3-trifluoromethylbenzyl bromide (286 mg, 1.2 mmol), followed by anhydrous $K_2CO_3$ (500 mg, powdered). The reaction was stirred at 40 to 45° C. for 18 h. The reaction mixture was diluted with water (20 mL) and extracted with ethyl acetate (3×20 mL). The combined organic layers were concentrated to give an oily residue. The crude was purified on pre-packed silica column (Biotage, Quad 3) eluting with ethyl acetate-hexane mixture to give the product. MS: m/z ($M^+$+1)=548.

The compounds below were also prepared in the same manner by alkylation of the 4-n-pentyltriazolinone derivative using the appropriate alkylhalide in the place of 3-trifluoromethylbenzyl bromide.

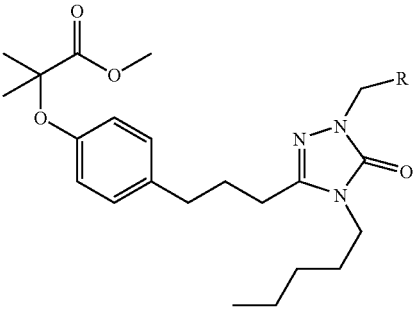

| R | MS: m/z (M+ + 1) |
|---|---|
| 3,5-bis-triflouromethylphenyl | 616 |
| phenyl | 480 |
| 4-cyanophenyl | 505 |
| 3,5-dimethylphenyl | 508 |
| 4-tert-butylphenyl | 536 |
| 4-methylphenyl | 494 |
| 2-biphenyl | 556 |
| 3,5-difluorophenyl | 516 |
| piperanyl | 524 |
| 3-heptyl | 502 |
| 2-naphthyl | |
| 3-cyanophenyl | |

Step B: Preparation of

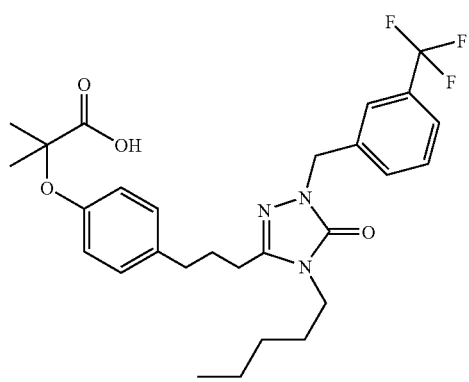

To a solution of the Step A ester (170 mg) in 2 mL of methanol was added 2N aqueous NaOH solution (2.5 mL). The reaction mixture was stirred at room temperature for 2 h. Methanol was removed on the rotary evaporator. The reaction mixture was acidified with 5N aqueous HCl (pH~3) and extracted with dichloromethane (2×25 mL). The oraganic layer was dried over $Na_2SO_4$ and concentrated to dryness to give the product as an oily residue. MS: m/z ($M^+$+1)=534.

The compounds below were also prepared by hydrolysis of the appropriate methyl ester.

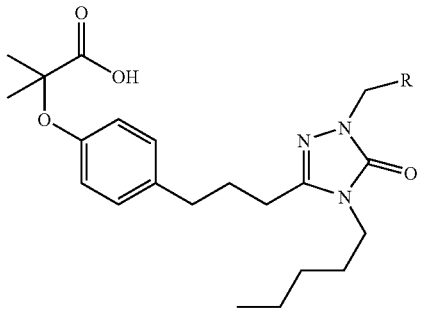

| Example Number | R | MS: m/z (M+ + 1) |
|---|---|---|
| 7 (2) | 3,5-bis-triflouromethylphenyl | 602 |
| 7 (3) | phenyl | 466 |
| 7 (4) | 4-cyanophenyl | 491 |
| 7 (5) | 3,5-dimethylphenyl | 494 |
| 7 (6) | 4-tert-butylphenyl | 522 |
| 7 (7) | 4-methylphenyl | 480 |
| 7 (8) | 2-biphenyl | 542 |
| 7 (9) | 3,5-difluorophenyl | 502 |
| 7 (10) | piperanyl | 510 |
| 7 (11) | 3-heptyl | 488 |
| 7 (12) | 2-naphthyl | 516 |
| 7 (13) | 3-cyanophenyl | 491 |

Example 8

Compound 8(1)

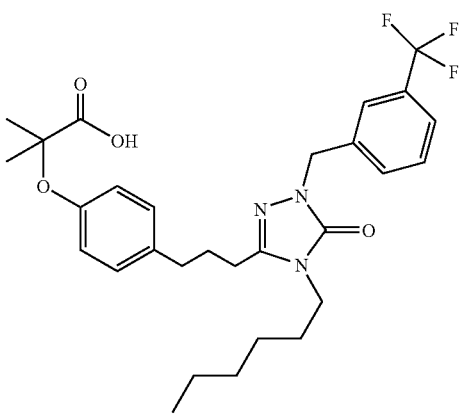

Step A: Preparation of

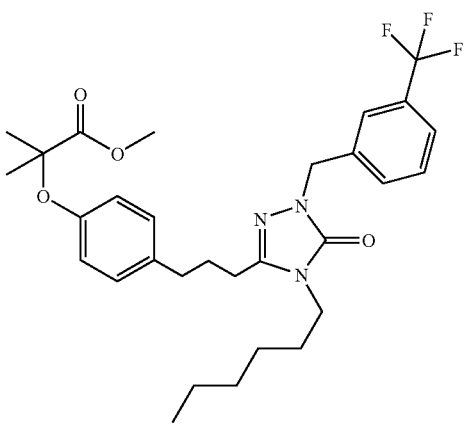

To a solution of the 4-hexyltriazolinone derivative, Compound 2(6) (150 mg, 0.39 mmol) in anhydrous DMF (3 mL), was added the 3-trifluoromethylbenzyl bromide (286 mg, 1.2 mmol), followed by anhydrous K₂CO₃ (500 mg, powdered). The reaction was strirred at 40 to 45° C. for 18 h. The reaction mixture was diluted with water (20 mL) and extracted with ethyl acetate (3×20 mL). The combined organic layers were concentrated to give an oily residue. The crude product was further purified on pre-packed silica column (Biotage, Quad 3) eluting with ethyl acetate-hexane mixture to give the products as oils.

The compounds listed below were prepared by alkylation of Compound 2(6) and using the appropriate alkylhalide in the place of 3-trifluoro-methylbenzyl bromide.

| R | MS: m/z (M⁺ + 1) |
|---|---|
| 2-naphthyl | |
| 3-cyanophenyl | |
| 3,5-bis-trifluoromethylphenyl | |

Step B: Preparation of

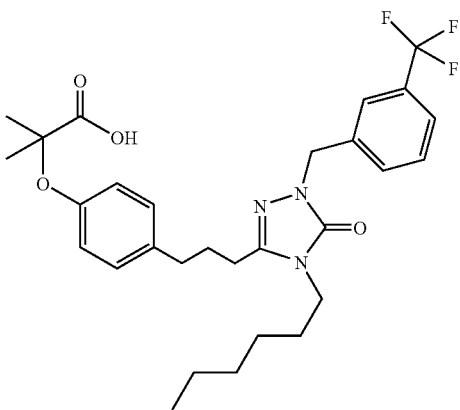

To a solution of the Step A ester (204 mg) in 2 mL of methanol was added 2N aqueous NaOH solution (2.5 mL). The reaction mixture was stirred at room temperature for 2 h. Methanol was removed on the rotary evaporator. The reaction mixture was acidified with 5N aqueous HCl (pH~3) and extracted with dichloromethane (2×25 mL). The oraganic layer was dried over Na₂SO₄ and concentrated to dryness to give the product as an oily residue. MS: m/z (M+1) 548.

The compounds listed below were prepared by hydrolysis of appropriate methyl ester.

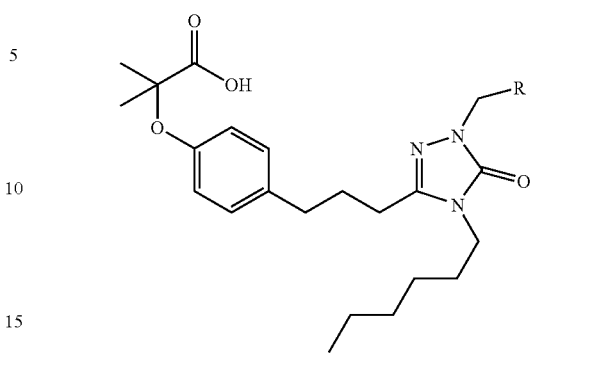

| Example Number | R | MS: m/z (M⁺ + 1) |
|---|---|---|
| 8 (2) | 2-naphthyl | 530 |
| 8 (3) | 3-cyanophenyl | 505 |
| 8 (4) | 3,5-bis-trifluoromethylphenyl | 616 |

Example 9

Compound 9(1)

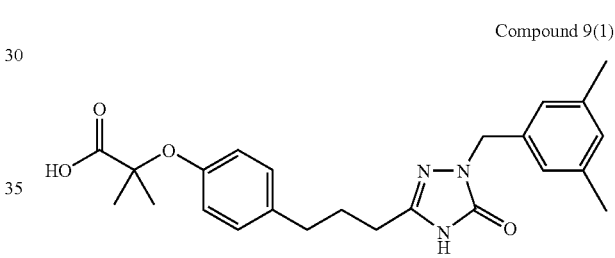

Step A: Preparation of

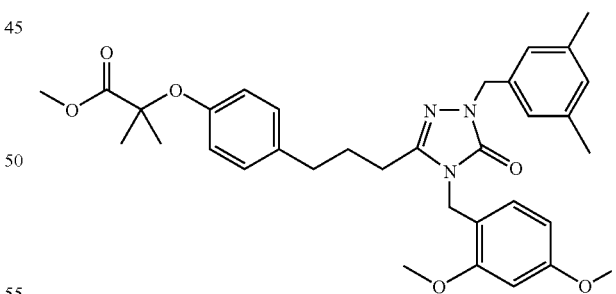

To a solution of the 4-(2,4-dimethoxybenzyl)-triazolinone derivative from Compound 2(7) (190 mg, 0.40 mmol) in DMF (2 mL), was added 3,5-dimethylbenzyl bromide (159 mg, 0.80 mmol) and powdered potassium carbonate (350 mg, 2.53 mmol), and the resulting mixture heated at 45° C. for 24 hours. After cooling to ambient temperature, the reaction mixture was diluted with water (10 mL) and extracted with ethyl acetate (3×3 mL). The combined organic extracts were concentrated to an oil which was purified by flash chromatography (gradient elution, 1:4 ethyl acetate:hexanes to 4:1 ethyl acetate:hexanes) to give the desired product as an oil. $C_{34}H_{41}N_3O_6$ (MW=587.72); MS: m/z (M$^+$+1)=588.

The following compounds were prepared utilizing the appropriate bromide in the place of 3,5-dimethylbenzyl bromide, as shown in the table.

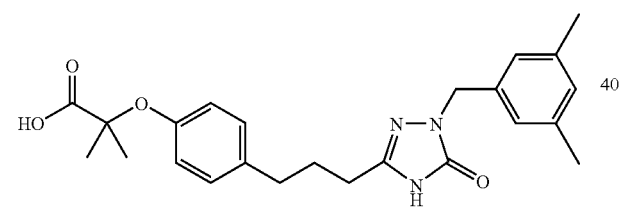

| R | MS: m/z (M$^+$ + 1) |
|---|---|
| 4-t-butylphenyl | 616 |
| 3-phenoxyphenyl | 652 |
| 3-methylphenyl | 574 |
| 3-trifluoromethylphenyl | 628 |
| 2-naphthyl | 610 |
| 3,5-dimethylphenyl | 588 |

Step B: Preparation of

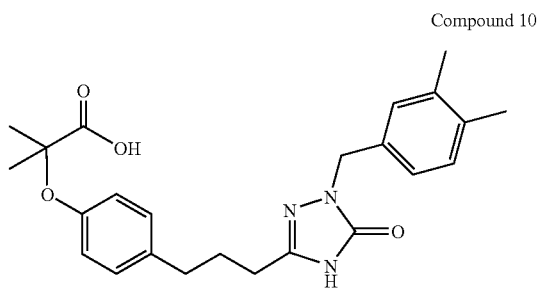

A solution of the Step A product (157mg, 0.26 mmol) in 33% (wt) hydrogen bromide in acetic acid (3 ml) was stirred at ambient temperature for 24 hours. The reaction mixture was treated with ice (30 g) and the mixture extracted with ethyl acetate (2×15 mL). The combined ethyl acetate extracts were washed with water, brine, dried and concentrated to an oil. The oil was dissolved in methanol (3 mL), treated with 5N aqueous NaOH (0.5 mL), and the resulting solution was stirred at ambient temperature for 18 hours. Concentration to remove methanol gave a residue which was dissolved in water (10 mL) and the resulting solution acidified to pH3 with concentrated hydrochloric acid. The suspension was extracted with methylene chloride (3×4 mL). The combined organic extracts were purified by reverse phase HPLC to give the desired product as a foam after lyophilization. $C_{24}H_{29}N_3O_4$ (MW=423.52); mass spectroscopy (MH$^+$)=424.

The compounds listed below were prepared from the corresponding methyl esters.

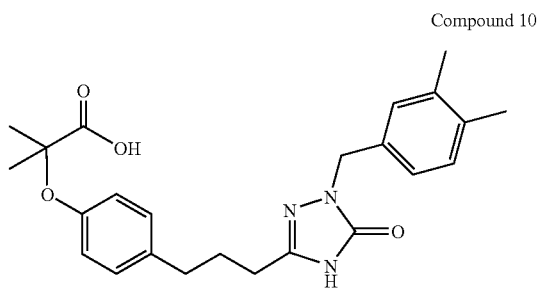

| Example Number | R | MS: m/z (M$^+$ + 1) |
|---|---|---|
| 9 (2) | 4-t-butylphenyl | 452 |
| 9 (3) | 3-phenoxyphenyl | 488 |
| 9 (4) | 3-methylphenyl | 410 |
| 9 (5) | 3-trifluoromethylphenyl | 464 |
| 9 (6) | 2-naphthyl | 446 |

Example 10

Compound 10

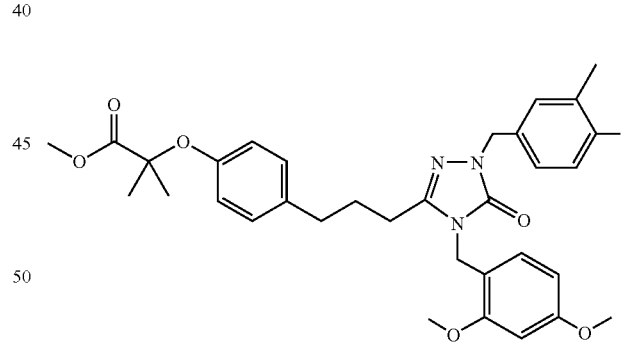

Step A: Preparation of

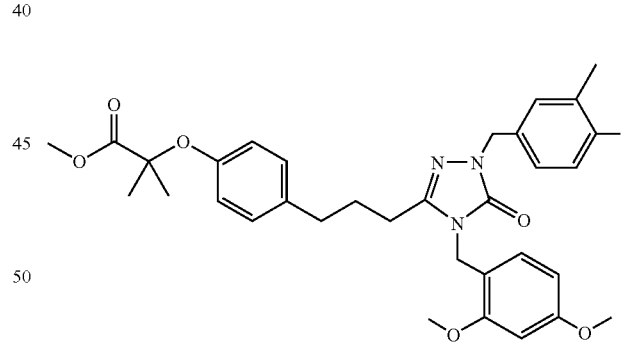

To a solution of the 4-(2,4-dimethoxybenzyl)-triazolinone derivative from Compound 2(7) (9.0, 21.3 mmol) in DMF (25 mL), was added 3,4-dimethylbenzyl bromide (4.62 g, 25 mmol) and powdered potassium carbonate (10 g), and the resulting mixture stirred at ambient temperature for 24 hours. The reaction mixture was diluted with water (100 mL) and extracted with ethyl acetate (3×75 mL). The combined organic extracts were concentrated to an oil. Alternatively the product could be further purified by flash chromatography (gradient elution, 1:4 ethyl acetate:hexanes to 4:1 ethyl acetate:hexanes) to give the desired product as an oil. MS: m/z (M$^+$+1)=588.

Step B: Preparation of

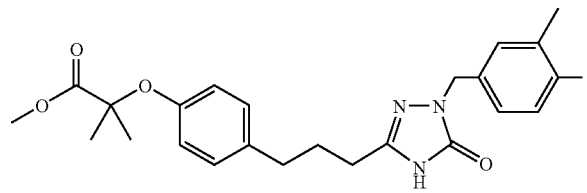

A solution of the Step A product (9.5 gm) in 33% (wt) hydrogen bromide in acetic acid (50 mL) was stirred at ambient temperature for 24 hours. The reaction mixture was treated with ice (100 g) and the mixture extracted with ethyl acetate (2×100 mL). The combined ethyl acetate extracts were washed with water, brine, dried and concentrated to an oil. The oil was dissolved in methanol (200 mL), treated with 2 mL of concentrated $H_2SO_4$, and the resulting solution was stirred at ambient temperature for 18 hours. Concentration to remove methanol gave a residue which was dissolved in methylene chloride (200 mL) and washed with water (2×100 mL) followed by saturated aqueous $NaHCO_3$. The combined organic extracts were dried ($Na_2SO_4$), concentrated, and purified by flash chromatography ($SiO_2$, EtOAc/Heanes) to give the desired product as a solid. MS: m/z ($M^+$+1)=438.

Step C: Preparation of

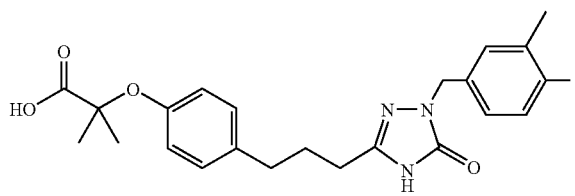

A solution of the Step B product (150 mg) in methanol (3 mL) was added 2N NaOH (2 mL) and the mixture was stirred at ambient temperature for 4 hours. The reaction mixture concentrated, diluted with methylene chloride (25 mL), water (5 mL) was added, and the mixture was acidified with concentrated HCl to pH~2. The layers were separated, and the aqueous layer was extracted (2×25 mL) methylene chloride. The combined organic extracts were dried ($Na_2SO_4$) and concentrated, to give the desired product as a solid. MS: m/z ($M^+$+1)=424.

Example 11

Compound 11

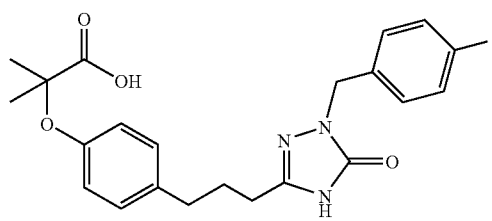

Step A: Preparation of

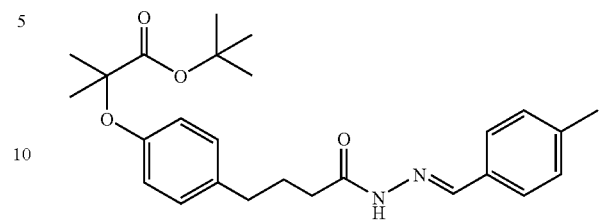

To the acyl hydrazide product of Example 2, Step C (5.4079 g, 16.07 mmol) in ethyl acetate (15 mL) was added p-methyl benzaldehyde (1.90 mL, 1.936 g, 16.11 mmol) via syringe. The resulting solution was stirred at room temperature and hexanes (30 mL) was added. Precipitate began to form and the resulting slurry was stirred for 16 h, then cooled to 0° C. and filtered. The filter cake was rinsed with cold hexanes and air dried to afford the desired imine (6.49 g, 92.1%) as a white solid. Anal. Calcd. for $C_{26}H_{34}N_2O_4$: C, 71.21; H, 7.81; N, 6.39. Found: C, 70.90; H, 7.79; N, 6.45.

Step B: Preparation of

To the product of Step A (4.0 g, 9.12 mmol) in THF (40 mL) was added platinum oxide (0.2012 g) and the resulting slurry hydrogenated at room temperature and 40 psi for 3 h. The solution was filtered and an additional charge of platinum oxide (0.303 g) was added, and the resulting slurry was hydrogenated at room temperature and 40 psi for 16 h. The slurry was filtered and concentrated in vacuo at 60° C. to afford the desired acyl hydrazide (3.88 g, 96.6%) as a viscous oil. $C_{26}H_{36}N_2O_4$ (MW=440.58); MS: m/z ($M^+$+1)=441.

Step C: Preparation of

Acyl hydrazide from Step B (287 g, 0.65 mol, 1 equiv) and isopropanol (1.7 L) were combined and heated to 50° C. Trimethylsilylisocyanate (85%, 112 g, 0.98 mol, 1.5 equiv)

was added rapidly. The reaction was stirred for 45 min, then cooled to 0° C. and stirred for 30 min. Colorless crystalline solid was collected by filtration and dried to provide product acyl semicarbazide (253.7 g, 81%). $C_{27}H_{37}N_3O_5$ (MW=483.60); MS: m/z (M$^+$+1)=484.

Step D: Preparation of

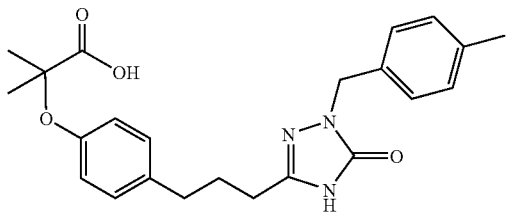

Acylsemicarbazide product from Step C (25.0 g, 0.0517 mol, 1.0 equiv), toluene (250 mL) and methanesulfonic acid (1.68 mL, 0.0258 mol, 0.5 equiv) were combined and the resulting solution was heated at reflux with azeotropic removal of water for 4 hrs. The reaction was concentrated in vacuo and the residue partitioned between $CH_2Cl_2$ (250 mL) and water (50 mL). The layers were separated and the organic phase was washed with 1N HCl (3×50 mL), dried (Na$_2$SO$_4$), filtered and the filter cake washed with $CH_2Cl_2$ (3×30 mL). The filtrate was concentrated to a white foamy film, dissolved in $CH_2Cl_2$ (200 mL) and washed with 1 N HCl (4×100 mL, then 5×200 mL), dried (Na$_2$SO$_4$) and concentrated to a white foam. Crude product was dissolved in warm ethyl acetate (75 mL) and seeded with authentic product. The resulting slurry was allowed to stand at rt for 1 h, then refrigerated overnight. Colorless crystals were collected by filtration, washed with a minimal amount of cold ethyl acetate and dried to afford desired triazolone (12.5 g, 59%). $C_{23}H_{27}N_3O_4$ (MW=409.48); MS: m/z (M$^+$+1)=410.

Example 12

Compound 12(1)

Step A: Preparation of

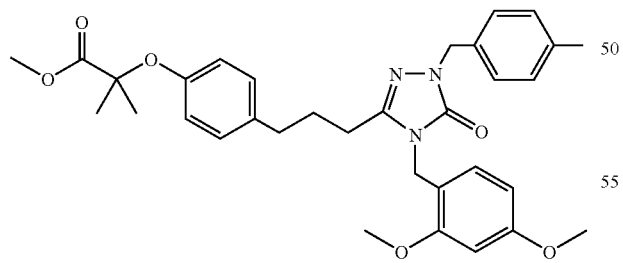

To a solution of the 4-(2,4-dimethoxybenzyl)-triazolinone derivative from Compound 2(7) (9.0, 21.3 mmol) in DMF (25 mL), was added 4-methylbenzyl bromide (4.62 g, 25 mmol) and powdered potassium carbonate (10 g), and the resulting mixture stirred at ambient temperature for 24 hours. The reaction mixture was diluted with water (100 mL) and extracted with ethyl acetate (3×75 mL). The combined organic extracts were concentrated to an oil. Alternatively the product could be further purified by flash chromatography (gradient elution, 1:4 ethyl acetate:hexanes to 4:1 ethyl acetate:hexanes) to give the desired product as an oil. MS: m/z (M$^+$+1)=588.

Step B. Preparation of

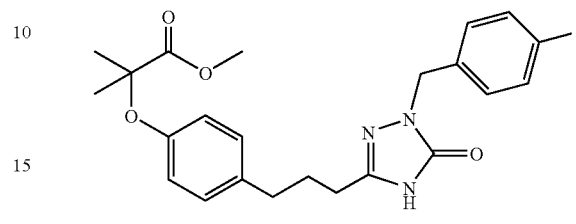

A mixture of 4-(2,4-dimethoxylbenzyl)triazolinone derivative, from Step A, (12.6 gm, 21.9 mmol) and HBr solution (50 mL, 32% w/v in glacial acetic acid) was stirred at room temp. for 24 h. Crushed ice (50 gm) was added to the reaction mixture and diluted with water (100 mL). The aqueous layer was extracted with ethyl acetate (400 mL). Wash ethyl acetate layer with water (2×250 mL), brine (100 mL), and dry over Na$_2$SO$_4$. The ethyl acetate layer was concentrated to dryness on a rotary evaporator to give an oily residue. The residue was taken up in methanol (300 mL). To this solution was added conc. Sulfuric acid (5 mL) with stirring. The reaction mixture was stirred at room temperature for 18 h. Methanol was removed to a small volume (25 mL) and the residue was diluted with ethyl acetate (200 mL), washed with water (2×200 mL), saturated NaHCO$_3$ solution (2×100 mL), brine (100 mL) and dried over Na$_2$SO$_4$. The ethyl acetate layer was concentrated to dryness to give a residue which was purified on a flash silica column to give the product as an oily residue. MS: m/z (M+1) 424.

Step C: Preparation of

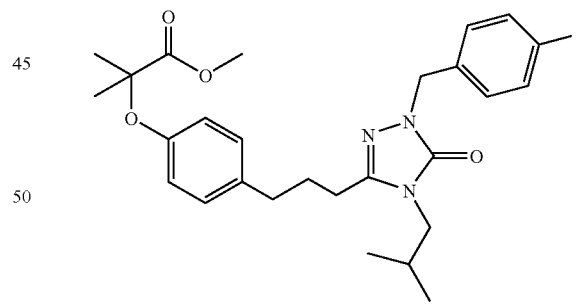

To a solution of the Step B product (50 mg, 0.12 mmol) in DMF (1 mL) was added isopropylmethyliodide followed by anhydrous (250 mg, powdered). The reaction mixture was stirred at 40-45° C. for 18 h. The reaction mixture was diluted with water (10 mL) and extracted with ethyl acetate (3×15 mL). Combined organic layer was concentrated to dryness on a rotary evaporator and then under high vacuum for 2 h. The crude was chromatographed on a prepacked silica column using Biotage Quad3 parallel chromatographic system eluting with ethyl acetate-hexane mixture (30-40% v/v) to give the product as an oily residue. MS: m/z (M+1) 480

The compounds below were prepared by alkylation of the Step B product, using the appropriate alkylhalide listed in the table.

| Alkyl halide | R | MS:m/z (M + 1) |
|---|---|---|
| 1-Iodo-2-methylpropane | Isobutyl | 480 |
| 2-bromoethyl methyl ether | 2-Methoxyethyl | 482 |
| 2-Bromoethyl ethyl ether | 2-Ethoxyethyl | 496 |
| 1-bromobutan-2-one | 2-Oxobutyl | 494 |
| 4-bromobutyl benzoate | 4-Hydroxybutyl | 496 |
| 2-bromoethyl acetate | 2-Hydroxyethyl | 468 |
|  | 2-(N,N-Diethyl)ethyl | 523 |
| 1-bromo-3,3-dimethylbutan-2-one | 3,3-Dimethyl-2-oxobutyl | 522 |
| Bromomethylcyclopropane | Cyclopropylmethyl | 478 |
|  | 1-Morpholinocarbonyl-2-isopropylmethyl | 593 |
| Methyl bromopropanoate | 2-methoxycarbonylethyl | 510 |
|  | 3-(2-tetrahydro-pyranyloxy)prop-1-yl | 566 |
| 1-bromo-3-hydroxypropane | 3-Hydroxy-propyl | 482 |
| Methyl bromoacetate | 2-methoxycarbonylmethyl | 496 |
| Isopropyliodide | Isopropyl | 466 |
|  | methoxyethoxyethyl | 526 |
|  | 3-Methoxy-2-hydroxypropyl | 512 |
| 2-chloromethylpyridien | 2-Pyridylmethyl | 515 |
| 4-chioromethyl pyridine | 4-Pyridylmethyl | 515 |
| Benzyl bromide | Benzyl | 514 |
|  | 2,2,2-trifluroethyl |  |
|  | 3,3,3-trifluropropyl |  |
|  | 4,4,4-triflurobutyl |  |

Step D: Preparation of

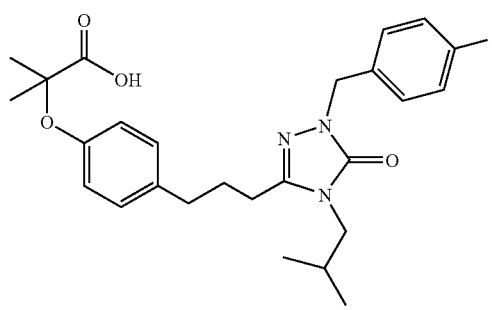

To a solution of the Step C product (15 mg,) in MeOH (1 mL) was added 2N NaOH (2 mL) and the mixture was stirred at ambient temperature for 16 hrs. The reaction mixture was concentrated, diluted with 15 mL water, and acidified to pH ~2 with concentrated HCl and extracted with methylene chloride (3×10 mL). The combined organic layers were dried ($Na_2SO_4$) and concentrated to give the product as an oil. MS: m/z (M+1) 466.

The compounds below were prepared from the corresponding methyl esters.

| Example Number | R | MS:m/z (M + 1) |
|---|---|---|
| 12 (2) | 2-Methoxyethyl | 468 |
| 12 (3) | 2-Ethoxyethyl | 482 |
| 12 (4) | 2-Oxobutyl | 480 |
| 12 (5) | 4-Hydroxybutyl | 482 |
| 12 (6) | 2-Hydroxyethyl | 454 |
| 12 (7) | 2-(N,N-Diethyl)ethyl | 509 |
| 12 (8) | 3,3-Dimethyl-2-oxobutyl | 508 |
| 12 (9) | Cyclopropylmethyl | 464 |
| 12 (10) | 1-Morpholinocarbonyl-2-methylpropyl | 579 |
| 12 (11) | 2 -Carboxyethyl | 482 |
| 12 (12) | THPether | 552 |
| 12 (13) | 3-Hydroxypropyl | 468 |
| 12 (14) | Carboxymethyl | 468 |
| 12 (15) | Isopropyl | 452 |
| 12 (16) | methoxyethyloxyethyl | 512 |
| 12 (17) | 3-Methoxy-2-hydroxypropyl | 498 |
| 12 (18) | 2-Pyridylmethyl | 501 |
| 12 (19) | 4-Pyridylmethyl | 501 |
| 12 (20) | Benzyl | 500 |
| 12 (21) | 2,2,2-trifluoroethyl | 492 |
| 12 (22) | 3,3,3-trifluoropropyl | 506 |
| 12 (23) | 4,4,4-trifluorobutyl | 520 |

Example 13

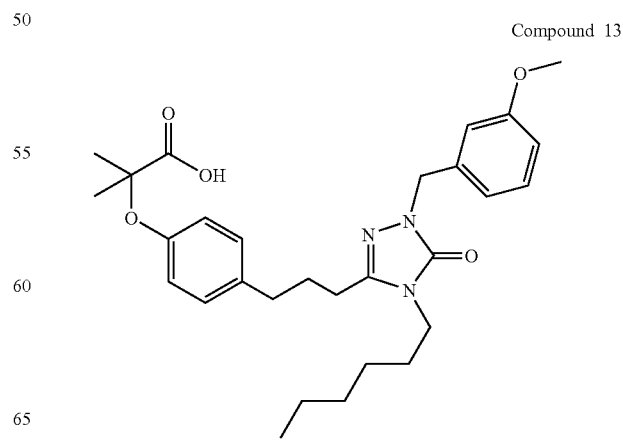

Compound 13

Step A: Preparation of

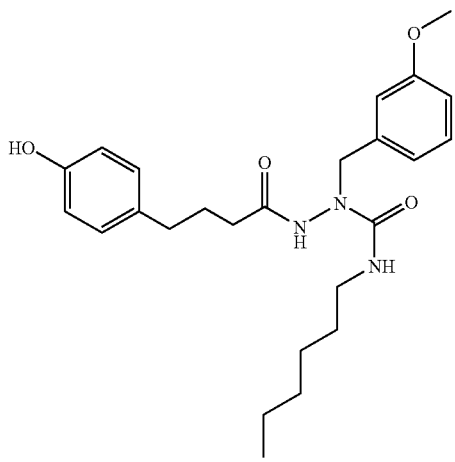

To a solution of hydrazide, specifically the 3-methoxyphenyl compound of Example 1, Step B (250 mg, 0.79 mmol) in anhydrous THF (5 mL) was added n-hexylisocyanate (202 mg, 1.59 mmol). The reaction mixture was stirred at room temp for 18 h. Methanol (1 mL) was added to the reaction mixture and it was stirred for an additional 30 min. The solvent was evaporated on a rotary evaporator to give the semicarbazate. MS: m/z (M+1) 442

Step B: Preparation of

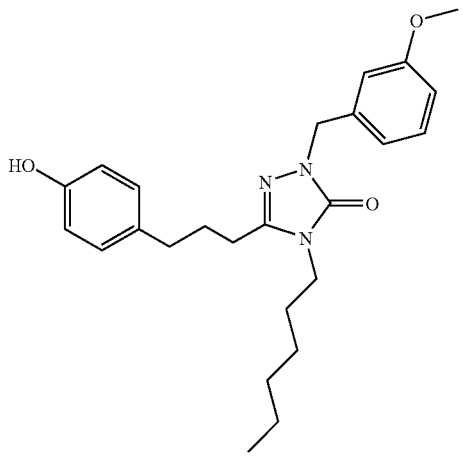

To a solution of the Step A product, in methanol (20 mL) and water (0.5 mL) was added KOH (500 mg). The reaction mixture was heated at reflux with stirring for 48 h. The reaction mixture was cooled to room temp and concentrated on a rotary evaporator to a small volume (5 mL). The reaction mixture was diluted with water (30 mL) and acidified with 5N HCl (pH 2-3) and extracted with ethyl acetate (2×35 mL). The combined organic layers were dried over $Na_2SO_4$ and concentrated on a rotary evaporator to give product as a colorless oily residue. MS: m/z (M+1) 424.

Step C: Preparation of

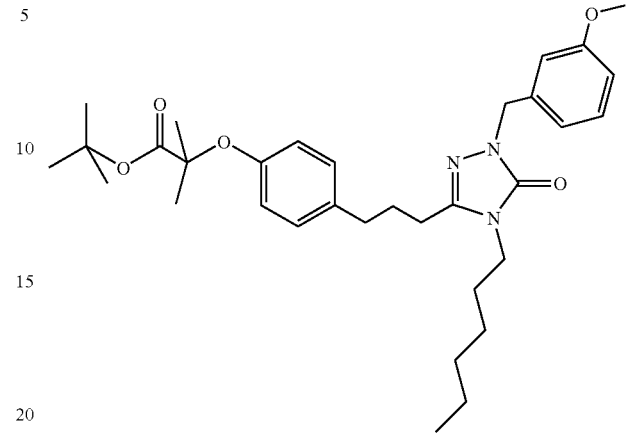

To a solution of the Step B product (300 mg, 0.71 mmol) in anhydrous DMF (5 mL) was added tert-butyl bromoisobutyrate (1 gm, 4.48 mmol) followed by powdered anhydrous $K_2CO_3$ (20 mmol). The reaction mixture was heated at 50° C. with stirring for 64 h. The reaction mixture was diluted with water (30 mL) and extracted with ethyl acetate (2×30 mL). Combined ethyl acetate layer dried ($Na_2SO_4$) and concentrated to dryness on rotary evaporator to give an oily residue. The crude was purified on a flash silica column eluting with 20% ethyl acetate-hexane mixture giving the product as a colorless oil. MS: m/z (M+1) 566

Step D: Preparation of

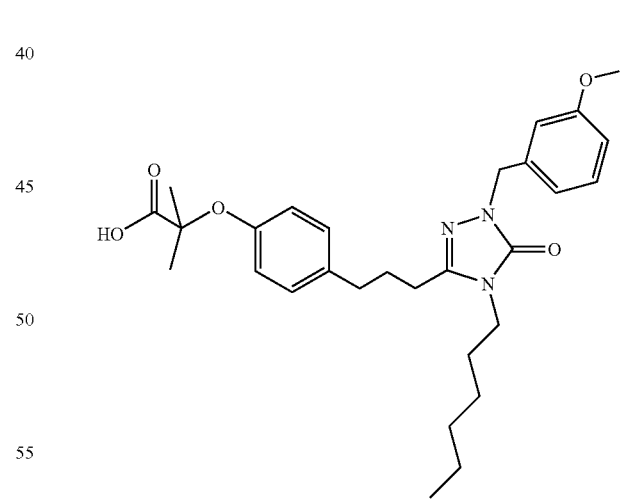

The Step C product (225 mg) was treated with a 50:50 mixture of TFA and dichloromethane (10 mL). The reaction was stirred at room temperature for 2 h. The solvent was removed on a rotary evaporator and the residue was dried under high vacuum to give the product as a colorless oil. MS: m/z (M+1) 510.

Example 14

Compound 14(1)

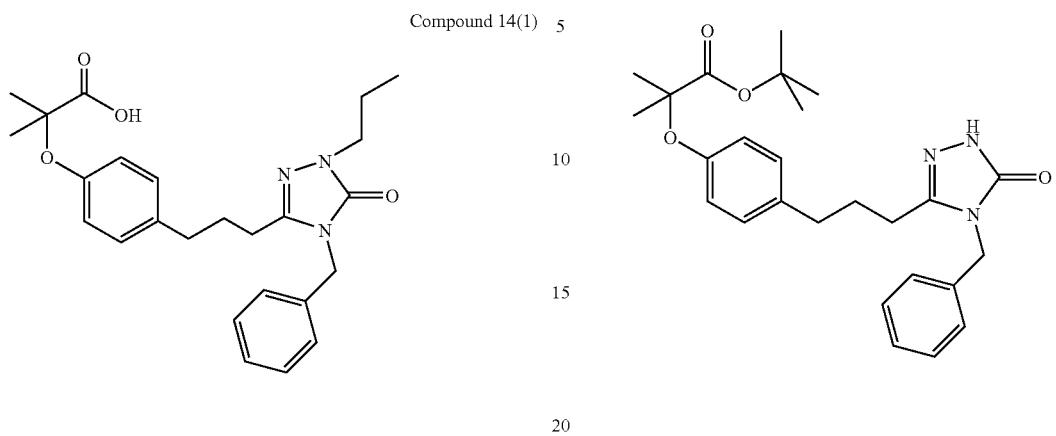

Step A: Preparation of

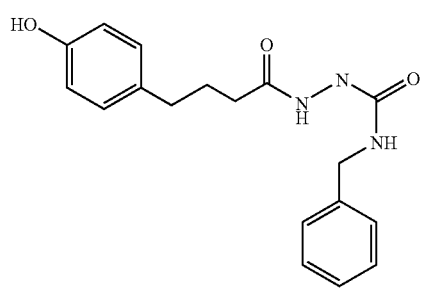

To a solution of 4-(4-hydroxyphenyl)butyrylhydrazine (200 mg, 1.03 mmol) in THF (5 mL) was added benzylisocyanate (200 mg, 1.5 mmol). The reaction mixture was stirred at room temperature for 48 h. Methanol (1 mL) was added to the reaction mixture and stirred for and additional 30 minutes. Solvent was removed on rotary evaporator to give the product as a white solid. MS: m/z (M+1) 328

Step B: Preparation of

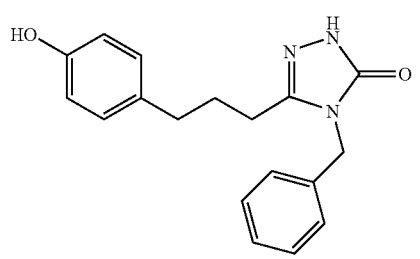

To a solution of the Step A semicarbazate (315 mg) in methanol (20 mL) was added solid KOH (1 gm). The reaction was heated at reflux with stirring for 20 h. The reaction mixture was concentrated to small volume (5 mL), acidified with 5N HCl to pH 3. It was then extracted with ethyl acetate (2×30 mL). Ethyl acetate layer was dried (Na2SO4) and concentrated to dryness to give the product as gummy solid. MS: m/z (M+1) 310

Step C: Preparation of

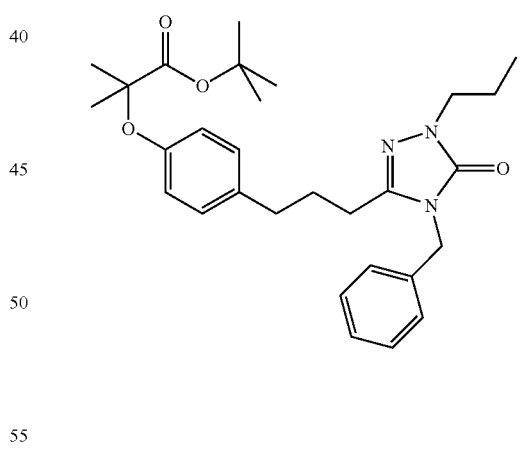

To a solution of the Step B benzyl triazolinone (270 mg) in DMF (7.5 mL) was added tert-butyl isobutyrate (1.1 g) followed by solid powdered anhydrous K2CO3 (500 mg). The reaction mixture was heated at 50° C. with stirring for 3 days. The reaction mixture was diluted with water (40 mL) and extracted with ethyl acetate (2×40 mL). Ethyl acetate layer dried (Na2SO4) and concentrated on a rotary evaporator to give a crude residue. The crude was purified on a flash silica column eluting with 60% ethyl acetate-hexane to give the product. MS: m/z (M+1) 452

Step D: Preparation of

To a solution of the Step C benzyltriazolinone (30 mg) in anhydrous THF (1 mL) was added 1-iodoproapane followed by 1M methanolic KOH solution (1 mL). Reaction initially stirred at room temp for 24 h. The reaction was then heated at 50° C. for and 18 h. The reaction mixture was diluted with water 920 mL) and extracted with ethyl acetate (2×20 mL). Ethyl acetate layer was dried (Na2SO4) and concentrated to dryness to give a residue. The residue was purified on flash silica column eluting with 40% ethyl acetate-hexane mixture to give the product. MS: m/z (M+1)=494.

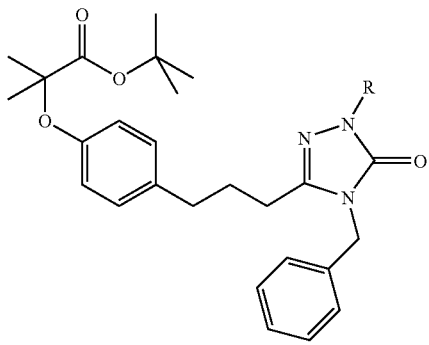

Step E: Preparation of

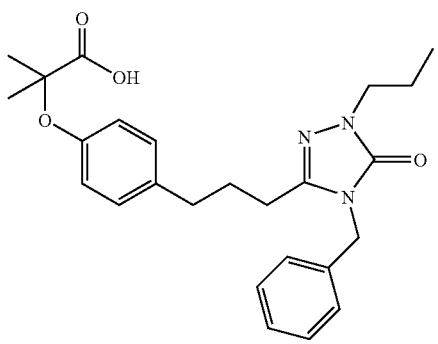

The Step D tert-butyl ester, described (16 mg) was treated with a 50% mixture of trifluoroacetic acid and dichloromethane (2 mL) for 2 h with stirring. The solvent was removed on a rotary evaporator and the residue dried under high vacuum to give the product as an oil. MS: m/z (M+1) 438

The compounds below were synthesized by alkylating benzyltriazolinone, using appropriate bromides to give the corresponding products.

| Example Number | R | MS: m/z (M + 1) |
|---|---|---|
| 14(2) | H | |
| 14(3) | Benzyl | |
| 14(4) | 4-tert-butylbenzyl | |

Example 15

Compound 15 (1)

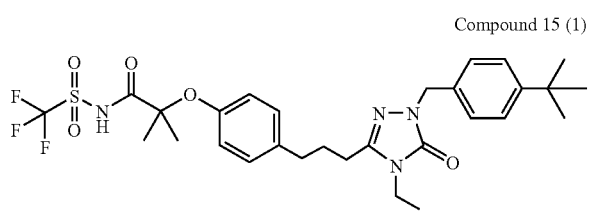

To a solution of the compound described in Example 4, Compound 4(19) (120 mg, 0.25 mmol), trifluoromethanesulfonamide (37 mg, 0.25 mmol), and 4-dimethylaminopyridine (31 mg, 0.25 mmol) in methylene chloride (2 mL) at ambient temperature was added N,N-diisopropylethylamine (65 mg, 0.50 mmol) and 1-[3-(dimethylamino)propyl]-3-ethylcarbo-diimide hydrochloride (77 mg, 0.40 mmol). After stirring for 24 hours, the reaction mixture was concentrated in vacuo to give a residue which was partitioned between ethyl acetate and 1N hydrochloric acid. The organic layer was washed with water, brine, dried ($Na_2SO_4$) and concentrated to an oil which was purified by flash chromatography (gradient elution, 1:4 ethyl acetate:hexanes to 100% ethyl acetate) to give the desired product as a white solid. $C_{29}H_{37}N_4O_5SF_3$ (MW=610.70); mass spectroscopy (M H$^+$)=611.

The following compounds were also prepared utilizing the appropriate sulfonamide (listed in the table) by the procedure of Compound 15(1).

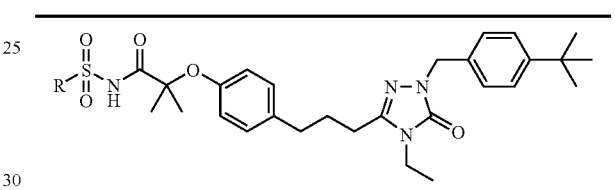

| Example Number | RSO$_2$NH$_2$ | R | (MH)$^+$ |
|---|---|---|---|
| 15 (2) | benzenesulfonamide | phenyl | 619 |
| 15 (3) | α-toluenesulfonamide | benzyl | 633 |
| 15 (4) | 4-methoxybenzenesulfonamide | 4-methoxyphenyl | 649 |
| 15 (5) | naphthalene-2-sulfonamide | β-naphthyl | 669 |
| 15 (6) | Methanesulfonamide | Methyl | 557 |
| 15 (7) | 5-bromothiophene-2-sulfonamide | 5-bromo-2-thienyl | 704 |
| 15 (8) | 3-chlorobenzenesulfonamide | 3-chlorophenyl | 654 |
| 15 (9) | 6-ethoxy-2-benzothiazolesulfonamide | 6-ethoxy-2-benzothiazolyl | 720 |

Example 16

Compound 16

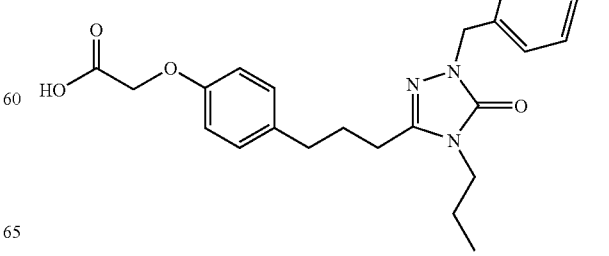

Step A: Preparation of Methyl 4-(4-methoxyphenyl)-butyrate

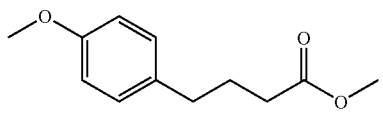

To a solution of 4-(4-methoxyphenyl)-butyric acid (25.1 g, 0.129 mol) in methanol (130 mL), was added sulfuric acid (concentrated, 1.0 mL) dropwise and it was stirred at room temperature overnight under nitrogen. The reaction mixture was concentrated on a rota-vapor, the residue was then partitioned between ethyl acetate (200 mL) and saturated sodium bicarbonate aqueous solution (200 mL). The organic phase was separated, washed with brine (3×200 mL), then dried over $Na_2SO_4$ and filtered. Evaporation of solvent gave the titled compound as an oil (26.8 g, 99%). Mass (MH+)=209.

Step B: Preparation of

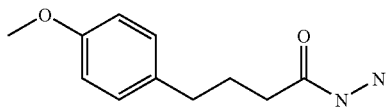

A mixture of methyl 4-(4-methoxyphenyl)-butyrate (10.4 g, 0.0500 mol) from Step A and hydrazine hydrate (25.0 g, 0.500 mol) in methanol (250 mL) was heated under reflux for an hour. It was then cooled down to room temperature and stirred overnight. The solvent was evaporated and the residue was partitioned between ethyl acetate (200 mL) and water (200 mL). The organic layer was washed with brine (3×200 mL), dried over $Na_2SO_4$, filtered and concentrated to dryness to give the titled compound as a white crystal (8.79 g, 85%). Mass (MH+)=209.

Step C: Preparation of

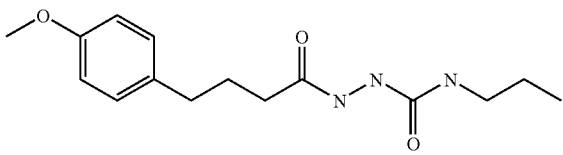

To a solution of the Step B product (8.76 g, 0.0421 mol) in THF (200 mL), was added n-propyl isocyanate (Aldrich, 4.34 mL, 0.0463 mol) dropwise and the mixture was stirred at room temperature for an hour. Evaporation of solvent gave the titled compound as an off-white powder (12.4 g, 100%). Mass (MH+)=294.

Step D: Preparation of

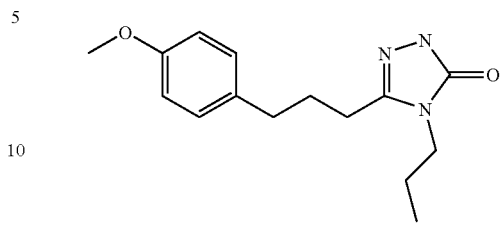

To a solution of the Step C product (12.4 g, 0.0421 mol) in methanol (200 mL), was added potassium hydroxide in one portion (35.4 g, 0.632 mol). The reaction mixture was heated at 70° C. for 36 hours. It was then concentrated on a rota-vapor, the residue was then partitioned between methylene chloride (150 mL) and water (150 mL), it was brought to pH=7 by concentrated HCl before the two layers was separated. The aqueous layer was extracted with more methylene chloride (150 mL). The combined organic layers was dried over $Na_2SO_4$ and filtered. Evaporation of solvent gave the titled compound as a off-white solid (11.2 g, 97%). Mass (MH+)=276.

Step E: Preparation of

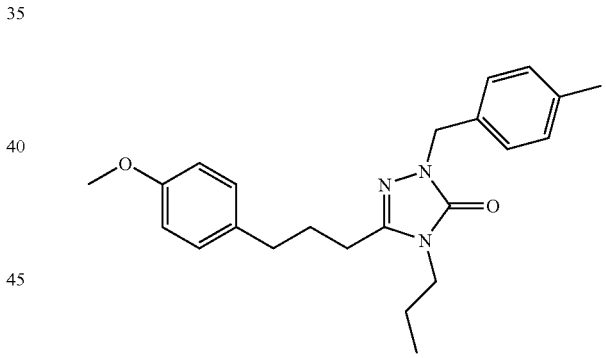

To a solution of the Step D product (5.51 g, 0.0200 mol) in DMF (100 mL), was added α-bromo-p-xylene (8.30 g, 0.0440) followed by potassium carbonate powder (13.8 g, 0.100 mol). It was heated to 70° C. under nitrogen overnight. The reaction mixture was partitioned between ethyl acetate (200 mL) and water (200 mL), the aqueous layer was extracted with ethyl acete (200 mL) one more time. The organic phase was combined, washed with brine (4×200 mL), then dried over $Na_2SO_4$ and filtered. Evaporation of solvent gave a crude product, which was purified on a silica gel column eluting with 20-60% ethyl acetate in hexane to give the titled compound as colorless oil (6.59 g, 87%). Mass (MH+)=380.

Step F: Preparation of

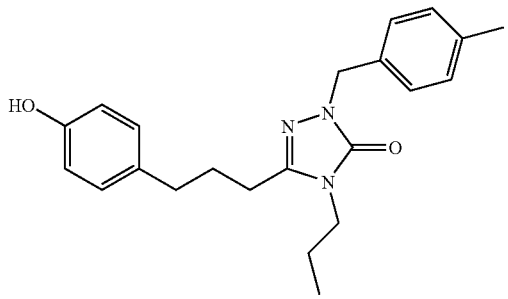

Step H: Preparation of

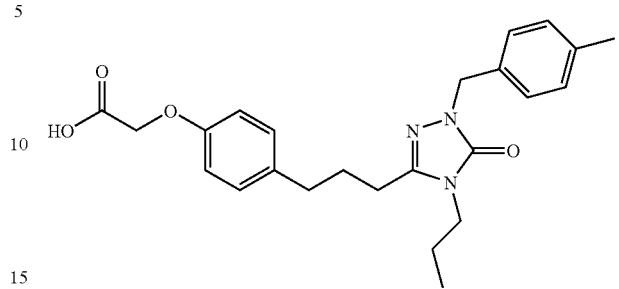

To a solution of the Step E product (6.55 g, 0.0173 mol) in DCM (100 mL) at 0° C., was added dropwise the solution of BBr$_3$ (4.91 mL, 0.0519 mL) in methylene chloride (25 mL). The reaction was kept at 0° C. and stirred for an hour. It was then quenched by 1:1 MeOH/DCM (20 mL), stirred for another hour at 0° C., then room temperature overnight. The reaction mixture was washed with water (3×100 mL), and the organic layer was separated, dried over Na$_2$SO$_4$, filtered and concentrated to an yellow oil, which was purified by chromatography on a silica gel column eluting with 20-60% ethyl acetate in hexane to give the titled compound as a white solid (2.39 g, 39%). Alternatively, the titled compound can also be made at −78° C. instead of 0° C. on the same scale, white solid (4.89 g, 78%). Mass (MH+)=366.

Step G: Preparation of

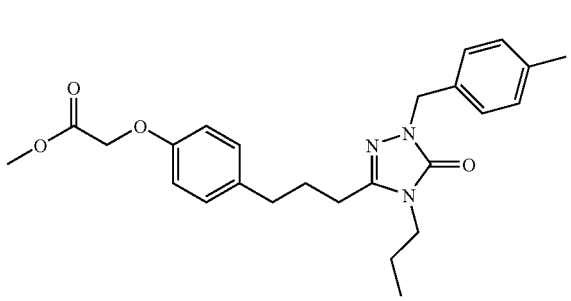

The Step F product (0.100 g, 0.000274 mol) was dissolved in DMF (1.0 mL), to it was added methyl bromoacetate (0.103 g, 0.000548 mol) followed by potassium carbonate (0.189 g, 0.00137 mol). After heated at 50° C. over weekend, the reaction mixture was diluted with ethyl acetate (2 mL), washed with water (2 mL), the separated organic layer was pass through a chem elut 1005 tube, and the tube was washed with more ethyl acetate (50 mL). Evaporation of solvent gave the methyl ester as an oil, which was purified on Biotage Quad3 (silica gel, 20-60% ethylacetate in hexane). Mass (MH+) 438.

The methyl ester obtained from Step G was treated with 1:1 MeOH/5.0N NaOH (6 mL) at room temperature overnight, and then concentrated. The resulting residue was diluted with water (2 mL), cooled down to 0° C., acidified to pH=2 by adding concentrated HCl dropwise. The aqueous suspension was loaded on a Chem elut 1005 tube, eluted with DCM (50 mL). Evaporation of methylene chloride gave the titled compound as an oil (0.103 g, 89%). Mass (MH+)=424.

The compounds listed below were prepared according to the procedure outlined above by using the appropriate methyl or ethyl α-substituted-α-bromo ester in Step G.

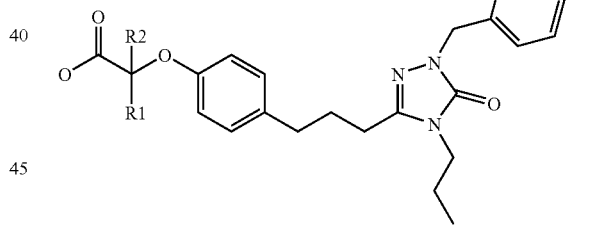

| Example Number | R1 | R2 | MS (m/z) |
| --- | --- | --- | --- |
| 16 (2) | Methyl | H | 438 |
| 16 (3) | Ethyl | H | 452 |
| 16 (4) | Isopropyl | H | 466 |
| 16 (5) | F | F | 460 |
| 16 (6) | —(CH$_2$)$_3$— | | 464 |
| 16 (7) | Cyclohexyl | H | 506 |
| 16 (8) | Phenyl | H | 500 |
| 16 (9) | Hydroxyethyl | H | 468 |
| 16 (10) | F | H | 442 |
| 16 (11) | n-Butyl | H | 480 |
| 16 (12) | n-Pentyl | H | 494 |
| 16 (13) | 4-fluoro phenyl | H | 518 |

Example 17

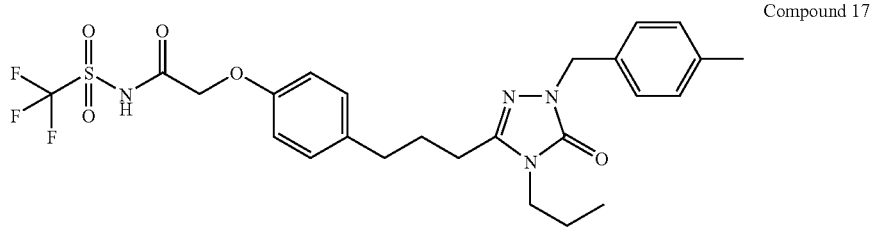

Compound 17

To a solution of the compound described in Example 16, **clarify, please . . . (45 mg, 0.10 mmol), trifluoromethanesulfonamide (15 mg, 0.10 mmol), and 4-dimethylaminopyridine (12 mg, 0.10 mmol) in methylene chloride (1 mL) at ambient temperature was added N,N-diisopropylethylamine (26 mg, 0.20 mmol) and 1-[3-(dimethylamino)propyl]-3-ethylcarbodiimide hydrochloride (31 mg, 0.16 mmol). After stirring for 24 hours, the reaction mixture was concentrated in vacuo to give a residue which was partitioned between ethyl acetate and 1N hydrochloric acid. The organic layer was washed with water, brine, dried ($Na_2SO_4$) and concentrated to an oil which was purified by flash chromatography (gradient elution, 1:4 ethyl acetate:hexanes to 100% ethyl acetate) to give the desired product as a white solid. $C_{25}H_{29}F_3N_4O_5S$ (MW=554.59); mass spectroscopy (M H$^+$)=555.

Example 18

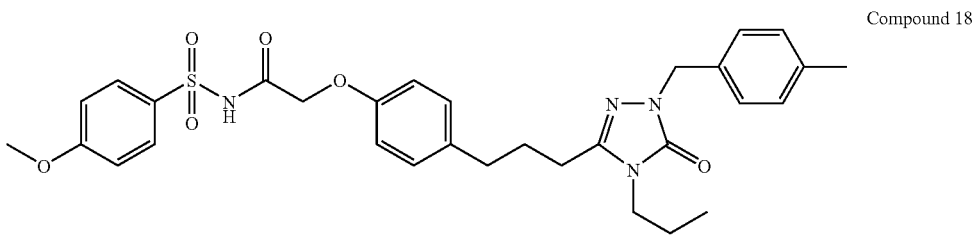

Compound 18

The title compound was prepared utilizing the Example 16 product and 4-methoxybenzenesulfonamide according to the procedure described in Example 17. $C_{31}H_{36}N_4O_6S$ (M=592.72); mass spectroscopy (MH$^+$)=593.

Example 19

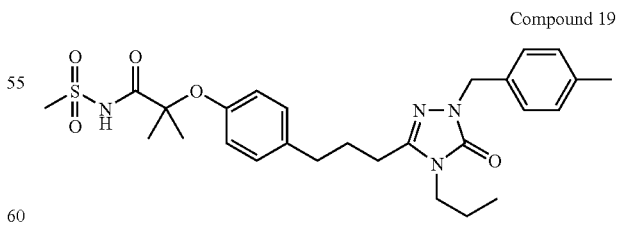

Compound 19

The title compound was prepared utilizing the compound described in Example 5, Compound 5(8), and methane sulfonamide according to the procedure described in Example 17. $C_{27}H_{36}N_4O_5S$ (MW=528.68); mass spectroscopy (MH$^+$)=529

Example 20

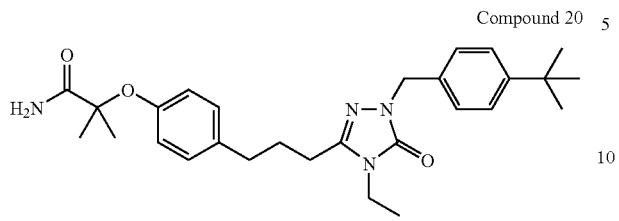

Compound 20

To a cooled (0° C.) solution of the compound described in Example 4, Compound 4(19) (164 mg, 0.34 mmol) in methylene chloride (3 mL) was added oxalyl chloride (178 μL, 2.0 mmol) followed by N,N-dimethylformamide (1 drop). After stirring in cold bath for 0.25 hour, the reaction mixture was stirred at room temperature for one hour, then concentrated to dryness. The residue was dissolved in tetrahydrofuran (15 mL) and the resulting solution added dropwise to chilled (0° C.) concentrated ammonium hydroxide (30 mL) with vigorous stirring. The mixture was stirred at 0° C. for one hour, then stirred at room temperature for 20 hours. Concentration gave a residue which was partitioned between ethyl acetate and saturated aqueous sodium bicarbonate. The ethyl acetate layer was washed with water, brine, dried ($Na_2SO_4$), and concentrated to give the desired product as a foam. $C_{28}H_{38}N_4O_3$ (MW=478.64); mass spectroscopy ($MH^+$)=479.

Example 21

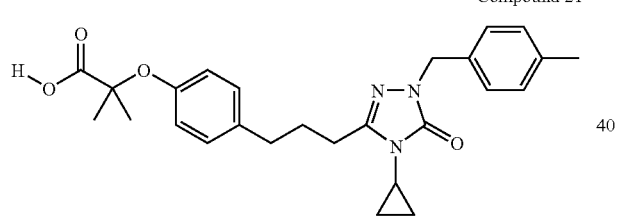

Compound 21

Step A: Preparation of

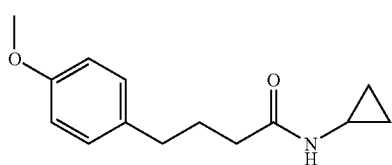

To a solution of 4-(4-methoxyphenyl)-butyric acid (2.13 g, 11 mmol), cyclopropylamine (1.14 mL, 16 mmol), HOAt (1.49 g, 11 mmol) and DMAP (134 mg, 1 mmol) in 70 mL of dry DMF, 3.07 g of EDC (16 mmol) was added in one portion. The resulting mixture was allowed to stand under $N_2$ for 8 h. Then the mixture was diluted with 50 mL of $Et_2O$. Organic layer was washed with 1N HCl (3×20 mL), brine (3×20 mL) and dried over $Na_2SO_4$, filtered. The organic solvent was then removed under vacuum. Residue was purified by column chromatography to give the title compound. MS ($M+1^+$) m/z 234.

Step B: Preparation of

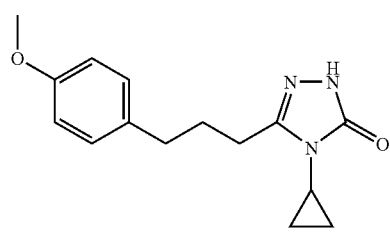

To a solution of the Step A product (1.72 g, 7.37 mmol) in 9 mL of dry $CH_2Cl_2$, 2.18 g of trimethyl-oxonium tetrafluoroborate (14.7 mmol) was added in one portion. The mixture was allowed to stand at r.t. for 4 h. Organic solvent was then removed under vacuum. Residue was redissolved in 50 mL of $Et_2O$ and washed with cold sat' aq. $K_2CO_3$ (3×10 mL), brine (3×10 mL). The ether layer was then dried over $Na_2SO_4$, filtered and concentrated. The residue was dissolved in 30 mL of dry toluene. To the solution, 0.79 g of ethylcarbazate was added. The mixture was heated to reflux for 38 h. Organic solvent was then removed under vacuum. Residue was purified by chromatography to give the title compound. MS ($M+1^+$) m/z 274.

Step C: Preparation of

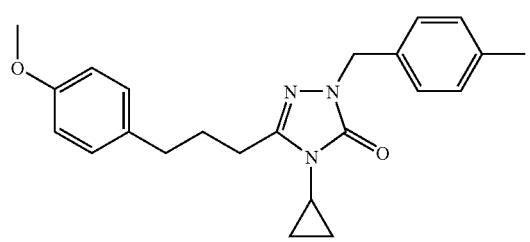

A mixture of the Step B product (1.53 g, 5.6 mmol), 4-methylbenzyl bromide (2.1 g, 11.2 mmol) and $K_2CO_3$ (7.7 g, 56 mmol) in 25 mL of dry DMF was heated at 60° C. for 12 h. The mixture was then diluted with 75 mL of $Et_2O$ and filtered. Organic layer was washed with 1N HCl (3×15 mL), brine (3×15 mL), dried over $MgSO_4$, filtered and concentrated. Residue was purified by chromatography to give the title compound. MS ($M+1^+$) m/z 377.

Step D: Preparation of

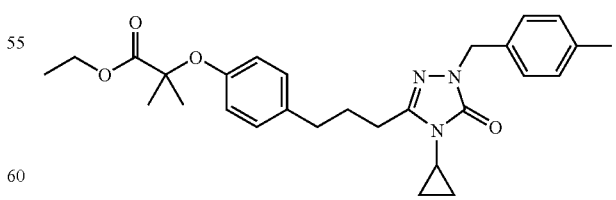

To a solution of the Step C product (1.01 g, 2.7 mmol) in 50 mL of dry $CH_2Cl_2$ at −78° C., 0.8 mL of $BBr_3$ (8.1 mmol) was added dropwise. The resulting solution was warmed up to 0° C. in 10 min. and maintained at same temperature for 2 h. The mixture was then diluted with 200 mL of $Et_2O$.

Organic layer was washed with H₂O (3×20 mL), brine (3×20 mL) and dried over Na₂SO₄, filtered. Organic solvent was removed under vacuum. Residue was dissolved in 25 mL of absolute EtOH. To the solution, 3.1 mL of 2-bromo-ethyl-butyrate (21.2 mmol), 1.26 g of K₂CO₃ (9.1 mmol) and 365 mg of MgSO₄ (3.03 mmol) were added. The resulting mixture was heated to 70° C. for 12 h. Solid was filtered off and organic solvent was removed under vacuum. The residue was then dissolved in 75 mL of CH₂Cl₂. The organic layer was washed with 1N HCl (3×10 mL), brine (3×10 mL), dried over Na₂SO₄, filtered and then concentrated. Residue was purified by chromatography to give the title compound. MS (M+1⁺) m/z 478.

Step E: Preparation of

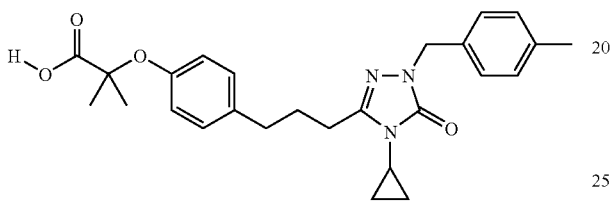

To a solution of the Step D product (490 mg, 1.03 mmol) in 20 mL of EtOH, 1.0 mL of 5N NaOH was added. The resulting solution was heated to reflux for 30 min. Organic solvent was removed under vacuum. Residue was dissolved in 30 mL of CH₂Cl₂ and washed with 1N HCl (2×10 mL), brine (2×10 mL). Organic layer was then dried over Na₂SO₄, filtered and concentrated. Residue was purified by chromatography to give the title compound. MS (M+1⁺) m/z 450.

Example 22

Compound 22

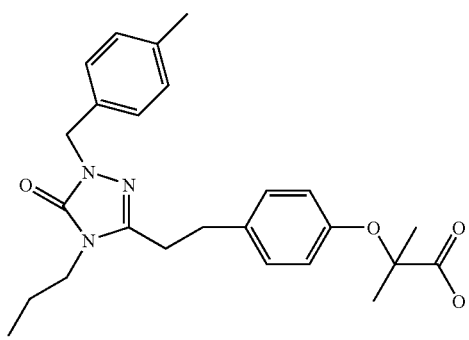

Step A: Preparation of

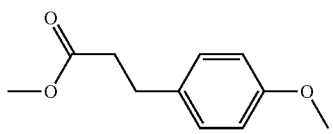

A methanol solution (500 mL) of 3-(4-methoxyphenyl)propionic acid (Aldrich, 10.15 g, 0.056 mol) was treated with H₂SO₄ (concentrated, 3 mL) and stirred at room temperature overnight. The solvent was evaporated and the residue diluted with CH₂Cl₂ (150 mL). The resulting solution was extracted with saturated aqueous sodium bicarbonate (1×150 mL) followed by brine (1×150 mL), then dried over Na₂SO₄. Upon evaporation of the solvent the desired methyl ester was obtained as a colorless oil. C₁₁H₁₄O₃ (MW=194.23); mass spectroscopy (MH⁺)=195.1

Step B: Preparation of

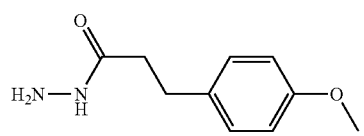

A methanol solution (60 mL) of methyl ester from Step A (10.6 g, 0.055 mol) was treated with hydrazine hydrate (30 g, 0.60 mol) and stirred overnight. The solvent was evaporated and the residue dissolved in ethyl acetate (300 mL). The resulting solution was extracted with H₂O (300 mL). The aqueous extract was back extracted with ethyl acetate (300 mL) then the combined organic extracts were dried over Na₂SO₄ and concentrated to give a white solid. The product was suspended in hexane (100 mL) then filtered to give the desired acyl hydrizide as a white solid. C₁₀H₁₄N₂O₂ (MW=194,23); mass spectroscopy (MH⁺)=195.1

Step C: Preparation of

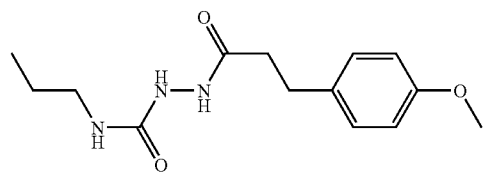

A THF solution (125 mL) of the acyl hydrizide from Step B (9.2 g, 0.047 mol) was treated with a THF solution (50 mL) of n-propyl isocyanate (Aldrich, 5.3 mL, 0.057 mol)—added dropwise over 15 minutes. The mixture was stirred overnight during which a thick precipitate formed. The resulting suspension was treated with methanol (100 mL) and stirred approximately 2 hours. The solvent was then concentrated to give the desired acyl semicarbazide as a white solid which was used without further purification.

Step D: Preparation of

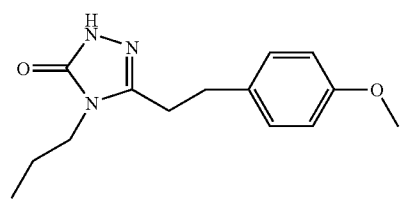

The acyl semicarbazide from Step C (13.4 g, 0.048 mol) was dissolved in methanol (100 mL), treated with KOH (27 g, 0.48 mol), then heated to 60° C. for 16 hr and 85° C. for an additional 6 hr. The reaction mixture was cooled to room temperature, poured into H$_2$O, then extracted with ethyl acetate (3×500 mL). The combined organic extracts were dried over Na$_2$SO$_4$ then concentrated to give the desired N4-propyl triazolinone as a slightly yellow solid. C$_{14}$H$_{19}$N$_3$O$_2$ (MW=261.33); mass spectroscopy (MH$^+$)=262.1

Step E: Preparation of

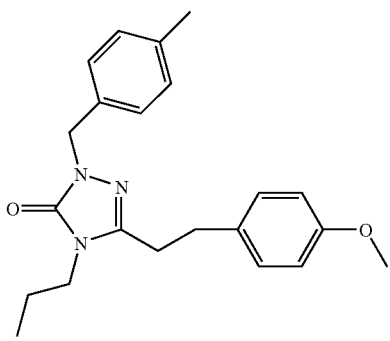

The N4-propyl triazolinone from Step D (1.05 g, 4.0 mmol) was dissolved in DMF (25 mL) and treated with α-bromo-p-xylene (1.17 g, 6.3 mmol) and powdered K$_2$CO$_3$ (3.17 g, 0.023 mol). The resulting mixture was heated to 50° C. under a drying tube overnight. The reaction mixture was cooled to room temperature, poured into aqueous HCl (1N, 75 mL) and extracted into ethyl acetate (75 mL). The organic extract was washed with brine, dried over Na$_2$SO$_4$, then concentrated to give the crude product. Purification by flash chromatography (1:1 hexanes:ethyl acetate) gave the desired N2-p-methylbenzyl triazolinone as a slightly yellow oil. C$_{22}$H$_{27}$N$_3$O$_2$ (MW=365.48); mass spectroscopy (MH$^+$)=366.1.

Step F: Preparation of

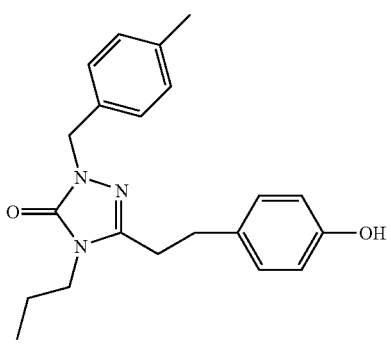

The N2-p-methylbenzyl triazolinone from Step E (0.95 g, 2.6 mmol) was dissolved in CH$_2$Cl$_2$ and cooled to 0° C. under N$_2$. To this solution was added, dropwise, a CH$_2$Cl$_2$ solution (10 mL) of BBr$_3$ (1.0 mL, 10.6 mmol). After stirring for 2 hr at 0° C., the reaction mixture was quenched by the dropwise addition of methanol/CH$_2$Cl$_2$. The resulting mixture was poured into H$_2$O and extracted with additional CH$_2$Cl$_2$ (50 mL). The organic extract was washed with brine, dried over Na$_2$SO$_4$, then concentrated to give the desired phenol as a slightly yellow oil. C$_{21}$H$_{25}$N$_3$O$_2$ (MW=351.45); mass spectroscopy (MH$^+$)=352.2.

Step G: Preparation of

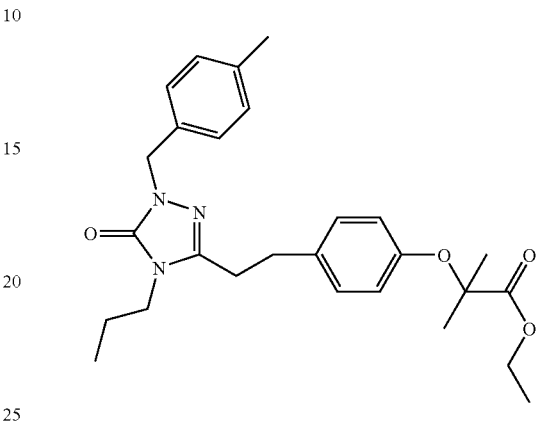

The phenol from Step F (0.81 g, 2.3 mmol) was dissolved in ethanol (absolute, 15 mL) and treated with ethyl 2-bromoisobutyrate (1.2 mL, 8.2 mmol), powdered K$_2$CO$_3$ (1.4 g, 10.1 mmol), and MgSO$_4$ (1.0 g, 8.3 mmol). The resulting mixture was heated to 60° C. under a drying tube overnight. After cooling to room temperature, the reaction mixture was filtered through a pad of celite and the filtrate was concentrated. The resulting residue was dissolved in CH$_2$Cl$_2$ (100 mL) and washed with aqueous HCl (1N, 100 mL) followed by brine. The organic extract was dried over Na$_2$SO$_4$ then concentrated to give the crude product. Purification by flash chromatography (1:1 hexanes:ethyl acetate) gave the desired ethyl ester as an oil. C$_{27}$H$_{35}$N$_3$O$_4$ (MW=465.60); mass spectroscopy (MH$^+$)=466.2.

Step H: Preparation of

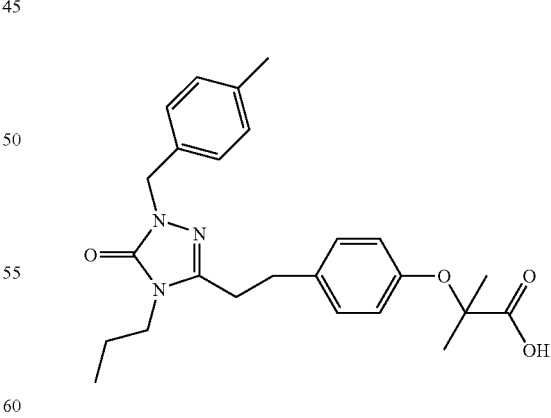

The ethyl ester from Step G (277.3 mg, 0.60 mmol) was dissolved in dioxane/H$_2$O (10 mL/3 mL) and treated with LiOH (44 mg, 1.8 mmol). The resulting mixture was stirred overnight then concentrated. The resulting residue was diluted with CH$_2$Cl$_2$ (25 mL) and extracted with aqueous NaOH (1N, 2×25 mL). The combined aqueous extracts were acidified by the careful addition of aqueous HCl (5N) then extracted into CH$_2$Cl$_2$ (2×25 mL). The combined organic extracts were dried over Na$_2$SO$_4$ and concentrated to give the desired carboxylic acid an a colorless oil. C$_{25}$H$_{31}$N$_3$O$_4$ (MW=437.54); Mass spectroscopy (MH$^+$)=438.2 (M H$^-$)=436.3

Example 23

Compound 23

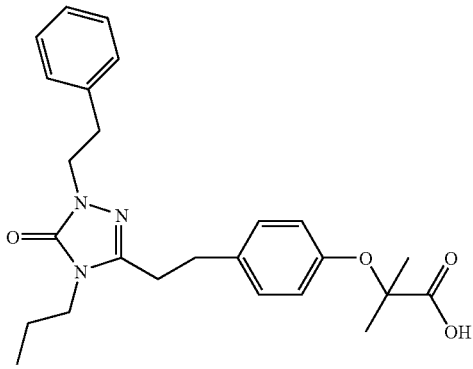

Step A: Preparation of

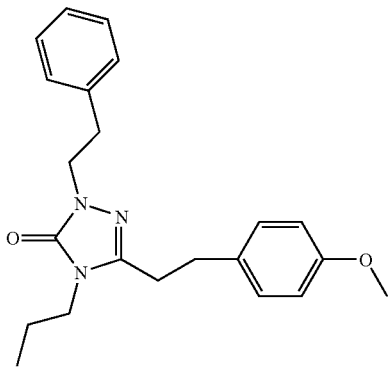

The N4-propyl triazolinone from Example 22, Step D (1.13 g, 4.3 mmol) was dissolved in DMF (25 mL) and treated with phenethylbromide (710 □L, 5.2 mmol) and powdered K$_2$CO$_3$ (1.25 g, 9.0 mmol). The resulting mixture was heated to 50-60° C. under a drying tube overnight. The reaction mixture was cooled to room temperature, poured into aqueous HCl (1N, 75 mL) and extracted into ethyl acetate (100 mL). The organic extract was washed with brine, dried over Na$_2$SO$_4$, then concentrated to give the crude product. Purification by flash chromatography (gradient 2:1 to 1:1 hexanes:ethyl acetate) gave the desired N2-phenethyl triazolinone as an oil. C$_{22}$H$_{27}$N$_3$O$_2$ (MW=365.48); mass spectroscopy (MH$^+$)=366.1.

Step B: Preparation of

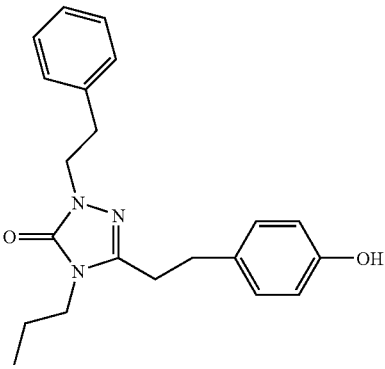

The N2-phenethyl triazolinone from Step A (0.83 g, 2.3 mmol) was dissolved in CH$_2$Cl$_2$ and cooled to 0° C. under N$_2$. To this solution was added, dropwise, a CH$_2$Cl$_2$ solution (10 mL) of BBr$_3$ (1.0 mL, 10.6 mmol). After stirring for 2 hr at 0° C., the reaction mixture was quenched by the dropwise addition of methanol/CH$_2$Cl$_2$. The resulting mixture was poured into H$_2$O and extracted with additional CH$_2$Cl$_2$ (50 mL). The organic extract was washed with brine, dried over Na$_2$SO$_4$, then concentrated to give the desired phenol as a slightly yellow oil. C$_{21}$H$_{25}$N$_3$O$_2$ (MW=351.45); mass spectroscopy (MH$^+$)=352.2.

Step C: Preparation of

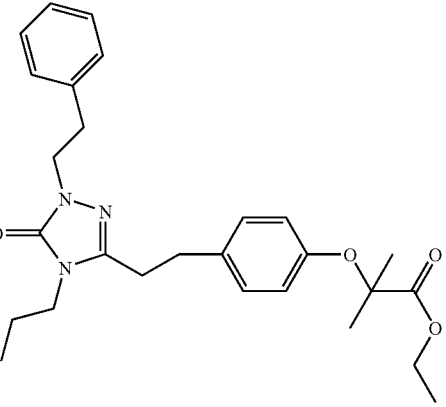

The phenol from Step B (0.78 g, 2.2 mmol) was dissolved in ethanol (absolute, 15 mL) and treated with ethyl 2-bromoisobutyrate (1.2 mL, 8.2 mmol), powdered K$_2$CO$_3$ (1.4 g, 10.1 mmol), and MgSO$_4$ (1.0 g, 8.3 mmol). The resulting mixture was heated to 60° C. under a drying tube overnight. After cooling to room temperature, the reaction mixture was filtered through a pad of celite and the filtrate was concentrated. The resulting residue was dissolved in CH$_2$Cl$_2$ (100 mL) and washed with aqueous HCl (1N, 100 mL) followed by brine. The organic extract was dried over Na$_2$SO$_4$ then concentrated to give the crude product. Purification by flash chromatography (1:1 hexanes:ethyl acetate) gave the desired ethyl ester as an oil. C$_{27}$H$_{35}$N$_3$O$_4$ (MW=465.60); mass spectroscopy (MH$^+$)=466.3.

Step D: Preparation of

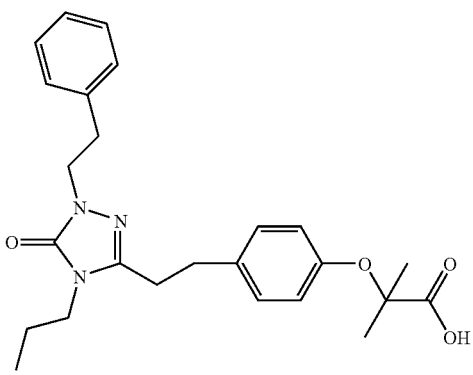

The ethyl ester from Step C (0.78 g, 1.7 mmol) was dissolved in dioxane/H$_2$O (20 mL, 3/1) and treated with LiOH (122 mg, 5.1 mmol). The resulting mixture was stirred overnight then concentrated. The resulting residue was diluted with ethyl acetate (50 mL) and extracted with aqueous HCl (1N, 50 mL). The organic extract was reextracted with aqueous NaOH (1N, 1×50 mL). The resulting aqueous washing was acidified by the addition of aqueous HCl (5N) then extracted with ethyl acetate (2×50 mL). The organic extracts were washed with brine, dried over Na$_2$SO$_4$ and concentrated to give the desired carboxylic acid an a colorless oil. C$_{25}$H$_{31}$N$_3$O$_4$ (MW=437.54); mass spectroscopy (MH$^+$)=438.2; (MH$^-$)=436.3

Example 24

Compound 24

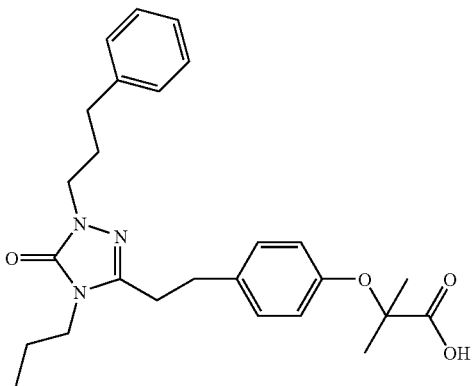

Step A: Preparation of

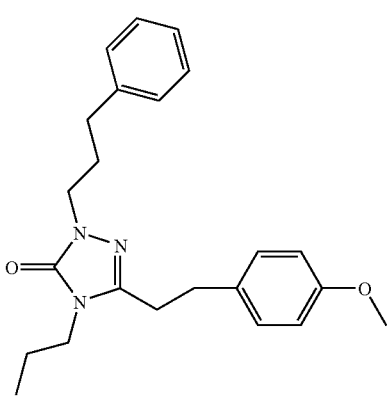

The N4-propyl triazolinone from Example 22, Step D (1.07 g, 4.1 mmol) was dissolved in DMF (25 mL) and treated with 3-phenylpropyl bromide (750 μL, 4.9 mmol) and powdered K$_2$CO$_3$ (1.2 g, 8.7 mmol). The resulting mixture was heated to 50-60° C. under a drying tube overnight. The reaction mixture was cooled to room temperature, poured into aqueous HCl (1N, 75 mL) and extracted into ethyl acetate (100 mL). The organic extract was washed with brine, dried over Na$_2$SO$_4$, then concentrated to give the crude product. Purification by flash chromatography (1:1 hexanes:ethyl acetate) gave the desired N2-(3-phenylpropyl)triazolinone as a slightly yellow oil. C$_{23}$H$_{29}$N$_3$O$_2$ (MW=379.51); mass spectroscopy (M H$^+$)=380.1

Step B: Preparation of

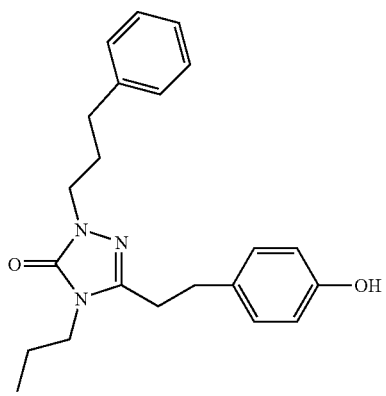

The N2-(3-phenylpropyl) triazolinone from Step A (0.92 g, 2.4 mmol) was dissolved in CH$_2$Cl$_2$ and cooled to 0° C. under N$_2$. To this solution was added, dropwise, a CH$_2$Cl$_2$ solution (10 mL) of BBr$_3$ (0.60 mL, 5.6 mmol). After stirring for approximately 1.5 hr at 0° C., the reaction mixture was quenched by the dropwise addition of methanol/CH$_2$Cl$_2$. The resulting mixture was poured into H$_2$O and extracted with additional CH$_2$Cl$_2$ (2×50 mL). The combined organic extracts were washed with brine, dried over Na$_2$SO$_4$, then concentrated to give the crude phenol as a colorless oil (used without further purification). C$_{22}$H$_{27}$N$_3$O$_2$ (MW=365.48); mass spectroscopy (MH$^+$)=366.2.

Step C: Preparation of

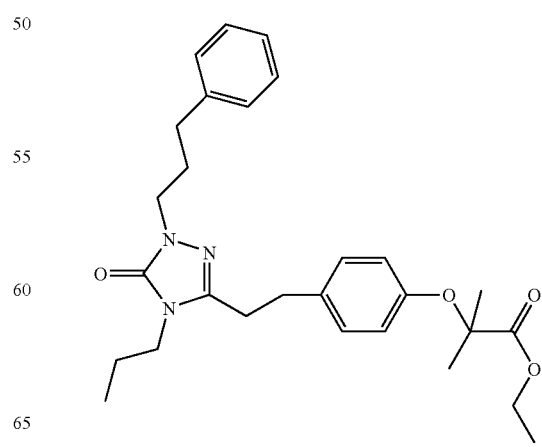

The phenol from Step B (0.91 g, 2.5 mmol) was dissolved in ethanol (absolute, 15 mL) and treated with ethyl 2-bromoisobutyrate (1.2 mL, 8.2 mmol), powdered $K_2CO_3$ (1.4 g, 10.1 mmol), and $MgSO_4$ (0.62 g, 5.2 mmol). The resulting mixture was heated to 60° C. under a drying tube overnight. After cooling to room temperature, the reaction mixture was filtered through a pad of celite and the filtrate was concentrated. The resulting residue was diluted with aqueous HCl (0.5N, 75 mL) and extracted with $CH_2Cl_2$ (2×75 mL). The combined organic extracts were washed with brine, dried over $Na_2SO_4$ then concentrated to give the crude product. Purification by flash chromatography (gradient 5:1 to 1:1 hexanes:ethyl acetate) gave the desired ethyl ester as a colorless oil. $C_{28}H_{37}N_3O_4$ (MW=479.62); mass spectroscopy (MH$^+$)=480.2.

Step D: Preparation of

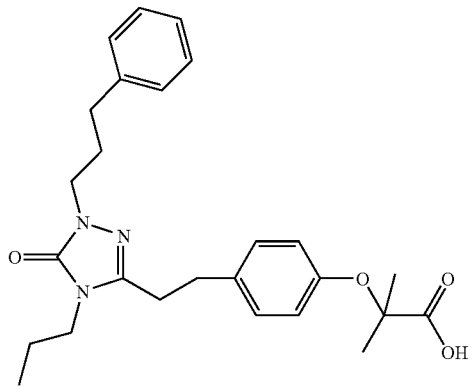

The ethyl ester from Step C (0.82 g, 1.7 mmol) was dissolved in dioxane/$H_2O$ (16 mL, 3/1) and treated with LiOH (140 mg, 5.8 mmol). The resulting mixture was stirred at room temperature for 2 hr then 45° C. for an additional 2 hr. The mixture was concentrated and the resulting residue was diluted with ethyl acetate (50 mL) and extracted with aqueous HCl. The organic extract was reextracted with aqueous NaOH (1N, 1×50 ml). The resulting aqueous washing was acidified by the addition of aqueous HCl (5N) then extracted with ethyl acetate (1×50 mL). The organic extract was dried over $Na_2SO_4$ and concentrated to give the desired carboxylic acid an a colorless oil. $C_{26}H_{33}N_3O_4$ (MW=451.25); mass spectroscopy (MH$^+$)=452.3; (M H$^-$)=450.3.

Example 25

Compound 25

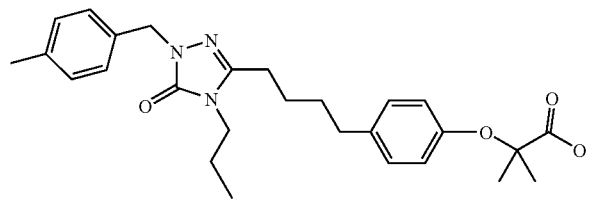

Step A: Preparation of

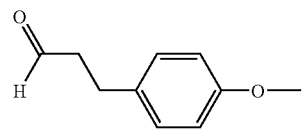

A methylene chloride solution (300 mL) of 3-(4-methoxyphenyl)-1-propanol (Aldrich, 15.0 g, 0.090 mol) was cooled to 0° C. and stirred. Pyridinium chlorochromate (Aldrich, 23.4 g, 0.108 mol) was slowly added to the solution which was then warmed to room temperature, placed under a drying tube and stirred over a weekend (approx. 72 hrs.). The reaction mixture was filtered through a pad of Florisil (Aldrich) and the filtrate was concentrated to give the crude product as a dark oil. Purification by flash chromatography (6:1 hexanes:ethyl acetate) gave the desired 3-(4-methoxyphenyl)propionaldehyde as a pale yellow oil.

Step B: Preparation of

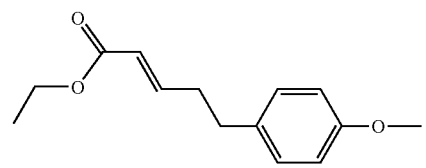

An aqueous (18 mL) solution of the aldehyde from Step A (8.5 g, 0.052 mol) was treated with triethylphosphonoacetate (Aldrich, 14.0 g, 0.062 mol) and potassium carbonate (14.4 g, 0.104 mol). The bi-phasic solution is stirred at room temperature overnight. Additional water (60 mL) was added to the mixture which was extracted with hexanes (3×). The combined organic layers were washed with brine then dried over sodium sulfate. Evaporation of the solvent gave the crude product as an oil. Purification by flash chromatography (10:1 hexanes:ethyl acetate) gave the desired unsaturated ethyl ester.

Step C: Preparation of

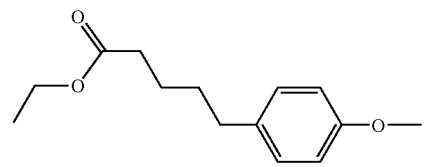

An ethyl acetate solution (100 mL) of the unsaturated ethyl ester from Step B (6.2 g, 0.026 mol) was stirred in a 3-neck flask. The atmosphere of the flask was replaced with nitrogen by alternating vacuum and nitrogen into the flask. Palladium on carbon (5%) was added, the atmosphere purged again then introduced to a balloon of hydrogen while stirring overnight. The hydrogen atmosphere was replaced with nitrogen as above, the resulting mixture was filtered through a pad of Celite and the filter cake washed with ethyl acetate. The filtrate was concentrated to give the desired saturated product as a clear oil.

Step D: Preparation of

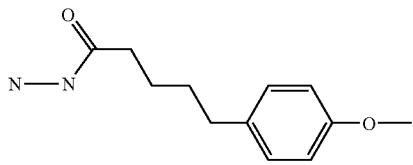

An ethanol solution of the ester from Step C (6.0 g, 0.025 mol) and hydrazine hydrate (EM Sciences, 12.7 g, 0.254 mol) was stirred and heated to 60° C. for 4 hours then cooled to room temperature and stirred over the weekend (about 72 hrs.). The resulting solution was concentrated, added to water and extracted with ethyl acetate (2×). The organic layers were combined and washed with brine then dried over sodium sulfate. Evaporation of the solvent gave a solid product which was washed with hexanes and filtered to give the desired acyl hydrazide as a white solid. $C_{12}H_{18}O_2N_2$ (MW=222.29); mass spectroscopy (MH$^+$)=223.2.

Step E: Preparation of

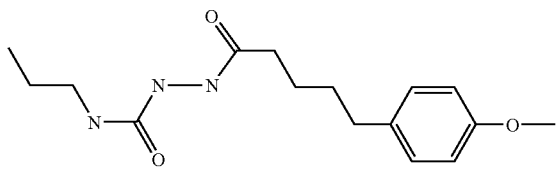

A tetrahydrofuran solution (25 mL) of the acyl hydrazide from Step D (2.6 g, 0.012 mol) was treated with propyl isocyanate (Aldrich, 1.2 g, 0.014 mol) and stirred at room temperature overnight, during which a precipitate forms. The resulting suspension was treated with methanol and stirred for an additional 30 minutes. The solvent was then evaporated to give the desired acyl semicarbazide as a white solid, which was used without further purification.

Step F: Preparation of

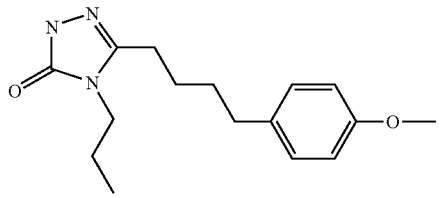

A methanol solution (50 mL) of the acyl semicarbazide from Step E (3.4 g, 0.011 mol) was stirred and treated with solid potassium hydroxide (6.2 g, 0.110 mol). The mixture was heated at 60° C. for 48 hrs. The resulting mixture was cooled, added to water (150 mL) and extracted with ethyl acetate (3×). The organic layers were combined, washed with brine and dried over sodium sulfate. Evaporation of the solvent gave a solid which was washed with hexane to give the desired N4-propyl triazolinone as a white solid. $C_{16}H_{23}N_3O_2$ (MW=289); mass spectroscopy (MH+)=290.2.

Step G: Preparation of

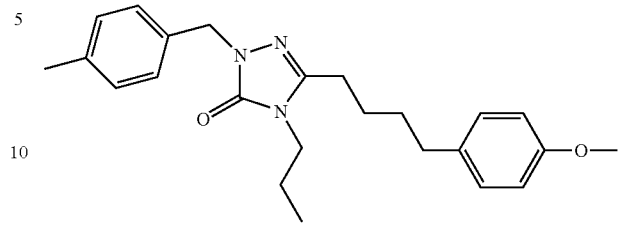

The N4-propyl triazolinone from Step F (1.2 g, 0.0042 mol) was dissolved in DMF (25 mL) and treated with α-bromo-p-xylene (Aldrich, 1.2 g, 0.0063 mol) and powdered potassium carbonate (Aldrich, 2.3 g, 0.0168 mol). The resulting mixture was heated to 45° C. for 2 hrs and then allowed to cool to room temperature and stir overnight. The reaction mixture was added to aqueous HCl (1N, 75 mL) and extracted with ethyl acetate (3×). The combined organic layers were washed with brine, dried over sodium sulfate and concentrated to give the crude product as an oil. Purification by flash chromatography (gradient: hexanes to 1:1 hexanes:ethyl acetate) gave the desired N2-p-methylbenzyl triazolinone.

Step H: Preparation of

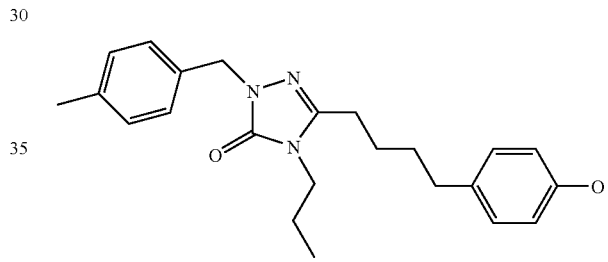

The N2-p-methylbenzyl triazolinone from Step G (1.2 g, 0.0031 mol) was dissolved in methylene chloride (25 mL) and cooled to 0° C. under a drying tube. A solution of boron tribromide (0.6 mL, 0.006 mol) in methylene chloride (5 mL) was added dropwise. The reaction mixture was stirred at 0° C. for 1 hr. An additional two equivalents of boron tribromide (0.6 mL, 0.006 mol) was added and stirring continued for an additional 0.5 hr. The reaction was quenched by the dropwise addition of methanol (4 mL) in methylene chloride (4 mL). The reaction was added to an additional 60 mL of methylene chloride and washed with water. The organic layer was then dried over sodium sulfate and concentrated to give the desired phenol as a yellow solid. $C_{23}H_{29}N_3O_2$ (MW=379.5); mass spectroscopy (MH$^+$)=380.3.

Step I: Preparation of

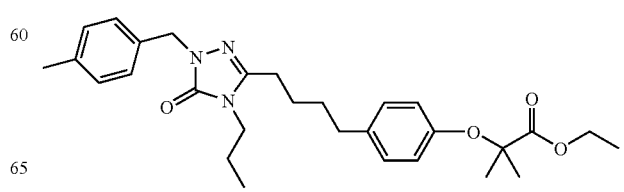

The phenol from Step H (1.0 g, 0.0026 mol) was dissolved in ethanol (absolute, 25 mL) and treated with ethyl 2-bromoisobutyrate (Aldrich, 1.5 g, 1.1 mL, 0.0078 mol), powdered potassium carbonate (Aldrich, 1.4 g, 0.010 mol) and magnesium sulfate (0.3 g, 0.0026 mol). The resulting mixture was stirred and heated to 60° C., under a drying tube, for 16 hrs. The reaction mixture was filtered through a pad of Celite and the filtrate was concentrated. The resulting residue was dissolved in ethyl acetate and washed with HCl (1N) and brine. The organic layer was then dried over sodium sulfate and concentrated to give the crude product. Purification by flash chromatography (1:1 hexanes:ethyl acetate) gave the desired ethyl ester. $C_{29}H_{39}N_3O_4$ (MW=493.6); mass spectroscopy (MH$^+$)=494.3.

Step J: Preparation of

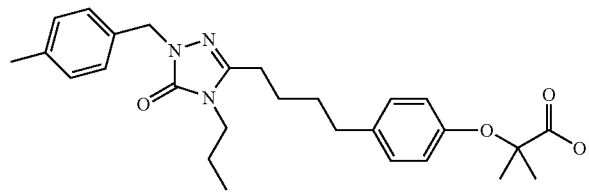

The ethyl ester from Step I (0.6 g, 0.0012 mol) was dissolved in methanol (6 mL) and an aqueous solution of lithium hydroxide (0.06 g, 0.0024 mol) in water (6 mL) added. The resulting mixture was heated to 60° C. for 2 hrs. After cooling to room temperature, the reaction mixture was added to ethyl acetate (70 mL) and washed with water, resulting in an emulsion, which was broken up by the addition of HCl(1N). This was extracted with ethyl acetate (2×). These two layers were combined and extracted with NaOH (1N), the aqueous layer was acidified with HCl (5N) and extracted with ethyl acetate (2×). These two organic layers were combined, dried over sodium sulfate and concentrated to give the desired carboxylic acid as an oil. $C_{27}H_{35}N_3O_4$ (MW=465.6); mass spectroscopy (M H$^+$)=466.3; (MH$^-$)=464.3.

Example 26

Compound 26

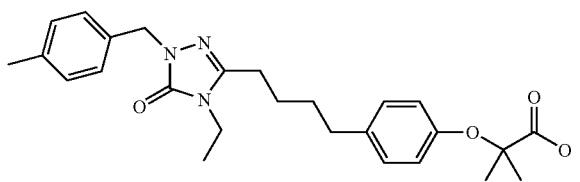

Step A: Preparation of

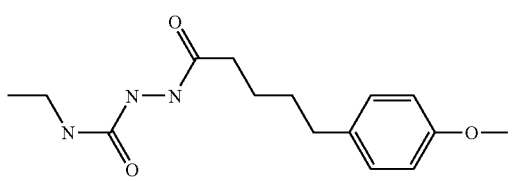

The acyl hydrazide from Example 25, Step D (2.6 g, 0.012 mol) was dissolved in tetrahydrofuran (25 mL) and treated with ethyl isocyanate (Aldrich, 1.2 g, 0.014 mol). The resulting mixture was stirred at room temperature overnight. The resulting suspension was treated with methanol and stirred for an additional 30 minutes. The solvent was then evaporated to give the desired acyl semicarbazide as a white solid which was used without further purification.

Step B: Preparation of

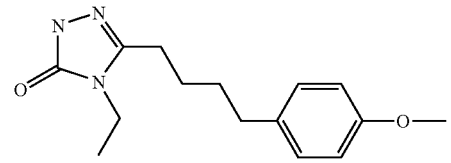

A methanol solution (50 mL) of the acyl semicarbazide from Step A (3.3 g, 0.011 mol) was stirred and treated with solid potassium hydroxide (6.2 g, 0.11 mol). The mixture was heated at 60° C. overnight. The resulting mixture was cooled, added to water (125 mL) and extracted with ethyl acetate (3×). The organic layers were combined, washed with brine and dried over sodium sulfate. Evaporation of the solvent gave the desired N4-ethyl triazolinone as a white solid. $C_{15}H_{21}N_3O_2$ (MW=275.35); mass spectroscopy (MH+)=276.1.

Step C: Preparation of

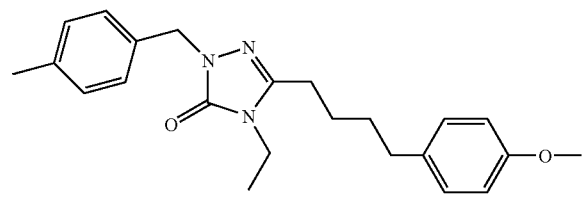

The N4-ethyl triazolinone from Step B (1.2 g, 0.0044 mol) was slowly added to a slurry of sodium hydride (60% dispersion in mineral oil, 0.3 g, 0.009 mol), under a stream of nitrogen. The resulting slurry was stirred for 45 min. and then treated with α-bromo-p-xylene (Aldrich, 1.2 g, 0.006 mol). The resulting mixture was stirred at room temperature overnight. The reaction mixture was added slowly to aqueous HCl (1N, 100 mL) and extracted with ethyl acetate (3×). The combined organic layers were washed with brine, dried over sodium sulfate and concentrated to give the crude product as an oil. Purification by flash chromatography (gradient: 1:1 hexanes:ethyl acetate to 4:1 ethyl acetate:hexanes) gave the desired N2-p-methylbenzyl triazolinone.

Step D: Preparation of

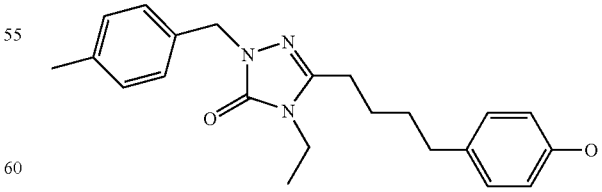

The N2-p-methylbenzyl triazolinone from Step C (1.1 g, 0.0029 mol) was dissolved in methylene chloride (25 mL) and cooled to 0° C. under a drying tube. A solution of boron tribromide (0.4 mL, 0.004 mol) in methylene chloride was added dropwise over 5 min. The reaction mixture was stirred at 0° C. for 10 min. then an additional solution of boron tribromide (0.4 mL, 0.004 mol) in methylene chloride was added and stirring continued for 1 hr. The reaction was quenched by the dropwise addition of methanol (2 mL). The reaction was added to an additional 100 mL water and extracted with methylene chloride (3×). The organic layers were combined, washed with brine and dried over sodium sulfate. Evaporation of the solvent gave the desired phenol as a white solid. $C_{22}H_{27}N_3O_2$ (MW=365.48); mass spectroscopy (MH+)=366.2.

Step E: Preparation of

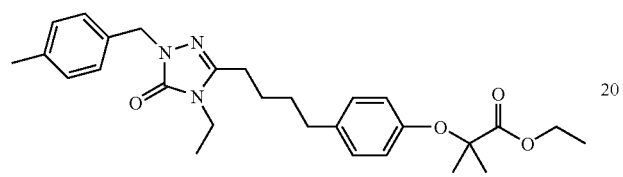

The phenol from Step D (0.8 g, 0.0022 mol) was dissolved in ethanol (absolute, 20 mL) and treated with ethyl 2-bromo-isobutyrate (Aldrich, 1.3 g, 0.0066 mol), powdered potassium carbonate (Aldrich, 1.2 g, 0.0088 mol) and magnesium sulfate (0.2 g, 0.002 mol). The resulting mixture was stirred and heated to 65° C., under a drying tube, for 48 hrs. The reaction mixture was filtered through a pad of Celite and the filtrate was concentrated to give the crude product. Purification by flash chromatography (gradient: 3:2 hexanes: ethyl acetate to 1:1 hexanes:ethyl acetate) gave the desired ethyl ester. $C_{28}H_{37}N_3O_4$ (MW=479.62); mass spectroscopy $(MH^+)$=480.3.

Step F: Preparation of:

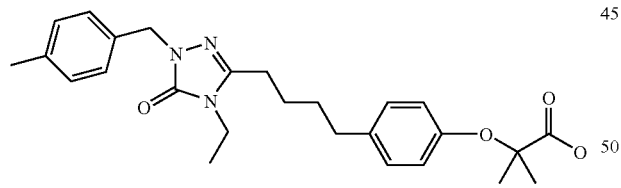

The ethyl ester from Step E (0.75 g, 0.0016 mol) was dissolved in methanol (7 mL) and an aqueous solution of lithium hydroxide (0.08 g, 0.0032 mol) in water (7 mL) added. The resulting mixture was heated to 60° C. for 1 hr. The reaction mixture was added to water (60 mL) and washed with ether. The aqueous layer was acidified with aqueous HCl (conc.) to a pH of 4 and extracted with ethyl acetate (2×). These two layers were combined, washed with brine and dried over sodium sulfate. The solvent was evaporated to give the desired carboxylic acid as an oil. $C_{26}H_{33}N_3O_4$ (MW=451.57); mass spectroscopy (M H$^+$)=452.2; (MH$^-$)=450.3.

Example 27

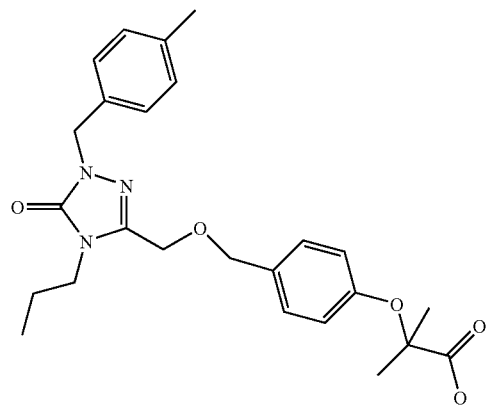

Compound 27

Step A: Preparation of

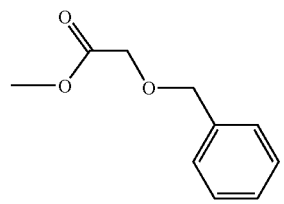

A methanol solution (75 mL) of benzyloxyacetic acid (Aldrich, 15.0 g, 0.090 mol) was treated with $H_2SO_4$ (concentrated, 1 mL) and stirred at room temperature overnight. The solvent was evaporated and the residue diluted with $CH_2Cl_2$ (150 mL). The resulting solution was extracted with saturated aqueous sodium bicarbonate (1×150 mL) followed by brine (1×150 mL), then dried over $Na_2SO_4$. Upon evaporation of the solvent the desired methyl ester was obtained as a colorless oil. $C_{10}H_{12}O_3$ (MW=180.21); mass spectroscopy (MH$^+$)=195.1.

Step B: Preparation of

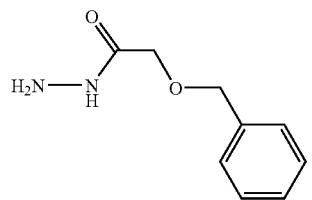

A methanol solution (100 mL) of methyl ester from Step A (6.45 g, 0.036 mol) was treated with hydrazine hydrate (20 mL, 0.41 mol) and stirred at room temperature several days. The solvent was evaporated and the residue dissolved in ethyl acetate (200 mL). The resulting solution was extracted with $H_2O$ (200 mL). The organic extract was dried over $Na_2SO_4$ and concentrated to give the desired acyl hydrizide as an oil.

Step C: Preparation of

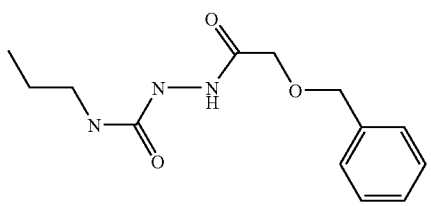

A THF solution (50 mL) of the acyl hydrizide from Step B (3.56 g, 0.020 mol) cooled to 0° C. and treated with a THF solution (25 mL) of n-propyl isocyanate (Aldrich, 2.3 mL, 0.024 mol)—added dropwise over 15 minutes. The mixture was warmed to room temperature and stirred overnight during which a thick precipitate formed. The resulting suspension was treated with methanol (25 mL) and stirred approximately 1 hour. The solvent was then concentrated to give the desired acyl semicarbazide as a white solid which was used without further purification. $C_{13}H_{19}N_3O_3$ (MW=265.31); mass spectroscopy (MH$^+$)=266.1.

Step D: Preparation of

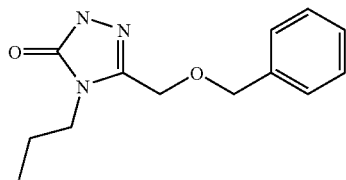

The acyl semicarbazide from Step C (5.02 g, 18.9 mmol) was dissolved in methanol (75 mL), treated with KOH (10.2 g, 18.2 mmol), then heated to reflux overnight. The reaction mixture was cooled to room temperature, poured into H$_2$O (300 mL), then extracted with ethyl acetate (3×300 mL). The combined organic extracts were washed with brine (1×300 mL), dried over Na$_2$SO$_4$ then concentrated to give the desired N4-propyl triazolinone as a slightly yellow solid. $C_{13}H_{17}N_3O_2$ (MW=247.30); mass spectroscopy (MH$^+$)=248.1.

Step E: Preparation of

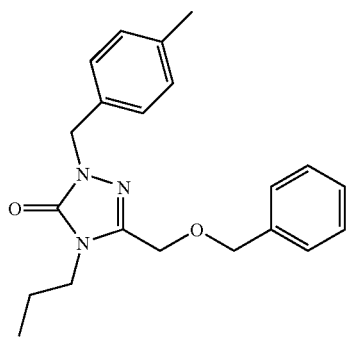

The N4-propyl triazolinone from Step D (4.32 g, 17.5 mmol) was dissolved in DMF (100 mL) and treated with α-bromo-p-xylene (4.0 g, 21.6 mmol) and powdered K$_2$CO$_3$ (5.2 g, 38 mmol). The resulting mixture was heated to 50° C. under a drying tube overnight. The reaction mixture was cooled to room temperature, poured into aqueous HCl (1N, 200 mL) and extracted into ethyl acetate (200 mL). The organic extract was washed with brine, dried over Na$_2$SO$_4$, then concentrated to give the crude product. Purification by flash chromatography gave the desired N2-p-methylbenzyl triazolinone as a slightly yellow oil. $C_{21}H_{25}N_3O_2$ (MW=351.45); mass spectroscopy (MH$^+$)=352.2.

Step F: Preparation of

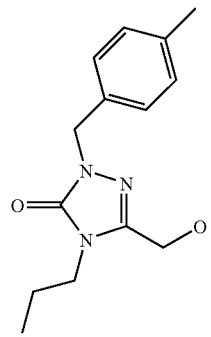

To a slurry containing 5% Pd/C (320 mg) in ethanol (50 mL) was added the benzyl ether from Step E (2.9 gm, 8.25 mmol) as a THF solution (50 mL). The resulting mixture was purged with nitrogen and then with hydrogen. An atmosphere of hydrogen was maintained over the reaction mixture by means of a balloon. After 48 hours, the reaction was judged (TLC and MS) to be only 50% complete. The catalyst was removed via filtration through a pad of celite. The resulting filtrate was concentrated to an oil and redissolved in CH$_3$OH (50 mL). A slurry containing 5% Pd/C (210 mg) in CH$_3$OH (10 mL) was added and the mixture was purged with nitrogen. An atmosphere of hydrogen was established as before and maintained for 5 days. Again the catalyst was removed via filtration through a pad of celite. Concentration of the filtrate gave the crude product which was purified by flash chromatography (gradient: 5:1 to 1:2 hexanes:ethyl acetate) to provide the desired alcohol as a white solid. $C_{14}H_{19}N_3O_2$ (MW=261.33); mass spectroscopy (MH$^+$)=262.0.

Step G: Preparation of

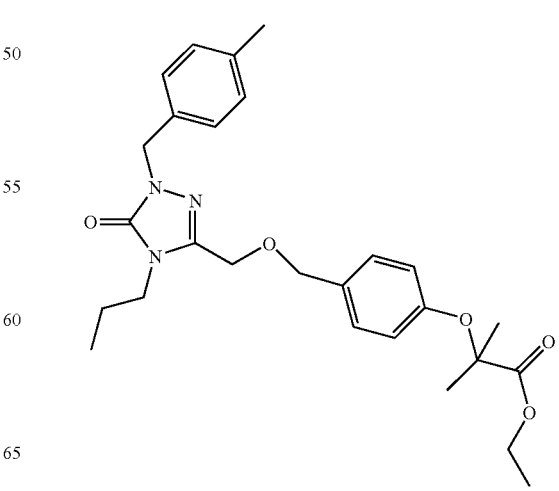

To a suspension of NaH (60% in oil, 130 mg, 3.25 mmol) in DMF (10 mL) at 0° C. was added a DMF solution (5 mL) of the alcohol from Step F (383.7 mg, 1.47 mmol). The resulting mixture was stirred 5 minutes then treated with a DMF solution (5 mL) of ethyl 2-[4-(bromomethyl)phenoxy]-2-methyl-propionate (registry 58336-71-3, 457.2 mg, 1.52 mmol). The reaction mixture was warmed to room temperature and stirred overnight. The mixture was then poured into aqueous HCl (1N, 100 mL) and extracted into $CH_2Cl_2$ (100 mL). The organic extract was washed a second time with aqueous HCl (1N) followed by brine, dried over $Na_2SO_4$, and concentrated. Flash chromatography (3:1 hexanes: ethyl acetate) gave the desired product as a yellow oil. NMR analysis indicated the presence of DMF so the oil was dissolved in $Et_2O$ (50 mL) and washed with aqueous HCl (1 N, 50 mL) followed by brine (1×50 mL). The organic solution was dried over $Na_2SO_4$ then concentrated. Purification by flash chromatography (3:1 hexanes:ethyl acetate) gave the desired ethyl ester. $C_{27}H_{35}N_3O_5$ (MW=481.60); mass spectroscopy $(MH^+)$=482.2.

Step H: Preparation of

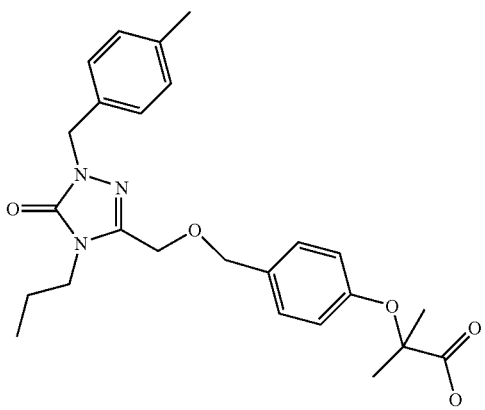

The ethyl ester from Step G (252.9 mg, 0.53 mmol) was dissolved in dioxane/$H_2O$ (15 mL/5 mL) and treated with LiOH (50 mg, 2.1 mmol). The resulting mixture was stirred overnight then concentrated. The resulting residue was diluted with $H_2O$ (70 mL) and washed with $Et_2O$ (1×75 mL). The aqueous extract was acidified with aqueous HCl then extracted with ethyl acetate (2×70 mL). The combined organic extracts were dried over $Na_2SO_4$ then concentrated to give the desired carboxylic acid as a thick, colorless oil. $C_{25}H_{31}N_3O_5$ (MW=453.54); mass spectroscopy $(MH^+)$= 454.2; $(MH^-)$=452.2.

Example 28

Compound 28

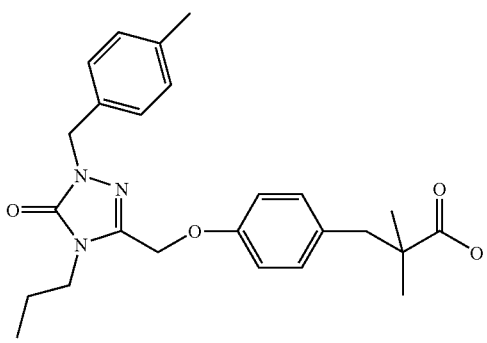

Step A: Preparation of

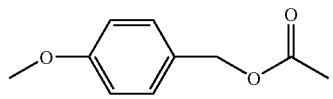

A solution of 4-methoxy benzyl alcohol (11 mL, 0.088 mol) in methylene chloride (865 mL) was cooled to 0° C. then treated with triethyl amine (18 mL, 0.129 mol). Acetyl chloride (7.2 mL, 0.101 mol) was added to the mixture. The reaction was allowed to stir for an hour. The solution was washed with 1N HCl, saturated $NaHCO_3$, and brine then dried over $Na_2SO_4$. The organic layer was concentrated to give the desired compound as a brown oil.

Step B: Preparation of

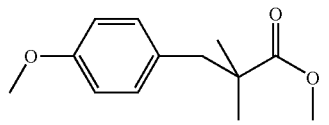

The acetate from Step A (13 g, 0.072 mol) was dissolved in methylene chloride (600 mL) and treated with 1-methoxy-1-trimethyl siloxy-2-methyl-1-propene (Aldrich, 29 mL, 0.193 mol) followed by $Mg(ClO_4)_2$ (1.7 g, 0.0073 mol). The mixture was stirred overnight at room temperature. The solution was washed with water then brine. The organic layer was concentrated to yield to a yellow oil. The material was carried forth without further purification.

Step C: Preparation of

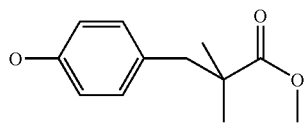

A solution of $BBr_3$ (9 mL, 0.048 mol) in methylene chloride (180 mL) was cooled to 0° C. and treated with a solution of the methyl ester from Step B (10.56 g, 0.095 mol) in methylene chloride (180 mL). The reaction was allowed to stir for thirty minutes. Methylene chloride and methanol (1:1, 70 ml) was added to quench the reaction. The solvent was concentrated. Purification of the residue by flash chromatography (3:1 hexanes:ethyl acetate) afforded the phenol as a colorless oil.

Step D: Preparation of

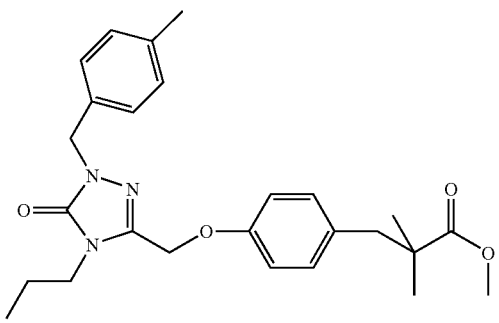

A THF solution of the phenol from Step C (173.3 mg, 0.83 mmol) and the alcohol from Example 27, Step F (204.5 mg, 0.78 mmol) was treated with triphenylphosphine (218.5 mg, 0.83 mmol) and diethyl azodicarboxylate (145 µL, 0.92 mmol). The resulting mixture was stirred overnight at room temperature under $N_2$. The mixture was concentrated and the residue dissolved in $CH_2Cl_2$ (50 mL). The organic solution was washed with $H_2O$ (1×50 mL) and brine (1×50 mL), dried over $Na_2SO_4$, and then concentrated to give the crude product. Purification by flash chromatography (4:1 hexanes:ethyl acetate) gave the desired methyl ester as an oil. $C_{26}H_{33}N_3O_4$ (MW=451.57); mass spectroscopy (MH$^+$)=452.2.

Step E: Preparation of

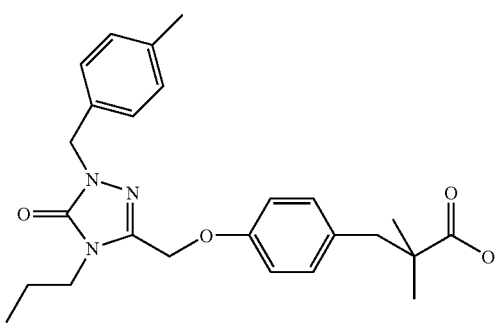

The methyl ester from Step D (190 mg, 0.42 mmol) was dissolved in dioxane/$H_2O$ (6 mL/3 mL) and treated with LiOH (50 mg, 2.1 mmol). The resulting mixture was stirred overnight then concentrated. The resulting residue was diluted with $H_2O$ (50 mL) and washed with $Et_2O$ (1×50 mL). The aqueous extract was acidified with aqueous HCl then extracted with ethyl acetate (1×50 mL). The organic extract was washed with brine (1×50 mL), dried over $Na_2SO_4$ then concentrated to give the crude product. Purification by flash chromatography (gradient 1:1 to 1:2 hexanes:ethyl acetate) gave the desired carboxylic acid as a colorless oil. $C_{25}H_{31}N_3O_4$ (MW=437.54); mass spectroscopy (MH$^+$)=438.1; (MH$^-$)=436.1.

Example 29

Compound 29

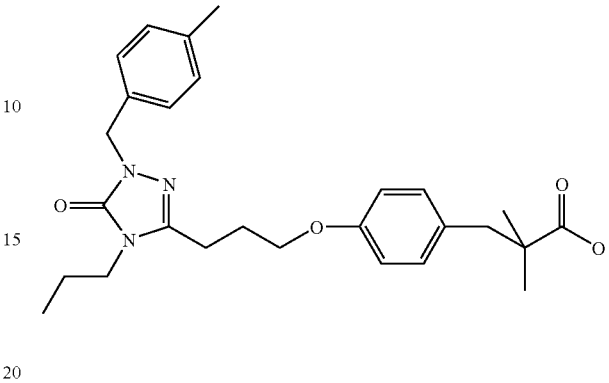

Step A: Preparation of

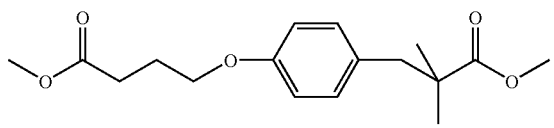

A DMF solution (65 mL) of the phenol from Example 28, Step C (2.1 g, 0.010 mol) and methyl 4-bromobutyrate (2.2 g, 0.012 mol) was treated with powdered $K_2CO_3$, (4.0 g, 0.030 mol) and $MgSO_4$ (4.0 g, 0.033 mol). The resulting mixture was heated to 60-70° C. under a drying tube. After heating overnight the mixture was cooled to room temperature and filtered through a pad of celite. The filtrate was diluted with aqueous HCl (1 N, 150 mL) and extracted with $Et_2O$. The organic solution was washed with brine, dried over $Na_2SO_4$, and concentrated. Purification by flash chromatography (10:1 hexanes:ethyl acetate) provided the desired methyl ester as a slightly yellow oil. $C_{17}H_{24}O_5$ (MW=308.38); mass spectroscopy (MH$^+$)=309.1.

Step B: Preparation of

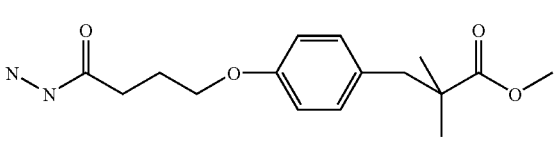

A methanol solution (76 mL) of the methyl ester from Step A (2 g, 0.0065 mol) was treated with hydrazine hydrate (0.95 mL, 0.019 mol) and stirred overnight. Additional hydrazine hydrate (0.95 mL, 0.019 mol) was added to drive the reaction to completion. The solvent was concentrated and the resulting residue was diluted with ethyl acetate. The organic layer was washed with water followed by brine then evaporated to yield the desired acyl hydrizide as a yellow oil. $C_{16}H_{24}N_2O_4$ (MW=308.38); mass spectroscopy (MH$^+$)=309.2.

Step C: Preparation of

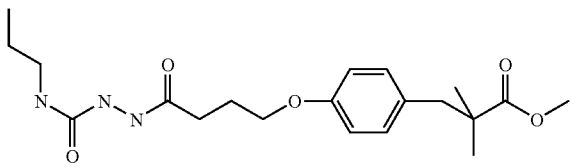

A THF solution (20 mL) of the acyl hydrizide from Step B (2 g, 0.006 mol) was treated with a THF solution (20 mL) of n-propyl isocyanate (Aldrich, 0.791 ml, 0.0084 mol), added dropwise. The mixture was stirred overnight. The solvent was concentrated to give a quantitative yield of the desired acyl semicarbazide which was carried forth without further purification.

Step D: Preparation of

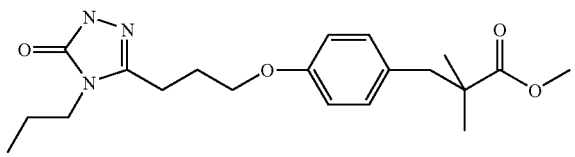

The acyl semicarbazide from Step C (2.68 g, 0.0068 mol) was dissolved in methanol and treated with KOH (3.82 g, 0.068 mol). The reaction was refluxed overnight. Upon cooling, water was added to the reaction mixture and the solution was then acidified using 1N HCl to pH=3. The acidified layer was then extracted with ethyl acetate. The organic layer was washed with brine, dried, and concentrated. The resulting material was diluted with methanol and treated with a catalytic amount of conc. $H_2SO_4$. The solution stirred overnight. The solvent was evaporated then the residue was diluted with methylene chloride and washed with water. The organic layer was concentrated to give the methyl ester. $C_{20}H_{29}N_3O_4$ (MW=375.47); mass spectroscopy (MH$^+$)=376.2.

Step E: Preparation of

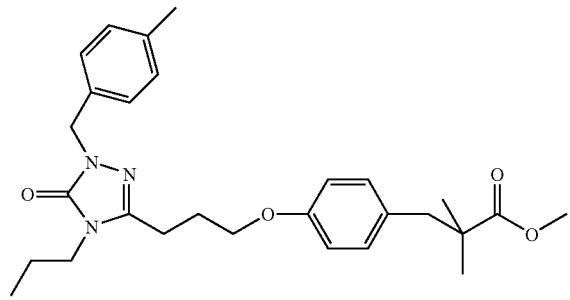

The N4-propyl triazolinone from Step D (1.5 g, 0.004 mol) was dissolved in DMF (7 ml) and treated with α-bromo-p-xylene (1.11 g, 0.006 mol) and powdered $K_2CO_3$ The resulting mixture was stirred overnight at 67° C. The heating source was removed and ethyl acetate was added to the reaction mixture. The organic layer was extracted with water followed by brine, dried then concentrated. Purification of the yellow oil by flash chromatography (4:1 hexanes:ethyl acetate) yielded the desired N4-p-methyl benzyl triazolinone. $C_{28}H_{37}N_3O_4$ (W=479.62); mass spectroscopy (MH$^+$)=480.3.

Step F:

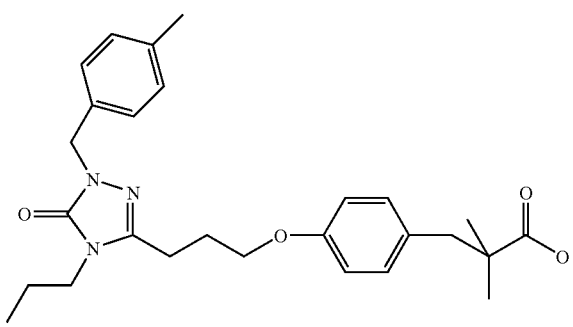

The methyl ester from Step E (0.160 g, 0.00033 mol) was dissolved in ethanol (6 mL) and treated with 2N NaOH (3 mL). The reaction was refluxed for one hour. The reaction was cooled and water (20 mL) was added to the solution. The solution was then acidified using 1N HCl to pH=3 then extracted with ethyl acetate. The organic layer was concentrated to afford the desired carboxylic acid as a colorless oil. $C_{27}H_{35}N_3O_4$ (MW=465.60); mass spectroscopy (M H$^+$)=466.3.

Example 30

Compound 30

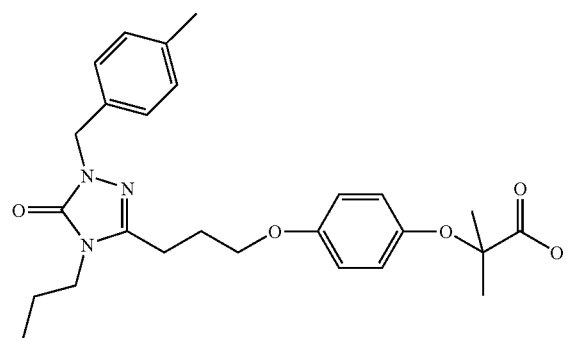

Step A: Preparation of

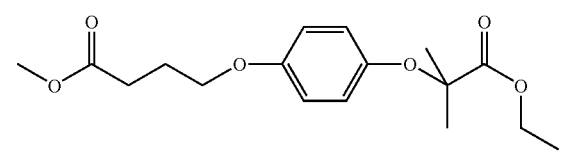

Methyl-4-bromo butyrate (3 g, 0.0166 mol) and 2-(4-hydroxyphenyl)-2-methyl propanoic acid ethyl ester (American Home Products U.S. Pat. No 3,795,691, 3.13 g, 0.014 mol) were combined in a flask and heated to 70° C. The reaction was stirred overnight. Upon cooling, the reaction mixture was filtered through celite. The filtrate was diluted with water and extracted with ethyl ether. The organic layer was washed with brine then concentrated. Purification by flash chromatography (4:1 hexanes:ethyl acetate) provided the desired diester as a yellow oil. $C_{17}H_{24}O_6$ (MW=324.38); mass spectroscopy (MH$^+$)=325.2.

Step B: Preparation of

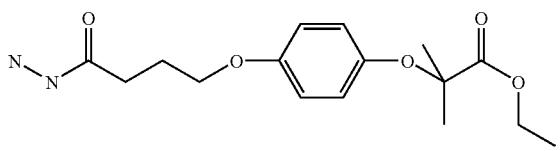

A methanol solution (60 mL) of the diester from Step A (1.64 g, 0.005 mol) was treated with hydrazine hydrate (1.23 mL, 0.025 mol) and stirred overnight. Additional hydrazine hydrate (2.46 mL, 0.050 mol) was added and the reaction was stirred overnight. The solvent was evaporated. The resulting residue was diluted with ethyl acetate and washed with water followed by brine. Concentration of the organic layer gave the acyl hydrizide.

Step C: Preparation of

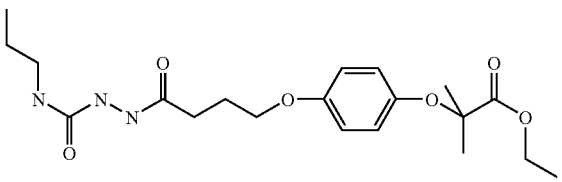

A THF solution (10 mL) of the acyl hydrizide from Step B (0.860 g, 0.00265 mol) was treated with a THF solution (10 mL) of n-propyl isocyanate (Aldrich, 0.323 ml, 0.00345 mol) added dropwise. The mixture was stirred overnight. The solvent was concentrated to give a quantitative yield of the desired acyl semicarbazide which was carried forth without further purification.

Step D: Preparation of

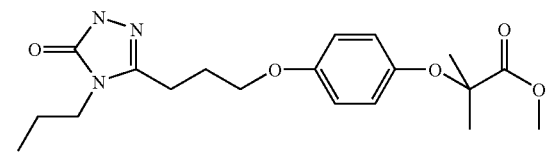

The acyl semicarbazide from Step C (1 g, 0.0026 mol) was dissolved in methanol and treated with KOH (1.48 g, 0.026 mol). The reaction was refluxed overnight. Upon cooling, water was added to the reaction mixture and the solution was then acidified using 1N HCl to pH=3. The acidified layer was then extracted with ethyl acetate. The organic layer was washed with brine, dried over $Na_2SO_4$, and concentrated. The resulting material was diluted with methanol and treated with a catalytic amount of conc. $H_2SO_4$. The solution was stirred overnight. The solvent was evaporated then the residue was diluted with methylene chloride and washed with water. The organic layer was concentrated to give the desired N4-propyl-triazolinone. $C_{19}H_{27}N_3O_5$ (MW=377.44); mass spectroscopy (MH$^+$)= 378.2.

Step E: Preparation of

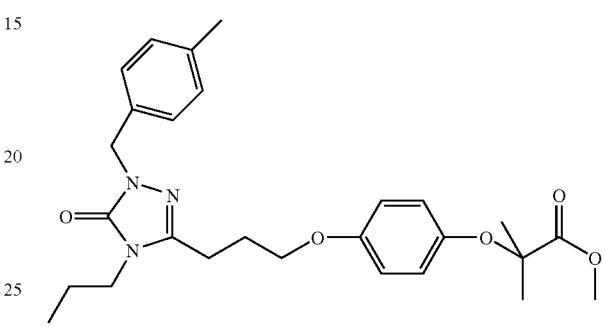

The N4-propyl triazolinone from Step D (0.92 g, 0.0024 mol) was dissolved in DMF (7 mL) and treated with α-bromo-p-xylene (0.476 mL, 0.0036 mol) and powdered $K_2CO_3$ (1.68 g, 0.012 mol). The resulting mixture was stirred for two hours at 67° C. The heating source was removed and ethyl acetate was added to the reaction mixture. The organic layer was extracted with water followed by brine, dried over $Na_2SO_4$, then concentrated. Purification of the yellow oil by flash chromatography (1:1 hexanes:ethyl acetate) yielded the desired N2-p-methyl benzyl triazolinone as a yellow oil. $C_{27}H_{35}N_3O_5$ (MW=481.60); mass spectroscopy (MH$^+$)= 482.3.

Step F: Preparation of

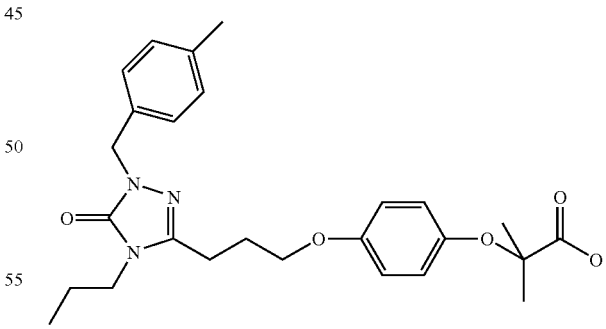

The methyl ester from Step E (0.250 g, 0.0005 mol) was dissolved in ethanol (8 mL) and treated with 2N NaOH (4 mL). The reaction was refluxed for thirty minutes. The reaction was cooled and water (10 mL) was added to the solution. The solution was then acidified using 1N HCl to pH=3 then extracted with ethyl acetate. The organic layer was concentrated to afford the desired carboxylic acid. $C_{26}H_{33}N_3O_5$ (MW=467.57); mass spectroscopy (MH$^+$)= 468.2.

Example 31

Compound 31

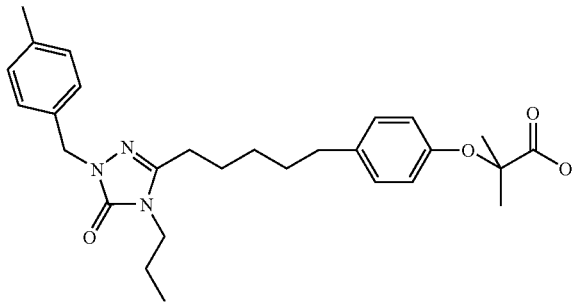

Step A: Preparation of

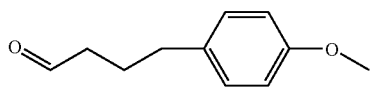

Pyridinium chlorochromate (14.2 g, 0.066 mol) was added slowly to a solution of 4-(4-methoxyphenyl)-1-butanol (10 g, 0.055 mol) in methylene chloride at 0° C. The reaction was warmed to room temperature and stirred overnight. The reaction mixture was filtered through a pad of Florisil and the solvent was evaporated. Purification by flash chromatography (4:1 hexanes:ethyl acetate) yielded the desired aldehyde as a colorless oil.

Step B: Preparation of

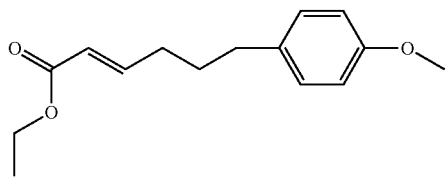

The aldehyde from Step A (6.28 g, 0.035 mol) was combined with triethyl phosphonoacetate (Aldrich, 8.39 mL, 0.042 mol) and potassium carbonate (9.66 g, 0.07 mol) in water (120 mL) and stirred overnight. Dioxane (120 mL) was added and the reaction was stirred for several days. The solution was extracted with hexanes. The organic layer was evaporated. The resulting material was purified by flash chromatography (4:1 hexanes:ethyl acetate) to give the olefin.

Step C: Preparation of

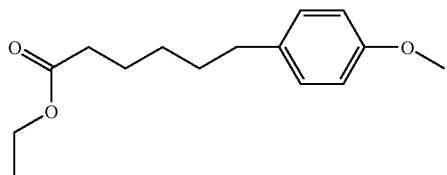

The olefin from Step B (2.5 g, 0.010 mol) was dissolved in ethyl acetate (40 mL) and purged with nitrogen. Upon the addition of the 5% Pd/C (0.40 g), the solution was purged with nitrogen and then $H_2$ gas was released across the system. The reaction was stirred overnight. The solution was filtered through a pad of celite. The solvent was concentrated to give the desired methy ether which was used without further purification.

Step D: Preparation of

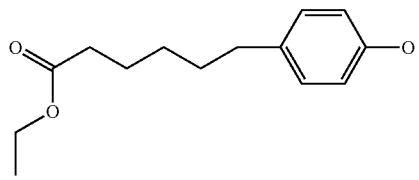

The methy ether, prepared as described in Step C (3.92 g, 0.016 mol), was dissolved in methylene chloride (50 mL) and cooled to 0° C. To this solution was added, dropwise, a solution of $BBr_3$ (4.5 mL, 0.48 mol) in methylene chloride. (20 mL). After stirring for about 45 minutes at room temperature, the reaction mixture was cooled to 0° C. and quenched by the dropwise addition of methanol/methylene chloride. During quenching, transesterification from the ethyl ester to the methyl ester occurred. The solvent was concentrated to give a dark oil. Purification by flash chromatography (4:1 hexanes:ethyl acetate) gave the desired phenol.

Step E: Preparation of

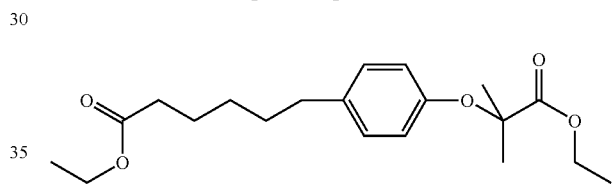

The phenol from Step D (2.5 g, 0.011 mol) was dissolved in ethanol (absolute, 40 mL) and treated with ethyl 2-bromoisobutyrate (11.56 mL. 0.079 mol), powdered $K_2CO_3$ (4.55 g, 0.033 mol), and $MgSO_4$. The reaction was stirred overnight at 75° C. Upon cooling, the reaction mixture was filtered and the filtrate was concentrated. The resulting residue was diluted with ethyl acetate and extracted with water followed by brine. The organic layer was concentrated to dryness. Purification by flashed chromatography (9:1 hexanes:ethyl acetate) gave the desired diester.

Step F: Preparation of

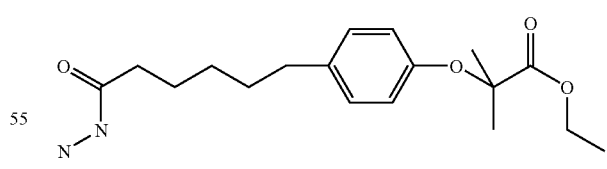

A methanol solution (76 mL) of the diester from Step E (2.65 g, 0.0076 mol) was treated with hydrazine hydrate (1.84 mL, 0.038 mol) and stirred overnight. After about six hours, additional hydrazine hydrate (1.84 mL, 0.038 mol) was added and the reaction was stirred overnight. Again, additional hydrazine hydrate (1.84 mL, 0.038 mol) was added. After several hours, the reaction was stopped and the solvent was evaporated. The resulting mixture was purified by flash chromatography (gradient 100% ethyl acetate to 6:1 ethyl acetate:methanol) to give the desired acyl hydrizide.

Step G: Preparation of

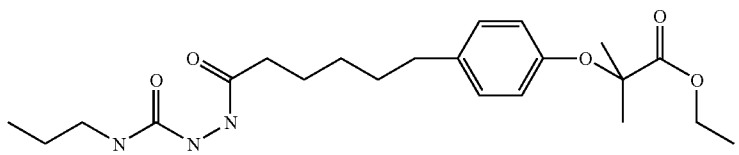

A THF solution (7 mL) of the acyl hydrizide from Step F (0.5 g, 0.0015 mol) was treated with a THF solution (7 mL) of n-propyl isocyanate (Aldrich, 0.181 mL, 0.0019 mol) added dropwise. The mixture was stirred overnight. The solvent was concentrated to give a quantitative yield of the desired acyl semicarbazide which was carried forth without further purification.

Step H: Preparation of

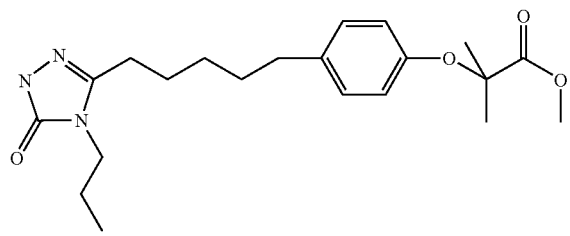

The acyl semicarbazide from Step G (1 g, 0.0024 mol) was dissolved in methanol and treated with KOH (1.34 g, 0.024 mol). The reaction was refluxed overnight. Upon cooling, water was added to the reaction mixture and the solution was then acidified using 1N HCl to pH=3. The acidified layer was then extracted with ethyl acetate. The organic layer was washed with brine, dried, and concentrated. The resulting material was diluted with methanol and treated with a catalytic amount of conc. $H_2SO_4$. The solution stirred overnight. The solvent was evaporated then the residue was diluted with methylene chloride and washed with water. The organic layer was concentrated to give the desired N4-propyl triazolinone. $C_{21}H_{31}N_3O_4$ (MW=389.50); mass spectroscopy (MH$^+$)=390.3.

Step I: Preparation of

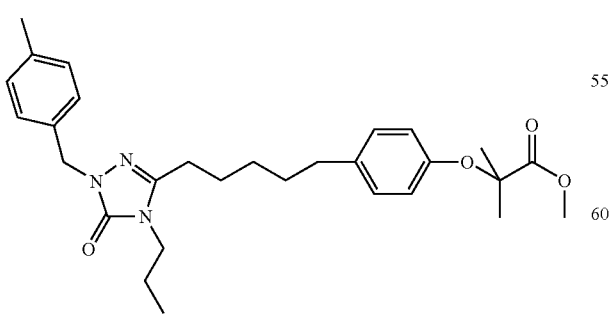

The N4-propyl triazolinone from Step H (0.5 g, 0.0013 mol) was dissolved in DMF (7 mL) and treated with α-bromo-p-xylene (0.885 g, 0.0064 mol) and powdered $K_2CO_3$ (0.885 g, 0.0064 mol). The resulting mixture was stirred for ninety minutes at 67° C. The heating source was removed and ethyl acetate was added to the reaction mixture. The organic layer was extracted with water followed by brine, dried then concentrated. Purification of the yellow oil by flash chromatography (2:1 hexanes:ethyl acetate) yielded the desired N2-p-methyl benzyl triazolinone. $C_{29}H_{39}N_3O_4$ (MW=493.65); mass spectroscopy (MH$^+$)=494.3.

Step J: Preparation of

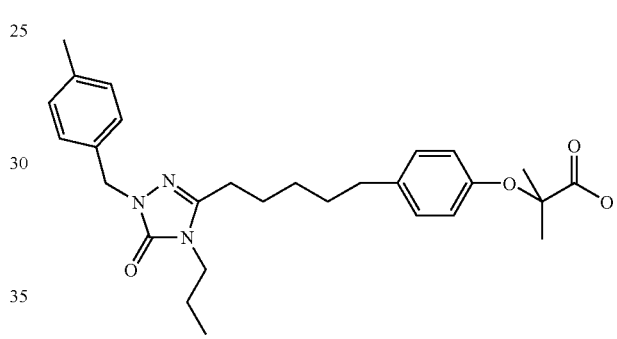

The methyl ester from Step I (0.129 g, 0.00026 mol) was dissolved in ethanol (4 mL) and treated with 2N NaOH (2 mL). The reaction was refluxed for forty-five minutes. The reaction was cooled and water (10 mL) was added to the solution. The solution was then acidified using 1N HCl to pH=3 then extracted with ethyl acetate. The organic layer was concentrated to afford the desired carboxylic acid as a colorless oil. $C_{28}H_{37}N_3O_2$ (MW=479.62); mass spectroscopy (MH$^+$)=480.3.

Example 32

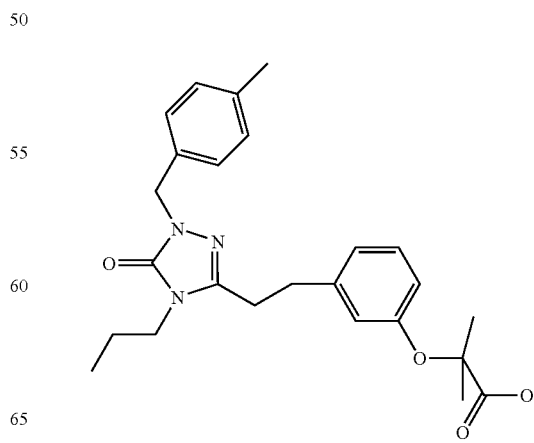

Step A: Preparation of

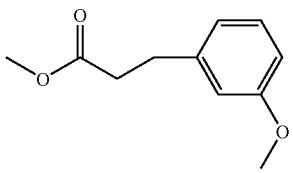

A methanol solution (75 mL) of 3-(3-methoxyphenyl)-propionic acid (Aldrich, 10.0 g, 0.055 mol) was treated with $H_2SO_4$ (concentrated, 2 mL) and stirred at room temperature for 2 days. The solvent was evaporated and the residue diluted with $CH_2Cl_2$ (150 mL). The resulting solution was extracted with saturated aqueous sodium bicarbonate (1×150 mL) followed by brine (1×150 mL), then dried over $Na_2SO_4$. Upon evaporation of the solvent the desired methyl ester was obtained as a yellowish oil. $C_{11}H_{14}O_3$ (MW=194.23); mass spectroscopy (MH$^+$)=195.0.

Step B: Preparation of

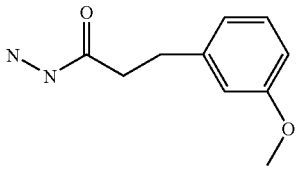

A methanol solution (100 mL) of methyl ester from Step A (10.3 g, 0.053 mol) was treated with hydrazine hydrate (30 mL, 0.60 mol) and stirred overnight. The solvent was evaporated and the residue dissolved in ethyl acetate (200 mL). The resulting solution was washed with $H_2O$ (200 mL), dried over $Na_2SO_4$ and concentrated to give the desired acyl hydrizide as a-white solid. $C_{10}H_{14}N_2O_2$ (MW=194,23); mass spectroscopy (MH$^+$)=195.1.

Step C: Preparation of

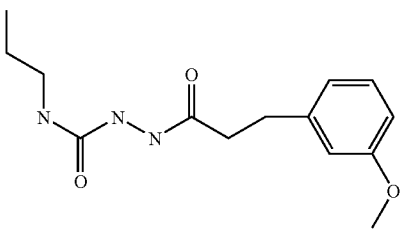

A THF solution (125 mL) of the acyl hydrizide from Step B (7.3 g, 0.038 mol) was treated with a THF solution (25 mL) of n-propyl isocyanate (Aldrich, 4.5 mL, 0.048 mol)—added dropwise over 15 minutes. The mixture was stirred overnight during which a thick precipitate formed. The resulting suspension was treated with methanol (100 mL) and stirred approximately 2 hours. The solvent was then concentrated to give the desired acyl semicarbazide as a white solid which was used without further purification. $C_{14}H_{21}N_3O_3$ (MW=279.34); mass spectroscopy (MH$^+$)= 280.2.

Step D: Preparation of

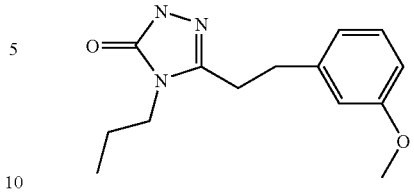

The acyl semicarbazide from Step C (10.0 g, 0.036 mol) was dissolved in methanol (200 mL), treated with KOH (20 g, 0.36 mol), then heated reflux overnight. The reaction mixture was cooled to room temperature, poured into $H_2O$ (500 mL) and extracted with ethyl acetate (2×500 mL). The combined organic extracts were washed with brine (1×500 mL), dried over $Na_2SO_4$ then concentrated to give the desired N4-propyl triazolinone as a yellow oil. $C_{14}H_{19}N_3O_2$ (MW=261.33); mass spectroscopy (MH$^+$)=262.1.

Step E: Preparation of

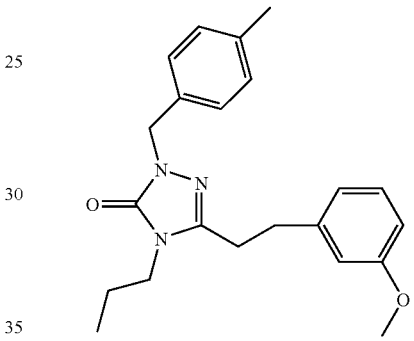

The N4-propyl triazolinone from Step D (1.25 g, 4.8 mmol) was dissolved in DMF (25 mL) and treated with α-bromo-p-xylene (1.36 g, 7.3 mmol) and powdered $K_2CO_3$ (4.2 g, 0.030 mol). The resulting mixture was heated to 50° C. under a drying tube overnight. The reaction mixture was cooled to room temperature, poured into aqueous HCl (1N, 200 mL) and extracted into ethyl acetate (200 mL). The organic extract was washed with brine (1×200 mL), dried over $Na_2SO_4$, then concentrated to give the crude product. Purification by flash chromatography (gradient 2:1 to 1:1 hexanes:ethyl acetate) gave the desired N2-p-methylbenzyl triazolinone as a colorless oil. $C_{22}H_{27}N_3O_2$ (MW=365.48); mass spectroscopy (MH$^+$)=366.1.

Step F: Preparation of

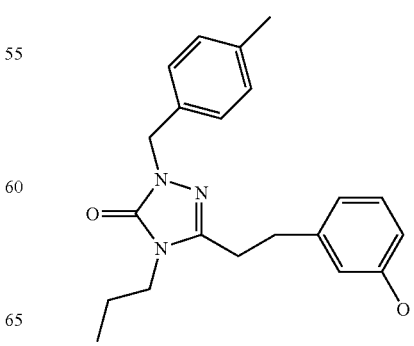

The N2-p-methylbenzyl triazolinone from Step E (1.06 g, 0.0029 mol) was dissolved in methylene chloride (15 mL) and cooled to 0° C. To this solution was added, dropwise, a solution of BBr$_3$ (0.548 mL, 0.0058 mol) in methylene chloride. (5 mL). After stirring for two hours, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the desired phenol was obtained. $C_{21}H_{25}N_3O_2$ (MW=351.45); mass spectroscopy (MH$^+$)=352.19.

Step G: Preparation of

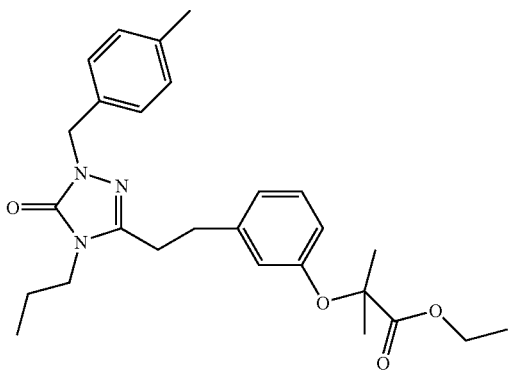

The phenol from Step F (1 g, 0.0028 mol) was dissolved in ethanol (absolute, 15 mL) and treated with ethyl 2-bromoisobutyrate (2.88 mL, 0.0196 mol), powdered K$_2$CO$_3$ (1.157 g, 0.0084 mol), and MgSO$_4$. The reaction was stirred overnight at 71° C. Upon cooling, the reaction mixture was filtered and the filtrate was concentrated. The resulting residue was diluted with methylene chloride and extracted with water followed by brine. An emulsion occurred. The organic layer was separated by the addition of brine then concentrated to dryness. Purification by flashed chromatography (gradient: 3:1 hexanes:ethyl acetate to 2:1 hexanes: ethyl acetate) gave the desired ester. $C_{27}H_{35}N_3O_4$ (MW=465.60); mass spectroscopy (MH$^+$)=466.3.

Step H: Preparation of

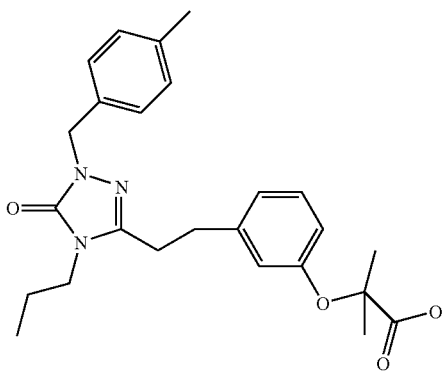

The ester from Step G (0.600 g, 0.0013 mol) was dissolved in methanol (6 mL) and treated with an aqueous solution of LiOH (0.062 g, 0.0026 mol). The reaction was stirred overnight at room temperature. Water (20 mL) was added to the reaction mixture and the solution was extracted with ethyl acetate. The aqueous layer was then acidified using 1N HCl to pH=3 then extracted with ethyl acetate. The organic layer was concentrated to afford the desired carboxylic acid. $C_{25}H_{31}N_3O_4$ (MW=437.54); mass spectroscopy (MH$^+$)=438.2.

Example 33

Compound 33

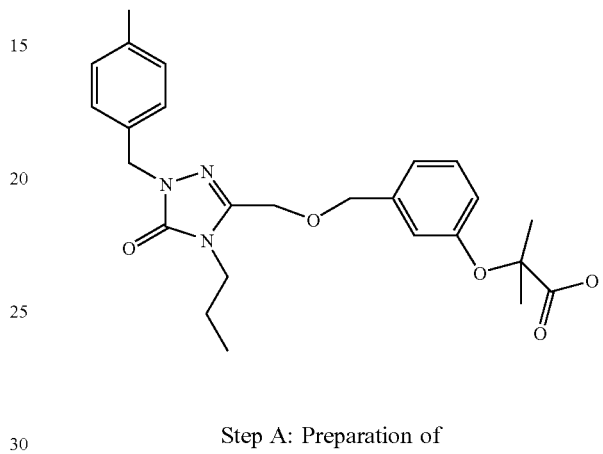

Step A: Preparation of

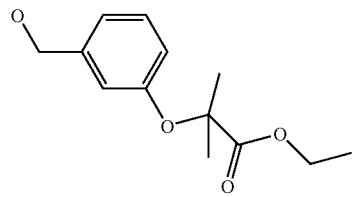

An ethanol solution of 3-hydroxybenzyl alcohol (Aldrich, 5 g, 0.040 mol) was combined with potassium carbonate (powdered, 18 g, 0.130 mol), ethyl 2-bromoisobutyrate (17 mL, 0.116 mol), and magnesium sulfate (15 g). The reaction was stirred overnight at 50° C. The reaction mixture was filtered and the filtrate was concentrated. The resulting residue was dissolved in methylene chloride and extracted with water followed by brine. Purification by flash chromatography (gradient 5:1 hexanes:ethyl acetate to 2:1 hexanes: ethyl acetate) gave the desired alcohol as a yellow oil.

Step B: Preparation of

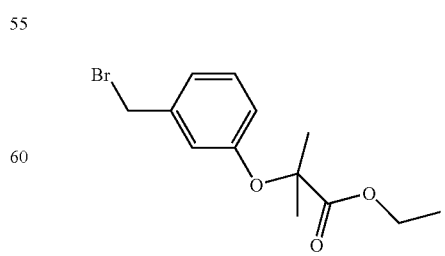

The alcohol from Step A (8.68 g, 0.036 mol) was dissolved in methylene chloride (150 mL) and cooled to 0° C.

Carbon tetrabromide (14.5 g, 0.044 mol) was added to the solution followed by the slow addition of triphenylphosphine (11.5 g, 0.044 mol). The solvent was evaporated and the resulting material was diluted with ethyl ether causing the triphenylphosphine oxide by-product to precipitate from the solution. The by-product was filtered and filtrate was concentrated. The resulting material was dissolved in hexane causing additional by-product to precipitate. A second filtration was performed and the filtrate was concentrated. A 5 g portion of the crude material was purified by flash chromatography (gradient 95:5 hexanes:ethyl acetate to 9:1 hexanes:ethyl acetate) to afford the ester. $C_{13}H_{17}BrO_3$ (MW=301.18); mass spectroscopy (MH$^+$)=302.0.

Step C: Preparation of

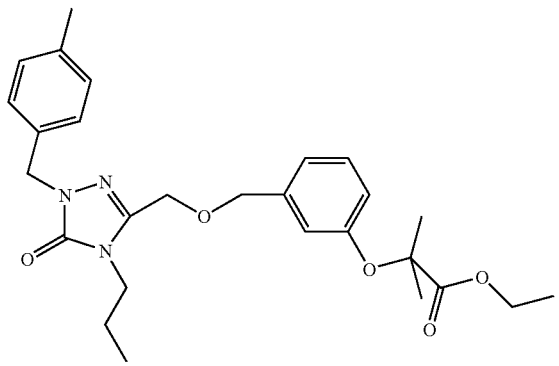

To a dry three-neck round bottom flask was added sodium hydride (60% oil dispersion, 0.134 g, 0.0033 mol) in THF (12 mL) and cooled to 0° C. A solution of the alcohol (0.4 g, 0.0015 mol) from Example 27, Step F in THF (12 mL) was added and the mixture was stirred for 5 minutes. The bromide from Step B was then added as a solution in THF (12 mL) and the resulting mixture was stirred overnight. The reaction mixture was poured into 1N HCl and extracted with methylene chloride. The organic layer was washed with water then brine. Purification by flash chromatography (1:1 hexanes:ethyl acetate) yielded the desired product. $C_{27}H_{35}N_3O_5$ (MW=481.60); mass spectroscopy (MH$^+$)=482.1.

Step D: Preparation of

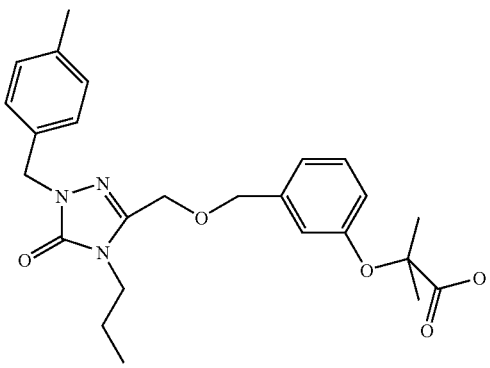

The ethyl ester from Step C (0.270 g, 0.00056 mol) was dissolved in ethanol (12 mL) and treated with 2N NaOH (6 mL). The reaction was refluxed for one hour. The reaction was cooled and water (25 mL) was added to the solution. The solution was then acidified using 1N HCl to pH=3 then extracted with ethyl acetate. The organic layer was concentrated to afford the desired carboxylic acid as a thick oil. $C_{25}H_{31}N_3O_5$ (MW=453.54); mass spectroscopy (MH$^+$)=454.2.

Example 34

Compound 34

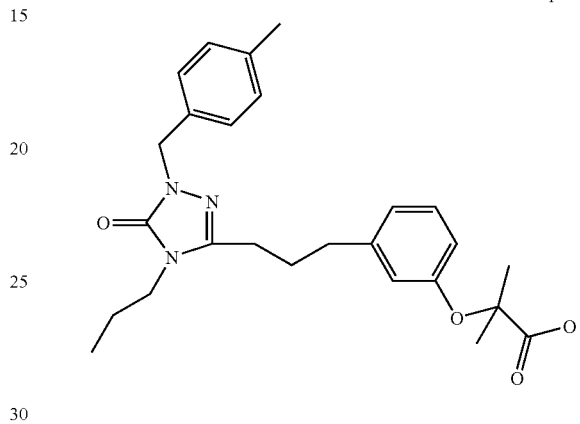

Step A: Preparation of

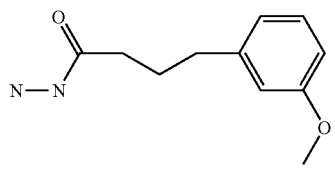

A methanol solution (15 mL) of ethyl 3-(3-methoxyphenyl)butyrate (Registry 57816-01-0, 1.91 g, 0.0086 mol) was treated with hydrazine hydrate (4.2 mL, 0.086 mol) and stirred overnight. The solvent was evaporated and the residue dissolved in ethyl acetate (50 mL). The resulting solution was washed with H$_2$O (50 mL) and brine (50 mL), then dried over Na$_2$SO$_4$ and concentrated to give the desired acyl hydrizide as a white solid. $C_{11}H_{16}N_2O_2$ (MW=208.26); mass spectroscopy (MH$^-$)=209.0.

Step B: Preparation of

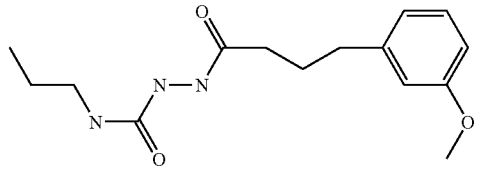

A THF solution (20 mL) of the acyl hydrizide from Step A (1.03 g, 0.0050 mol) was treated with a THF solution of n-propyl isocyanate (Aldrich, 0.60 mL, 0.0064 mol)—added dropwise over 15 minutes. The mixture was stirred then treated with $H_2O$ (50 mL) and stirred approximately 2 hours. The mixture was concentrated to an aqueous solution which was extracted with $CH_2Cl_2$ (2×75 mL). The combined organic extracts were dried over $Na_2SO_4$ then concentrated to give the desired acyl semicarbazide as a white solid, which was used without further purification. $C_{15}H_{23}N_3O_3$ (MW=293.37); mass spectroscopy ($MH^-$)=292.2.

Step C: Preparation of

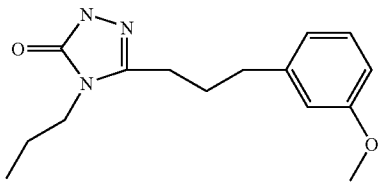

The acyl semicarbazide from Step B was dissolved in methanol (60 mL), treated with KOH (3.0 g, 0.053 mol), then heated to reflux for 48 hours. The reaction mixture was cooled to room temperature, poured into $H_2O$ (200 mL), then extracted with ethyl acetate (2×200 mL). The combined organic extracts were washed with brine (250 mL), dried over $Na_2SO_4$ then concentrated to give the desired N4-propyl triazolinone as a solid. $C_{15}H_{21}N_3O_2$ (MW=275.35); mass spectroscopy ($MH^+$)=276.1.

Step D: Preparation of

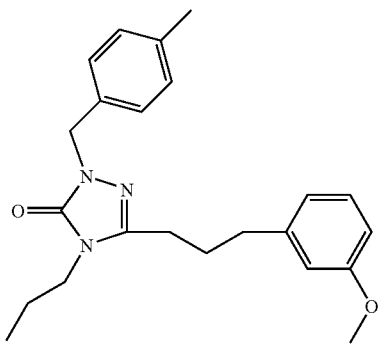

The N4-propyl triazolinone from Step C (1.20 g, 4.4 mmol) was dissolved in DMF (20 mL) and treated with p-methylbenzyl bromide (1.60 g, 8.6 mmol), powdered $K_2CO_3$ (3.2 g, 0.023 mol), and $MgSO_4$ (1.2 g, 0.010 mol). The resulting mixture was heated to 80° C. under a drying tube overnight. The reaction mixture was cooled to room temperature, poured into aqueous HCl (1N, 100 mL) and extracted into $Et_2O$ (2×100 mL). The combined organic extracts were washed with brine (1×200 mL), dried over $Na_2SO_4$, then concentrated to give the crude product. Purification by flash chromatography (2:1 hexanes:ethyl acetate) gave the desired N2-p-methylbenzyl triazolinone as a colorless oil. $C_{23}H_{29}N_3O_2$ (MW=379.51); mass spectroscopy ($MH^+$)=380.2.

Step E: Preparation of

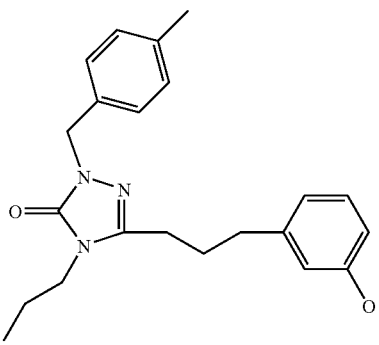

The N2-p-methylbenzyl triazolinone from Step D (0.7879 g, 0.002 mol) was dissolved in methylene chloride (15 mL) and cooled to 0° C. To this solution was added, dropwise, a solution of $BBr_3$ (0.392 mL, 0.004 mol) in methylene chloride (5 mL). After stirring for about 90 minutes, the reaction mixture was cooled to 0° C. and quenched by the dropwise addition of methanol/methylene chloride. The solvent was concentrated and the resulting material was dissolved in methylene chloride. The organic layer was extracted with water followed by brine. Upon evaporation of the solvent, the desired phenol was obtained. $C_{22}H_{27}N_3O_2$ (MW=365.48); mass spectroscopy (MH+)=366.3.

Step F: Preparation of

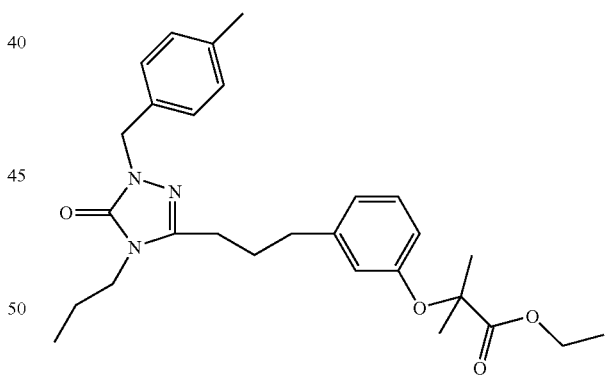

The phenol from Step E (0.70 g, 0.0019 mol) was dissolved in DMF (40 mL) and treated with ethyl 2-bromoisobutyrate (1.97 mL, 0.013 mol), powdered $K_2CO_3$ (0.797 g, 0.0057 mol), and $MgSO_4$. The reaction was stirred overnight at 75° C. Upon cooling, the reaction mixture was filtered and the filtrate was concentrated. The resulting residue was diluted with ethyl acetate and extracted with water followed by brine. The organic layer was concentrated to dryness. Purification by flashed chromatography (1:1 hexanes:ethyl acetate) gave the desired ester. $C_{28}H_{37}N_3O_4$ (MW=479.62); mass spectroscopy ($MH^+$)=480.3.

Step G: Preparation of

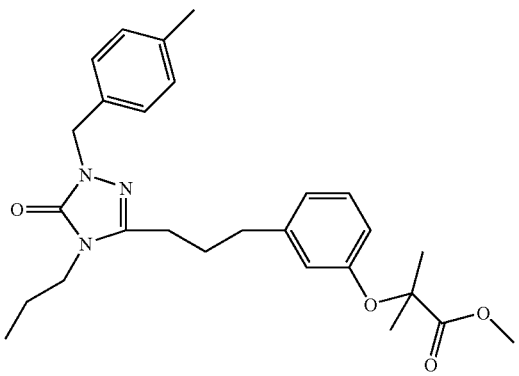

The ester from Step F (0.250 g, 0.00052 mol) was dissolved in ethanol (8 mL) and treated with 2N NaOH (4 mL). The reaction was refluxed for thirty minutes. The reaction was cooled and water (20 mL) was added to the solution. The solution was then acidified using 1N HCl to pH=3 then extracted with ethyl acetate. The organic layer was concentrated to afford the desired carboxylic acid. $C_{26}H_{33}N_3O_4$ (MW=451.57); mass spectroscopy (MH$^+$)= 452.3.

Example 35

Compound 35

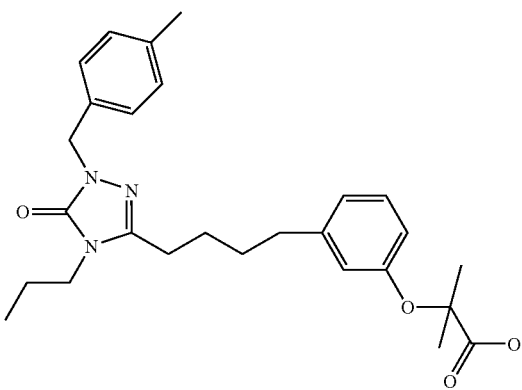

Step A: Preparation of

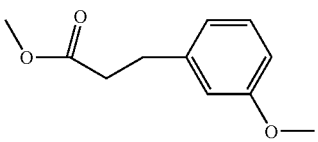

A methanol solution (75 mL) of 3-(3-methoxyphenyl)-propionic acid (Aldrich, 10 g, 0.055 mol) was treated with a catalytic amount of concentrated $H_2SO_4$ and stirred at room temperature overnight. The solvent was concentrated and the residue was diluted with methylene chloride (150 mL). The resulting solution was extracted with saturated aqueous sodium bicarbonate (1×150 mL) followed by brine (1×150 mL), then dried over $Na_2SO_4$. Upon evaporation of the solvent, the desired methyl ester was obtained as a colorless oil. $C_{11}H_{14}O_3$ (MW=194.23); mass spectroscopy (MH$^+$)=195.1.

Step B: Preparation of

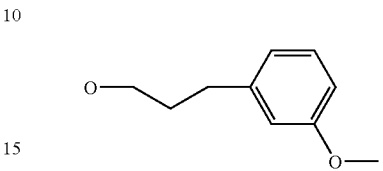

The ester from Step A (5 g, 0.0257 mol) was dissolved in toluene (100 mL) and cooled to 0° C. An excess of DIBAL (1M, 50 mL, 0.050 mol) was slowly added to the solution. The reaction stirred for 1 hour. An aqueous solution of Rochelle's salt (saturated) was added and the mixture was stirred over the weekend. The resulting biphasic solution was diluted with water and extracted with ethyl acetate. The organic layer was washed with brine, dried over Na$_2$SO4, then concentrated. Purification by flash chromatography (gradient 4:1 to 3:1 hexanes:ethyl acetate) gave the desired alcohol.

Step C: Preparation of

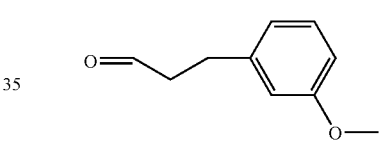

The alcohol, prepared as described in Step B (5.5 g, 0.033 mol), was dissolved in methylene chloride (165 mL) and cooled to 0° C. Pyridinium chlorochromate (8.57 g, 0.040 mol) was added slowly to the solution. The reaction was warmed to room temperature and stirred overnight. The reaction mixture was filtered through a pad of celite then concentrated. Purification by flash chromatography (4:1 hexanes:ethyl acetate) yielded the desired aldehyde.

Step D: Preparation of

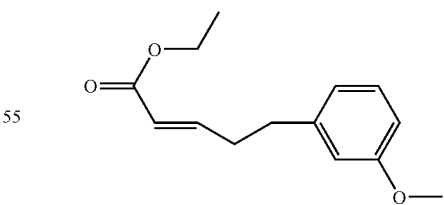

The aldehyde (3.73 g, 0.023 mol) from Step C was combined with triethyl phosphonoacetate (Aldrich, 6.12 g, 0.027 mol) and potassium carbonate (6.26 g, 0.045 mol) in water and stirred overnight. Dioxane was added and the reaction was stirred overnight again. The reaction solution was diluted with hexanes and extracted. The organic layer was concentrated. Purification by flash chromatography (15:1 hexanes:ethyl acetate) gave the desired olefin.

Step E: Preparation of

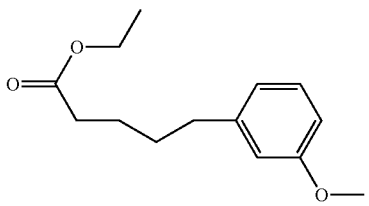

The olefin from Step D (2.5 g, 0.010 mol) was dissolved in ethyl acetate and purged with nitrogen. Upon the addition of 5% Pd/C (0.250 g), the solution was purged with nitrogen then subjected to $H_2$ gas. The reaction was stirred overnight. The solution was filtered through a pad of celite. The solvent was concentrated to give the saturated ester which was used without further purification.

Step F: Preparation of

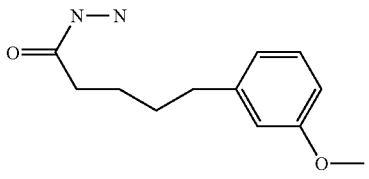

A methanol solution (60 mL) of the ester from Step E (2.5 g, 0.0105 mol) was treated with hydrazine hydrate (5.14 mL, 0.105 mol) and stirred for three days. The solvent was evaporated. The resulting mixture was dissolved in ethyl acetate and the solution was extracted with water then brine. The organic layer was concentrated to give the desired acyl hydrizide. $C_{12}H_{18}N_2O_2$ (MW=222.29); mass spectroscopy $(MH^+)=223$.

Step G: Preparation of

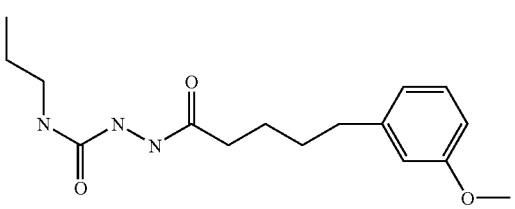

A THF solution (20 mL) of the acyl hydrizide from Step F (2.1 g, 0.0095 mol) was treated with a THF solution (20 mL) of n-propyl isocyanate (Aldrich, 1.15 mL, 0.012 mol) added dropwise. The mixture was stirred overnight. The solvent was concentrated to give the desired acyl semicarbazide which was carried forth without further purification. $C_{16}H_{25}N_3O_3$

Step H: Preparation of

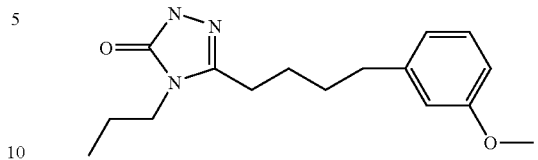

The acyl semicarbazide from Step G (2.95 g, 0.0096 mol) was dissolved in methanol and treated with KOH (5.39 g, 0.096 mol). The reaction was refluxed overnight. Upon cooling, water was added to the reaction mixture and the solution was then acidified using 1N HCl to pH=3. The acidified layer was then extracted with ethyl acetate. The organic layer was washed with brine, dried, and concentrated. Purification by flash chromatography (1:1 hexanes:ethyl acetate) gave the desired $N^4$-propyl triazolinone. $C_{16}H_{23}N_3O_2$ (MW=289.38); mass spectroscopy $(MH^+)=290.2$.

Step I: Preparation of

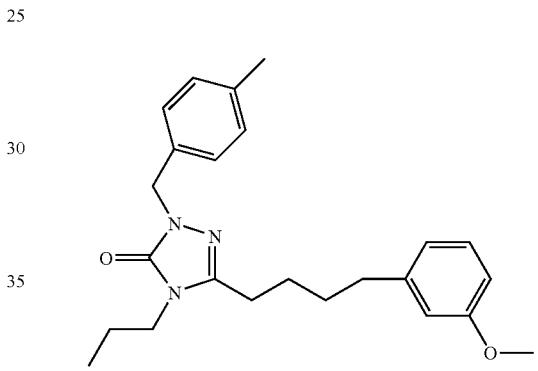

The N4-propyl triazolinone from Step H (2.13 g, 0.0073 mol) was dissolved in DMF (75 mL) and treated with (α-chloro-p-xylene (1.54, 0.0110 mol) and powdered $K_2CO_3$ (5.09 g, 0.037 mol). The resulting mixture was stirred overnight at 67° C. The heating source was removed and ethyl acetate was added to the reaction mixture. The organic layer was extracted with water followed by brine, dried over $Na_2SO_4$ then concentrated. Purification of the residue by flash chromatography (2:1 hexanes:ethyl acetate) yielded the desired N2-p-methyl benzyl triazolinone. $C_{24}H_{31}N_3O_2$ (MW=393.53); mass spectroscopy $(MH^+)=394.3$.

Step J: Preparation of

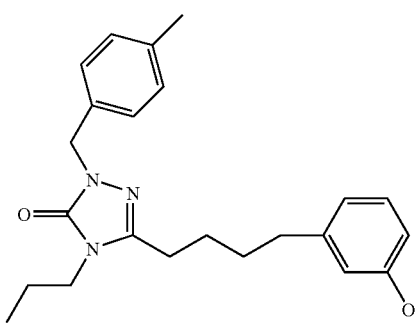

The N2-p-methyl benzyl triazolinone from Step I (1.96 g, 0.005 mol) was dissolved in methylene chloride (30 mL) and cooled to 0° C. To this solution was added, dropwise, a solution of BBr$_3$ (0.942 mL, 0.010 mol) in methylene chloride (10 mL). After stirring for about one hour, two additional equivalents of BBr$_3$ was added. The reaction mixture was cooled to 0° C. and quenched by the dropwise addition of methanol/methylene chloride. The solvent was concentrated to give the desired phenol which was used without further purification. C$_{23}$H$_{29}$N$_3$O$_2$ (MW=379.51); mass spectroscopy (MH$^+$)=380.3.

Step K: Preparation of

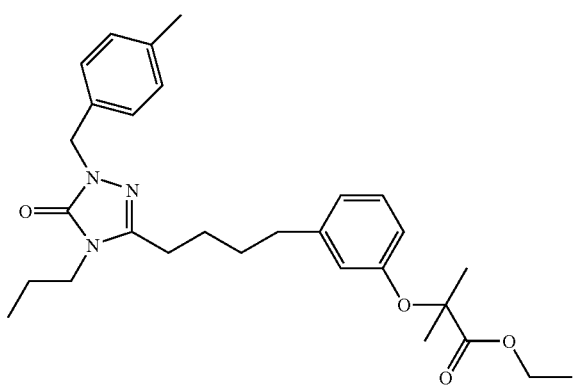

The phenol from Step J (1.75 g, 0.0046 mol) was dissolved in ethanol (absolute, 20 mL) and treated with ethyl 2-bromoisobutyrate (4.74 mL, 0.032 mol), powdered K$_2$CO$_3$ (1.90 g, 0.014 mol), and MgSO$_4$. The reaction was stirred overnight at 77° C. Upon cooling, the reaction mixture was filtered and the filtrate was concentrated. The resulting residue was diluted with ethyl acetate and extracted with water followed by brine. The organic layer was concentrated to dryness. Purification by flashed chromatography (1:1 hexanes:ethyl acetate) gave the ester as a colorless oil. C$_{29}$H$_{39}$N$_3$O$_4$ (MW=493.65); mass spectroscopy (MH$^+$)=494.3.

Step L: Preparation of

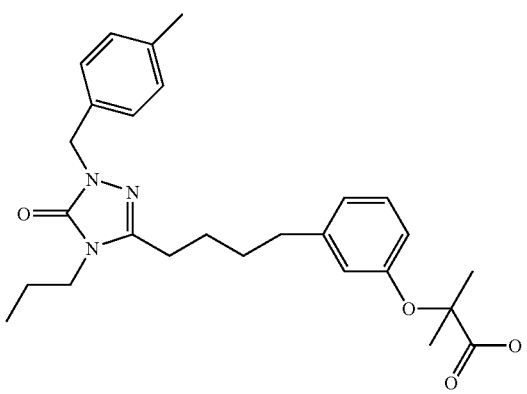

The ethyl ester from Step K (1 g, 0.002 mol) was dissolved in ethanol (24 mL) and treated with 2N NaOH (12 mL). The reaction was refluxed for one hour. The reaction was cooled and water (25 mL) was added to the solution. The solution was then acidified using 1N HCl to pH=3 then extracted with ethyl acetate. The organic layer was concentrated to afford the desired carboxylic acid as a colorless oil. C$_{27}$H$_{35}$N$_3$O$_4$ (MW=465.6); mass spectroscopy (MH$^+$)=466.7.

Example 36

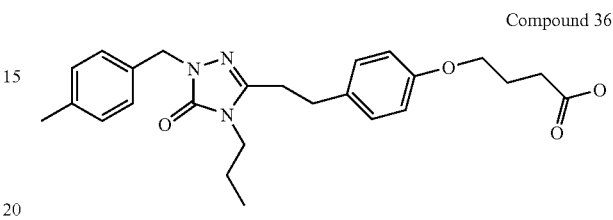

Compound 36

Step A: Preparation of

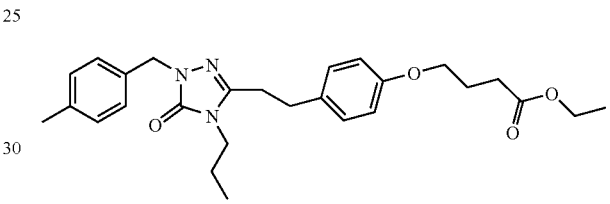

The phenol (2.1 g, 0.0060 mol), prepared as in Example 22, Step F, was dissolved in DMF (25 mL) and treated with ethyl 4-bromobutyrate (Aldrich, 1.4 g, 0.0072 mol), powdered potassium carbonate (Aldrich, 3.3 g, 0.0240 mol) and small amount of magnesium sulfate. The resulting mixture was stirred and heated to 65° C. for 18 hrs. The resulting reaction mixture was added slowly to HCl (1N, 100 mL) and extracted with ether (3×). the ether layers were combined, washed with water and dried over sodium sulfate. Evaporation of the solvent gave the crude product. Purification by flash chromatography (1:1 hexanes:ethyl acetate) gave the desired ethyl ester as a clear oil.

Step B: Preparation of

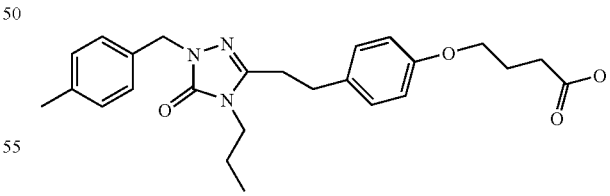

The ethyl ester from Step A (0.1 g, 0.0002 mol) was dissolved in methanol (2 mL) and treated with an aqueous solution of lithium hydroxide (0.01 g, 0.0004 mol) in water (2 mL). The resulting mixture was heated to 50° C. for 2 hrs., then stirred at room temperature overnight. The reaction mixture was added to water and acidified with aqueous HCl (conc.) to a pH of 3 and extracted with ethyl acetate (2×). These two layers were combined, washed with brine and dried over sodium sulfate. The solvent was evaporated to give the desired carboxylic acid as an oil. C$_{25}$H$_{31}$N$_3$O$_4$ (MW=437.54); mass spectroscopy (MH$^+$)=438.1.

Example 37

Compound 37

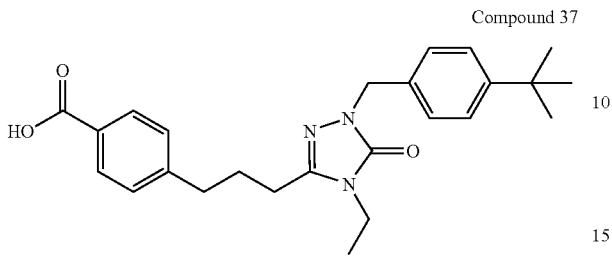

Step A: Preparation of methyl 4-(4-iodophenyl)-butyrate

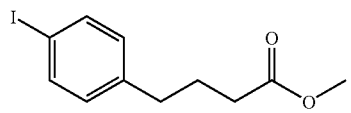

To a solution of 4-(p-iodophenyl)-butyric acid (45.0 g, 0.155 mol) in methanol (1.3 L), was added sulfuric acid (concentrated, 8.4 mL) dropwise and it was stirred at room temperature under nitrogen for 3 hours. The reaction mixture was concentrated on a rota-vapor, the residue was then partitioned between ethyl acetate (700 mL) and saturated sodium bicarbonate aqueous solution (500 mL). The organic phase was separated, washed with brine (2×200 mL), then dried over Na$_2$SO$_4$ and filtered. Evaporation of solvent gave the titled compound as an oil that was used in step B without further purification.

Step B: Preparation of

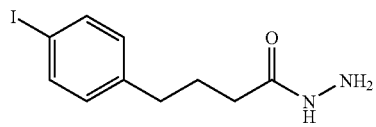

A mixture of methyl 4-(4-iodophenyl)-butyrate (47.0 g, 0.155 mol) from Step A and hydrazine hydrate (38.8 g, 0.775 mol) in methanol (200 mL) at room temperature was stirred overnight. The solvent was evaporated and the residue was partitioned between ethyl acetate (500 mL) and water (100 mL). The organic layer was washed water (3×100 mL) and brine (2×100 mL), dried over Na$_2$SO$_4$, filtered and concentrated to dryness to give the titled compound as a white crystal that was used in step C without further purification.

Step C: Preparation of

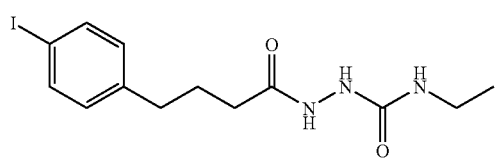

To a solution of the Step B product (47.0 g, 0.155 mol) in THF (500 mL), was added a solution of ethyl isocyanate (Aldrich, 14.7 mL, 0.186 mol) in THF (200 mL) dropwise and the mixture was stirred at room temperature for an hour. Evaporation of solvent gave the titled compound as an off-white powder that was used in step D without further purification.

Step D: Preparation of

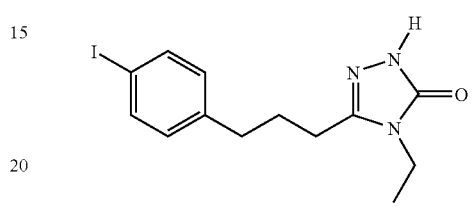

To a solution of the Step C product (58 g, 0.155 mol) in methanol (775 mL), was added potassium hydroxide in one portion (43.5 g, 0.775 mol). The reaction mixture was heated at 85° C. for 48 hours. Half of the volume was then evaporated on a rota-vapor, the residue was then partitioned between ethyl acetate (1.0 L) and water (500 mL), and the two layers were separated. The aqueous layer was extracted with ethyl acetate (2×200 mL). The combined organic layers was dried over Na$_2$SO$_4$ and filtered. Evaporation of solvent gave the titled compound as a white solid.

Step E: Preparation of

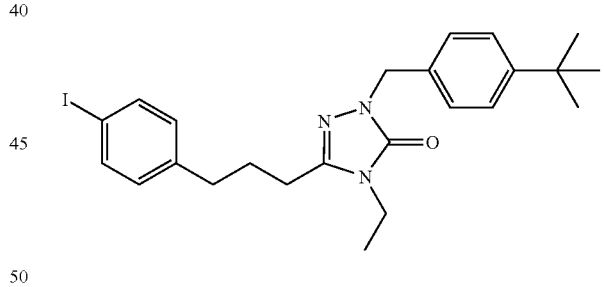

To a solution of the Step D product (2.05 g, 0.00574 mol) in methyl ethyl ketone (60 mL), was added 4-(tert-butyl) benzyl bromide (1.93 mL, 0.00861 mol) followed by potassium carbonate powder (4.75 g, 0.0344 mol).The resulting mixture was stirred under reflux under a drying tube for 24 hours. The reaction mixture was cooled to room temperature and then partitioned between ethyl acetate (100 mL) and NH$_4$Cl saturated aqueous solution (100 mL). The aqueous layer was extracted with ethyl acete (100 mL) and the combined organic phase dried over Na$_2$SO$_4$ and filtered. Evaporation of solvent gave a crude product, which was purified on a silica gel column eluting with 50% ethyl acetate in hexane to give the titled compound as colorless oil.

Step F: Preparation of

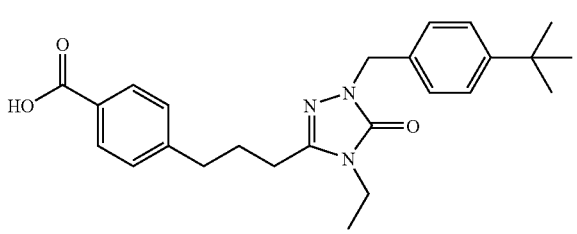

To a solution of the Step E product (2.4 g, 0.0048 mol) in benzene (5 mL) at room temperature, a solution of KOH (5.35 g, 0.0953 mol) in water (8.9 mL), chloroform (19.2 mL) and Pd(Ph$_3$P)$_2$Cl$_2$ (0.34 g, 0.00048 mol) were added and mixture stirred for 24 hours. Then, mixture was diluted with diethyl ether (20 mL) and pH adjusted to pH=1-2 by addition of 1N HCl. Layers were separated and the aqueous layer extracted with diethyl ether (3×100 mL). The combined organic layers were dried over Na$_2$SO$_4$, filtered and evaporated to give a crude product, which was purified on a silica gel column eluting, first with 70% ethyl acetate in hexane and then with ethyl acetate. The titled compound was obtained as white solid. Mass (MH+=422.5).

Example 38

Compound 38

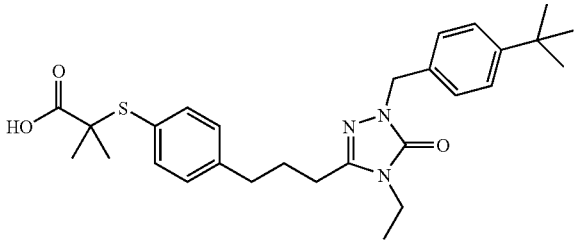

Step A: Preparation of methyl 4-benzyloxybutyrate

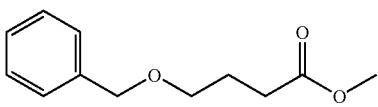

To a solution of 4-benzyloxybutyric acid (54.8 g, 0.282 mol) in methanol (1.4 L), was added sulfuric acid (concentrated, 1.4 mL) dropwise and it was stirred at room temperature under nitrogen overnight. The reaction mixture was concentrated on a rota-vapor, the residue was then partitioned between ethyl acetate (700 mL) and saturated sodium bicarbonate aqueous solution (200 mL). The organic phase was separated, washed with brine (2×100 mL), then dried over Na$_2$SO$_4$ and filtered. Evaporation of solvent gave the titled compound as an oil that was used in step B without further purification.

Step B: Preparation of

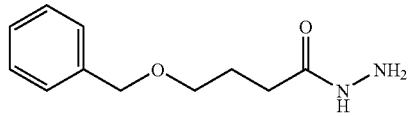

A mixture of methyl 4-benzyloxybutyrate (58.7 g, 0.282 mol) from Step A and hydrazine hydrate (56.4 g, 1.13 mol) in methanol (300 mL) at room temperature was stirred overnight. The solvent was evaporated and the residue was partitioned between ethyl acetate (1 L) and water (100 mL). The organic layer was washed water (3×100 mL) and brine (2×100 mL), dried over Na$_2$SO$_4$, filtered and concentrated to dryness to give the titled compound as a white crystal that was used in step C without further purification.

Step C: Preparation of

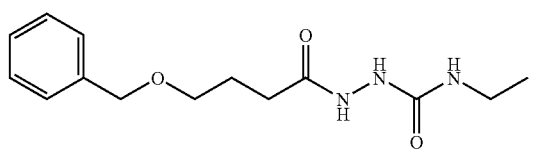

To a solution of the Step B product (58.7 g, 0.282 mol) in THF (600 mL), was added a solution of ethyl isocyanate (Aldrich, 26.8 mL, 0.338 mol) in THF (300 mL) dropwise and the mixture was stirred at room temperature for an hour. Evaporation of solvent gave the titled compound as an off-white powder that was used in step D without further purification.

Step D: Preparation of

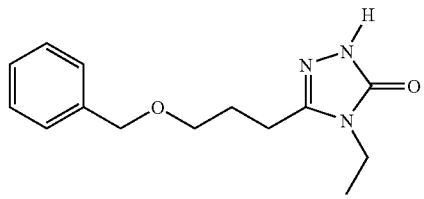

A suspension of the Step C product (78.6 g, 0.282 mol) in a solution of KOH (19.0 g, 0.339 mol) in water (380 mL) (1.2 eq of 5% KOH aqueous solution) was heated at 110° C. for 1 hour (as soon as the temperature is increased, suspension disappear). At that time, TLC showed no starting material remained and reaction was cooled to room temperature. Then, pH was adjusted to pH=6-7 by addition of 1N HCl, and extracted with AcOEt (3×500 mL). The combined organic layers were dried over Na$_2$SO$_4$, filtered and evaporated to give the titled compound as white solid.

Step E: Preparation of

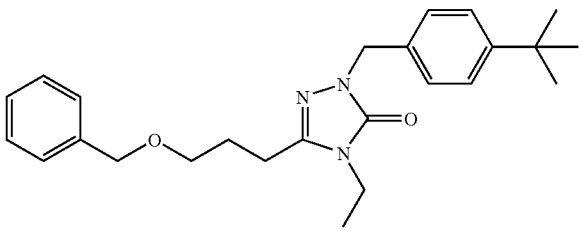

To a solution of the Step D product (9.7 g, 0.00374 mol) in methyl ethyl ketone (400 mL), was added 4-(tert-butyl)benzyl bromide (17.2 mL, 0.00935 mol) followed by potassium carbonate powder (25.8 g, 0.187 mol). The resulting mixture was stirred at 80-85° C. under a drying tube for 24 hours. The reaction mixture was cooled to room temperature and then partitioned between ethyl acetate (300 mL) and NH₄Cl saturated aqueous solution (300 mL). The aqueous layer was extracted with ethyl acetate (200 mL) and the combined organic phase dried over Na₂SO₄ and filtered. Evaporation of solvent gave a crude product, which was purified on a silica gel column eluting with 50% ethyl acetate in hexane to give the titled compound as colorless oil.

Step F: Preparation of

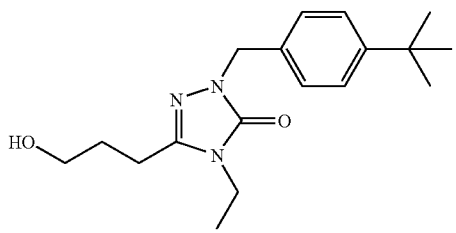

To a solution of the Step E product (4.2 g, 0.0103 mol) in ethanol (100 mL) at room temperature, palladium, 10% on activated carbon (1.03 g) was added. Mixture was stirred under hydrogen atmosphere (balloon) for 3 hours and then filtered through a plug of celite. Evaporation of the solvent gave the titled compound as white solid that was used in Step G without further purification.

Step G: Preparation of

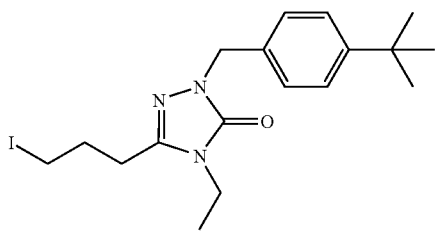

To a solution of triphenylphosphine (1.23 g, 4.68 mmol) and imidazole (0.32 g, 4.68 mmol) in a 3:1 mixture of Et₂O—CH₃CN (20 mL) at 0° C. under nitrogen atmosphere, iodine (1.19 g, 4.68 mmol) was added in small portions with vigorous stirring. The resulting mixture was warmed at room temperature and stirred for 30 minutes. Then, mixture was cooled to 0° C. and a solution of the Step F product (1.35 g, 4.25 mmol) in a 1:1 mixture of Et₂O—CH₃CN (5 mL) was added. Reaction was stirred at 0° C. for 15 min and at room temperature for 30 minutes and then poured onto 0.5N HCl (50 mL). The aqueous layer was extracted twice with a 1:1 mixture of Et₂O-hexanes (100 mL) and the combined organic phase dried over Na₂SO₄ and filtered. Evaporation of solvent gave a crude product, which was purified on a silica gel column eluting with 50% ethyl acetate in hexane to give the titled compound as yellow oil.

Step H: Preparation of

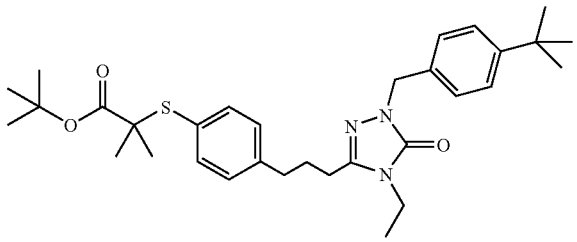

To a stirred slurry of zinc dust (0.21 g, 3.22 mmol) in anhydrous THF (0.5 mL) under nitrogen atmosphere at 60° C. was added 1,2-dibromoethane (13.9 μL, 0.16 mmol). After 15 minutes of vigorous stirring, the slurry was allowed to cool to room temperature and chlorotrimethylsilane (17.1 μL, 0.135 mmol) was added. Mixture was stirred for 30 minutes and then was reheated to 60° C. Then, a solution of the Step G product (0.23 g, 0.54 mmol) in anhydrous THF (1 mL) was added dropwise and mixture stirred for 30 minutes. A solution of tert-butyl 2-(4-bromophenylsulfanyl)-2-methylpropionate (0.36 g, 1.08 mmol), Pd(dba)₂ (0.0155 g, 0.027 mmol) and tri-o-tolylphosphine (0.0164 g, 0.054 mmol) in anhydrous THF (1 mL) was added and the resulting solution maintained at 60° C. for 2 h. Reaction was then cooled at room temperature and poured onto saturated NH₄Cl aqueous solution (20 mL). The aqueous layer was extracted with ethyl acetate (50 mL) and the organic layer washed with saturated NH₄Cl aqueous solution (2×10 mL). The combined aqueous phase was extracted with ethyl acetate (50 mL) and the combined organic phase dried over Na₂SO₄ and filtered. Evaporation of solvent gave a crude product, which was purified on a silica gel column eluting with 40% ethyl acetate in hexane to give the titled compound as colorless oil. MS: m/z (M⁺+1): 552.4.

Step I: Preparation of

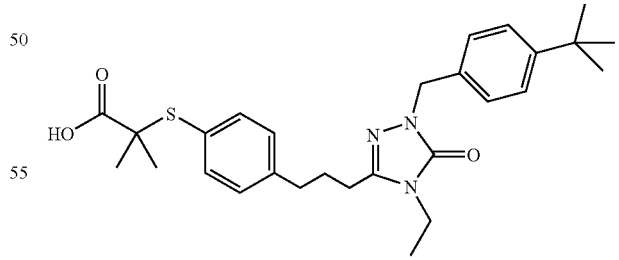

The Step I product (180 mg) was treated a mixture of triflouroacetic acid and dichloromethane (10 mL, 50% v/v) with stirring for 3 h. The solvent was removed on a rotary evaporator and the residue dried under high vacuum to give the titled compound.

Example 39

Compound 39

2-(4-{3-[1-(4-tert-Butylbenzyl)-4-methyl-5-oxo-4,5-dihydro-1H-[1,2,4]triazol-3yl[propyl}phenoxy)-2-methyl-3-phenylpropionic acid

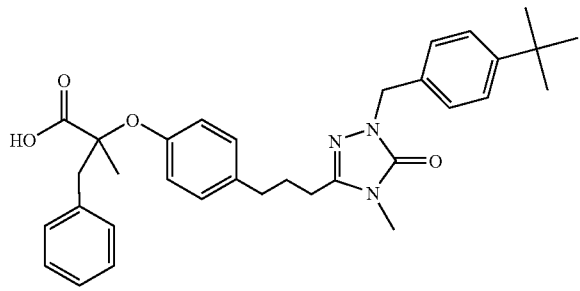

Step A: Preparation of 4-(4-Hydroxyphenyl)butyric acid hydrazide

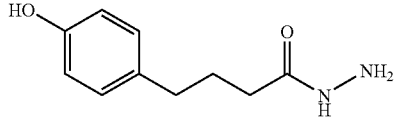

A mixture of methyl 4-(4-hydroxyphenyl)butyrate (4.93 g, 0.025 mol) and hydrazine hydrate (25.4 g, 0.254 mol) in methanol (64 mL) was heated under reflux for an hour. It was then cooled down to room temperature and stirred overnight. The solvent was evaporated and the residue was partitioned between ethyl acetate (100 mL) and water (100 mL). The organic layer was dried over $Na_2SO_4$, filtered and concentrated to dryness to give the titled compound as a white crystal (3.30 g, 67%). 400 MHz $^1$H NMR (DMSO-d$^6$) δ 9.10 (s, 1H), 8.89 (s, 1H), 6.93 (d, J=8.8 Hz, 2H), 6.63 (d, J=8.8 Hz, 2H), 3.32 (s, 2H), 2.40 (t, J=7.6 Hz, 2H), 1.97 (t, J=7.2 Hz, 2H), 1.71–1.67 (m, 2H); Mass (M–H$^-$)=193.27.

Step B: Preparation of

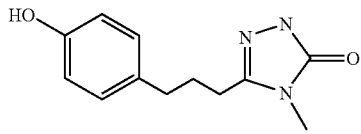

To a solution of the Step A product (3.49 g, 0.0180 mol) in THF (900 mL), was added methyl isocyanate (Aldrich, 1.17 mL, 0.0198 mol) dropwise and the mixture was stirred at room temperature for an hour. Evaporation of solvent gave the titled compound as an off-white powder (3.2 g, 71%). Mass (M–H$^-$)=250.30.

Step C: Preparation of 5-[3-(4-hydroxyphenyl)propyl]-4-methyl-2,4-dihydro-[1,2,4]triazol-3-one

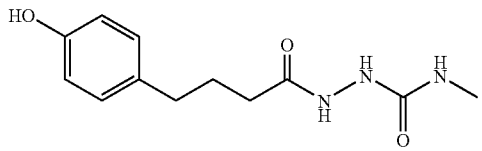

To a solution of the Step B product (3.21 g, 0.0128 mol) in methanol (64 mL), was added potassium hydroxide in one portion (10.8 g, 0.181 mol). The reaction mixture was heated at 70° C. for 36 hours. The residue was concentrated under reduced pressure and dissolved in water (80 mL). The aqueous solution was acidified to pH=2 by concentrated HCl, resulting in product precipitation. The heterogeneous mixture was stirred for 18 h, and the product was collected by filtration, yielding the titled compound as an off-white solid (4.5 g, in excess of theoretical yield). 400 MHz $^1$H NMR (DMSO-d$^6$) δ 11.37 (s, 1H), 6.97 (d, J=8.0 Hz, 2H), 6.65 (d, J=8.4 Hz, 2H), 3.01 (s, 3H), 2.50 (t, J=7.6 Hz, 2H), 2.42 (t, J=7.6 Hz, 2H), 1.80–1.77 (m, 2H); Mass (M+H$^+$)=234.21, (M–H$^-$)=232.29.

Step D: Preparation of 2-(4-tert-Butylbenzyl)-5-{3-[4-(4-tertbutylbenzyloxy)-phenyl]propyl}-4-methyl-2,4-dihydro[1,2,4]triazol-3-one

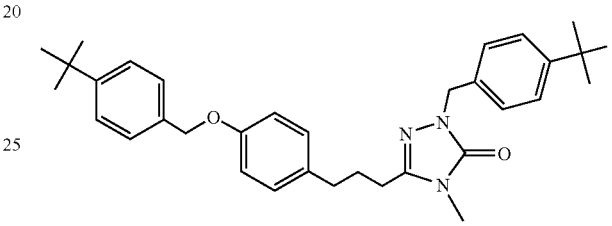

To a solution of the Step C product (1.00 g, 4.3 mmol) in DMF (21.2 mL), was added 4-t-butylbenzyl bromide (3.86 g, 17 mmol) followed by potassium carbonate powder (2.92 g, 22 mmol). The mixture was stirred at rt under nitrogen overnight. The reaction mixture was partitioned between ethyl acetate (20 mL) and water (20 mL). The organic phase was dried over $Na_2SO_4$ and filtered. Evaporation of solvent gave a crude product, which was purified on a silica gel column eluting with 20% ethyl acetate in hexane to give the titled compound as colorless oil (1.12 g, 59%). 400 MHz $^1$H NMR (CDCl$_3$) δ 7.42–7.26 (m, 8H), 7.06 (d, J=8.8 Hz, 2H), 6.90 (d, J=8.8 Hz, 2H), 5.00 (s, 2H), 4.89 (s, 2H), 3.15 (s, 3H), 2.63 (t, J=7.2 Hz, 2H), 2.46 (t, J=7.6 Hz, 2H), 1.95 (quintet, J=7.6 Hz, 2H); 1.29 (m, 18H); Mass (M+H$^+$)=526.43.

Step E: Preparation of 2-(4-tert-butylbenzyl)-5-[3-(4-hydroxyphenyl)propyl]-4-methyl-2,4-dihydro-[1,2,4]triazol-3-one

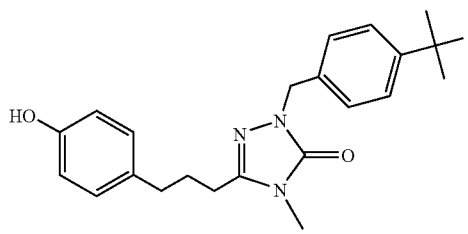

To a solution of the Step D product (1.12 g, 2.1 mmol) in EtOH (21 mL) was added 5% Pd/C (22 mg) and a hydrogen balloon. The reaction was stirred for 18 h. After filtering away the catalyst on celite, the filtrate was concentrated to produce the titled compound as a white solid (0.746 mg, 92%). 400 MHz $^1$H NMR (CDCl$_3$) δ 7.33 (d, J=8.4 Hz, 2H), 7.28 (d, J=8.4 Hz, 2H), δ 6.99 (d, J=8.4 Hz, 2H), 6.74 (d, J=8.4 Hz, 2H), 4.89 (s, 2H), 3.15 (s, 3H), 2.61 (t, J=7.6 Hz, 2H), 2.46 (t, J=7.2 Hz, 2H), 1.97-1.92 (m, 2H); 1.28 (s, 9H); Mass (M+H$^+$)=380.26.

Step F: Preparation of 2-(4-{3-[1-(4-tert-Butylbenzyl)-4-methyl-5-oxo-4,5-dihydro-1H-[1,2,4]triazol-3-yl]propyl}phenoxy)propionic acid ethyl ester

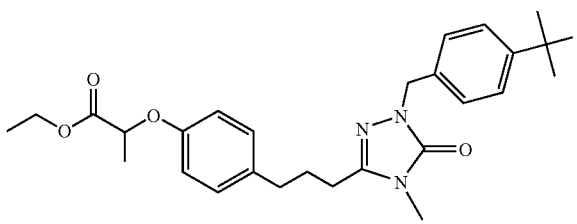

To a solution of the Step E product (0.746 g, 1.97 mmol) in DMF (7.9 mL) was added ethyl bromopropionate (0.713 g, 3.94 mmol) followed by powdered potassium carbonate (1.36 g, 9.85 mmol). The reaction was stirred at rt overnight, then diluted with ethyl acetate (20 mL) and washed with water (10 mL). The aqueous layer was back-extracted with ethyl acetate (20 mL), then the combined organics were dried over Na$_2$SO$_4$ and concentrated. The product was purified by column chromatography (90 g SiO$_2$, 50% ethyl acetate in hexane to 100% ethyl acetate) providing the ethyl ester as an oil (0.754 g, 80%). 400 MHz $^1$H NMR (CDCl$_3$) δ 7.33 (d, J=8.4 Hz, 2H), 7.28 (d, J=8.4 Hz, 2H), 7.04 (d, J=8.4 Hz, 2H), 6.79 (d, J=8.4 Hz, 2H), 4.89 (s, 2H), 4.70 (q, J=6.8 Hz, 2H), 4.21 (q, J=7.2 Hz, 2H), 3.15 (s, 3H), 2.62 (t, J=7.6 Hz, 2H), 2.45 (t, J=7.2 Hz, 2H), 1.94 (quintet, J=7.2 Hz, 2H), 1.60 (d, J=6.8 Hz, 3H),1.28-1.23 (m, 12H); Mass (M+H$^+$)=480.2.

Step G: Preparation of 2-(4-{3-[1-(4-tert-Butylbenzyl)-4-methyl-5-oxo-4,5-dihydro-1H-[1,2,4]triazol-3-yl]propyl}phenoxy)-2-methyl-3-phenyl-propionic acid ethyl ester

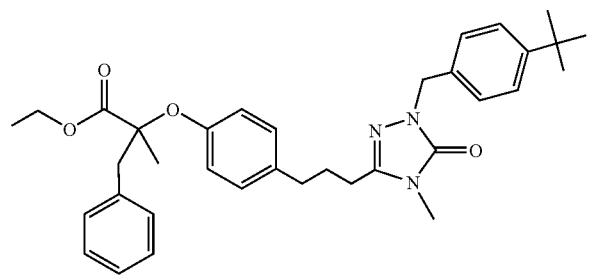

A magnetically stirred solution of the Step F product (0.752 g, 1.6 mmol) in THF (12 mL) was cooled to −78° C. under nitrogen. LHMDS (1M solution in THF, 1.96 mL) was added dropwise via syringe, followed by syringe addition of a mixture of benzyl bromide (0.992 g, 5.8 mmol) and tetrabutyl ammonium iodide (57 mg, 0.15 mmol). The reaction proceeded for 1 h at −78° C., then for 4 h at −20° C., and finally for 1 h at rt. The reaction was quenched with saturated aqueous ammonium chloride, and ethyl acetate was added. Layers were separated, and the organic phase was washed with brine, dried over Na$_2$SO$_4$, then concentrated. The product was purified by column chromatography (50 g SiO$_2$, 50% ethyl acetate in hexane to 100% ethyl acetate) providing the ethyl ester as an oil (0.224 g, 25%). 400 MHz $^1$H NMR (CDCl$_3$) δ 7.34-7.25 (m, 9H), 6.99 (d, J=8.8 Hz, 2H), 6.75 (d, J=8.8 Hz, 2H), 4.88 (s, 2H), 4.12 (q, J=7.2 Hz, 2H), 3.31 (d, J=9.6 Hz, 2H), 3.16 (d, J=9.6 Hz, 2H), 3.14 (s, 3H), 2.60 (t, J=7.6 Hz, 2H), 2.44 (t, J=7.2 Hz, 2H), 1.95-1.91 (m, 2H), 1.34 (s, 3H), 1.27-1.20 (m, 12H); Mass (M+H$^+$)=570.3, (M+NH$_4^+$)=587.3.

Step H: Preparation of 2-(4-{3-[1-(4-tert-Butylbenzyl)-4-methyl-5-oxo-4,5-dihydro-1H-[1,2,4]triazol-3-yl]propyl}phenoxy)-2-methyl-3-phenyl-propionic acid

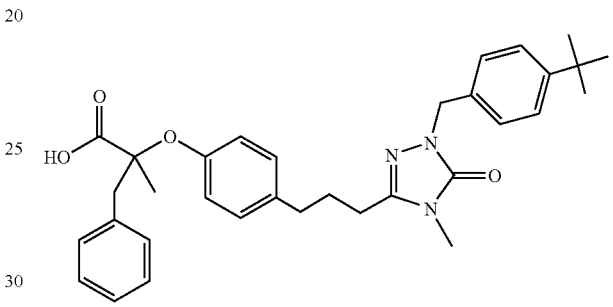

A magnetically stirred solution of the Step G product (0.073 g, 0.13 mmol) in EtOH (1.3 mL) was treated with NaOH (5M aqueous solution, 0.128 mL) and heated at reflux for 18 h. The reaction mixture was acidified to pH=1 using 1M HCl, and cooled to rt. Ethyl acetate was added (10 mL), layers were separated, and the aqueous phase was back-extracted with EtOAc (3×10 mL). Combined organic phases were dried over Na$_2$SO$_4$, and concentrated to provide the product as a tacky solid (0.054 g, 77%). Mass (M+H$^+$)=542.2, (M−H$^-$)=540.2.

Example 40

Compound 40

2-(4-{3-[1-(4-tert-Butylbenzyl)-4-methyl-5-oxo-4,5-dihydro-1H-[1,2,4]triazol-3-yl]propyl}phenoxy)-3-(4-fluorophenyl)-2-methylpropionic acid ethyl ester

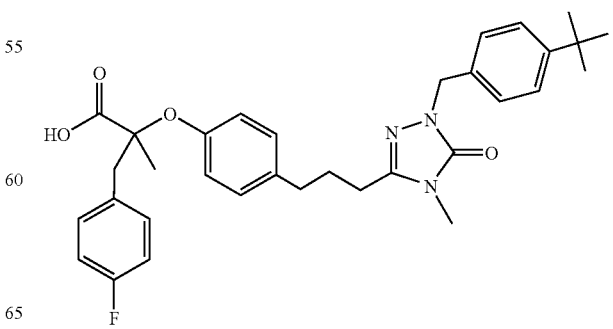

Step A: Preparation of 2-(4-{3-[1-(4-tert-Butylbenzyl)-4-methyl-5-oxo-4,5-dihydro-1H-[1,2,4]triazol-3-yl]propyl}phenoxy)-3-(4-fluorophenyl)-2-methyl-propionic acid ethyl ester

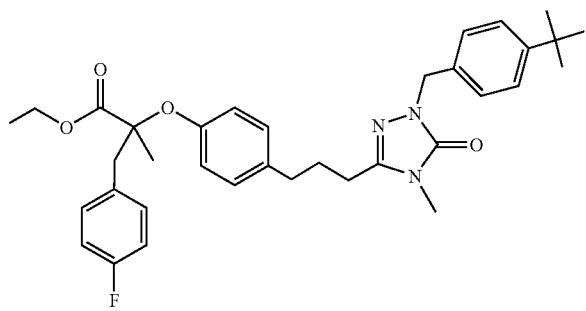

A magnetically stirred solution of the 2-(4-{3-[1-(4-tert-butylbenzyl)-4-methyl-5-oxo-4,5-dihydro-1H-[1,2,4]triazol-3-yl]propyl}phenoxy)propionic acid ethyl ester (Example 1, step F)(0.119 g, 0.25 mmol) in THF (1.7 mL) was cooled to −78° C. under nitrogen. LHMDS (1M solution in THF, 0.31 mL) was added dropwise via syringe, followed by syringe addition of a mixture of 4-fluorobenzyl bromide (0.173 g, 0.91 mmol) and tetrabutyl ammonium iodide (10 mg, 0.03 mmol). The reaction proceeded for 1 h at −78° C., then for 4 h at −20° C., and finally for 1 h at rt. The reaction was quenched with saturated aqueous ammonium chloride, and ethyl acetate was added. Layers were separated, and the organic phase was washed with brine, dried over $Na_2SO_4$, then concentrated. The product was purified by column chromatography (30 g $SiO_2$, 50% ethyl acetate in hexane) providing the ethyl ester as an oil (0.051 g, 35%). 400 MHz $^1$H NMR (CDCl$_3$) δ 7.34–7.22 (m, 8H), 7.00 (d, J=8.4 Hz, 2H), 6.74 (d, J=8.4 Hz, 2H), 4.88 (s, 2H), 4.20 (q, J=7.2 Hz, 2H), 3.28 (d, J=14.0 Hz, 2H), 3.14 (s, 3H), 3.12 (d, J=14.0 Hz, 2H), 2.61 (t, J=7.6 Hz, 2H), 2.44 (t, J=7.2 Hz, 2H), 1.95–1.91 (m, 2H), 1.28–1.22 (m, 18H).

Step B: Preparation of 2-(4-{3-[1-(4-tert-Butylbenzyl)-4-methyl-5-oxo-4,5-dihydro-1H-[1,2,4]triazol-3-yl]propyl}-phenoxy)-3-(4-fluorophenyl)-2-methyl-propionic acid

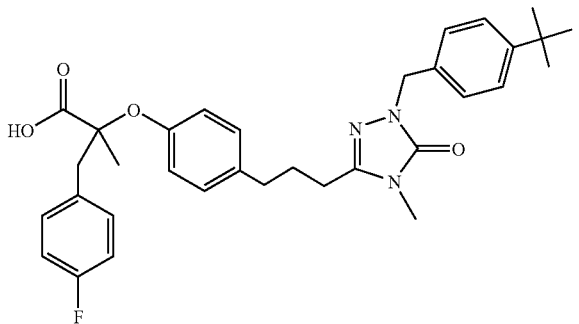

A magnetically stirred solution of the Step A product (54 mg, 0.09 mmol) in EtOH (0.9 mL) was treated with NaOH (5M aqueous solution, 0.091 mL) and heated at reflux for 18 h. The reaction mixture was acidified to pH=1 using 1M HCl, and cooled to rt. Ethyl acetate was added (10 mL), layers were separated, and the aqueous phase was back-extracted with EtOAc (3×10 mL). Combined organic phases were dried over $Na_2SO_4$, and concentrated to provide the product as a tacky solid (0.029 g, 57%). 400 MHz $^1$H NMR (DMSO-d$^6$) δ 7.15 (d, J=8.0 Hz, 2H), 7.26 (d, J=8.4 Hz, 2H), 7.14 (d, J=8.0 Hz, 2H), 7.09 (d, J=8.4 Hz, 2H), 7.05 (d, J=8.4 Hz, 2H), 6.72 (d, J=8.4 Hz, 2H), 4.76 (s, 2H), 3.08 (s, 2H), 2.53–2.45 (m, 4H), 1.82–1.78 (m, 2H), 1.25 (s, 3H), 1.22 (s, 9H); Mass (M+H$^+$)=560.3, (M−H$^-$)=558.3.

Example 41

Compound 41

2-Methyl-2-(4-{3-[4-methyl-5-oxo-1-(3-trifluoromethyl-benzyl)-4,5-dihydro-1H-[1,2,4]triazol-3-yl]-propyl}-phenoxy)-3-phenyl-propionic acid

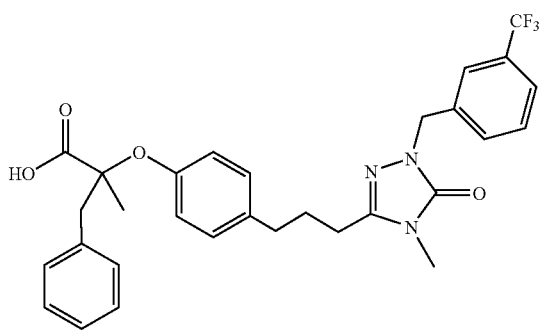

Step A: Preparation of 4-Methyl-2-(3-trifluoromethyl-benzyl)-5-{3-[4-(3-trifluoromethyl-benzyloxy)-phenyl]-propyl}-2,4-dihydro-[1,2,4]triazol-3-one

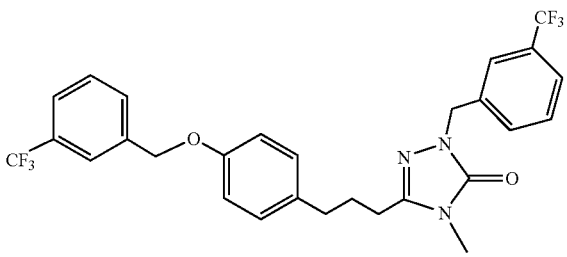

To a solution of 5-[3-(4-hydroxyphenyl)propyl]-4-methyl-2,4-dihydro-[1,2,4]triazol-3-one (Example 1, step C) (0.350 g, 1.50 mmol) in DMF (5 mL), was added 3-trifluorobenzyl bromide (1.03 g, 4.29 mmol) followed by potassium carbonate powder (0.74 g, 5.35 mmol). The mixture was stirred at rt under nitrogen overnight. The reaction mixture was partitioned between ethyl acetate (20 mL) and water (20 mL). The organic phase was dried over MgSO$_4$ and filtered. Evaporation of solvent gave a crude product, which was purified on a silica gel column (125 mL SiO$_2$) eluting with 50% EtOAc/hexanes to give the titled compound as colorless oil (0.675 g, 82%). 400 MHz $^1$H NMR (CDCl$_3$) δ 7.70 (s, 1H), 7.63–7.42 (m, 7H), 7.08 (d, J=8.4

Hz, 2H), 6.89 (d, J=8.4 Hz, 2H), 5.09 (s, 2H), 4.98 (s, 2H), 3.18 (s, 3H), 2.64 (t, J=7.2 Hz, 2H), 2.48 (t, J=7.6 Hz, 2H), 1.97 (quintet, J=7.6 Hz, 2H); Mass (M+H$^+$)=550.3.

Step B: Preparation of 5-[3-(4-Hydroxy-phenyl)-propyl]-4-methyl-2-(3-trifluoromethyl-benzyl)-2,4-dihydro-[1,2,4]triazol-3-one

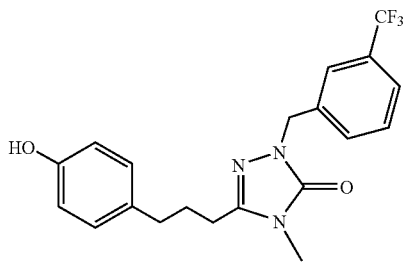

To a solution of the Step A product (0.67 g, 1.22 mmol) in EtOH (50 mL) was added 5% Pd/C (85 mg) and a hydrogen balloon. The reaction was stirred for 18 h. After filtering away the catalyst on celite, the filtrate was concentrated to produce the titled compound (oil, 0.29 g, 60%). Mass (M+H$^+$)=392.2.

Step C: Preparation of 2-Methyl-3-(4-{3-[4-methyl-5-oxo-1-(3-trifluoromethyl-benzyl)-4,5-dihydro-1H-[1,2,4]triazol-3-yl]-propyl}-phenoxy)-propionic acid ethyl ester

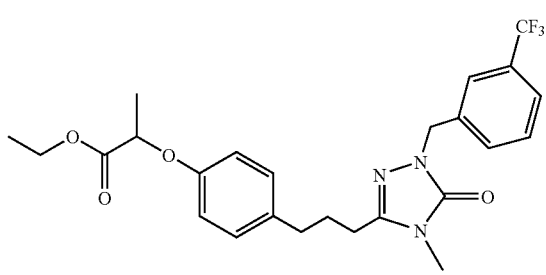

To a solution of the Step B product (0.29 g, 0.74 mmol) in DMF (3 mL) was added ethyl bromopropionate (0.27 g, 1.47 mmol, 0.19 mL) followed by powdered potassium carbonate (0.51 g, 3.7 mmol). The reaction was stirred at rt overnight, then diluted with ethyl acetate (20 mL) and washed with water (10 mL). The aqueous layer was back-extracted with ethyl acetate (20 mL), then the combined organics were dried over MgSO$_4$ and concentrated. The product was purified by column chromatography (100 mL SiO$_2$, 50% ethyl acetate in hexane to 100% ethyl acetate) providing the ethyl ester as an oil (0.754 g, 80%). 400 MHz $^1$H NMR (CDCl$_3$) δ 7.57 (s, 1H), 7.51–7.49 (m, 2H), 7.42 (d, J=8.0 Hz, 1H), 7.02 (d, J=8.6 Hz, 2H), 6.78 (d, J=8.4 Hz, 2H), 4.95 (s, 2H), 4.68 (q, J=7.2 Hz, 2H), 4.19 (q, J=7.2 Hz, 2H), 3.15 (s, 3H), 2.60 (t, J=7.6 Hz, 2H), 2.44 (t, J=7.2 Hz, 2H), 1.93 (quintet, J=7.6 Hz, 2H), 1.58 (d, J=6.8 Hz, 3H), 1.22 (t, J=7.2 Hz, 3H); Mass (M+H$^+$)=492.1.

Step D: Preparation 2-Methyl-2-(4-{3-[4-methyl-5-oxo-1-(3-trifluoromethyl-benzyl)-4,5-dihydro-1H-[1,2,4]triazol-3-yl]-propyl}-phenoxy)-3-phenyl-propionic acid ethyl ester

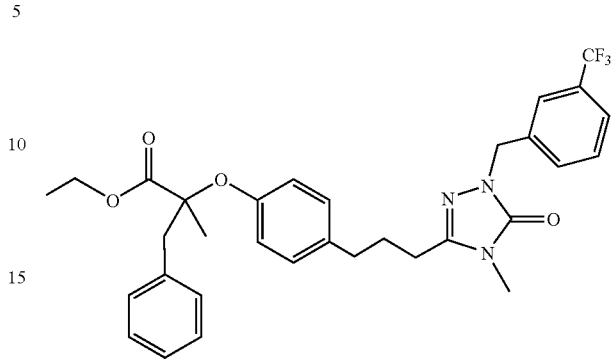

A magnetically stirred solution of the part C product (0.22 g, 0.45 mmol) in THF (2.8 mL) was cooled to −78° C. under nitrogen. LHMDS (1M solution in THF, 0.56 mL) was added dropwise via syringe, followed by syringe addition of a mixture of benzyl bromide (0.27 g, 1.6 mmol) and tetrabutyl ammonium iodide (16 mg, 0.045 mmol). The reaction proceeded for 1 h at −78° C., then for 4 h at −20° C., and finally for 1 h at rt. The reaction was quenched with saturated aqueous ammonium chloride, and ethyl acetate was added. Layers were separated, and the organic phase was washed with brine, dried over Na$_2$SO$_4$, then concentrated. The product was purified by column chromatography (100 mL SiO$_2$, 15% EtOAc/hexanes to 70% EtOAc/hexanes) providing the ethyl ester as an oil (23 mg, 9%). 400 MHz $^1$H NMR (CDCl$_3$) δ 7.34–7.22 (m, 9H), 7.00 (d, J=8.4 Hz, 2H), 6.74 (d, J=8.4 Hz, 2H), 4.97 (s, 2H), 4.20 (q, J=7.2 Hz, 2H), 3.28 (d, J=14.0 Hz, 2H), 3.14 (s, 3H), 3.12 (d, J=14.0 Hz, 2H), 2.61 (t, J=7.6 Hz, 2H), 2.44 (t, J=7.6 Hz, 2H), 1.95–1.91 (m, 2H), 1.38 (s, 3H), 1.28 (s, 3H), 1.21 (t, J=7.2 Hz, 3H); Mass (M+H$^+$)=582.4; (M+NH$_4^+$)=599.4.

Step E: Preparation of 2-Methyl-2-(4-{3-[4-methyl-5-oxo-1-(3-trifluoromethyl-benzyl)-4,5-dihydro-1H-[1,2,4]triazol-3-yl]-propyl}-phenoxy)-3-phenyl-propionic acid

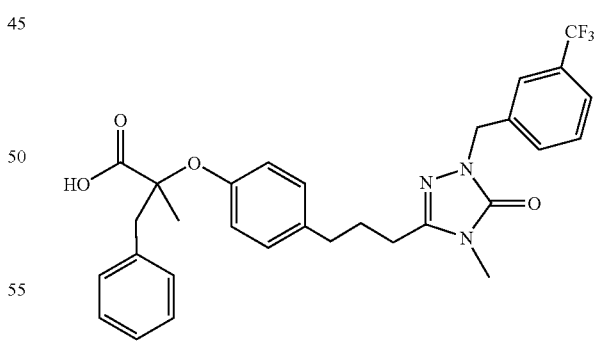

A magnetically stirred solution of the Step D product (20 mg, 0.034 mmol) in EtOH (2 mL) was treated with NaOH (5M aqueous solution, 40 µL) and heated at reflux for 18 h. The reaction mixture was acidified to pH=1 using 1M HCl, and cooled to rt. Ethyl acetate was added (10 mL), layers were separated, and the aqueous phase was back-extracted with EtOAc (3×10 mL). Combined organic phases were dried over MgSO$_4$, and concentrated to provide the product as a tacky solid (10.3 mg, 54%). Mass (M+H$^+$)=554.3, (M−H$^-$)=552.3.

Example 42

Compound 42

2-Methyl-2-(4-{3-[4-methyl-5-oxo-1-(3-phenoxy-benzyl)-4,5-dihydro-1H-[1,2,4]triazol-3-yl]propyl}phenoxy)-3-phenylpropionic acid

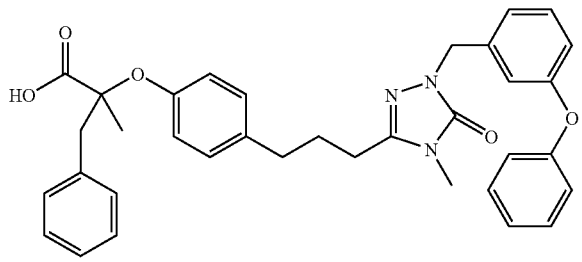

Step A: Preparation of 4-Methyl-2-(3-phenoxy-benzyl)-5-{3-[4-(3-phenoxy-benzyloxy)-phenyl]-propyl}-2,4-dihydro-[1,2,4]triazol-3-one

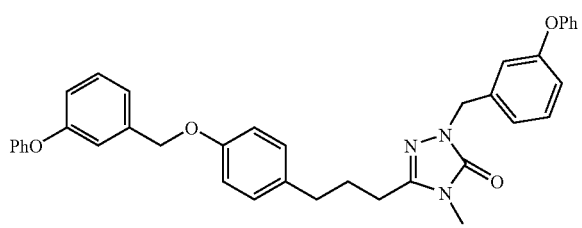

To a solution of 5-[3-(4-hydroxyphenyl)propyl]-4-methyl-2,4-dihydro-[1,2,4]triazol-3-one (Example 1, step C) (0.350 g, 1.50 mmol) in DMF (5 mL), was added 3-phenoxybenzyl chloride (0.94 g, 4.29 mmol) followed by potassium carbonate powder (0.74 g, 5.35 mmol). The mixture was stirred at rt under nitrogen overnight. The reaction mixture was partitioned between ethyl acetate (20 mL) and water (20 mL). The organic phase was dried over MgSO$_4$ and filtered. Evaporation of solvent gave a crude product, which was purified on a silica gel column (125 mL SiO$_2$) eluting with 50% EtOAc/hexanes to give the titled compound as colorless oil (0.0.78 g, 87%). 400 MHz $^1$H NMR (CDCl$_3$) δ 7.32 (q, J=7.6 Hz, 4H), 7.30–7.25 (m, 3H), 7.20–6.90 (m, 10H), 6.97 (d, J=8.8 Hz, 2H), 6.87 (d, J=8.8 Hz, 2H), 5.01 (s, 2H), 4.91 (s, 2H), 3.16 (s, 3H), 2.63 (t, J=7.2 Hz, 2H), 2.46 (t, J=7.6 Hz, 2H), 1.94 (quintet, J=7.6 Hz, 2H); Mass (M+H$^+$)=598.4.

Step B: Preparation of 5-[3-(4-Hydroxy-phenyl)-propyl]-4-methyl-2-(3-phenoxy-benzyl)-2,4-dihydro-[1,2,4]triazol-3-one

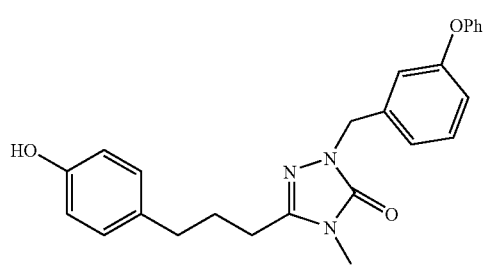

To a solution of the Step A product (0.78 g, 1.30 mmol) in EtOH (10 mL) and EtOAc (2 mL) was added 5% Pd/C (85 mg) and a hydrogen balloon. The reaction was stirred for 72 h. After filtering away the catalyst on celite, the filtrate was concentrated to produce the titled compound as a oil (0.138 g, 25%). Mass (M+H$^+$)=416.1.

Step C: Preparation of 2-(4-{3-[4-Methyl-5-oxo-1-(3-phenoxybenzyl)-4,5-dihydro-1H-[1,2,4]triazol-3-yl]propyl}phenoxy)propionic acid ethyl ester

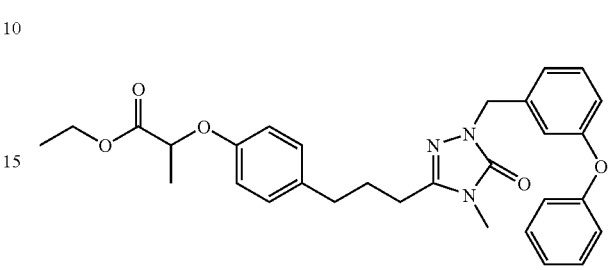

To a solution of the Step B product (0.138 g, 0.33 mmol) in DMF (1.3 mL) was added ethyl bromopropionate (0.120 g, 0.66 mmol) followed by powdered potassium carbonate (0.23 g, 0.0017 mol). The reaction was stirred at rt overnight, then diluted with ethyl acetate (20 mL) and washed with water (10 mL). The aqueous layer was back-extracted with ethyl acetate (20 mL), then the combined organics were dried over Na$_2$SO$_4$ and concentrated. The product was purified by column chromatography (20 g SiO$_2$, 50% ethyl acetate in hexane) providing the ethyl ester as an oil (0.144 g, 84%). 400 MHz $^1$H NMR (CDCl$_3$) δ 7.22–7.15 (m, 4H), 7.00–6.69 (m, 9H), 4.81 (s, 2H), 4.61 (q, J=6.8 Hz, 2H), 4.12 (q, J=7.2 Hz, 2H), 3.07 (s, 3H), 2.52 (t, J=7.2 Hz, 2H), 2.36 (t, J=7.2 Hz, 2H), 1.86–1.82 (m, 2H), 1.51 (d, J=6.8 Hz, 3H), 1.16 (d, J=7.2 Hz, 3H); Mass (M+H$^+$)=516.3, (M+NH$_4^+$)=533.3.

Step D: Preparation of 2-Methyl-2-(4-{3-[4-methyl-5-oxo-1-(3-phenoxybenzyl)-4,5-dihydro-1H-[1,2,4]triazol-3-yl]propyl}phenoxy)-3-phenylpropionic acid ethyl ester

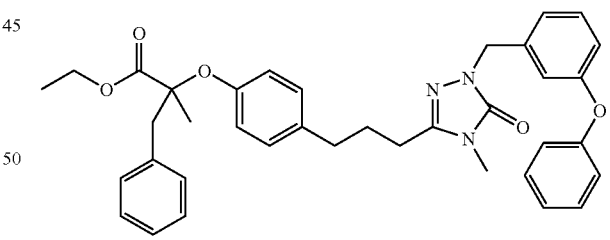

A magnetically stirred solution of the Step C product (0.144 g, 0.00028 mol) in THF (2 mL) was cooled to −78° C. under nitrogen. LHMDS (1M solution in THF, 0.348 mL) was added dropwise via syringe, followed by syringe addition of a mixture of benzyl bromide (0.176 g, 0.00103 mol) and tetrabutyl ammonium iodide (0.010 g, 0.00003 mol). The reaction proceeded for 1 h at −78° C., then for 4 h at −20° C., and finally for 1 h at rt. The reaction was quenched with saturated aqueous ammonium chloride, and ethyl acetate was added. Layers were separated, and the organic phase was washed with brine, dried over Na$_2$SO$_4$, then concentrated. The product was purified by column chromatography (50 g SiO$_2$, 50% ethyl acetate in hexane) providing the ethyl ester as an oil (0.146 g, 87%). 400 MHz $^1$H NMR (CDCl$_3$) δ 7.31–7.24 (m, 8H), 7.09–6.74 (m, 10 H), 4.90 (s, 2H), 4.20 (q, J=7.2 Hz, 2H), 3.30–3.15 (m, 5H), 2.60 (t, J=7.2 Hz, 2H), 2.44 (t, J=7.2 Hz, 2H), 1.94–1.91 (m, 2H), 1.38 (s, 3H), 1.27–1.20 (m, 3H); Mass (M+H$^+$)=606.2, (M+NH$_4^+$)=623.2.

Step E: Preparation of 2-Methyl-2-(4-{3-[4-methyl-5-oxo-1-(3-phenoxybenzyl)-4,5-dihydro-1H-[1,2,4]triazol-3-yl]propyl}phenoxy)-3-phenylpropionic acid

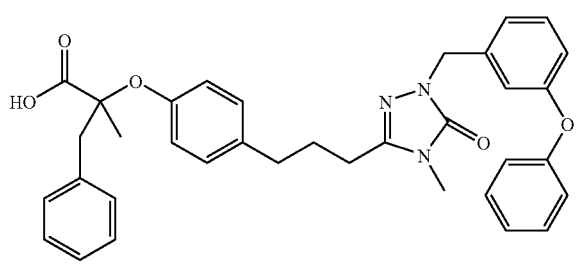

A magnetically stirred solution of the Step D product (0.120 g, 0.00020 mol) in EtOH (2.0 mL) was treated with NaOH (5M aqueous solution, 0.198 mL) and heated at reflux for 48 h. The reaction mixture was acidified to pH=1 using 1M HCl, and cooled to rt. Ethyl acetate was added (10 mL), layers were separated, and the aqueous-phase was back-extracted with EtOAc (3×10 mL). Combined organic phases were dried over Na$_2$SO$_4$, and concentrated to provide the product as a tacky solid (0.097 g, 85%). 400 MHz $^1$H NMR (DMSO-d$^6$) δ 7.38–7.24 (m, 8H), 7.14–6.73 (m, 10 H), 4.81 (s, 2H), 3.25–3.07 (m, 5H), 2.52 (m, 4H), 1.82–1.76 (m, 2H), 1.26 (s, 3H); Mass (M+H$^+$)=578.3, (M–H$^-$)=576.3.

Additional compounds of the present invention, having the structural formula shown below, were synthesized by methods similar to those described in the previous examples.

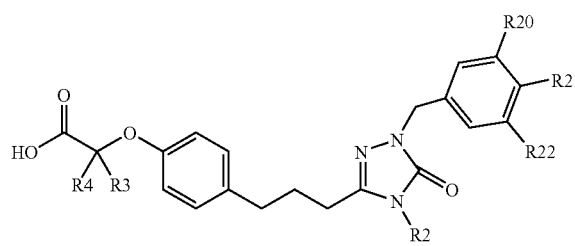

These additional compounds are further exemplified in the following table.

TABLE I

| Example Number | R4 | R3 | R2 | R20 | R21 | R22 |
|---|---|---|---|---|---|---|
| 43 | CH3 | CH3 | propyl | OH | H | H |
| 44 | CH3 | CH3 | butyl | H | H | OCH3 |
| 45 | CH3 | CH3 | CH3 | H | H | OCH3 |
| 46 | CH3 | CH3 | propyl | H | NO2 | H |
| 47 | CH3 | CH3 | ethyl | H | H | OCH3 |
| 48 | ethyl | CH3 | propyl | H | CH3 | H |
| 49 | benzyl | CH3 | propyl | H | CH3 | H |
| 50 | H | H | propyl | CH3 | CH3 | H |

TABLE I-continued

| Example Number | R4 | R3 | R2 | R20 | R21 | R22 |
|---|---|---|---|---|---|---|
| 51 | CH3 | H | propyl | CH3 | CH3 | H |
| 52 | ethyl | H | propyl | CH3 | CH3 | H |
| 53 | isopropyl | H | propyl | CH3 | CH3 | H |
| 54 | F | F | propyl | CH3 | CH3 | H |
| 55 | cyclohexyl | H | propyl | CH3 | CH3 | H |
| 56 | phenyl | H | propyl | CH3 | CH3 | H |
| 57 | 2-hydroxyethyl | H | propyl | CH3 | CH3 | H |
| 58 | F | H | propyl | CH3 | CH3 | H |
| 59 | butyl | H | propyl | CH3 | CH3 | H |
| 60 | pentyl | H | propyl | CH3 | CH3 | H |
| 61 | H | H | propyl | H | t-butyl | H |
| 62 | CH3 | H | propyl | H | t-butyl | H |
| 63 | ethyl | H | propyl | H | t-butyl | H |
| 64 | isopropyl | H | propyl | H | t-butyl | H |
| 65 | F | F | propyl | H | t-butyl | H |
| 66 | cyclohexyl | H | propyl | H | t-butyl | H |
| 67 | phenyl | H | propyl | H | t-butyl | H |
| 68 | 2-hydroxyethyl | H | propyl | H | t-butyl | H |
| 69 | butyl | H | propyl | H | t-butyl | H |
| 70 | pentyl | H | propyl | H | t-butyl | H |
| 71 | CH3 | CH3 | 2-methoxyethyl | CH3 | CH3 | H |
| 72 | H | H | ethyl | H | CH3 | H |
| 73 | CH3 | H | ethyl | H | CH3 | H |
| 74 | ethyl | H | ethyl | H | CH3 | H |
| 75 | isopropyl | H | ethyl | H | CH3 | H |
| 76 | cyclohexyl | H | ethyl | H | CH3 | H |
| 77 | phenyl | H | ethyl | H | CH3 | H |
| 78 | CH3 | CH3 | t-butyl | CH3 | CH3 | H |
| 79 | CH3 | CH3 | i-propyl | CH3 | CH3 | H |
| 80 | CH3 | CH3 | H | H | H | Cl |
| 81 | CH3 | CH3 | H | CF3 | H | CF3 |
| 82 | CH3 | CH3 | H | H | Cl | Cl |
| 83 | CH3 | CH3 | H | H | F | F |
| 84 | OCH3 | H | propyl | H | t-butyl | H |
| 85 | CH3 | CH3 | H | H | t-amyl | H |
| 86 | CH3 | CH3 | H | H | CF3 | H |
| 87 | CH3 | CH3 | H | H | OCF3 | H |
| 88 | CH3 | CH3 | H | H | CF3 | F |
| 89 | CH3 | CH3 | 2-phenoxyethyl | CH3 | CH3 | H |
| 90 | CH3 | CH3 | cyclopropyl-methyl | CH3 | CH3 | H |
| 91 | CH3 | CH3 | propyl | H | amino | H |
| 92 | CH3 | CH3 | 2,4-dimethoxybenzyl | H | CH3 | H |
| 93 | CH3 | CH3 | 2,4-dimethoxybenzyl | CH3 | H | CH3 |
| 94 | CH3 | CH3 | 2,4-dimethoxybenzyl | H | t-butyl | H |
| 95 | CH3 | CH3 | 2,4-dimethoxybenzyl | H | H | phenoxy |
| 96 | CH3 | CH3 | 2,4-dimethoxybenzyl | H | H | CH3 |
| 97 | CH3 | CH3 | 2,4-dimethoxybenzyl | H | H | CF3 |
| 98 | CH3 | CH3 | 2,4-dimethoxybenzyl | CH3 | CH3 | H |
| 99 | CH3 | CH3 | 2,4,6-trimethoxybenzyl | H | CH3 | H |

Other compounds of the present invention, having the structural formula shown below, were also synthesized by methods similar to those described in the previous examples.

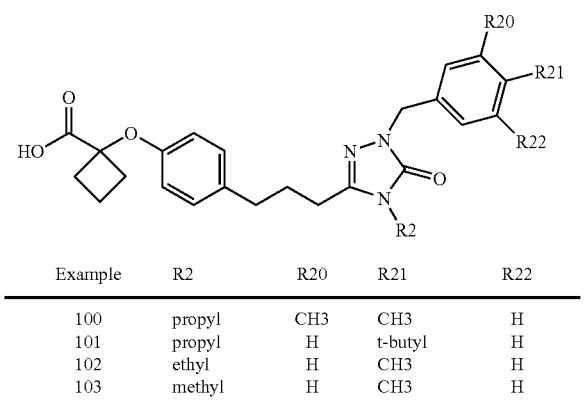

| Example | R2 | R20 | R21 | R22 |
|---|---|---|---|---|
| 100 | propyl | CH3 | CH3 | H |
| 101 | propyl | H | t-butyl | H |
| 102 | ethyl | H | CH3 | H |
| 103 | methyl | H | CH3 | H |

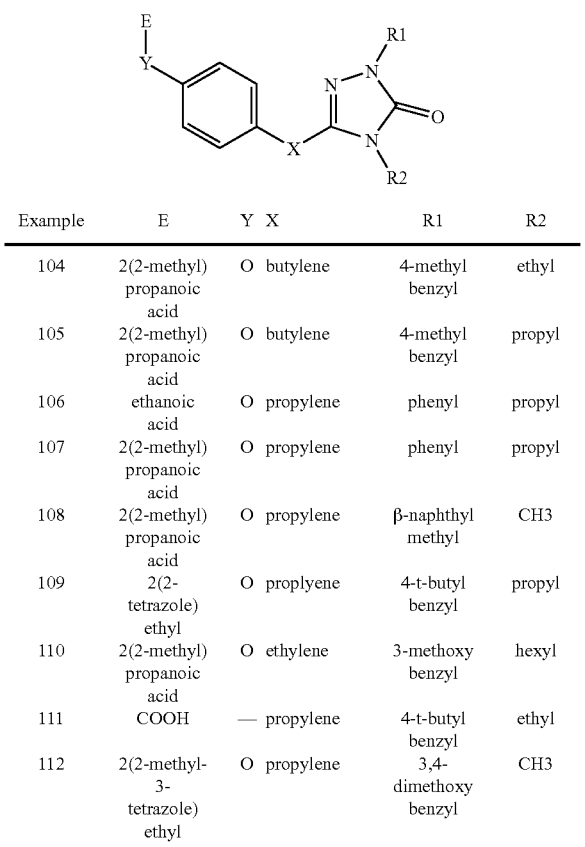

| Example | E | Y X | R1 | R2 |
|---|---|---|---|---|
| 104 | 2(2-methyl) propanoic acid | O butylene | 4-methyl benzyl | ethyl |
| 105 | 2(2-methyl) propanoic acid | O butylene | 4-methyl benzyl | propyl |
| 106 | ethanoic acid | O propylene | phenyl | propyl |
| 107 | 2(2-methyl) propanoic acid | O propylene | phenyl | propyl |
| 108 | 2(2-methyl) propanoic acid | O propylene | β-naphthyl methyl | CH3 |
| 109 | 2(2-tetrazole) ethyl | O proplyene | 4-t-butyl benzyl | propyl |
| 110 | 2(2-methyl) propanoic acid | O ethylene | 3-methoxy benzyl | hexyl |
| 111 | COOH | — propylene | 4-t-butyl benzyl | ethyl |
| 112 | 2(2-methyl-3-tetrazole) ethyl | O propylene | 3,4-dimethoxy benzyl | CH3 |

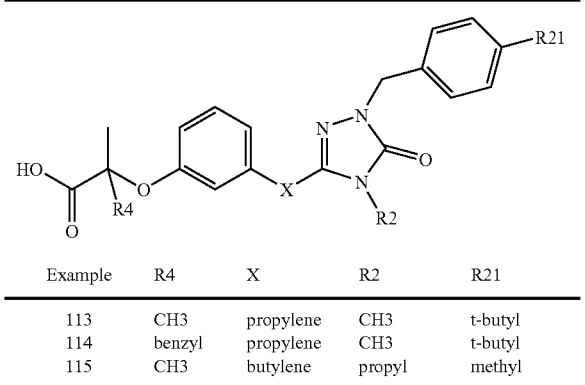

| Example | R4 | X | R2 | R21 |
|---|---|---|---|---|
| 113 | CH3 | propylene | CH3 | t-butyl |
| 114 | benzyl | propylene | CH3 | t-butyl |
| 115 | CH3 | butylene | propyl | methyl |

Example 116

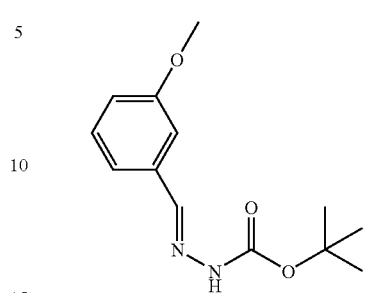

(3-methoxyphenyl)methylenehydrazinecarboxylic acid, 1,1-dimethylethyl ester

To a solution of t-butyl carbazate (5.59 g, 42.3 mmol) in ethyl acetate (15 mL) was added with stirring m-anisaldehyde (5.17 mL, 5.76 g, 42.3 mmol). Hexanes (70 mL) was added slowly and crystallization occurred. The resulting slurry was stirred at rt for 45 min and then cooled to 0° C. The slurry was stirred at 0° C. for 60 min, then filtered and rinsed with cold hexanes (20 mL), and dried in vacuo at 40° C. to afford the title compound as a solid (9.68 g, 91.4%): mp 135.6–137.4° C.; $^1$H NMR (DMSO-$d_6$) δ 10.93 (s, 1H), 7.29 (t, 1H, J=8 Hz), 7.14 (d, 2H, J=7 Hz), 6.92 (q, 1H, J=7 Hz), 3.75 (s, 3H), 1.45 (s, 9H); $^{13}$C NMR (DMSO-$d_6$) δ 160.2, 153.1, 143.7, 136.8, 130.5, 120.0, 116.2, 111.3, 80.1, 55.7, 28.7; IR (KBr mull): 3360, 3010, 2982, 2838, 1510, 1487 cm$^{-1}$; A portion was recrystallized from ethyl acetate and submitted for elemental analysis. Anal. Calcd. for $C_{13}H_{18}N_2O_3$: C, 62.38; H, 7.25; N, 11.19. Found: C, 62.34.; H, 7.46; N, 11.19.

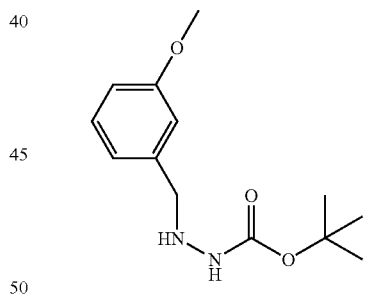

(3-methoxybenzyl)hydrazinecarboxylic acid, 1,1-dimethylethyl ester (3-methoxyphenyl) methylenehydrazinecarboxilic acid, 1,1-dimethylethyl ester (7.03 g, 28.1 mmol) and Pt/C (5%, dry, 5.07 g) were slurried in THF (80 mL) and hydrogenated at rt and 50 psig for 8 hr. The slurry was then filtered through celite and concentrated in vacuo at 50° C. to afford the title compound as a clear oil (6.68 g, 94.0%): $^1$H NMR (DMSO-$d_6$) δ 8.22 (s, 1H), 7.19 (t, 1H, J=8 Hz), 6.85 (d, 1H, J=7 Hz), 6.77 (d, 1H, J=7 Hz), 3.84 (s, 2H), 3.72 (s, 3H), 1.37 (s, 9H); $^{13}$C NMR (DMSO-$d_6$) δ 159.9, 157.1, 141.1, 129.7, 121.1, 114.1, 113.1, 78.9, 55.5, 54.9, 28.9; IR (CHCl$_3$): 3008, 2982, 2935, 1712 cm$^{-1}$; Exact Mass: Calc'd. m/z for $C_{13}H_{20}N_2O_3Na$: 275.1372, Found: 275.1381.

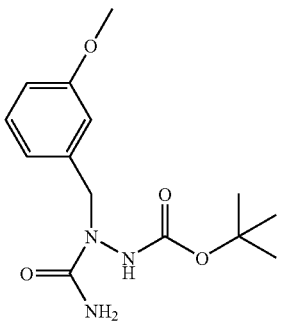

3-(aminocarbonyl)-2-(3-methoxyphenylmethyl)hydrazine carboxylic acid, 1,1-dimethylethyl ester (3-methoxybenzyl) hydrazinecarboxilic acid, 1,1-dimethylethyl ester (6.30 g, 25.0 mmol) was dissolved in isopropyl alcohol (IPA, 65 mL). Trimethylsilyl isocyanate (4.73 g, 34.9 mmol) was added in one portion via syringe and the solution was allowed to stir at ambient temperature for 7 h. The slurry was cooled to 0-5° C., filtered, and the solids rinsed with cold IPA. The solids were dried in vacuo at 40° C. overnight to afford the title compound as a white solid (4.71 g, 63.9%). The filtrate was concentrated and purified by column chromatography (SiO$_2$, EtOAc) to afford additional compound (0.91 g, 12.3%). These two portions were combined to yield 5.82 g (76.2%) of the title compound: mp 136.3-138.5° C.; $^1$H NMR (DMSO-d$_6$, 60° C.) δ 8.70 (s, 1H), 7.20 (t, 1H, J=8 Hz), 6.80 (m, 3H), 5.90 (s, 2H), 4.50 (s, 2H), 3.74 (s, 3H), 1.36 (s, 9H); $^{13}$C NMR (DMSO-d$_6$, 20° C.) δ 159.9, 159.6, 155.0, 140.2, 129.8, 120.9, 114.0, 113.2, 80.2, 55.6, 51.1, 28.7; IR (CHCl$_3$): 3003, 2984, 2938, 1745, 1680 cm$^{-1}$; Anal. Calcd. for C$_{14}$H$_{21}$N$_3$O$_4$: C, 56.94; H, 7.17; N, 14.23. Found: C, 56.54; H, 7.17; N, 13.98.

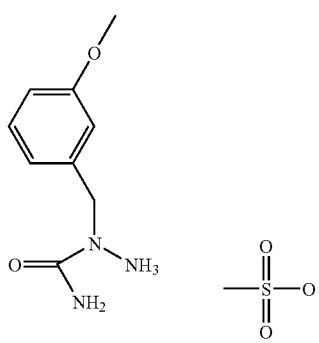

1-(3-methoxyphenylmethyl)hydrazine carboxamide methanesulfonate 3-(aminocarbonyl)-2-(3-methoxyphenylmethyl)hydrazine carboxylic acid, 1,1-dimethylethyl ester (5.30 g, 17.9 mmol) was dissolved in dichloromethane (60 mL)). Methanesulfonic acid (1.93 g, 19.9 mmol) was added in one portion and the solution was allowed to stir at rt overnight. The resulting slurry was cooled to 0-5° C., filtered, and the solids rinsed with cold dichloromethane. The solids were dried in vacuo at 40° C. overnight to afford the title compound as a white solid (5.05 g, 96.6%). mp 130.3-132.1° C.; $^1$H NMR (DMSO-d$_6$) δ 9.7 (broad s, 3H), 7.30 (t, 1H, J=8 Hz), 7.05 (broad s, 2 H), 6.88 (s, 3H), 4.69 (s, 2H), 3.74 (s, 3H), 3.34 (s, 3 H); $^{13}$C NMR (DMSO-d$_6$) δ 160.1, 158.2, 137.3, 130.5, 120.7, 114.3, 114.0, 55.7, 52.7, 40.4; IR (KBr mull): 3186, 2939, 1719, 1707, 1168 cm$^{-1}$; Anal. Calcd. for C$_9$H$_{13}$N$_3$O$_2$: C, 41.23.; H, 5.88; N, 14.42. Found: C, 40.86.; H, 5.92; N, 14.61.

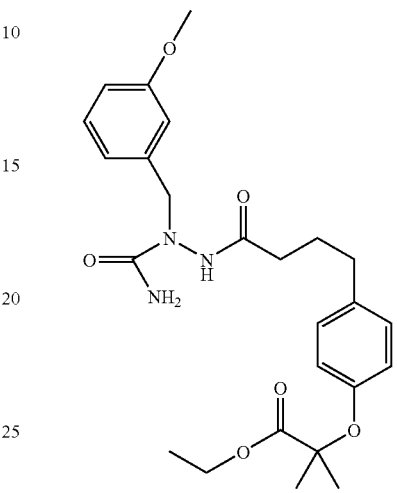

1-[4-[4-(1-Ethoxycarbonyl-1-methylethoxy)phenyl]butyryl]-2-(3-methoxyphenylmethyl)semicarbazide 4-[4-(1-Ethoxycarbonyl-1-methyl-ethoxy)-phenyl]butyric acid (4.86 g, 16.5 mmol) was dissolved in ethyl acetate (40 mL). Oxalyl chloride (2.43 g, 19.14 mmol) was added to this solution dropwise in the presence of a catalytic amount of N,N-dimethylformamide (100 mg, 1.37 mmol). Completion of acid chloride formation was verified by HPLC. This solution was then added dropwise to a suspension of 1-(3-methoxyphenylmethyl)hydrazine carboxamide methanesulfonate (4.80 g, 16.5 mmol) and pyridine (1.30 g, 16.5 mmol) in ethyl acetate (55 mL) at 0-5° C. After stirring at 0-5° C. for 6 h, an additional charge of pyridine was added (1.30 g, 16.5 mmol) and the solution was stirred at 0-5° C. for 1 h at which time the reaction was complete. The solution was warmed to rt and washed twice with 1N HCl (80 mL) and twice with 5% aq. NaHCO$_3$ (80 mL). The organic layer was dried (MgSO$_4$), filtered and concentrated to a waxy solid. The solids were recrystallized from a mixture of toluene (17 mL) and n-heptane (7 mL) at 60° C., cooled to 0-5° C. and filtered. The solids were dried in vacuo at 40° C. overnight, affording the title compound as a white solid (5.05 g, 65%): $^1$H NMR (DMSO-d$_6$, 60° C.) δ 9.60 (s, 1H), 7.19 (t, 1H, J=8 Hz), 7.00 (d, 2H), 6.80 (m, 3H), 6.71 (d, 2 H, J=8 Hz), 5.92 (s, 2H), 4.52 (s, 2H), 4.15 (q, J=7 Hz), 3.71 (s, 3H), 2.45 (t, 2H, J=7 Hz ), 2.07 (t, 2H, J=7 Hz ), 1.73 (quint, 2H, J=7 Hz), 1.48 (s, 6H), 1.17 (t, 3H, J=7 Hz); $^{13}$C NMR (DMSO-d$_6$) δ 174.0, 171.9, 159.9, 159.3, 153.7, 140.5, 135.9, 129.9, 129.7, 120.9, 119.4, 114.1, 113.1, 79.2, 61.6, 55.5, 50.9, 34.3, 33.4, 27.2, 25.7, 14.6; IR (KBr mull): 3450, 3320, 3275, 3202, 2997, 2940, 1730, 1646, 1511 cm$^{-1}$; Anal. Calcd. for C$_{25}$H$_{33}$N$_3$O$_6$: C, 63.68; H, 7.05; N, 8.91. Found: 63.49; H, 7.02; N, 8.99.

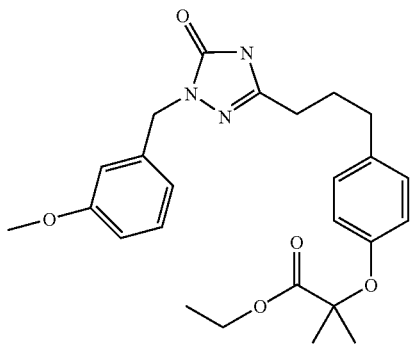

2-(4-(3-[1-(3-Methoxy-benzyl)-5-oxo-4,5-dihydro-1H-[1,2,4]triazol-3-yl]-propyl}-phenoxy)-2-methyl-propionic acid ethyl ester 1-[4-[4-(1-Ethoxycarbonyl-1-methylethoxy)phenyl]butyryl]-2-(3-methoxyphenylmethyl)semicarbazide (4.08 g, 8.65 mmol) was dissolved in ethyl acetate (7.5 mL). 1S (+)-10-camphorsulfonic acid (2.21 g, 9.51 mmol) was added in one portion and the solution was heated to reflux overnight. The solution was cooled to rt and washed with sat'd aq. NaHCO₃ (40 mL×2) followed by 1N HCl (40 mL×2). The organic was concentrated to an orange oil. This oil was redissolved in ethyl acetate (40 mL). Amberlyst-15 resin (4.41 g) was added and the mixture was heated to 50° C. and stirred for 4 hours to remove de-ureated impurity. The mixture was then cooled to ambient temperature, filtered, concentrated, and purified by column chromatography (SiO₂, 9:1 ethyl acetate: hexanes) to afford the title compound as an orange oil (1.93 g, 49.2%). ¹H NMR (DMSO-d₆) δ 11.47 (s, 1 H), 7.22 (t, 1H, J=8 Hz), 7.04 (d, 2H, J=8 Hz), 6.82 (d, 1H, J=2 Hz), 6.76 (m, 2H), 6.68 (d, 2H, J=2 Hz), 4.73 (s, 2H), 4.13 (q, 2H, J=7 Hz), 3.69 (s, 3H), 2.48 (t, 2H, J=8 Hz), 2.36 (t, 2H, J=8 Hz), 1.80 (quint, 2 H, J=7 Hz), 1.47 (s, 6H), 1.14 (t, 3H, J=7 Hz); ¹³C NMR (DMSO-d₆) δ 174.0, 160.0, 155.0, 153.8, 146.7, 139.8, 135.5, 130.2, 129.8, 120.1, 119.5, 113.8, 113.2, 79.2, 61.6, 55.6, 47.8, 34.0, 28.4, 26.2, 25.7, 14.6; IR (CHCl₃) 2940, 1692, 1508, 1467 cm⁻¹; Anal. Calcd. for C₂₅H₃₁N₃O₅: C, 66.21.; H, 6.89; N, 9.26. Found: C, 66.29; H, 6.75; N, 9.19.

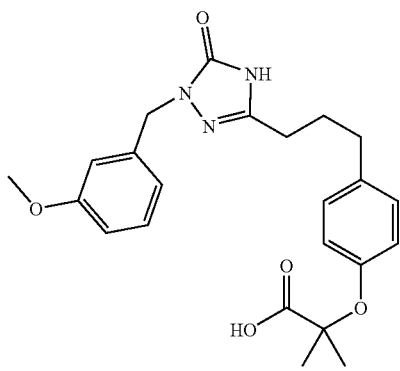

2-(4-{3-[1-(3-Methoxy-benzyl)-5-oxo-4,5-dihydro-1H-[1,2,4]triazol-3-yl]-propyl}-phenoxy)-2-methyl-propionic acid 2-(4-{3-[1-(3-Methoxy-benzyl)-5-oxo-4,5-dihydro-1H-[1,2,4]triazol-3-yl]-propyl}-phenoxy)-2-methyl-propionic acid ethyl ester (1.55 g, 3.42 mmol) was dissolved in a mixture of ethanol (7.5 mL) and deionized water (7.5 mL). Solid sodium hydroxide (0.36 g, 8.73 mmol) was added in one portion and the solution was warmed to 70° C. and stirred for one hour. The solution was cooled to ambient temperature and the pH adjusted to 7 with 6N HCl. The solution was concentrated to a hazy yellow oil. This oil was partitioned between 1N HCl (10 mL) and ethyl acetate (15 mL). The aqueous layer was then re-extracted with ethyl acetate (15 mL) and the organic layers combined, dried (MgSO₄), filtered and concentrated in vacuo at 50° C. overnight to afford the title compound as a clear oil (1.41 g, 97.0%). ¹H NMR (DMSO-d₆) δ 13.0 (broad s, 1H), 11.47 (s, 1H), 7.23 (t, 1H, J=8 Hz), 7.03 (d, 2H, J=8 Hz), 6.82 (d, 1H, J=2 Hz), 6.75 (m, 5H), 4.73 (s, 2H), 3.70 (s, 3H), 3.35 (broad s, 1H), 2.48 (t, 2H, J=8 Hz), 2.36 (t, 2H, J=8 Hz), 1.80 (quint, 2H, J=7 Hz), 1.46 (s, 6H); ¹³C NMR (DMSO-d₆, 20° C.) δ 175.8, 160.0, 155.0, 154.1, 146.8, 139.8, 135.0, 130.3, 129.7, 120.1, 119.1, 113.8, 113.2, 78.9, 55.6, 47.8, 40.6, 40.5, 34.0, 28.4, 27.5, 26.2, 25.7; IR (CHCl3) 1707, 1603, 1509, 1159 cm⁻¹; Anal. Calcd. for C₂₃H₂₇N₃O₅: C, 64.93; H, 6.40; N, 9.88. Found: C, 65.02; H, 6.65; N, 9.57.

Example 117

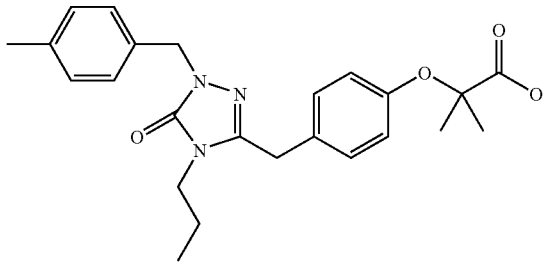

Step A

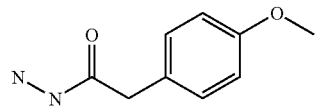

A methanol solution of methyl 4-methoxyphenylacetate (Aldrich, 10.0 g, 0.056 mol) and hydrazine hydrate (EM Sciences, 27.8 g, 0.556 mol) was stirred at ambient temperature overnight. The resulting solution was concentrated, added to water and extracted with ethyl acetate (2×). The organic layers were combined and washed with aqueous brine then dried over sodium sulfate. Evaporation of the solvent gives a solid product which is washed with hexanes/ether and filtered to give the desired acyl hydrazide as a white solid.

C₉H₁₂O₂N₂ (MW=180.21); mass spectroscopy (MH⁺)=181.0

Step B

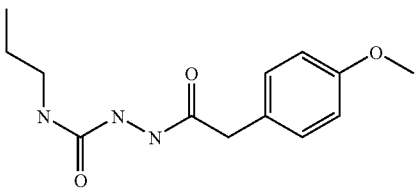

A tetrahydrofuran solution (150 mL) of the acyl hydrazide from Step A (8.0 g, 0.044 mol) was treated with propyl isocyanate (Aldrich, 1.2 g, 0.014 mol) and stirred at room temperature overnight, during which a precipitate forms. The resulting suspension was treated with methanol (20 ml) and stirred for an additional 30 minutes. Hexane was then added and the mixture was filtered to give the desired acyl semicarbazide as a white solid which was used without further purification.

$C_{13}H_{19}N_3O_3$ (MW=265.31)

Step C

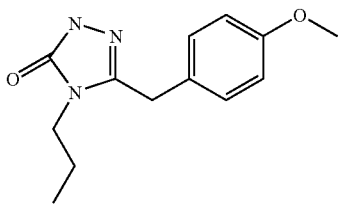

A methanol solution (150 mL) of the acyl semicarbazide from Step B (10.0 g, 0.038 mol) was stirred and treated with solid potassium hydroxide (21.1 g, 0.377 mol). The mixture was heated at 60° C. for 24 hrs then cooled to ambient temperature and stirred for 48 hrs. The solvent was reduced to about 75 ml, added to water, acidified to pH 6 with conc. HCl and extracted with ethyl acetate (3×). The organic layers were combined, washed with aqueous brine and dried over sodium sulfate. Evaporation of the solvent gives a solid that was washed with hexane/ether to give the desired N4-propyl triazolinone as a white solid.

$C_{13}H_{17}N_3O_2$ (MW=247.30); mass spectroscopy (MH+)= 248.1

Step D

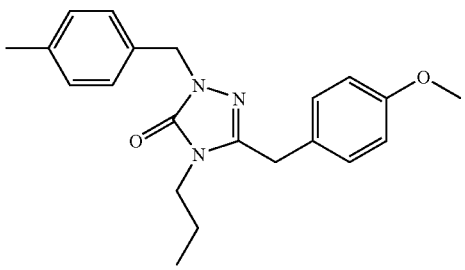

The N4-propyl triazolinone from Step C (7.0 g, 0.028 mol) is dissolved in DMF (75 mL) and treated with chloro-p-xylene (Aldrich, 6.0 g, 0.043 mol) and powdered potassium carbonate (Aldrich, 15.6 g, 0.113 mol). The resulting mixture was heated to 60° C. overnight. The cooled reaction mixture was added to aqueous HCl (1N, 200 mL) and extracted with ethyl acetate (3×). The combined organic layers were washed with aqueous brine, dried over sodium sulfate and concentrated to give the crude product as an oil. Purification by flash chromatography (gradient: 100% hexanes to 2:1 hexanes:ethyl acetate) gives the desired N2-p-methylbenzyl triazolinone.

$C_{21}H_{25}N_3O_2$ (MW=351.45); mass spectroscopy (MH+)= 352.2

Step E

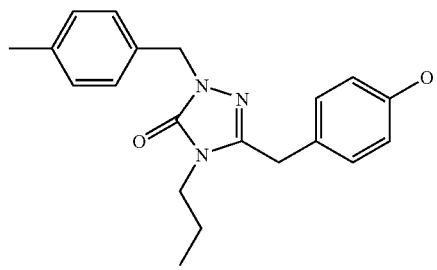

The N2-p-methylbenzyl triazolinone from Step D (1.5 g, 0.004 mol) was dissolved in methylene chloride (25 mL) and cooled under a drying tube. A solution of boron tribromide (3.1 g, 1.2 mL, 0.013 mol) was added dropwise. The reaction mixture was then allowed to warm to ambient temperature and stirred for 2 hrs. The reaction was quenched by the dropwise addition of methanol (5 mL), added to water and extracted with methylene chloride (2×). The organic layers were combined, dried over sodium sulfate and concentrated to give the desired phenol as an oil which is used without purification.

$C_{20}H_{23}N_3O_2$ (MW=337.4); mass spectroscopy (MH$^+$)= 338.3

Step F

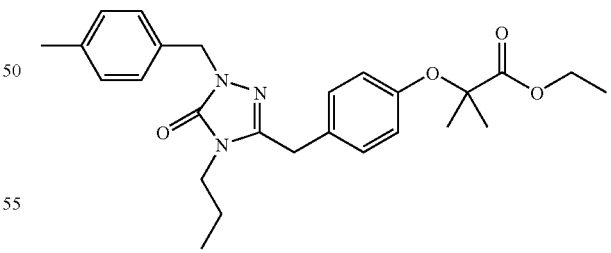

The phenol from Step E (1.3 g, 0.004 mol) was dissolved in ethanol (50 mL) and treated with ethyl 2-bromoisobutyrate (Aldrich, 2.3 g, 1.7 mL, 0.012 mol), powdered potassium carbonate (Aldrich, 2.2 g, 0.016 mol) and magnesium sulfate (0.6 g, 0.005 mol). The resulting mixture was stirred and heated to 55° C., under a drying tube, overnight. The cooled reaction mixture was added to HCl (5N. 70 ml) and extracted with ethyl acetate (2×). The combined organic layers were dried over sodium sulfate and concentrated to give the crude product. Purification by flash chromatography (gradient: 100% hexanes to 3:2 ethyl acetate:hexanes) gives the desired ethyl ester.

$C_{26}H_{33}N_3O_4$ (MW=451. 6); mass spectroscopy (MH$^+$)=452.3

Step G

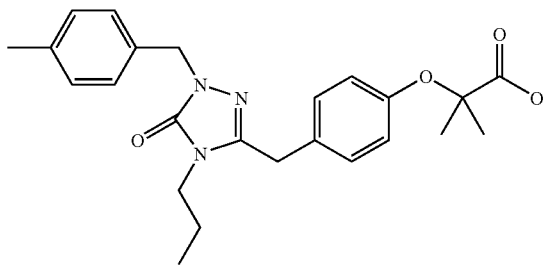

The ethyl ester from Step F (0.8 g, 0.002 mol) was dissolved in methanol (12 mL) and sodium hydroxide (2N, 3.0 ml, 0.006 mol) added. The resulting mixture was stirred at ambient temperature overnight. The reaction mixture was added to HCl (5N, 15 ml) and extracted with ethyl acetate (2×). The organic layers were combined, dried over sodium sulfate and concentrated to give the crude product. Purification by flash chromatography (gradient: 100% hexanes to 1:1 ethyl acetate/hexane then 10% methanol in ethylacetate) gives the desired carboxylic acid as a white foam.

$C_{24}H_{29}N_3O_4$ (MW=423.5); mass spectroscopy (MH$^+$)=424.3; (MH$^-$)=422.1

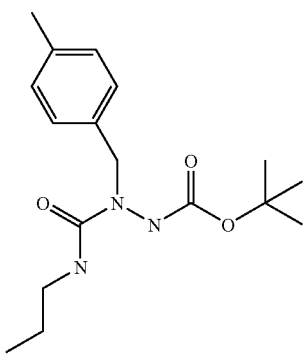

Example 118

2-(n-Propylaminocarbonyl)-2-(4-methylphenylmethyl)hydrazine carboxylic acid, 1,1-dimethylethyl ester 4-Methylphenylmethyl hydrazine carboxylic acid, 1,1-dimethylethyl ester (5.02 g, 21.2 mmol) was dissolved in isopropanol (50 mL). Propyl isocyanate (2.71 g, 31.9 mmol) was added in one portion via syringe and the solution was allowed to stir at ambient temperature for 1 h. The solution was concentrated to a clear yellow oil, and purified by column chromatography (SiO$_2$, 2:3 ethyl acetate:hexanes) to afford the title compound as a white solid (5.58 g, 82%): mp 87.8-89.4° C.; $^1$H NMR (DMSO-d$_6$, 60° C.) δ 8.45 (s, 1H), 7.10 (d-d, 4H, J=8.2 Hz), 6.21 (s, 1H), 4.43 (s, 1H), 3.01 (q, 2H, J=6.4 Hz), 2.27 (s, 3H), 1.41 (sext., 2H, J=7.3 Hz), 1.35 (s, 9H), 0.82 (t, 3H, J=7.4 Hz); $^{13}$C NMR (DMSO-d$_6$, 20° C.) δ 158.6, 155.1, 136.6, 135.5, 129.3, 129.0, 80.2, 51.0, 42.2, 28.6, 23.7, 21.4, 11.8; Anal. Calcd. for $C_{17}H_{27}N_3O_3$: C, 63.53; H, 8.47; N, 13.07.

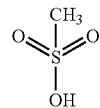

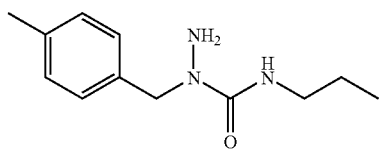

N-Propyl-1-(4-methylphenylmethyl)hydrazinecarboxamide methanesulfonate

To a solution of 2-(propylaminocarbonyl)-2-(4-methylphenylmethyl)hydrazinecarboxylic acid, 1,1-dimethylethyl ester (3.0204 g, 9.397 mmol) in dichloromethane (25 mL) was added methanesulfonic acid (762 µL, 11.7 mmol) and the mixture stirred for 21 h. The mixture was then concentrated in vacuo to an oil and recrystallized (ethyl acetate) to afford the title compound as a white solid (2.0639 g, 6.502 mmol, 69%): mp 108.5-111.4° C.; $^1$H NMR (DMSO-d$_6$) δ 7.56 (s, 1H), 7.18 (s, 4H), 4.67 (s, 2H), 3.06 (t, 2H, J=7.0 Hz), 2.35 (s, 3H), 2.81 (s, 3 H), 1.44 (m, 2H), 0.82 (t,. 3H, J=7.5 Hz); $^{13}$C NMR (DMSO-d$_6$) δ 157.7, 138.0, 132.5, 129.9, 128.8, 52.7, 42.7, 40.6, 23.3, 21.4, 11.9; IR (CHCl$_3$) 3416, 3009, 2967, 2936, 2877, 1691, 1543 cm$^{-1}$. Anal. Calcd. for $C_{12}H_{19}N_3O \cdot CH_4O_3S$: C, 49.19; H, 7.30; N, 13.24. Found: C, 48.87; H, 7.32; N, 13.28.

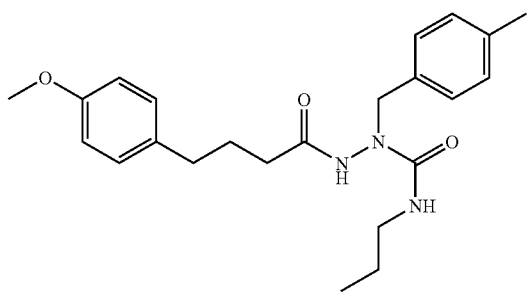

1-[(4-Methoxyphenyl)butyryl]-2-(4-methylphenylmethyl)-4-propyl)semicarbazide

To a solution of 4-(4-methoxyphenyl)butyric acid (2.0207 g, 10.42 mmol) and N,N-dimethylformamide (2 drops) in ethyl acetate (25 mL) was added dropwise over 5 min oxalyl chloride (1.13 mL, 13.02 mmol). The resulting mixture was stirred for 30 min and then concentrated in vacuo to remove excess oxalyl chloride. The resulting oil was redissolved in ethyl acetate (15 mL) and then added in one portion to a solution of N-Propyl-2-(4-methylphenylmethyl)hydrazinecarboxamide methanesulfonate (3.1578 g, 9.95 mmol,) and pyridine (2 mL, 24 mmol) in ethyl acetate (10 mL) at 0-5° C. The reaction was stirred for 1 hour at room temperature, then washed with 1N HCl (2×50 mL), saturated aq. NaHCO$_3$ (2×50 mL), and saturated aq. NaCl (25 mL). The organic layer was dried (MgSO$_4$), filtered, concentrated and purified by silica gel chromatography (3:1 ethyl acetate:hexanes) to afford the title compound as a white solid (3.76 g, 9.47 mmol, 95%):. mp 86.5-88.2° C.; $^1$H NMR (DMSO-d$_6$, 60°

C.) δ 9.45 (s, 1H), 7.10 (m, 4H), 6.92 (AB, 4H, J=8.0 Hz), 6.25 (s, 1H), 4.50 (s, 1H), 3.71 (2, 3H), 2.99 (m, 2H), 2.45 (t, 2H, J=8.0 Hz), 2.26 (s, 3H), 2.06 (t, 2H, J=7.5 Hz), 1.72 (t, 2H, J=7.5 Hz) , 1.40 (m, 2H) , 0.81 (t, 3H, J=8.0 Hz); $^{13}$C NMR (DMSO-d$_6$) δ 172.0, 158.2, 158.1, 136.7, 135.8, 134.1, 129.9, 129.4, 128.9, 114.3, 55.6, 50.8, 42.3, 34.3, 33.4, 27.3, 23.7, 21.4, 11.9; IR (CHCl$_3$) 3456, 2996, 2963, 2936, 2876, 1708, 1669 cm$^{-1}$. Anal. Calcd. for C$_{23}$H$_{31}$N$_3$O$_3$: C, 69.49; H, 7.86; N, 10.57. Found: C, 69.36; H, 7.71; N, 10.54.

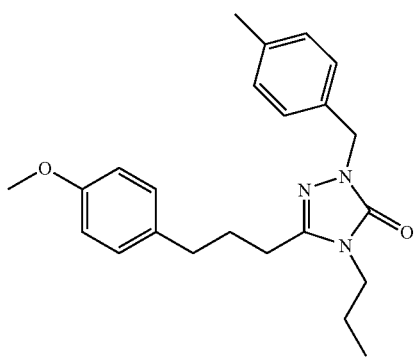

5-[3-(4-Methoxyphenyl)-propyl]-2-(4-methylbenzyl)-4-propyl-2,4-dihydro[1,2,4]tria-zol-3-one To a solution of 1-[(4-methoxyphenyl)butyryl]-2-(4-methylphenylmethyl)-4-propyl)semicarbazide (1.24 g, 3.12 mmol) in ethyl acetate (25 mL) was added camphorsulfonic acid (0.80 g, 3.43 mmol) and the resulting mixture stirred at reflux for 2 hours. The organic layer was washed with saturated aq. NaHCO$_3$ (2×25 mL) and 1 N HCl (2×25 mL) followed by saturated aq. NaCl (25 mL). The organic layer was then dried (MgSO$_4$), filtered, and concentrated to afford the title compound as an oil (1.14 g, 3.00 mmol, 96%): $^1$H NMR (DMSO-d$_6$) δ 7.10 (s, 4H), 7.06 (d, 2H, J=8.5 Hz), 6.81 (q, 2H, J=5.0 Hz), 4.77 (s, 2H), 3.69 (s, 3H), 3.46 (t, 2H, J=7.5 Hz), 2.54 (t, 2H, J=7.5 Hz), 2.47 (t, 2H, J=7.5 Hz), 2.23, (s, 3H), 1.82 (m, 2H), 1.52 (m, 2H), 0.79 (t, 3H, J=7.5 Hz); $^{13}$C NMR (DMSO-d$_6$) δ 158.2, 154.1, 146.8, 137.2, 135.1, 133.9, 129.9, 129.7, 128.1, 114.4, 55.6, 48.3, 42.8, 34.0, 28.1, 24.8, 22.5, 21.3, 11.5; IR (CHCl$_3$) 1691, 1513, 1465, 1247, 1225 cm$^{-1}$. Anal. Calcd. for C$_{23}$H$_{29}$N$_3$O$_2$: C, 72.79; H, 7.70; N, 11.07. Found: C, 72.82; H, 7.87; N, 11.11.

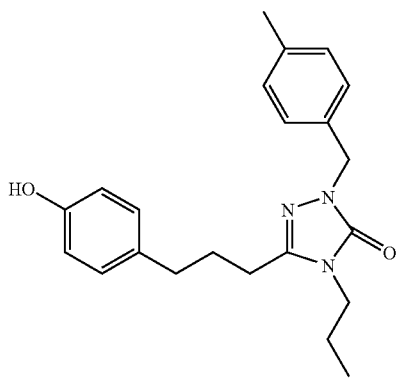

Example 119

5-[3-(4-Hydroxyphenyl)-propyl]-2-(4-methylbenzyl)-4-propyl-2,4-dihydro-[1,2,4]triazol-3-one 5-[3-(4-Methoxyphenyl)-propyl]-2-(4-methylbenzyl)-4-propyl-2,4-dihydro-[1,2,4]triazol-3-one (0.770 g, 2.03 mmol) and excess pyridine hydrochloride were melted together for 2 hours with stirring at 180° C. After cooling to room temperature, the contents were diluted in ethyl acetate (50 mL) and water (50 mL). The aqueous layer was extracted with ethyl acetate (2×25 mL). The combined organics were washed with 5 N HCl (50 mL), saturated aq. NaCl (25 mL), dried (MgSO$_4$), filtered and concentrated to afford the title compound as a yellow oil (0.670 g, 1.83 mmol, 90%): $^1$H NMR (DMSO-d$_6$) δ 9.13 (s, 1 H), 7.10 (q, 4H, J=3.0 Hz), 6.79 (AB, 4H, J=8.5 Hz), 4.77 (s, 2H), 2.5 (t, 2H, J=7.5 Hz), 2.46 (t, 2H, J=7.5 Hz), 2.24 (s, 3H), 1.79 (m, 2H), 1.51 (m, 2H), 0.79 (t, 3H, J=7.5 Hz); $^{13}$C NMR (DMSO-d$_6$) δ 156.1, 154.1, 146.8, 137.2, 135.1, 132.1, 129.9, 129.7, 128.1, 115.7, 48.3, 42.8, 34.1, 28.2, 24.7, 22.5, 21.3, 11.5; IR (CHCl$_3$) 3007, 2937, 1690, 1515, 1463 cm$^{-1}$. Exact Mass Calcd. for C$_{22}$H$_{28}$N$_3$O$_2$: 366.2182. Found: 366.2191.

Example 120

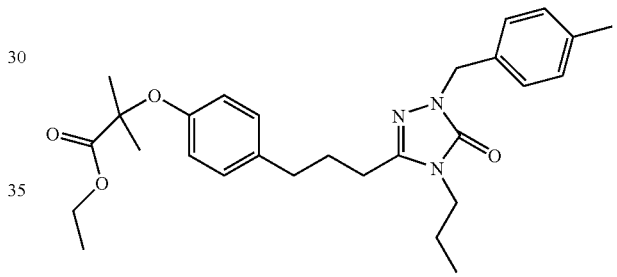

2-Methyl-2-(4-(3-[1-(4-methylbenzyl)-5-oxo-4-propyl-4,5-dihydro-1H-[1,2,4]triazol-3-yl]-propyl}-phenoxy)-propionic acid ethyl ester To a mixture of sodium ethoxide (1.22 mL, 3.28 mmol) and ethyl acetate (322 μL, 3.28 mmol) was added 5-[3-(4-hydroxyphenyl)-propyl]-2-(4-methylbenzyl)-4-propyl-2,4-dihydro-[1,2,4]triazol-3-one (1.2 g, 3.28 mmol) in ethanol (10 mL) and the resulting mixture stirred at reflux for 1 hour. Then ethyl-2-butyl isobutyrate (1.08 mL, 7.38 mmol) was added and the reaction continued at reflux for 1 hour. Then sodium ethoxide (1.22 mL, 3.28 mmol) was added dropwise over 5 min and the reaction continued at reflux for 4.5 hour. Additional sodium ethoxide (520 μL, 1.4 mmol) and ethyl-2-butyl isobutyrate (205 μL, 1.4 mmol) were added and reaction continued at reflux for 4 hour. Additional sodium ethoxide (336 μL, 0.903 mmol) and ethyl-2-butyl isobutyrate (132 μL, 0.903 mmol) were added and the reaction continued at reflux for 3 hours. Finally, additional sodium ethoxide (200 μL, 0.54 mmol) and ethyl-2-butyl isobutyrate (100 μL, 0.133 mmol) were added and the reaction continued at reflux for 1.5 hours. The mixture was allowed to cool to room temperature and is then quenched into a solution of conc. HCl (1.5 g, 41 mmol) in water (50 mL). The resulting solution was then concentrated in vacuo, taken up in ethyl acetate (100 mL) and the aqueous layer was discarded. The organic layer was washed with saturated aq. NaHCO$_3$ (2×50 mL) followed by saturated aq. NaCl (2×25 mL). The organic layer was dried (MgSO$_4$), filtered, concentrated, and purified by silica gel chromatography (1:1 ethyl acetate:hexanes) to afford the title compound as a yellow oil (990 mg, 2.06 mmol, 63%):

$^1$H NMR (DMSO-d$_6$) δ 7.10 (s, 4H), 6.87 (AB, 4H, J=8.0 Hz), 4.77 (s, 2H), 4.14 (q, 2H, J=7.0 Hz), 3.46 (t, 2H, J=6.5 Hz), 2.54 (t, 2H, J=7.5 Hz), 2.47 (t, 2H, J=7.5 Hz), 2.24 (s, 3H), 1.82 (m, 2H), 1.51 (m, 2H), 1.47 (s, 6 H), 1.14 (t, 3H, J=7.5 Hz), 0.79 (t, 3H, J=7.0 Hz); $^{13}$C NMR (DMSO-d$_6$) δ 174.0, 154.1, 153.8, 146.7, 137.2, 135.6, 135.1, 129.75, 129.66, 128.1, 119.6, 79.2, 61.6, 48.3, 42.8, 34.0, 27.8, 25.7, 24.8, 22.5, 21.3, 14.5, 11.5; IR (CHCl$_3$) 3005, 2939, 2878, 1729, 1692, 1509 cm$^{-1}$. Anal. Calcd. for C$_{28}$H$_{37}$N$_3$O$_4$: C, 70.12; H, 7.78; N, 8.76. Found: C, 69.92; H, 7.84; N, 8.77.

Example 121

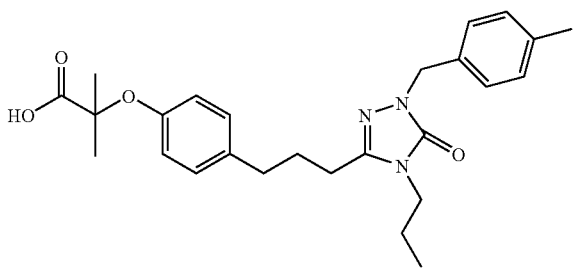

To a solution of 2-methyl-2-(4-{3-[1-(4-methylbenzyl)-5-oxo-4-propyl-4,5-dihydro-1H-[1,2,4]triazol-3-yl]-propyl}-phenoxy)-propionic acid ethyl ester (0.45 g, 0.938 mmol) in methanol (7 mL) was added with stirring aq. 1N NaOH (2 mL, 2 mmol) at room temperature for 18 hours. The reaction mixture was concentrated to a thin film and partitioned between ethyl acetate (25 mL) and 1N HCl (25 mL). The organic layer was washed with saturated aq. NaCl (25 mL), dried (MgSO$_4$), filtered, and concentrated to afford the title compound as a yellow solid (0.400 g, 0.886 mmol, 94%): mp 94.0-96.5° C.; $^1$H NMR (DMSO-d$_6$) δ 12.92 (br. s, 1H), 7.10 (s, 4H), 6.88 (AB, 4H, J=8.5 Hz), 4.77 (s, 2H), 3.46 (t, 2H, J=7.5 Hz), 2.54 (t, 2H, J=7.5 Hz), 2.48 (m, 2 H), 2.24 (s, 3H), 1.82 (m, 2H), 1.52 (t, 2H, J=7.5 Hz), 1.46 (s, 6H), 0.79 (t, 3H, J=8.0 Hz); $^{13}$C NMR (DMSO-d$_6$) δ 175.8, 154.1, 146.8, 137.2, 135.2, 135.1, 129.7, 128.1, 119.3, 79.0, 60.4, 48.3, 42.8, 34.0, 27.9, 25.7, 24.8, 22.5, 21.3, 14.8, 11.5; IR (CHCl$_3$) 3007, 2939, 2878, 1692, 1573, 1508 cm$^{-1}$; Anal. Calcd. for C$_{26}$H$_{33}$N$_3$O$_4$: C, 69.16; H, 7.37; N, 9.31. Found: C, 68.90; H, 7.55; N, 9.14.

Example 122

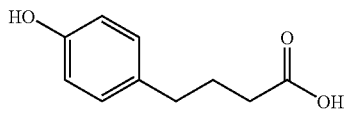

4-(4-Hydroxyphenyl)butyric Acid

A 22-L 4-necked round bottom flask was equipped with a condenser, nitrogen inlet, thermometer lead and overhead stirring apparatus. The flask was charged with 4-(4-methoxyphenyl)butyric acid (2250 g, 11.58 moles) followed by pyridine hydrochloride (5360 g, 46.34 moles, 4 eq). The resulting mixture of the two solids was heated under nitrogen to 185-195° C., with stirring commencing by 50° C. The flask contents were held at 185-195° C., and reaction progress was monitored by TLC (50/50 v/v hexanes/ethyl acetate+1% v/v acetic acid, panisaldehyde stain for visualization). After two hours, TLC analysis indicated complete consumption of starting material. The heat source was removed and the mixture allowed to cool to 90° C., after which 5N HCl (2900 mL, 14.47 moles, 1.25 eq) and H$_2$O (2700 mL) were added sequentially. Stirring was continued until the pot temperature reached 35° C. The mixture was transferred to a 22-L bottom-outlet flask and diluted with t-butyl methyl ether (MTBE, 6000 mL). The layers were separated and the aqueous portion was reextracted with MTBE (3×4000 mL). The organic portions were combined and back-washed with 5N HCl (750 mL). After drying (Na$_2$SO$_4$) and filtration, the solution was concentrated in vacuo to afford the title compound as a white solid (2020 g, 96.7%). $^1$H NMR (500 MHz, DMSO-d$_6$) δ 1.70 (m, 2H), 2.15 (t, 2H), 2.45 (t, 2H), 3.33 (s, 1H), 6.65 (d, 2H), 6.95 (d, 2H). $^{13}$C NMR (DMSO-d$_6$) δ 26.5, 32.5, 33.5, 114.6, 129.0, 131.2, 155.3, 174.2.

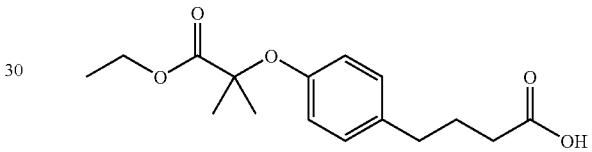

4-[4-(1-Ethoxycarbonyl-1-methylethoxy)phenyl]butyric acid

A 12-L 3-neck round-bottom flask was equipped with an overhead air-driven stirrer apparatus, condenser, nitrogen inlet, thermometer/thermocouple, and heating mantle. The flask was charged with ethyl acetate (450 mL) and 21% (wt.) sodium ethoxide in ethanol solution (3318 mL, 8.87 moles, 2 eq). The resulting mixture was heated to reflux under a nitrogen atmosphere and maintained at reflux for 30 min. The mixture was then allowed to cool slightly below reflux, and 4-(4-hydroxyphenyl)butyric acid (800 g, 4.43 moles) was added. The flask contents were re-heated to reflux for 30 min, at which point ethyl 2-bromoisobutyrate (EBIB, 1954 mL, 13.32 moles, 3.0 eqs.) was added. After 1 h at reflux, the flask was equipped with a 2-L addition funnel, which was charged sodium ethoxide in ethanol solution (1660 mL, 4.43 moles, 1 eq.). The sodium ethoxide solution was added dropwise to the refluxing reaction over 1 h. After an additional 30 min at reflux, HPLC analysis showed the reaction was complete. The heat source was removed and the flask contents were cooled to 5-10° C. and then transferred to a 22-L bottom-outlet flask. While stirring, the mixture was quenched with dilute phosphoric acid (6000 mL), transferred to a 20-L Buchi flask, and concentrated in vacuo to remove ethanol. The resulting aqueous mixture of crystals and excess EBIB was refrigerated overnight. The crystals were then filtered and washed with water (2000 mL). The solids were removed from the funnel and placed in a 20-L Buchi flask equipped with an overhead stirring apparatus. After the addition of water (2000 mL), the solids were stirred at ambient temperature for 30 min, then filtered and washed with heptane (2×2500 mL)). The solids were then placed in the vacuum oven and dried at 45° C. to afford the title compound as an off-white solid (1247 g, 95.5%). $^1$H NMR (500 MHz, CDCl$_3$) δ 1.25 (t, 3 H), 1.57 (s, 6 H), 1.92 (m, 2 H), 2.35 (t, 2 H), 2.60 (t, 2 H), 4.23 (q, 2 H), 6.76 (d, 2 H), 7.03 (d, 2 H). $^{13}$C NMR (CDCl$_3$) δ 14.1, 25.4, 26.3, 33.3, 34.2, 61.4, 119.4, 129.1, 134.9, 153.7, 174.4, 179.7.

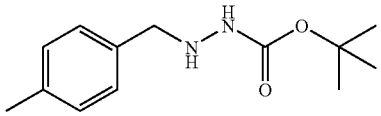

(4-Methylbenzyl)hydrazinecarboxylic acid, 1,1-dimethylethyl ester

To a 10-gal stainless steel autoclave containing isopropanol (10 L) under nitrogen was charged t-butyl carbazate (1.25 kg, 9.46 mol)followed by isopropanol (2 L). The contents were stirred and heated at 35° C. for 30 min, then 4-methylbenzaldehyde (1.142 kg, 9.51 mol) was added, followed by isopropanol (0.3 L). The contents were heated to 45° C., and a slurry of 5% Pd/C (0.3 kg) in water (0.3 L) and isopropanol (4 L) was added, followed by rinses of isopropanol (2×1 L). The contents were hydrogenated at 40 psig and 45° C. for 4 h, then a second charge of 5% Pd/C (0.3 kg) in water (0.3 L) and isopropanol (4 L) was added, followed by rinses of isopropanol (2×1 L). Hydrogenation was continued at 40 psig and 45° C. for 14 h, at which the reaction was determined to be complete by HPLC. The contents were then cooled to 15° C. and filtered, and the filter cake rinsed with isopropanol (15 L). The filtrate was concentrated in vacuo to afford the title compound (1.97 kg, 88.2%) as a 33.8 wt-% solution in isopropanol.

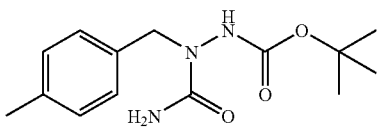

2-(Aminocarbonyl)-2-(4-methylphenylmethyl)hydrazine carboxylic acid, 1,1-dimethylethyl ester A 22-L 4-neck flask was equipped with an overhead stirring apparatus, cooling bath, thermometer probe, and 2-L addition funnel. The flask was charged with a solution of (4-methylbenzyl)hydrazinecarboxylic acid, 1,1-dimethyl-ethyl ester in isopropanol (4988 g of a 31.73% wt/wt solution, 1583 g, 6.70 moles). Additional isopropanol (3130 mL) was added to dilute the solution to a total volume of 8933 mL. Trimethylsilyl isocyanate (1179 mL, 8.71 mol, 1.3 eq) was charged to the 2-L addition funnel and was added dropwise to the stirring reaction solution over 45 minutes, while the temperature was maintained between 15-25° C. using a cool water bath. Reaction progress was monitored by TLC (50/50 v/v hexane/ethyl acetate, I$_2$; Rf(sm)=0.6, Rf(prod)=0.1). After overnight stir at room temperature, TLC indicated the reaction was essentially complete. The reaction mixture was treated with heptane (7800 mL), cooled to 5-10° C. and stirred for 0.5 hr. The mixture was filtered and the cake was washed with heptane (2×1000 mL). The material was dried in a vacuum oven at 30-35° C. to yield the title compound as a white solid (1423 g, 96%). $^1$H NMR (DMSO-d$_6$, 300 MHz): □ 1.35 (s, 9 H), 2.26 (s, 1 H), 4.45 (br s, 2 H), 6.06 (s, 2 H), 7.10 (s, 4 H), 8.88 (br s, 1 H); Anal. Calcd. for C$_{14}$H$_{21}$N$_3$O$_3$: C, 60.20; H, 7.58; N, 15.04. Found: C, 59.65; H, 7.34; N, 14.87.

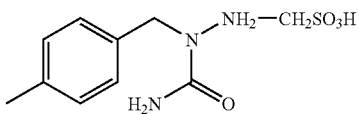

1-(4-Methylphenylmethyl)hydrazinecarboxamide methanesulfonate

A 22-L 4-neck flask was equipped with an overhead stirring apparatus, warming/cooling bath, thermometer probe, condenser, and 500-mL addition funnel. The flask was charged with 2-(Aminocarbonyl)-2-(4-methylphenylmethyl)-hydrazine carboxylic acid, 1,1-dimethylethyl ester (1100 g, 3.94 moles) and dichloromethane (12 L). The mixture was warmed to 30-35° C. to completely dissolve all solids, then cooled to 25-30° C. and methanesulfonic acid (MsOH) (398 g, 4.14 moles) was added over 30 min. The water bath was replaced with a heating mantle and the reaction solution was heated at reflux for 12-20 hours, and, monitored by TLC analysis (Ethyl Acetate 100%; I$_2$, Rf(sm) =0.3, Rf(prod)=0.1) When complete, the reaction mixture was diluted with heptane (4000 mL), cooled to 10-20° C., and stirred for 30 min. After filtration, the cake was washed with heptane (2×1000 mL) and dried in vacuo at 35-45° C., to afford the title compound as a white solid (1070 g, 98.6%). $^1$H NMR (DMSO-d$_6$, 300 MHz): δ 1.35 (s, 9 H), 2.26 (s, 1 H), 4.45 (br s, 2 H), 6.06 (s, 2 H), 7.10 (s, 4 H), 8.88 (br s, 1 H); Anal. Calcd. for C$_{10}$H$_{17}$N$_3$O$_4$S,: C, 43.62; H, 6.22; N, 15.26; S, 11.64. Found: C, 43.33; H, 6.21; N, 14.97.

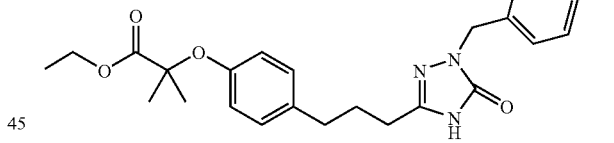

2-(4-{3-[1-(4-Methylphenylmethyl)-4-methyl-5-oxo-4,5-dihydro-1H-[1,2,4]triazol-3-yl]propyl}phenoxy)-2-methylpropionic acid ethyl ester A 22-L 4-neck flask was equipped with a thermometer/thermocouple, addition funnel, overhead stirring apparatus, nitrogen inlet, and cooling bath. The flask was charged with 4-[4-(1-Ethoxycarbonyl-1-methylethoxy)phenyl]butyric acid (1250 g, 4.247 moles), ethyl acetate (11,250 mL) and DMF (16.4 mL), and the resulting mixture was stirred to dissolve solids. Oxalyl chloride (426 mL, 4.88 moles, 1.15 eq) was added dropwise to the reaction mixture over 45 min, using a water bath to keep the temperature below 30° C. The reaction mixture was then concentrated in vacuo to remove both the solvent and excess oxalyl choride to afford crude 4-[4-(1-ethoxycarbonyl-1-methylethoxy)phenyl]butyric acid chloride. A separate 22-L 4-neck flask was equipped with a thermometer/thermocouple, addition funnel, nitrogen inlet, overhead stirring apparatus, and cooling bath. The flask was charged with 1-(4-methylphenylmethyl)hydrazine-carboxamide methanesulfonate (1169 g, 4.247 moles, 1 eq.), ethyl acetate (8750 mL), and pyridine (790 mL, 9.77 moles, 2.3 eqs.). The contents of the flask were cooled to 0-5° C. The crude acid chloride was dissolved in ethyl acetate (1000 mL) and added dropwise to the mixture containing 1-(4-methylphenylmethyl)hydrazinecarboxamide methanesulfonate over 20 min, while maintaining the pot temperature below 25° C. The resulting mixture was stirred at ambient temperature for 1 h, then (±)-camphorsulfonic acid (1973 g, 8.494 moles, 2 eq) was added. The flask contents were then heated to reflux for 16 h. The reaction was cooled to 20° C. and transferred into a flask containing 1N HCl (7500 mL). After stirring, the layers were separated and the organic layer was washed with saturated $Na_2CO_3$ solution (7500 mL) and water (1000 mL)), then dried over $MgSO_4$. The ethyl acetate solution was transferred to a 4-neck flask equipped with a condenser, nitrogen inlet, thermometer/thermocouple, and a heating mantle. The flask was charged with Amberlyst-15 resin (1975 g) and the mixture was heated to reflux for 1 h. After cooling to 20° C., the material was filtered to remove the resin and the resin was washed with ethyl acetate (2×2000 mL). The filtrate was concentrated in vacuo to afford a tan solid. MTBE (5000 mL) was added to the crude material and the mixture warmed to 45-50° C. until all solids were dissolved. While slowly rotating the flask, the solution was allowed to cool, whereupon crystallization occurred. The slurry was cooled to 0-5° C. for 1 hour, filtered, rinsed with cold MTBE (1500 mL) and dried in vacuo at 45° C. to afford the title compound as a white solid (1027 g, 55.2%). $^1$H NMR (500 MHz, DMSO-$d_6$) δ 1.14 (t, 3 H), 1.47 (s, 6 H), 1.76, (m, 2 H), 2.26 (t, 2 H), 2.49 (t, 2 H), 3.55 (s, 3 H), 4.15 (q, 2 H), 6.69 (d, 2 H), 7.05 (d, 2 H).). $^{13}$C NMR (CDCl$_3$) δ 14.0, 21.0, 25.3, 26.1, 28.1, 34.1, 48.3, 61.2, 79.0, 119.3, 127.8, 128.1, 129.0, 129.3, 133.2, 134.8, 137.5, 147.2, 148.3, 153.6, 155.8, 174.3.

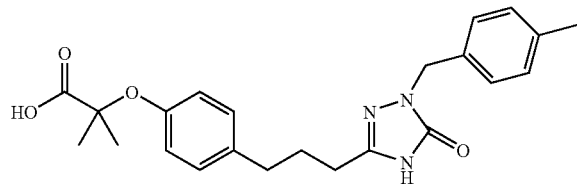

2-[4-[3-[2,5-dihydro-1-[(4-Methylphenyl)methyl]-5-oxo-1H-1,2,4-triazol-3-yl]propyl]phenoxy]-2-methyl-propanoic Acid A 4-neck flask was equipped with overhead stirring apparatus and thermometer probe. The flask was charged with 2-(4-{3-[1-(4-Methylphenylmethyl)-4-methyl-5-oxo-4,5-dihydro-1H-[1,2,4]triazol-3-yl]-propyl}phenoxy)-2-methyl-propionic acid, ethyl ester (800 g, 1.828 moles), and toluene (4000 mL) followed by 1N NaOH (4023 mL, 2.194 mol, 1.2 eq). The resulting mixture was stirred at ambient temperature for 5 h. The mixture was transferred to a 22-L bottom outlet flask and layers separated. The aqueous layer from the above layer separation was charged to the flask and acidified to pH 2 with concentrated HCl (337 mL). Ethyl acetate was added (8000 mL) and the mixture was transferred to a 22-L bottom-outlet flask. The layers were separated and the organic solution was transferred to a 22-L 3-neck round-bottom flask equipped with a distillation head and overhead stirring apparatus. The mixture was concentrated by distillation of the ethyl acetate to approximately 4000 mL, and fresh ethyl acetate (3600 mL) was added to the reaction vessel. Distillation was continued until 3600 mL of distillate were recovered. Heating was stopped and the mixture was allowed to cool slowly to 60-65° C., at which point seed crystals (0.8 g) of the desired product were added. The flask contents were allowed to cool slowly until crystallization initiated (55-57° C.), then the mixture was cooled to 0-5° C. and stirred for 1 h. The product was filtered, washed with cold ethyl acetate, and dried in vacuo at 55° C. to afford the title compound as a white solid (713.6 g, 95.3%). $^1$H NMR (DMSO-$d_6$, 500 MHz): δ 1.46 (s, 6 H), 1.79 (m, 2 H), 2.25 (s, 3H), 2.35 (t, 2 H), 2.47 (t, 2 H), 4.70 (s, 2 H), 6.71 (d, 2H), 7.03 (d, 2H), 7.10 (m, 4 H). $^{13}$C NMR (DMSO-$d_6$), δ 20.6, 25.0, 25.5, 27.7, 47.0, 78.3, 118.6, 127.4, 127.7, 128.9, 128.9, 134.4, 134.5, 136.4, 145.9, 153.4, 154.3, 175.0.

Example 123

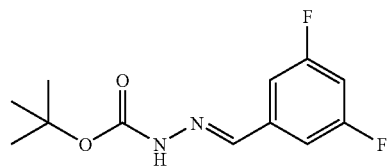

(3,5-Difluorophenyl)methylenehydrazinecarboxylic acid, 1,1-dimethylethyl ester

To a solution of t-butyl carbazate (4.99 g, 37.76 mmol) in ethyl acetate (10 mL) was added with stirring 3,5-difluorobenzaldehyde (5.50 g, 38.7 mmol) followed by hexanes (50 mL). Crystallization occurred and the resulting slurry was stirred at rt for 15 min, then cooled to 0° C. and held at that temperature for 45 min. The solids were filtered, rinsed with cold hexanes and dried in vacuo at 60° C. to afford the title compound as a solid (9.04 g, 93.3%): mp 196.4-196.8° C. (dec); $^1$H NMR (DMSO-$d_6$) δ 11.16 (br s, 1 H), 7.96 (s, 1 H), 7.28 (m, 2 H), 7.21 (t, 1 H, J=2.2 Hz), 1.45 (s, 9 H); $^{13}$C NMR (DMSO-$d_6$) δ 163.3 (dd, J=246.1, 13.5 Hz), 152.9, 141.2, 139.2 (t, J=9.6 Hz), 109.9 (dd, J=20.2, 5.8 Hz), 105.1 (t, J=25.9 Hz), 80.5, 28.7; IR (KBr mull) 3263, 2987, 1709, 1584, 1536 cm$^{-1}$. A portion was recrystallized (ethyl acetate) for analysis. Anal. Calcd. for $C_{12}H_{14}F_2N_2O_2$: C, 56.25; H, 5.51; F, 14.83; N, 10.93. Found: C, 56.11; H, 5.49; N, 10.86.

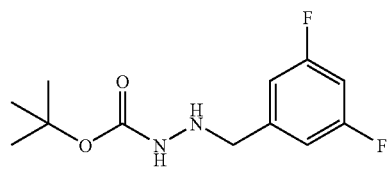

2-(3,5-Difluorophenylmethyl)hydrazinecarboxylic acid, 1,1-dimethylethyl ester

To substrate imine (7.00 g, 27.3 mmol) and 5% Pt/C (5.05 g) was added tetrahydrofuran (70 mL) and the resulting suspension hydrogenated at rt and 50 psi. After 4 h, an additional charge of 5% Pt/C (5.00 g) was added and hydrogenation continued for 12 h. The contents were filtered and concentrated to an oil, then reconstituted in THF (70 mL) along with 5% Pt/C (5.00 g) and hydrogenation continued for 60 h at rt and 50 psi. The contents were then filtered and concentrated. SiO$_2$ gel chromatography (20% ethyl acetate in hexanes) gave the title compound as an oil (4.96 g, 19.2 mmol, 70%). $^1$H NMR (DMSO-d$_6$) δ 8.28 (br s, 1 H), 7.03 (m, 3 H), 5.03 (br s, 1 H), 3.88 (s, 2 H), 1.35 (s, 9 H); $^{13}$C NMR (DMSO-d$_6$) δ 162.9 (dd, J=243.6, 12.4 Hz), 144.9 (t, J=9.6 Hz), 111.5 (d, J=23.0 Hz), 102.5 (t, J=25.9 Hz), 79.0, 53.9, 28.8; IR (CHCl$_3$) 3444, 2982, 2933, 1712, 1628, 1597 cm$^{-1}$; HRMS calcd for C$_{12}$H$_{16}$F$_2$N$_2$O$_2$ (M+H)$^+$: 259.1258. Found: 259.1252.

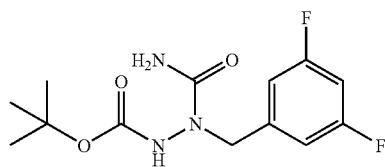

2-(Aminocarbonyl)-2-(3,5-Difluorophenylmethyl) hydrazinecarboxylic acid, 1,1-dimethylethyl ester To substrate difluorobenzyl hydrazine (2.5649 g, 9.93 mmol) in isopropanol (20 mL) at rt was added trimethylsilyl isocyanate (1.808 g, 15.7 mmol) in one portion. The reaction was stirred at rt for 36 h, then concentrated to a solid. Recrystallization (1:1 ethyl acetate:hexanes) followed by dilution with hexanes (100 mL) to facilitate stirring gave the title compound as a solid (2.84 g, 9.43 mmol, 95%): mp 128.7-129.9° C.; $^1$H NMR (DMSO-d$_6$, 60° C.) δ 88.86 (br s, 1 H), 6.97 (m, 3 H), 6.00 (s, 2 H), 4.52 (s, 2 H), 1.36 (s, 9 H); $^{13}$C NMR (DMSO-d$_6$,) δ 162.7 (dd, J=245, 13 Hz), 159.5, 155.1, 143.7 (t, J=9 Hz), 111.4 (d, J =23 Hz), 102.8 (t, J=26 Hz), 80.4, 51.4, 28.6; IR (KBr mull) 3540, 3227, 3004, 2988, 1744, 1682 cm$^{-1}$. Anal. Calcd. for C$_{13}$H$_{17}$F$_2$N$_3$O$_3$: C, 51.82; H, 5.69; N, 13.95. Found: C, 51.59; H, 5.61; N, 13.81.

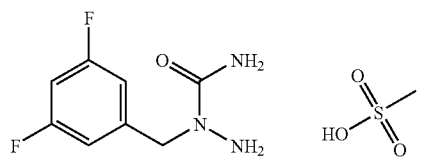

1-(3,5-Difluorophenylmethyl)hydrazinecarboxamide methanesulfonate

To substrate Boc semicarbazide (1.81 g, 6.00 mmol) in tetrahydrofuran (25 mL) at rt was added methanesulfonic acid (0.725 g, 6.3 mmol, 1.05 equiv) in one portion. The reaction was stirred at rt for 24 h, then heated to reflux for 22 h. The reaction mixture was cooled to rt, filtered and the filter cake rinsed with dichloromethane. The solids were dried in vacuo overnight at 60° C. to afford title compound as a solid (1.32 g, 4.44 mmol, 74%): mp 138.4-139.5° C. (dec); $^1$H NMR (DMSO-d$_6$, 60° C.) δ 7.94 (br s, 4 H), 7.10 (m, 1 H), 6.98 (m, 2 H), 4.70, 4.06 (s, s, 2 H total, pair of rotamers), 2.48, 2.41 (s, s, 3 H total, pair of rotamers); $^{13}$C NMR (DMSO-d$_6$,) δ 163.6 (dd, J=246, 13 Hz), 158.0, 140.9, 111.6 (dd, J=20, 6 Hz), 104.0 (t, J=26 Hz), 52.1; IR (KBr mull) 3411, 3281, 3211, 1706, 1685, 1457, 1209 cm$^{-1}$. HRMS calcd. for C$_8$H$_9$F$_2$N$_3$O (M+H)$^+$: 202.0792. Found: 202.0797.

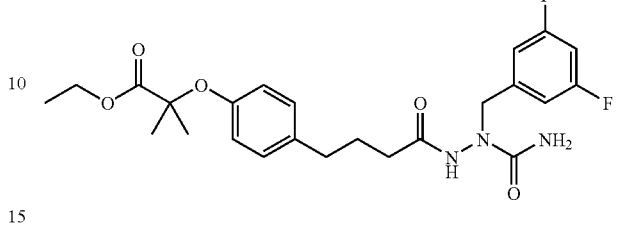

1-[4-[4-(1-Ethoxycarbonyl-1-methylethoxy)phenyl] butyryl]-2-(3,5-difluorophenyl-methyl)semicarbazide To 4-[4-(1Ethoxycarbonyl-1-methylethoxy)phenyl]butyric acid (1.0072 g, 3.42 mmol) in ethyl acetate (10 mL) at rt was added DMF (1 pipette drop), followed by oxalyl chloride (0.728 g, 5.73 mmol) dropwise over 5 min. The resulting solution was stirred for 30 min at rt, then concentrated to an oil. The oil was twice reconstituted into toluene (20 mL) and concentrated to an oil, then dissolved in ethyl acetate (3 mL). 1-(3,5-Difluorophenylmethyl)hydrazine carboxamide methanesulfonate (1.025 g, 3.45 mmol) was suspended in ethyl acetate (10 mL) at 0° C., and pyridine (0.65 mL, 636 mg, 8.04 mmol) was added. The solution of acid chloride in ethyl acetate was then added dropwise over 15 min, and the resulting mixture stirred for 30 min at 0° C. The mixture was then diluted with ethyl acetate and washed with 1 N HCl (2×) followed by sat'd aq. NaCl. It was then dried (MgSO$_4$), filtered and concentrated to an oil, which was chromatographed on silica gel (ethyl acetate) to afford the title compound as a solid (1.1436 g, 70%): mp 108.1-109.4° C.; $^1$H NMR (DMSO-d$_6$, 60° C.) δ 9.73 (s, 1 H), 7.00 (m, 5 H), 6.70 (d, 2 H, J=6.5 Hz), 6.03 (s, 2 H), 4.54 (br s, 2 H), 4.15 (q, 2 H, J=7 Hz), 2.45 (m, 2 H), 2.09 (m, 2 H), 1.74 (m, 2 H), 1.48 (s, 6 H), 1.17 (t, 3 H, J=7 Hz); $^{13}$C NMR (DMSO-d$_6$) δ 174.0, 172.0, 162.5 (dd, J=244, 13 Hz), 159.2, 153.8, 144.1, 135.8, 129.7, 119.4, 111.3 (d, J=25 Hz), 102.8 (t, J=26 Hz), 79.2, 51.1, 47.3, 34.3, 33.1, 27.0, 25.7, 14.6; IR (KBr) 3456, 3324, 1726, 1643, 1509, 1445 cm$^{-1}$; Anal. Calcd. for C$_{24}$H$_{29}$N$_3$O$_5$F$_2$: C, 60.37; H, 6.12; N, 8.80; F, 7.96. Found: C, 60.48; H, 6.28; N, 8.67; F, 7.75.

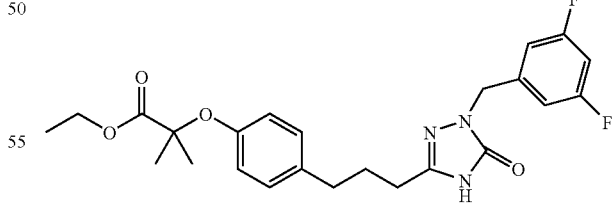

2-(4-{3-[1-(3,5-Difluorobenzyl)-5-oxo-4,5-dihydro-1H-[1,2,4]triazol-3-yl]-propyl}-phenoxy)-2-methyl-propionic acid, ethyl ester To substrate 1-[4-[4-(1-Ethoxycarbonyl-1-methylethoxy) phenyl]butyryl]-2-(3,4-dichlororophenylmethyl)-4-(n-propyl)semicarb-azide (1.06 g, 2.26 mmol) and camphorsulfonic acid (0.5283 g, 2.27 mmol) was added ethyl acetate (12 mL) and the resulting solution heated to reflux for 22 h. The solution was diluted with ethyl acetate, then washed with sat'd aq. NaHCO₃ followed by sat'd aq. NaCl. It was then dried (MgSO₄), filtered and concentrated to an oil, which was chromatographed on silica gel (1:1 ethyl acetate: hexanes) to afford the title compound as an oil (0.3836 g, 37%): ¹H NMR (DMSO-d₆) δ 11.54 (s, 1 H), 7.13 (t, 1 H, J=9.3 Hz), 7.04 (d, 2 H, J=8.5 Hz), 6.91 (d, 2 H, J=6.5 Hz), 6.68 (d, 2 H. J=8.5 Hz), 4.81 (s, 2 H), 4.13 (q, 2 H, J=7.0 Hz), 2.49 (t, 2 H, J=7.5 Hz), 2.38 (t, 2 H, J=7.5 Hz), 1.81 (m, 2 H), 1.47 (s, 6 H), 1.14 (t, 3 H, J=7.0 Hz); ¹³C NMR (DMSO-d₆) δ 174.0, 162.6 (dd, J=245, 13 Hz), 155.0, 153.8, 147.3, 142.9 (d, J=9 Hz), 135.5, 129.8, 119.5, 111.1 (t, J=26, 6 Hz), 103.5 (t, J=26 Hz), 79.2, 61.6, 47.1, 34.0, 28.3, 26.2, 25.7; IR (CHCl₃) 3004, 1727, 1695, 1601, 1509, 1464 cm⁻¹; Anal. Calcd. for C₂₄H₂₇F₂N₃O₄: C, 62.74; H, 5.92; N, 9.14. Found: C, 62.65; H, 5.99; N, 8.98.

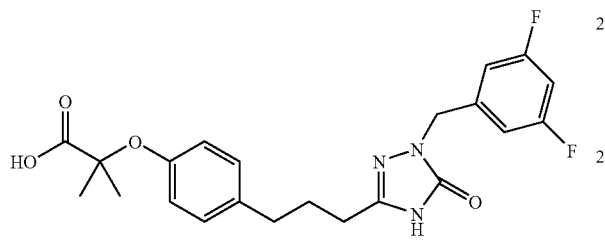

2-(4-{3-[1-(3,5-Difluorobenzyl)-5-oxo-4,5-dihydro-1H-[1,2,4]triazol-3-yl]-propyl}-phenoxy)-2-methyl-propionic acid To substrate triazolone ethyl ester (0.2971 g, 0.647 mmol) in methanol (3 mL) at rt was added 1 N NaOH (2 mL, 2.0 mmol) and the resulting mixture stirred at rt for 16 h. The mixture was then acidified by addition of 1 N HCl and concentrated to an oil, which was partitioned between ethyl acetate (35 mL) and water (25 mL). The layers were separated and the organic phase washed with sat'd aq. NaCl, then dried (Mg SO₄), filtered and concentrated to afford the title compound as an oil (0.2643 g, 95%): ¹H NMR (DMSO-d₆, 60° C.) δ 12.96 (br s, 1 H), 11.54 (s, 1 H), 7.13 (t, 1 H, J=9.5 Hz), 7.04 (d, 2 H, J=8 Hz), 6.91 (d, 2 H, J=7 Hz), 6.72 (d, 2 H, J=8 Hz), 4.81 (s, 2 H), 2.49 (t, 2 H, J=7 Hz), 2.38 (t, 2 H, J=7 Hz), 1.82 (m, 2 H), 1.46 (s, 6 H); ¹³C NMR (DMSO-d₆) δ 175.8, 163.0 (dd, J=245, 13 Hz), 155.0, 154.1, 147.3, 142.9, 135.0, 129.7, 119.2, 111.1 (m), 103.5 (t, J=26 Hz), 78.9, 47.1, 34.0, 28.3, 26.2, 25.7; IR (CHCl₃) 3096, 3005, 2865, 1708, 1601, 1509, 1465, 1158, 1121 cm⁻¹; Anal. Calcd. for C₂₂H₂₃F₂N₃O₄: C, 61.25; H, 5.37; N, 9.74. Found: C, 61.21, H, 5.46; N, 9.48.

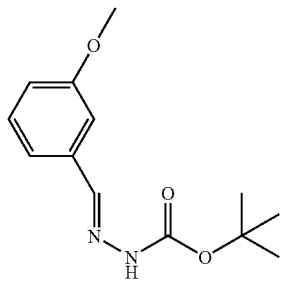

Example 124

(3-Methoxyphenyl)methylenehydrazinecarboxylic acid, 1,1-dimethylethyl ester

To a solution of t-butyl carbazate (5.59 g, 42.3 mmol) in ethyl acetate (15 mL) was added with stirring m-anisaldehyde (5.17 mL, 5.76 g, 42.3 mmol). Hexanes (70 mL) was added slowly and crystallization occurred. The resulting slurry was stirred at rt for 45 min and then cooled to 0° C. The slurry was stirred at 0° C. for 60 min, then filtered and rinsed with cold hexanes (20 mL), and dried in vacuo at 40° C. to afford the title compound as a solid (9.68 g, 91.4%): mp 135.6-137.4° C.; ¹H NMR (DMSO-d₆) δ 10.93 (s, 1H), 7.29 (t, 1 H, J=8 Hz), 7.14 (d, 2 H, J=7 Hz), 6.92 (q, 1 H, J=7 Hz), 3.75 (s, 3 H), 1.45 (s, 9 H); ¹³C NMR (DMSO-d₆) δ 160.2, 153.1, 143.7, 136.8, 130.5, 120.0, 116.2, 111.3, 80.1, 55.7, 28.7; IR (KBr mull) 3360, 3010, 2982, 2838, 1510, 1487 cm⁻¹. A portion was recrystallized from ethyl acetate and submitted for elemental analysis. Anal. Calcd. for C₁₃H₁₈N₂O₃: C, 62.38; H, 7.25; N, 11.19. Found: C, 62.34.; H, 7.46; N, 11.19.

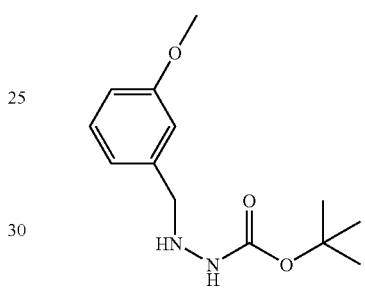

(3-Methoxybenzyl)hydrazinecarboxylic acid, 1,1-dimethylethyl ester (3-Methoxyphenyl)methylenehydrazinecarboxilic acid, 1,1-dimethylethyl ester (7.03 g, 28.1 mmol) and Pt/C (5%, 5.07 g) were slurried in THF (80 mL) and hydrogenated at rt and 50 psig for 8 hr. The slurry was then filtered through celite and concentrated in vacuo at 50° C. to afford the title compound as oil (6.68 g, 94.0%): ¹H NMR (DMSO-d₆) δ 8.22 (s, 1H), 7.19 (t, 1 H, J=8 Hz), 6.85 (d, 1 H, J=7 Hz), 6.77 (d, 1 H, J=7 Hz), 3.84 (s, 2 H), 3.72 (s, 3 H), 1.37 (s, 9 H); ¹³C NMR (DMSO-d₆) δ 159.9, 157.1, 141.1, 129.7, 121.1, 114.1, 113.1, 78.9, 55.5, 54.9, 28.9; IR (CHCl₃) 3008, 2982, 2935, 1712 cm⁻¹; Exact Mass: Calcd. for C₁₃H₂₀N₂O₃Na: 275.1372, Found: 275.1381.

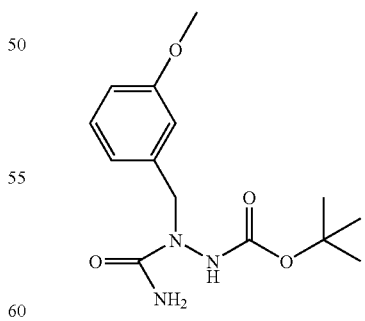

3-(Aminocarbonyl)-2-(3-methoxyphenylmethyl)hydrazine carboxylic acid, 1,1-dimethylethyl ester (3-Methoxybenzyl)hydrazinecarboxylic acid, 1,1-dimethylethyl ester (6.30 g, 25.0 mmol) was dissolved in isopropyl alcohol (65 mL). Trimethylsilyl isocyanate (4.73 g, 34.9 mmol) was added in one portion via syringe and the solution was allowed to stir at rt for 7 h. The slurry was cooled to 0° C., filtered, and the solids rinsed with cold isopropanol. The solids were dried in vacuo at 40° C. to afford the title compound as a white solid (4.71 g, 63.9%). The filtrate was concentrated and purified by column chromatography (SiO$_2$, EtOAc) to afford additional compound (0.91 g, 12.3%). These two portions were combined to yield 5.82 g (76.2%) of the title compound: mp 136.3-138.5° C.; $^1$H NMR (DMSO-d$_6$, 60° C.) δ 8.70 (s, 1H), 7.20 (t, 1 H, J=8 Hz), 6.80 (m, 3 H), 5.90 (s, 2 H), 4.50 (s, 2 H), 3.74 (s, 3 H), 1.36 (s, 9 H); $^{13}$C NMR (DMSO-d$_6$) δ 159.9, 159.6, 155.0, 140.2, 129.8, 120.9, 114.0, 113.2, 80.2, 55.6, 51.1, 28.7; IR (CHCl$_3$) 3003, 2984, 2938, 1745, 1680 cm$^{-1}$; Anal. Calcd. for C$_{14}$H$_{21}$N$_3$O$_4$: C, 56.94; H, 7.17; N, 14.23. Found: C, 56.54; H, 7.17; N, 13.98.

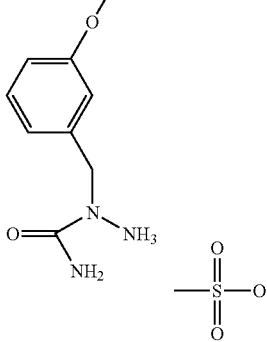

1-(3-Methoxyphenylmethyl)hydrazine carboxamide methanesulfonate 3-(Amino-carbonyl)-2-(3-methoxyphenylmethyl)hydrazine carboxylic acid, 1,1-dimethyl-ethyl ester (5.30 g, 17.9 mmol) was dissolved in dichloromethane (60 mL). Methanesulfonic acid (1.93 g, 19.9 mmol) was added in one portion and the solution was allowed to stir at rt overnight. The resulting slurry was cooled to 0° C., filtered, and the solids rinsed with cold dichloromethane. The solids were dried in vacuo at 40° C. to afford the title compound as a white solid (5.05 g, 96.6%): mp 130.3-132.1° C.; $^1$H NMR (DMSO-d$_6$) δ 9.7 (broad s, 3 H), 7.30 (t, 1 H, J=8 Hz), 7.05 (broad s, 2 H), 6.88 (s, 3 H), 4.69 (s, 2 H), 3.74 (s, 3 H), 3.34 (s, 3 H); $^{13}$C NMR (DMSO-d$_6$) δ 160.1, 158.2, 137.3, 130.5, 120.7, 114.3, 114.0, 55.7, 52.7, 40.4; IR (KBr mull) 3186, 2939, 1719, 1707, 1168 cm$^{-1}$; Anal. Calcd. for C$_9$H$_{13}$N$_3$O$_2$: C, 41.23.; H, 5.88; N, 14.42. Found: C, 40.86.; H, 5.92; N, 14.61.

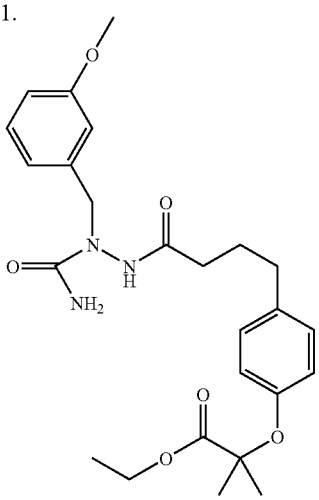

1-[4-[4-(1-Ethoxycarbonyl-1-methylethoxy)phenyl] butyryl]-2-(3-methoxyphenyl-methyl)semicarbazide 4-[4-(1-Ethoxycarbonyl-1-methyl-ethoxy)-phenyl] butyric acid (4.86 g, 16.5 mmol) was dissolved in ethyl acetate (40 mL). Oxalyl chloride (2.43 g, 19.14 mmol) was added to this solution dropwise in the presence of a catalytic amount of N,N-dimethylformamide (100 mg, 1.37 mmol). Completion of acid chloride formation was verified by HPLC. This solution was then added dropwise to a suspension of 1-(3-methoxyphenylmethyl)hydrazine carboxamide methanesulfonate (4.80 g, 16.5 mmol) and pyridine (1.30 g, 16.5 mmol) in ethyl acetate (55 mL) at 0° C. After stirring at 0° C. for 6 h, an additional charge of pyridine was added (1.30 g, 16.5 mmol) and the solution was stirred at 0° C. for 1 h. The solution was warmed to rt and washed with 1N HCl (2×80 mL) and 5% aq. NaHCO$_3$ (2×80 mL). The organic layer was dried (MgSO$_4$), filtered and concentrated to a waxy solid. The solids were recrystallized from a mixture of toluene (17 mL) and heptane (7 mL) at 60° C., cooled to 0° C. and filtered. The solids were dried in vacuo at 40° C. to afford the title compound as a white solid (5.05 g, 65%): mp 91.9-93.4° C.; $^1$H NMR (DMSO-d$_6$, 60° C.) δ 9.60 (s, 1 H), 7.19 (t, 1 H, J=8 Hz), 7.00 (d, 2 H), 6.80 (m, 3 H), 6.71 (d, 2 H, J=8 Hz), 5.92 (s, 2 H), 4.52 (s, 2 H), 4.15 (q, J=7 Hz), 3.71 (s, 3 H), 2.45 (t, 2 H, J=7 Hz ), 2.07 (t, 2 H, J=7 Hz ), 1.73 (quint, 2 H, J=7 Hz), 1.48 (s, 6 H), 1.17 (t, 3 H,. J=7 Hz); $^{13}$C NMR (DMSO-d$_6$) δ 174.0, 171.9, 159.9, 159.3, 153.7, 140.5, 135.9, 129.9, 129.7, 120.9, 119.4, 114.1, 113.1, 79.2, 61.6, 55.5, 50.9, 34.3, 33.4, 27.2, 25.7, 14.6; IR (KBr mull) 3450, 3320, 3275, 3202, 2997, 2940, 1730, 1646, 1511 cm$^{-1}$; Anal. Calcd. for C$_{25}$H$_{33}$N$_3$O$_6$: C, 63.68; H, 7.05; N, 8.91. Found: C, 63.49; H, 7.02; N, 8.99.

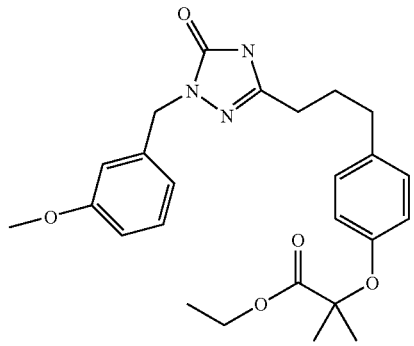

2-(4-{3-[1-(3-Methoxybenzyl)-5-oxo-4,5-dihydro-1H-[1,2,4]triazol-3-yl]-propyl}-phenoxy)-2-methyl-propionic acid ethyl ester 1-[4-[4-(1-Ethoxycarbonyl-1-methyl-ethoxy)phenyl]butyryl]-2-(3-methoxyphenylmethyl)semicarbazide (4.08 g, 8.65 mmol) was dissolved in ethyl acetate (7.5 mL). Camphorsulfonic acid (2.21 g, 9.51 mmol) was added in one portion and the solution was heated to reflux overnight. The solution was cooled to rt and washed with sat'd aq. NaHCO$_3$ (2×40 mL) followed by 1N HCl (2×40 mL). The organic was concentrated to an oil, which was redissolved in ethyl acetate (40 mL). Amberlyst-15 resin (4.41 g) was added and the mixture was heated to 50° C. and stirred for 4 h. The mixture was then cooled to rt, filtered, concentrated, and purified by column chromatography (SiO$_2$, 9:1 ethyl acetate: hexanes) to afford the title compound as an oil (1.93 g, 49.2%). $^1$H NMR (DMSO-d$_6$) δ 11.47 (s, 1 H), 7.22 (t, 1 H, J=8 Hz), 7.04 (d, 2 H, J=8 Hz), 6.82 (d, 1 H, J=2 Hz), 6.76

(m, 2 H), 6.68 (d, 2 H, J=2 Hz), 4.73 (s, 2 H), 4.13 (q, 2 H, J=7 Hz), 3.69 (s, 3 H), 2.48 (t, 2 H, J=8 Hz), 2.36 (t, 2 H, J=8 Hz), 1.80 (quint, 2 H, J=7 Hz), 1.47 (s, 6 H), 1.14 (t, 3 H, J=7 Hz); $^{13}$C NMR (DMSO-d$_6$) δ 174.0, 160.0, 155.0, 153.8, 146.7, 139.8, 135.5, 130.2, 129.8, 120.1, 119.5, 113.8, 113.2, 79.2, 61.6, 55.6, 47.8, 34.0, 28.4, 26.2, 25.7, 14.6; IR (CHCl$_3$) 2940, 1692, 1508, 1467 cm$^{-1}$; Anal. Calcd. for C$_{25}$H$_{31}$N$_3$O$_5$: C, 66.21.; H, 6.89; N, 9.26. Found: C, 66.29; H, 6.75; N, 9.19.

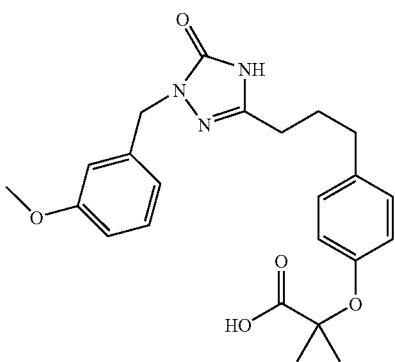

2-(4-{3-[1-(3-Methoxy-benzyl)-5-oxo-4,5-dihydro-1H-[1,2,4]triazol-3-yl]-propyl}-phenoxy)-2-methyl-propionic acid 2-(4-{3-[1-(3-Methoxy-benzyl)-5-oxo-4,5-dihydro-1H-[1,2,4]triazol-3-yl]-propyl}-phenoxy)-2-methyl-propionic acid ethyl ester (1.55 g, 3.42 mmol) was dissolved in a mixture of ethanol (7.5 mL) and water (7.5 mL). Solid sodium hydroxide (0.36 g, 8.73 mmol) was added in one portion and the solution was warmed to 70° C. and stirred for 1 h. The solution was cooled to rt and the pH adjusted to 7 with 6N HCl. The solution was concentrated to an oil, which was partitioned between 1N HCl (10 mL) and ethyl acetate (15 mL). The aqueous layer was then reextracted with ethyl acetate (15 mL) and the combined organic layers were dried (MgSO$_4$), filtered and concentrated in vacuo at 50° C. to afford the title compound as an oil (1.41 g, 97.0%). $^1$H NMR (DMSO-d$_6$) δ 13.0 (broad s, 1 H), 11.47 (s, 1 H), 7.23 (t, 1 H, J=8 Hz), 7.03 (d, 2 H, J=8 Hz), 6.82 (d, 1 H, J=2 Hz), 6.75 (m, 5 H), 4.73 (s, 2 H), 3.70 (s, 3 H), 3.35 (broad s, 1 H), 2.48 (t, 2 H, J=8 Hz), 2.36 (t, 2 H, J=8 Hz), 1.80 (quint, 2 H, J=7 Hz), 1.46 (s, 6 H); $^{13}$C NMR (DMSO-d$_6$, 20° C.) δ 175.8, 160.0, 155.0, 154.1, 146.8, 139.8, 135.0, 130.3, 129.7, 120.1, 119.1, 113.8, 113.2, 78.9, 55.6, 47.8, 40.6, 40.5, 34.0, 28.4, 27.5, 26.2, 25.7; IR (CHCl$_3$) 1707, 1603, 1509, 1159 cm$^{-1}$; Anal. Calcd. for C$_{23}$H$_{27}$N$_3$O$_5$: C, 64.93; H, 6.40; N, 9.88. Found: C, 65.02; H, 6.65; N, 9.57.

Example 125

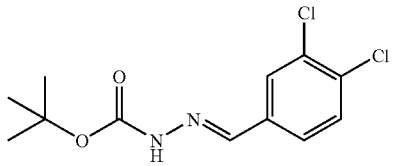

(3, 4-Dichlorophenyl)methylenehydrazinecarboxylic acid, 1,1-dimethylethyl ester

To a solution of t-butyl carbazate (4.99 g, 37.76 mmol) in ethyl acetate (10 mL) was added with vigorous stirring a solution of 3,4-dichlorobenzaldehyde (6.77 g, 38.6 mmol) in ethyl acetate (10 mL) followed by hexanes (40 mL). Crystallization occurred and the resulting slurry was stirred at rt for 15 min, then cooled to 0° C. and held at that temperature for 45 min. The solids were filtered, rinsed with cold hexanes and dried in vacuo at 60° C. to afford the title compound as a solid (10.10 g, 92.4%): mp 173.8-174.4° C. (dec); $^1$H NMR (DMSO-d$_6$) δ 11.16 (br s, 1 H), 7.79 (s, 1 H), 7.62 (d, 1 H, J=1.8 Hz), 7.57 (d, 1 H, J=8.5 Hz), 7.55 (m, 1 H), 1.44 (s, 9 H); $^{13}$C NMR (DMSO-d$_6$) δ 152.9, 141.1, 136.1, 132.3, 132.1, 131.6, 128.6, 127.0, 80.4, 28.7; IR (KBr mull) 3358, 3010, 2983, 1736, 1508, 1475 cm$^{-1}$. A portion was recrystallized (ethyl acetate) for analysis. Anal. Calcd. for C$_{12}$H$_{14}$Cl$_2$N$_2$O$_2$: C, 49.84; H, 4.88; Cl, 24.52; N, 9.69. Found: C, 49.59; H, 4.71; Cl, 24.43; N, 9.57.

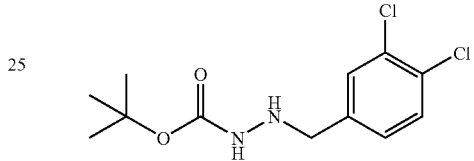

2-(3,4-Dichlorophenylmethyl)hydrazinecarboxylic acid, 1,1-dimethylethyl ester

To substrate imine (2.90 g, 10.03 mmol) and 5% Pt/S/C (4.31 g of 55% wet catalyst, 1.94 g) was added tetrahydrofuran (30 mL) and the resulting slurry hydrogenated at 50 psi hydrogen at rt for 16 h. The slurry was filtered and the filtrate concentrated to an oil, which was chromatographed on silica gel (gradient of hexanes to 15% ethyl acetate in hexanes) to afford the title compound as an oil (2.56 g, 8.79 mmol, 88%): $^1$H NMR (DMSO-d$_6$, 60° C.) δ 8.05 (br s, 1 H), 7.56 (s, 1 H), 7.52 (dd, 1 H, J=7.5, 1.5 Hz), 7.27 (d, 1 H, J=7.5 Hz), 3.87 (s, 2 H), 1.36 (s, 9 H); $^{13}$C NMR (DMSO-d$_6$) δ 157.0, 141.0, 131.4, 130.8, 129.8, 129.3, 79.1, 53.6, 28.8; IR (CHCl$_3$) 3443, 2983, 1713, 1472, 1455, 1369 cm$^{-1}$; Anal. Calcd. for C$_{12}$H$_{16}$Cl$_2$N$_2$O$_2$: C, 49.50; H, 5.54; N, 9.62. Found: C, 49.82; H, 5.39; N, 9.50.

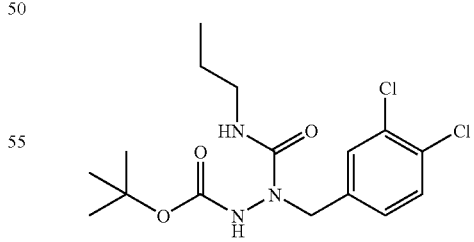

2-(Propylaminocarbonyl)-2-(3,4-dichlorophenylmethyl)hydrazinecarboxylic acid, 1,1-dimethylethyl ester To substrate hydrazide (2.30 g, 7.90 mmol) in isopropanol (25 mL) at rt was added propyl isocyanate (0.89 mL, 0.808 g, 9.50 mmol). After stirring for 30 min, the solution was concentrated to an oil, and chromatographed on silica gel (40% ethyl acetate in hexanes) to afford the title compound as an oil (2.63 g, 88%): $^1$H NMR (DMSO-$d_6$, 60° C.) δ 8.72 (br s, 1 H), 7.52 (dd, 1 H, J=8.0, 2.0 Hz), 7.48 (s, 1 H), 7.24 (d, 1 H, J=8.0 Hz), 6.39 (br s, 1 H), 4.50 (br s, 2 H), 3.13 (m, 2 H), 1.41 (m, 2 H), 1.35 (s, 9 H), 0.82 (m, 3 H); $^{13}$C NMR (DMSO-$d_6$) δ 158.4, 155.1, 140.1, 131.3, 130.9, 130.1, 129.3, 80.4, 51.2, 28.6, 23.7, 11.8; IR (CHCl$_3$) 3454, 3007, 2971, 2936, 2876, 1743, 1671, 1524 cm$^{-1}$; Anal. Calcd. for $C_{16}H_{23}Cl_2N_3O_3$: C, 51.07; H, 6.16; N, 11.17. Found: C, 51.01, H, 6.09; N, 11.15.

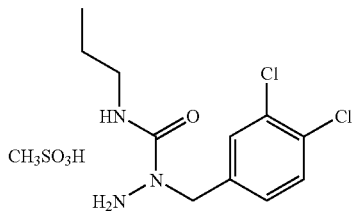

N-Propyl-1-(3,4-dichlorophenylmethyl)hydrazin-ecarboxamide methanesulfonate

To substrate BOC semicarbazide (2.15 g, 5.71 mmol) in dichloromethane (20 mL) at rt was added methanesulfonic acid (0.39 mL, 0.578 g, 6.01 mmol) in one portion. The resulting solution was stirred at rt for 16 h, then heated to reflux for 16 h. The solution was cooled and concentrated to a foam, which was triturated with t-butyl methyl ether to afford the title compound as a solid (2.03 g, 5.53 mmol, 95%). A portion was recrystallized (ethyl acetate/ethanol) for analysis: mp 134.6-135.5° C.; $^1$H NMR (DMSO-$d_6$, 60° C.) δ 8.35 (br 2, 4 H), 7.60 (d, 1 H, J=8.5 Hz), 7.51 (d, 1 H, J=2.0 Hz), 7.27 (dd, 1 H, J=8.5, 2.0 Hz), 4.66 (s, 2 H), 3.06 (t, 2 H, J=7.0 Hz), 2.42 (s, 3 H), 1.45 (m, 2 H), 0.83 (t, 3 H, J=7.5 Hz); $^{13}$C NMR (DMSO-$d_6$) δ 157.6, 137.4, 131.8, 131.4, 131.2, 130.8, 129.1, 52.0, 42.7, 40.4, 23.3, 11.9; IR (KBr mull) 3385, 2958, 2933, 2874, 1687, 1525, 1189 cm$^{-1}$; Anal. Calcd. for $C_{11}H_{15}Cl_2N_3O\cdot CH_4O_3S$: C, 38.72; H, 5.14; N, 11.29. Found: C, 38.76; H, 5.14; N, 11.26.

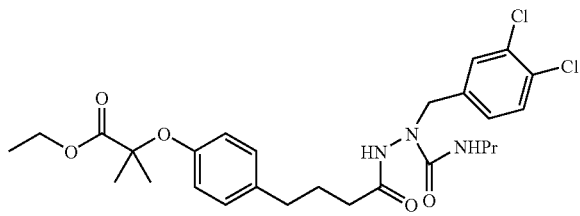

1-[4-[4-(1-Ethoxycarbonyl-1-methylethoxy)phenyl]butyryl]-2-(3,4-dichlorophenyl-methyl)-4-(propyl)semicarbazide To 4-[4-(1-Ethoxycarbonyl-1-methylethoxy)phenyl]-butyric acid (1.005 g, 3.41 mmol) in ethyl acetate (10 mL) at rt was added DMF (1 pipette drop), followed by oxalyl chloride (0.4 mL, 0.582 g, 4.58 mmol) dropwise over 3 min. The resulting solution was stirred for 30 min at rt, then concentrated to an oil. The oil was twice reconstituted into toluene (20 mL) and concentrated to an oil, then dissolved in ethyl acetate (3 mL). N-Propyl-1-(3,4-dichlorophenylm-ethyl)hydrazine methane-sulfonate (1.1458 g, 3.08 mmol) was suspended in ethyl acetate (10 mL) at 0° C., and pyridine (0.65 mL, 636 mg, 8.04 mmol) was added. The solution of acid chloride in ethyl acetate was then added dropwise over 2 min, and the resulting mixture stirred for 15 min at 0° C. The mixture was then diluted with ethyl acetate and washed with 1 N HCl (2×) followed by sat'd aq. NaCl. It was then dried (MgSO$_4$), filtered and concentrated to an oil, which was chromatographed on silica gel (3:2 ethyl acetate:hexanes) to afford the title compound as an oil (1.4397 g, 85%): $^1$H NMR (DMSO-$d_6$, 60° C.) δ 9.61 (s, 1 H), 7.50 (d, 1 H, J=8 Hz), 7.47 (d, 1 H, J=2 Hz), 7.23 (dd, 1 H, J=8, 2 Hz), 7.01 (d, 2 H, J=8.5 Hz), 6.71 (d, 2 H, J=8.5 Hz), 6.41 (br m, 1 H), 4.53 (br s, 2 H), 4.15 (q, 2 H. J=7 Hz), 3.00 (m, 2 H), 2.43 (m, 2 H), 2.09 (t, 2 H, J=7 Hz), 1.74 (m, 2 H), 1.48 (s, 6 H), 1.40 (m, 2 H), 0.81 (t, 3 H, J=7.5 Hz); $^{13}$C NMR (DMSO-$d_6$) δ 174.0, 172.1, 158.1, 153.8, 140.4, 135.8, 131.4, 130.9, 130.6, 130.1, 129.7, 129.1, 119.5, 79.2, 61.6, 50.9, 42.3, 34.4, 33.5, 27.1, 25.7, 23.7, 14.6, 11.9; IR (CHCl$_3$) 3457, 3008, 2876, 1727, 1673, 1509 cm$^{-1}$; Anal. Calcd. for $C_{27}H_{35}Cl_2N_3O_5$: C, 58.70; H, 6.39; N, 7.61. Found: C, 58.60; H, 6.49; N, 7.67.

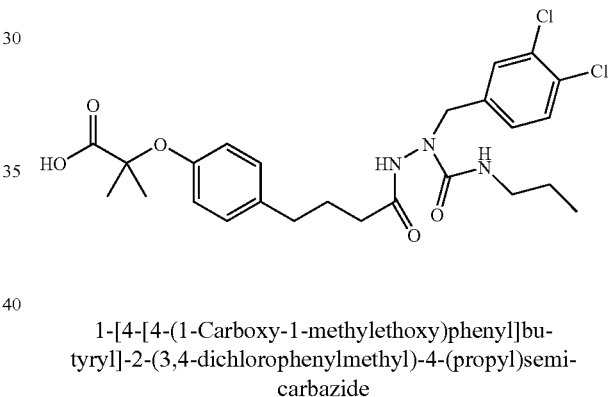

1-[4-[4-(1-Carboxy-1-methylethoxy)phenyl]bu-tyryl]-2-(3,4-dichlorophenylmethyl)-4-(propyl)semi-carbazide To substrate 1-[4-[4-(1-Ethoxycarbonyl-1-methyl-ethoxy)-phenyl]butyryl]-2-(3,4-dichlorophenylmethyl)-4-(propyl)semicarbazide (0.609 g, 1.10 mmol) in methanol (5 mL) at rt was added 1 N NaOH (2.0 mL, 2.0 mmol) and the resulting solution stirred for 16 h. The solution was then concentrated to an oil, and partitioned between ethyl acetate and 1 N HCl. The organic phase was then washed with sat'd aq. NaCl, dried (MgSO$_4$), filtered and concentrated to afford the title compound as an amorphous solid (0.5563 g, 1.06 mmol, 96%): $^1$H NMR (DMSO-$d_6$, 60° C.) δ 9.61 (s, 1 H), 7.50 (d, 1 H, J=8 Hz), 7.47 (d, 1 H, J=1.5 Hz), 7.23 (dd, 1 H, J=8, 1.5 Hz), 7.01 (d, 2 H, J=8.5 Hz), 6.75 d, 2 H, J=8.5 Hz), 6.40 (br m, 1 H), 4.53 (br s, 2 H), 2.99 (q, 2 H, J=6.5 Hz), 2.46 (t, 2 H, J=7.5 Hz), 2.09 (t, 2 H, J=7.5 Hz), 1.74 (m, 2 H), 1.47 (s, 6 H), 1.40 (q, 2 H, J=7.5 Hz), 0.81 (t, 3 H, J=7.5 Hz); $^{13}$C NMR (DMSO-$d_6$) δ 175.8, 172.1, 158.1, 154.1, 140.4, 135.3, 131.5, 130.9, 130.6, 130.1, 129.6, 129.1, 119.1, 78.9, 50.9, 42.3, 40.7, 34.4, 33.5, 27.1, 25.7, 23.7, 11.9; IR (CHCl$_3$) 3379, 3291, 2960, 2915, 1719, 1671, 1618, 1542, 1508 cm$^{-1}$; Anal. Calcd. for $C_{25}H_{31}Cl_2N_3O_5$: C, 57.26; H, 5.96; N, 8.01. Found: C, 57.15; H, 5.89; N, 7.94.

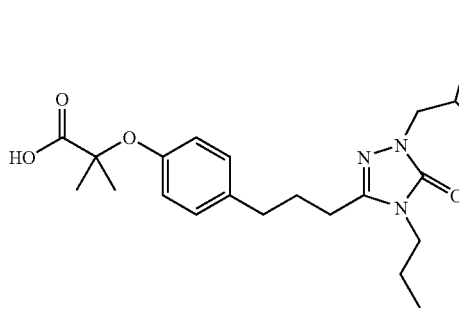

2-(4-{3-[1-(3,4-Dichlorobenzyl)-5-oxo-4,5-dihydro-1H-[1,2,4]triazol-3-yl]-propyl}-phenoxy)-2-methyl-propionic acid To substrate 1-[4-[4-(1-Carboxy-1-methylethoxy)-phenyl]butyryl]-2-(3,4-dichlorophenylmethyl)-4-(propyl)semicarbazide (0.3658 g, 0.697 mmol) and camphorsulfonic acid (0.1658 g, 0.714 mmol) was added toluene (10 mL) and the resulting solution heated to 90° C. for 1 h. The solution was concentrated to an oil, and chromatographed on silica gel (7:3 ethyl acetate:hexanes) to afford title compound as an oil (0.2397 g, 0.473 mmol, 68%): $^1$H NMR (DMSO-$d_6$) δ 12.95 (br s, 1 H), 7.58 (d, 2 H, J=8 Hz), 7.46 (d, 1 H, J=1.5 Hz), 7.19 (dd, 1 H, J=8, 1.5 Hz), 7.03 (d, 2 H, J=8.5 Hz), 6.72 (d, 2 H, J=8.5 Hz), 4.85 (s, 2 H), 3.47 (t, 2 H, J=7 Hz), 2.54 (t, 2 H, J=7.5 Hz), 1.83 (m, 2 H), 1.52 (q, 2 H, J=7 Hz), 1.45 (s, 6 H), 0.79 (t, 3 H, J=7 Hz); $^{13}$C NMR (DMSO-$d_6$) δ 175.8, 154.1, 147.3, 139.2, 135.2, 131.7, 131.5, 130.8, 130.1, 129.7, 128.4, 119.3, 79.0, 47.3, 42.9, 34.0, 27.8, 25.7, 24.8, 22.5, 11.5; IR (CHCl$_3$) 3028, 3005, 2939, 2878, 1696, 1574, 1509, 1472 cm$^{-1}$; Anal. Calcd. for $C_{25}H_{29}Cl_2N_3O_4$: C, 59.29; H, 5.77; N, 8.30. Found: C, 59.33; H, 5.63; N, 8.10.

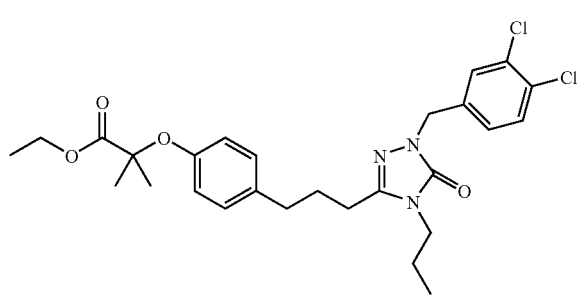

2-(4-{3-[1-(3,4-Dichlorobenzyl)-5-oxo-4,5-dihydro-1H-[1,2,4]triazol-3-yl]-propyl}-phenoxy)-2-methyl-propionic acid, ethyl ester To substrate 1-[4-[4-(1-Ethoxycarbonyl-1-methylethoxy)phenyl]butyryl]-2-(3,4-dichlorophenylmethyl)-4-(propyl) semicarbazide (0.4976 g, 0.901 mmol) and camphorsulfonic acid (0.2078 g, 0.895 mmol) was added ethyl acetate (10 mL) and the resulting solution heated to reflux for 12 h. The solution was diluted with ethyl acetate, then washed with sat'd aq. NaHCO$_3$ followed by sat'd aq. NaCl. It was then dried (MgSO$_4$), filtered and concentrated to afford the title compound as an oil (0.4532 g, 0.848 mmol, 94%): $^1$H NMR (DMSO-$d_6$) δ 7.59 (d, 1H, J=8.5 Hz), 7.47 (d, 1H, J=2 Hz), 7.19 (dd, 1H, J=8.5, 2 Hz), 7.03 (d, 2 H, J=8.5 Hz), 6.69 (d, 2H, J=8.5 Hz), 4.85 (s, 2H), 4.13 (q, 2H, J=7 Hz), 3.48 (t, 2H, J=8 Hz), 2.55 (t, 2H, J=7 Hz), 1.83 (m, 2H), 1.52 (q, 2H, J=7 Hz), 1.47 (s, 6H), 1.14 (t, 3H, J=7 Hz), 0.79 (t, 3H, J=7 Hz); $^{13}$C NMR (DMSO-$d_6$) δ 174.0, 154.1, 153.8, 147.3, 139.2, 135.6, 131.7, 131.5, 130.8, 130.1, 129.8, 128.4, 119.6, 79.3, 61.6, 47.3, 42.9, 34.0, 27.7, 25.7, 24.7, 22.4, 14.6, 11.5; IR (CHCl$_3$) 3003, 2939, 1728, 1696, 1509 cm$^{-1}$; HRMS calcd. for $C_{27}H_{34}Cl_2N_3O_4$ (M+H)$^+$: 524.1926. Found: 534.1935

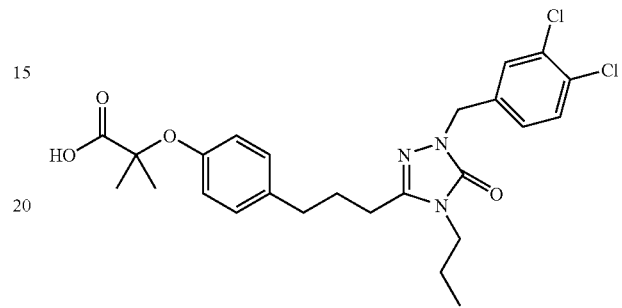

2-(4-{3-[1-(3,4-Dichlorobenzyl)-5-oxo-4,5-dihydro-1H-[1,2,4]triazol-3-yl]-propyl}-phenoxy)-2-methyl-propionic acid To substrate triazolone ethyl ester (0.3879 g, 0.726 mmol) in methanol (5 mL) at rt was added sodium hydroxide (2.0 mL of 2.0 M solution, 2.0 mmol) and the resulting mixture stirred at rt for 16 h. The mixture was then concentrated to an oil and partitioned between ethyl acetate and 1 N HCl. The organic phase was washed with sat'd aq. NaCl, dried (MgSO$_4$), filtered and concentrated to afford the title compound (0.336 g, 0.646 mmol, 89%) as an oil.

Example 126

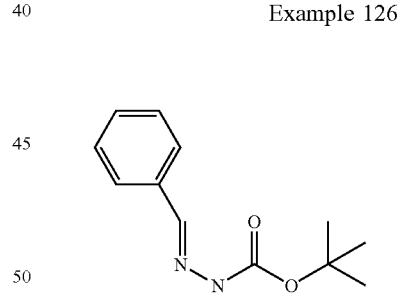

Phenylmethylenehydrazinecarboxylic acid, 1,1-dimethylethyl ester

To a solution of t-butyl carbazate (5.62 g, 42.5 mmol) in ethyl acetate (15 mL) was added with stirring benzaldehyde (4.51 g, 42.5 mmol). Crystallization occurred and the resulting slurry was stirred at rt for 45 min. Hexanes (70 mL) was added and the slurry was cooled to 0° C. The slurry was stirred at 0° C. for 60 min, then filtered and rinsed with cold hexanes (20 mL) and dried in vacuo at 40° C. to afford the title compound as a solid (8.34 g, 89.0%): mp 184.1-184.9° C.; $^1$H NMR (DMSO-$d_6$) δ 10.91 (s, 1H), 7.99 (s, 1H), 7.58 (d, 2H, J=3 Hz), 7.39 (m, 3H), 1.45 (s, 9H); $^{13}$C NMR (DMSO-$d_6$) δ 153.0, 143.8, 135.3, 130.0, 129.4, 127.2, 80.1, 28.8; IR (KBr mull) 2983, 1735, 1511, 1157 cm$^{-1}$; A portion was recrystallized (ethyl acetate) for analysis. Anal. Calcd. For $C_{12}H_{16}N_2O_2$: C, 65.43; H, 7.32; N, 12.72. Found: C, 65.16; H, 7.43; N, 12.62.

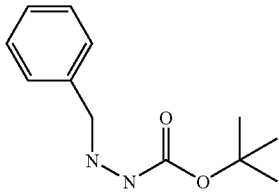

Phenylmethylhydrazinecarboxylic acid, 1,1-dimethylethyl ester

Phenylmethylene-hydrazinecarboxylic acid, 1,1-dimethylethyl ester (7.00 g, 31.8 mmol) and 5% Pt/C (5.32 g) were slurried in THF (70 mL) and stirred and hydrogenated (50 psig) at rt for 3 hr. The slurry was then filtered through celite to remove the catalyst and concentrated in vacuo at 50° C. to afford the title compound as a clear oil (6.36 g, 90.0%): $^1$H NMR (DMSO-d$_6$) δ 8.23 (s, 1H), 7.29 (m, 4H), 7.20 (m, 1H), 4.62 (br s, 1H), 3.85 (s, 2H), 1.37 (s, 9H); $^{13}$C NMR (DMSO-d$_6$) δ 157.1, 139.4, 129.1, 128.7, 127.4, 79.0, 55.1, 28.9; IR (CHCl$_3$) 2982, 1712, 1454, 1273, 1159 cm$^{-1}$; Exact Mass Calcd for $C_{12}H_{21}N_2O_2$: 245.1266. Found: 245.1273.

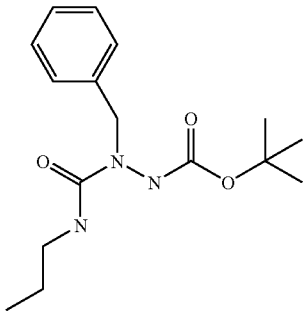

2-(Propylaminocarbonyl)-2-(phenylmethyl)hydrazine carboxylic acid, 1,1-dimethylethyl ester To a solution of phenylmethylhydrazinecarboxylic acid, 1,1-dimethylethyl ester (2.54 g, 11.4 mmol) in isopropanol (25 mL) was added propyl isocyanate (1.51 g, 17.6 mmol) and the solution was stirred at rt for 1 h. The solution was concentrated to a white solid. This solid was dissolved in ethyl acetate (25 mL) and washed with water (25 mL) and 10% aq. NaCl (25 mL), dried (MgSO$_4$), filtered and concentrated to an off-white solid. It was then recrystallized (2:3 ethyl acetate:hexanes) and dried in vacuo to afford the title compound as a white solid (2.53 g, 72.1%): mp 122.8-124.5° C.; $^1$H NMR (DMSO-d$_6$, 60° C.) δ 8.58 (s, 1H), 7.28 (m, 2H), 7.23 (m, 3H), 6.26 (s, 1H), 4.53 (s, 2H), 3.02 (q, 2H, J=7 Hz), 1.41 (quint, 2H, J=7 Hz), 1.35 (s, 9H), 0.83 (t, J=7 Hz); $^{13}$C NMR (DMSO-d$_6$) δ 158.6, 155.0, 138.7, 128.9, 128.8, 127.6, 80.2, 51.5, 42.3, 28.6, 23.7, 11.8 ; IR (CHCl$_3$) 3007, 1745, 1665, 1523 cm$^{-1}$. Anal. Calcd. For $C_{16}H_{25}N_3O_3$: C, 62.52; H, 8.20; N, 13.67. Found: C, 62.28.; H, 8.14; N, 13.51.

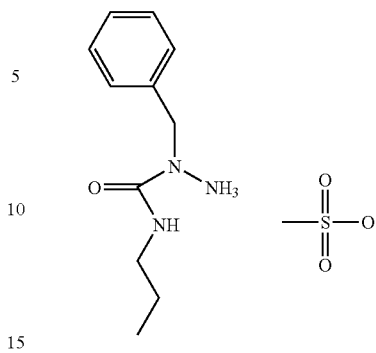

N-Propyl-1-phenylmethylhydrazine carboxamide methanesulfonate 2-(Propylaminocarbonyl)-2-(phenylmethyl)hydrazine carboxylic acid, 1,1-dimethylethyl ester (2.33 g, 7.58 mmol) was dissolved in dichloromethane (25 mL). Methanesulfonic acid (615 μL, 9.48 mmol) was added in one portion and the solution was allowed to stir at rt overnight. The solution was heated to reflux for 8 h, then concentrated to afford the title compound as a crude white solid (2.47 g, 107%): mp 78.1-82.9° C.; $^1$H NMR (DMSO-d$_6$) δ 9.7 (br s, 3H), 7.61 (br s, 1H), 7.38 (t, 1H, J=8 Hz), 7.32 (m, 4H), 4.74 (s, 2H), 3.07 (t, 2H, J=8 Hz), 2.38 (s, 3H), 1.43, (quint, 2H, J=8 Hz), 0.81 (t, 3H, J=8 Hz); $^{13}$C NMR (DMSO-d$_6$) δ 157.5, 135.6, 129.3, 128.7, 128.6, 52.8, 42.7, 40.3, 23.3, 11.9; IR (CHCl$_3$) 3009, 1691, 1543, 1196 cm$^{-1}$; Exact Mass Calcd. For $C_{11}H_{17}N_3O$: 208.1450. Found: 208.1462.

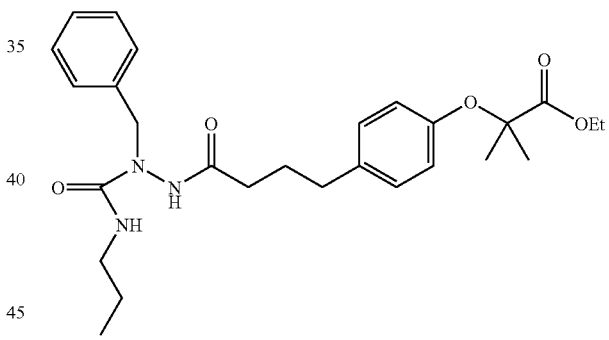

1-[4-[4-(1-Ethoxycarbonyl-1-methylethoxy)phenyl] butyryl]-2-phenylmethyl-4-(propyl)semicarbazide 4-[4-(1-Ethoxycarbonyl-1-methyl-ethoxy)-phenyl] butyric acid (1.50 g, 5.04 mmol) was dissolved in ethyl acetate (10 mL). Oxalyl chloride (524 μL, 6.01 mmol) was added to this solution dropwise in the presence of a catalytic amount of N,N-dimethylformamide (30.1 μL, 0.41 mmol). Completion of acid chloride formation was verified by HPLC. This solution was then concentrated to remove residual oxalyl chloride and the resulting oil was redissolved in ethyl acetate (10 mL). This solution was then added dropwise to a suspension of N-propyl-1-phenylmethylhydrazine carboxamide methanesulfonate (1.52 g, 5.01 mmol) and pyridine (970 μL, 12.6 mmol) in ethyl acetate (15 mL) at 0° C. After stirring at 0° C. for 1 h, the solution was warmed to rt and washed with 1N HCl (2×20 mL) and 5% aq. NaHCO$_3$ (2×20 mL) followed by sat'd aq. NaCl (20 mL). The organic layer was dried (MgSO$_4$), filtered and concentrated to a yellow oil. The oil was purified by column chromatography (SiO₂, 1:1 ethyl acetate:hexanes) to afford the title compound as a clear oil (1.42 g, 59%): ¹H NMR (DMSO-d₆, 60° C.) δ 9.51 (s, 1H), 7.20 (m, 5H), 7.01 (d, 2H, J=8 Hz), 6.71 (t, 1H, J=7 Hz), 4.55 (s, 2H), 4.17 (q, J=7 Hz), 3.00 (q, 2H, J=7 Hz ), 2.45 (t, 2H, J=2Hz ), 2.07 (t, 2H, J=2 Hz), 1.73 (quint, 2H, J=7 Hz), 1.48 (s, 6H), 1.40 (q, 2H, J=7 Hz ), 1.17 (t, 3H, J=7 Hz), 0.81 (t, 3H, J=7 Hz); ¹³C NMR (DMSO-d₆) δ 174. 0, 172.0, 158.2, 153.8, 139.0, 135.8, 129.7, 128.84, 128.79, 127.6, 119.4, 79.2, 61.6, 51.3, 42.3, 34.3, 33.4, 27.1, 25.7, 23.7, 14.6, 11.9 ; IR (CHCl₃) 3009, 1726, 1672, 1143 cm⁻¹; Anal. Calcd. For C₂₇H₃₇N₃O₅: C, 67.05; H, 7.71; N, 8.69. Found: C, 66.65.; H, 7.63; N, 8.57.

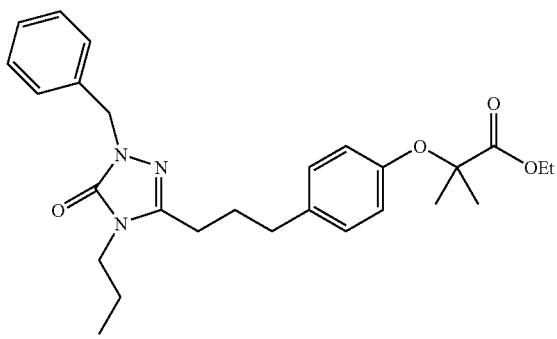

2-{4-[3-(1-Phenylmethyl-5-oxo-4-propyl-4,5-dihydro-1H-[1,2,4]triazol-3-yl)-propyl]-phenoxy}-2-methylpropionic acid ethyl ester 1-[4-[4-(1-Ethoxycarbonyl-1-methyl-ethoxy)phenyl]butyryl]-2-phenylmethyl-4-(propyl) semicarbazide (1.26 g, 2.61 mmol) was dissolved in ethyl acetate (15 mL). Camphorsulfonic acid (670 mg, 2.88 mmol) was added in one portion and the solution was heated to reflux for 1 h. The solution was cooled to rt and washed with sat'd aq. NaHCO3(2×10 mL) followed by 1N HCl (2×10 mL). The organic phase was dried (MgSO4) and concentrated to a clear, colorless oil. The material was purified by plug silica gel filtration (gradient dichloromethane to ethyl acetate) to afford the title compound as a clear, colorless oil (0.86 g, 71%). 1H NMR (DMSO-d6) □ 7.30 (t, 3H, J=7 Hz), 7.24 (d, 1H, J=7 Hz), 7.20 (d, 2H, J=7 Hz ), 7.04 (d, 2H, J=8 Hz), 6.69 (d, 2H, J=8 Hz), 4.13 (q, 2H, J=7 Hz), 3.47 (t, 2H, J=7 Hz), 2.55 (t, 2H, J=7 Hz), 2.48 (t, 2H, J=7 Hz), 1.83 (quint, 2H, J=7 Hz), 1.52, (m, 2H), 1.47 (s, 6H), 1.14 (t, 3H, J=7 Hz), 0.79 (t, 3H, J=7 Hz); 13C NMR (DMSO-d6) □ 174.0, 154.1, 153.8, 146.9, 138.1, 135.6, 129.8, 129.1, 128.0, 119.6, 79.3, 61.6, 48.5, 42.8, 34.0, 27.8, 25.7, 24.8, 22.5, 14.5, 11.5; IR (CHCl13) 2878, 1692, 1509, 1143 cm-1; Anal. Calcd. For C27H35N3O4: C, 69.65; H, 7.58; N, 9.03. Found: C, 69.28; H, 7.96; N, 8.84.

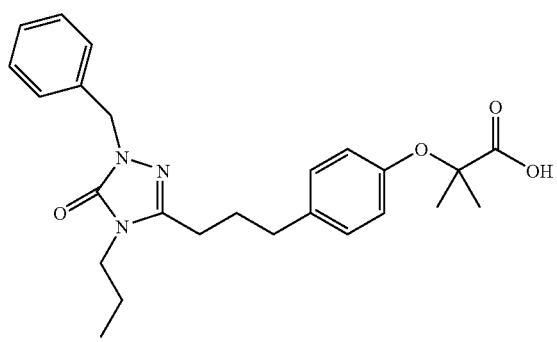

2-(4-{3-[1-(Phenylmethyl)-5-oxo-4,5-dihydro-1H-[1,2,4]triazol-3-yl]-propyl}-phenoxy)-2-methylpropionic acid 2-(4-{3-[1-(Phenylmethyl)-5-oxo-4,5-dihydro-1H-[1,2,4]triazol-3-yl]-propyl}-phenoxy)-2-methylpropionic acid ethyl ester (557 mg, 1.20 mmol) was dissolved in ethanol (5 mL) and 1N aq. NaOH (3.6 mL, 3.6 mmol) was added in one portion and the solution was stirred at room temperature for 16 h. The solution was then concentrated to a hazy colorless oil. This oil was diluted with water (5 mL) and washed with t-butyl methyl ether (5 mL). The pH of the aqueous layer was adjusted to <1with conc. HCl and the aqueous was extracted with ethyl acetate (10 mL, then 5 mL). This solution was washed with 1 N aqueous HCl (5 mL) and sat'd aq. NaCl (5 mL), dried (MgSO₄), and concentrated in vacuo to afford the title compound as a clear colorless oil (442 mg, 84.5%). ¹H NMR (DMSO-d₆) δ 12.9 (br s, 1H), 7.30 (t, 2H, J=7 Hz), 7.25 (d, 1H, J=7 Hz), 7.20 (d, 2H, J=7 Hz), 7.04 (d, 2H J=8 Hz), 6.72 (d, 2H, J=8 Hz), 4.83 (s, 2H), 3.47 (t, 2H, J=7 Hz), 2.54 (t, 2H, J=8 Hz), 2.49 (t, 2H, J=8 Hz), 1.83 (quint, 2H, J=7 Hz), 1.53, (m, 2H), 1.46 (s, 6H), 0.80 (t, 3H, J=7 Hz); ¹³C NMR (DMSO-d₆) δ 175.8, 154.1, 146.0, 138.1, 135.2, 129.7, 129.2, 128.0, 119.3, 79.0, 48.5, 42.8, 34.0, 27.9, 25.7, 24.8, 22.5, 11.5; IR (CHCl₃) 2938, 1509, 1468, 1233, 1155 cm⁻¹; Anal. Calcd. For C₂₅H₃₁N₃O₄: C, 68.63; H, 7.14; N, 9.60. Found: C, 68.24; H, 6.95; N, 9.40.

Example 127

Step A

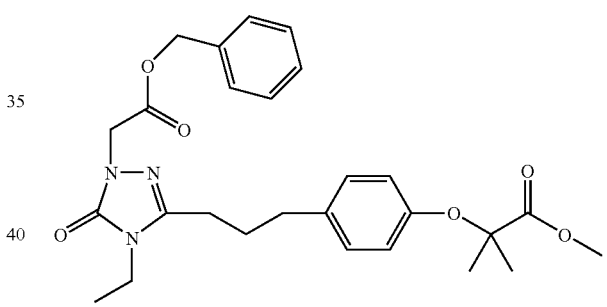

The N-4ethyl triazolinone (1 g, 0.003 mol) was combined with benzyl bromoacetate (0.089 ml, 0.0056 mol) and powdered K₂CO₃ (1.99 g, 0.014 mol) in DMF (28 ml) and stirred at 67° C. overnight. Ether was added to the reaction mixture and the solution was extracted with water. Purification by flash chromatography (2:1 hexanes: ethyl acetate) gave the desired amide.

C₂₇H₃₃N₃O₆ (MW=495.65); mass spectroscopy (MH⁺)= 496.2

Step B

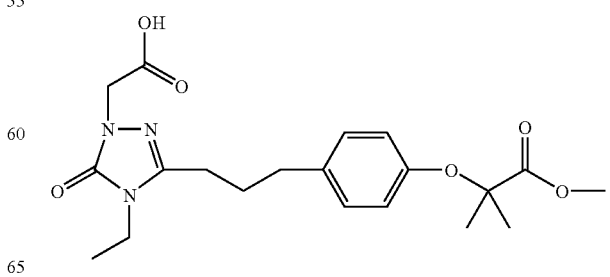

The amide from Step A (1.28 g, 0.0026 mol) was dissolved in ethyl acetate (20 ml) and purged with nitrogen.

Palladium catalyst (0.128 g, 10%) was added to the solution. The reaction mixture was purged again. Hydrogen gas was released across the system and the reaction was stirred overnight. The reaction mixture was filtered and the filtrate was concentrated. The resulting residue was carried forth without further purification.

$C_{20}H_{27}N_3O_6$ (MW=405.45); mass spectroscopy (MH$^+$)= 406.3

Step C

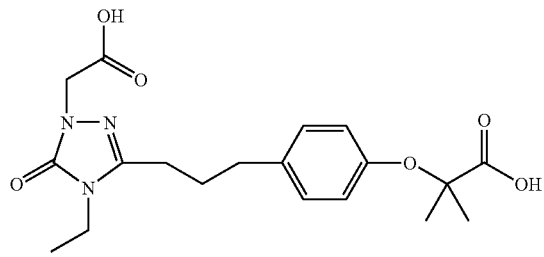

The ester from Step B (0.200 g, 0.00049 mol) was dissolved in ethanol (6 ml) and treated with 2N NaOH (3 ml). The solution was refluxed for one hour. Water was added to the mixture and the layer was extracted with ether. The aqueous layer was acidified with 1N HCl and extracted with ethyl acetate. The organic layer was washed with brine, dried over Na$_2$SO$_4$ then concentrated to yield the desired product as a white foam.

$C_{19}H_{25}N_3O_6$ (MW=391.43); mass spectroscopy (MH$^+$)= 392.3

Example 128

Step A

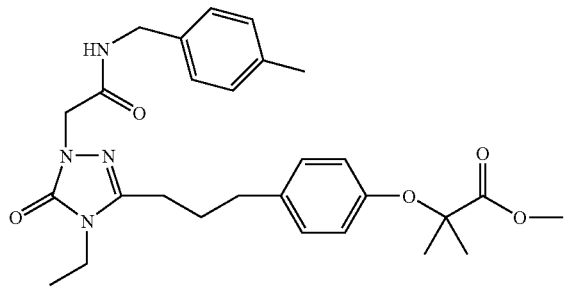

A THF solution of the acid described in Example 127, Step B (0.190 g, 0.00047 mol) was treated with EDC (0.134 g, 0.0007 mol) and HOAt (0.064 g, 0.0047 mol). An equivalent of 4-methyl benzyl amine (0.060 ml, 0.00047 mol) was added and the reaction was stirred overnight. The solvent was concentrated and the residue was redissolved in methylene chloride and extracted with water. Purification by flash chromatography (100% ethyl acetate) gave the desired amide.

$C_{28}H_{36}N_4O_5$ (MW=508.62); mass spectroscopy (MH$^+$)= 509.4

Step B

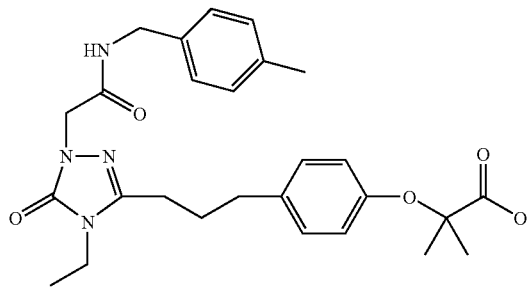

The amide from Step A (0.150 g, 0.00029 mol) was dissolved in dioxane (3 ml) and water (3 ml) then treated with LiOH (0.007 g, 0.00029 mol). The reaction was stirred for two hours. Water was added to the mixture and the layer was extracted with ether. The aqueous layer was acidified with 1N HCl and extracted with ethyl acetate. The organic layer was washed with brine, dried over Na$_2$SO$_4$ then concentrated to yield the desired product as a white foam.

$C_{27}H_{34}N_4O_5$ (MW=494.60); mass spectroscopy (MH$^+$)= 495.4

Example 129

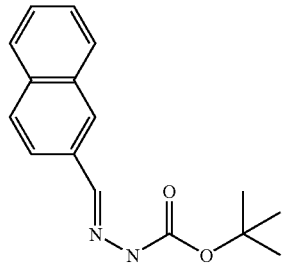

(Naphthalen-2-yl)methylenehydrazinecarboxylic acid, 1,1-dimethylethyl ester

To a solution of t-butyl carbazate (7.59 g, 57.4 mmol) in ethyl acetate (22 mL) was added with stirring 2-napthaldehyde (8.98 g, 57.5 mmol). This clear yellow solution was stirred at rt for 15 min. Hexanes (105 mL) was added dropwise and solids precipitated from solution. The slurry was cooled to 0° C., the solids were then filtered and rinsed with cold hexanes (20 mL). A second crop of solids was obtained from the filtrate, filtered and combined with the first crop. The combined solids were recrystallized (EtOAc) and filtered. A second crop was collected by concentrating the filtrate to half its original volume and filtering the resulting solids at 0° C. The two crops of solids were combined and dried in vacuo at 40° C. to afford the title compound as a solid (13.17 g, 85.0%): mp 182.1-190° C. (dec.); $^1$H NMR (DMSO-d$_6$) δ 11.04 (s, 1H), 8.17 (s, 1H), 7.99 (s, 1H), 7.93-7.86 (m, 4H), 7.52-7.49 (m, 2H), 1.47 (s, 9H); $^{13}$C N (DMSO-d$_6$) δ 153.1, 143.9, 134.1, 133.6, 133.1, 129.1, 128.9, 128.5, 128.4, 127.5, 127.3, 123.1, 80.1, 28.8; IR (CHCl$_3$) 3061, 3010, 2982, 1733, 1505, 1369 cm$^{-1}$; Anal. Calcd. for $C_{16}H_{18}N_2O_2$: C, 71.09; H, 6.71; N, 10.36. Found: C, 70.95; H, 6.89; N, 10.31.

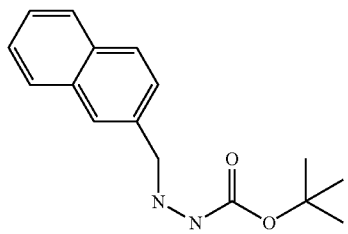

(Naphthalen-2-yl)methylhydrazinecarboxylic acid,
1,1-dimethylethyl ester (Naphthalen-2-yl)methylenehydrazinecarboxylic acid, 1,1-dimethylethyl ester (7.08 g, 26.2 mmol) and 5% Pt/C (7.11 g) were slurried in THF (70 mL) and hydrogenated at 50 psig at rt for 4 hr. A second charge of 5% Pt/C (1.78 g) was added and hydrogenation continued for 16 h. The slurry was then filtered through celite to remove the catalyst and concentrated in vacuo at 50° C. to afford the title compound as a clear oil (7.01 g, 98.3%): $^1$H NMR (DMSO-$d_6$) δ 8.27 (s, 1H), 7.83 (m, 4H), 7.48 (m, 3H), 6.97 (m, 1H), 4.88 (s, 1H), 4.04 (s, 2H), 1.37 (s, 9H); $^{13}$C NMR (DMSO-$d_6$) δ 137.1, 133.6, 132.9, 128.2, 128.1, 127.7, 127.3, 126.6, 126.4, 126.2, 79.0, 55.1, 28.9, 23.5; IR (CHCl$_3$) 3445, 1711, 1454, 1393, 1331 cm$^{-1}$; Exact Mass Calcd for $C_{16}H_{20}N_2O_2$: 295.1422. Found: 295.1414.

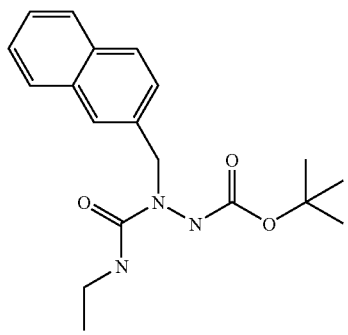

2-(Ethylaminocarbonyl)-2-(Naphthalen-2-yl)methyl-
hydrazine carboxylic acid, 1,1-dimethylethyl ester (Naphthalen-2-yl)methyl-hydrazinecarboxylic acid, 1,1-dimethylethyl ester (2.84 g, 10.4 mmol) was dissolved in isopropanol (30 mL). Ethyl isocyanate (1.23 mL, 15.6 mmol) was added in one portion and the solution was stirred at rt for 1 h, then concentrated to a yellow oil. Column chomatography (SiO$_2$, 2:3 EtOAc: hexanes) afforded the title compound as a clear, colorless oil (2.66 g, 55%): $^1$H NMR (DMSO-$d_6$, 60° C.) δ 8.60 (s, 1H), 7.8 (m, 3H), 7.72, (s, 1H), 7.4 (m, 3H), 6.37 (s, 1H), 4.71 (s, 2H), 3.11 (quint, 2H, J=6 Hz), 1.32 (s, 9H), 1.04 (t, 3H, J=7 Hz); $^{13}$C NMR (DMSO-$d_6$) δ 158.6, 155.0, 136.2, 133.5, 133.0, 129.3, 128.2, 128.1, 127.5, 126.7, 126.3, 60.4, 35.4, 28.6, 16.3, 14.7; IR (CHCl$_3$) 3453, 2983, 1664, 1370, 1156 cm$^{-1}$; Exact Mass Calcd for $C_{19}H_{25}N_3O_3$: 366.1794. Found: 366.1797.

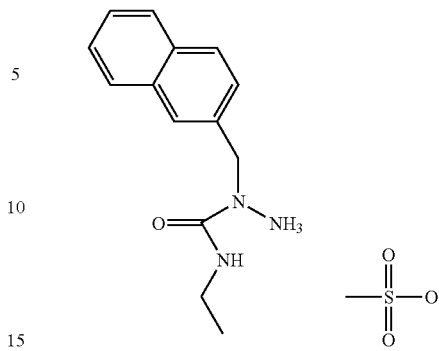

N-Ethyl-2-(naphthalen-2-yl)methylhydrazine
carboxamide methanesulfonate 2-(Ethylaminocarbonyl)-2-(naphthalen-2-yl)methylhydrazine carboxylic acid, 1,1-dimethylethyl ester (2.52 g, 7.34 mmol) was dissolved in dichloromethane (25 mL). Methanesulfonic acid (524 µL, 8.07 mmol) was added in one portion and the solution was stirred at rt overnight. The solution was then heated to reflux for 8 h, then concentrated to afford the title compound as a white amorphous solid (2.49 g, 96%): m. p. 46.2-48.1° C.; $^1$H NMR (DMSO-$d_6$) δ 9.7 (br s, 3H), 7.9 (m, 3H), 7.82, s, 1H, 7.61 (br s, 1H), 7.52 (m, 2H,), 7.44 (d, 1H, J=7 Hz), 3.18 (quint, 2H, J=8 Hz), 2.38 (s, 3H), 1.07 (t, 3H, J=7 Hz); $^{13}$C NMR (DMSO-$d_6$) δ 157.5, 133.4, 133.3, 133.1, 129.0, 128.5, 128.3, 127.7, 127.1, 126.9, 126.7, 53.2, 40.4, 35.9, 15.8; IR (CHCl$_3$) 3415, 2939, 1543, 1191, 1043 cm$^{-1}$; Exact Mass Calcd. for $C_{14}H_{17}N_3O$: 244.1450. Found: 244.1460.

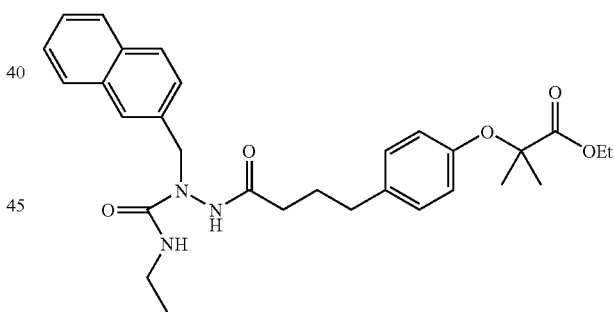

1-[4-[4-(1-Ethoxycarbonyl-1-methylethoxy)phenyl]
butyryl]-2-(naphthalen-2-yl)methyl-4-(propyl)semi-
carbazide 4-[4-(1-Ethoxycarbonyl-1-methyl-ethoxy)-phenyl] butyric acid (1.35 g, 4.59 mmol) was dissolved in ethyl acetate (10 mL). Oxalyl chloride (425 µL, 4.86 mmol) was added to this solution dropwise in the presence of a catalytic amount of N,N-dimethylformamide (25 µL, 0.34 mmol). Completion of acid chloride formation was verified by HPLC. This solution was then concentrated to remove residual oxalyl chloride and the resulting oil dissolved in ethyl acetate (10 mL). This solution was then added dropwise to a suspension of N-ethyl-2-(naphthalen-2-yl)methylhydrazine carboxamide methanesulfonate (1.50 g, 4.42 mmol) and pyridine (895 µL, 11.1 mmol) in ethyl acetate (15 mL) at 0° C. After stirring at 0° C. for 4 h, the solution was warmed to rt and washed with 1N HCl (2×25 mL) and 5% aq. NaHCO₃ (2×25 mL) followed by sat'd aq. NaCl (25 mL). The organic layer was dried (MgSO₄), filtered and concentrated to a yellow oil, which was purified by column chromatography (SiO₂, 7:3 ethyl acetate: hexanes) to afford the title compound as an oil (1.59 g, 69%): ¹H NMR (DMSO-d₆, 60° C.) □ 9.51 (s, 1H), 7.85 (m, 3H), 7.70 (s, 1H), 7.42 (m, 3H), 6.94 (d, 2H, J=7 Hz), 6.67 (d, 2H, J=7 Hz), 6.38 (s, 1H), 4.72 (s, 2H), 4.16 (q, J=7 Hz), 3.08 (t, 2H, J=7 Hz ), 2.41 (t, 2H, J=8 Hz ), 2.07 (t, 2H, J=8 Hz), 1.72 (quint, 2H, J=7 Hz), 1.47 (s, 6H), 1.17 (t, 3H, J=7 Hz), 1.01 (t, 3H, J=7 Hz); ¹³C NM (DNSO-d₆) □ 174.0, 172.1, 158.2, 153.7, 136.4, 135.8, 133.5, 133.0, 129.7, 128.4, 128.2, 128.1, 127.4, 126.7, 126.3, 119.4, 79.2, 61.6, 51.3, 35.4, 34.3, 33.5, 27.2, 25.7, 16.3, 14.6; IR (CHCl₃) 3454, 2938, 1727, 1670, 1509, 1233, 1142 cm⁻¹; Anal. Calcd. for C₃₀H₃₇N₃O₅: C, 69.34; H, 7.18; N, 8.09. Found: C, 69.19; H, 7.49; N, 7.93.

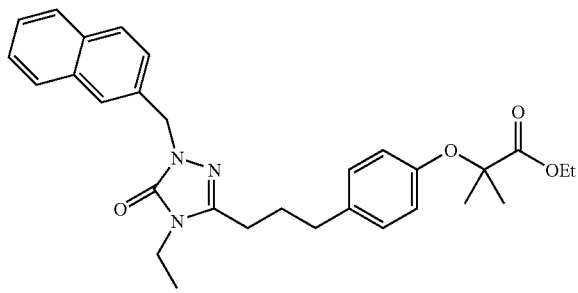

2-{4-[3-(4-Ethyl-1-(naphthalen-2-yl)methyl-5-oxo-4,5-dihydro-1H-[1,2,4]triazol-3-yl)-propyl]-phenoxy}-2-methylpropionic acid ethyl ester 1-[4-[4-(1-Ethoxycarbonyl-1-methylethoxy)phenyl]butyryl]-2-(naphthalen-2-yl)methyl-4-(propyl)semicarbazide (1.30 g, 2.51 mmol) was dissolved in ethyl acetate (15 mL). Camphorsulfonic acid (0.645 g, 2.78 mmol) was added in one portion and the solution was heated to reflux for 4 h. The solution was cooled to rt and washed with sat'd aq. NaHCO₃ (2×20 mL) followed by 1N HCl (2×20 mL). The organic was dried (MgSO₄) and concentrated to afford the title compound as a clear, colorless oil (1.23 g, 98%). ¹H NMR (DMSO-d₆) □ 7.85 (t, 3H, J=8 Hz), 7.73 (s, 1H), 7.48 (quint, 2H, J=4 Hz), 7.38 (d, 1H, J=8 Hz), 7.02 (d, 2H, J=8 Hz), 6.66 (d, 2H, J=8 Hz), 4.99 (s, 2H), 4.13 (q, 2H, J=7 Hz), 3.57 (q, 2H, J=8 Hz), 2.53 (m, 4H), 1.82 (quint, 2H, J=7 Hz), 1.46 (s, 6H), 1.13 (m, 6H); ¹³C NMR (DMSO-d₆) □ 174.0, 154.0, 146.7, 135.6, 135.5, 133.5, 132.9, 129.7, 128.9, 128.3, 128.2, 127.0, 126.8, 126.4, 119.5, 79.2, 61.6, 48.7, 36.4, 34.0, 27.9, 25.7, 24.8, 14.9, 14.5; IR (CHCl₃) 2940, 1729, 1693, 1509, 1233, 1179, 1142 cm⁻¹; Anal. Calcd. for C₃₀H₃₅N₃O₄: C, 71.83; H, 7.03; N, 8.38. Found: C, 71.64; H, 7.12; N, 8.19.

2-{4-[3-(4-Ethyl-1-(naphthal n-2-yl)methyl-5-oxo-4,5-dihydro-1H-[1,2,4]triazol-3-yl)-propyl]-phenoxy}-2-methylpropionic acid 2-{4-[3-(4-Ethyl-1-(naphthalen-2-yl)-methyl-5-oxo-4,5-dihydro-1H-[1,2,4]triazol-3-yl)-propyl]-phenoxy}-2-methylpropionic acid ethyl ester (725 mg, 1.45 mmol) was dissolved in ethanol (10 mL) and 1N NaOH (4.3 mL, 4.3 mmol) was added in one portion and the solution was stirred at room temperature for 1 h. The solution was then concentrated to an oil, which was washed with t-butyl methyl ether (5 mL). The pH of the aqueous phase was adjusted to <1 with conc. HCl, and extracted with ethyl acetate (2×10 mL). The combined extracts dried (MgSO₄), filtered and concentrated to afford the title compound as a clear yellow oil (0.570 g, 83%). ¹H NMR (DMSO-d₆) δ 12.9 (br s, 1H), 7.86 (t, 2H, J=8 Hz), 7.73 (s, 1H), 7.48 (quint, 2H, J=4 Hz), 7.38 (d, 1H), 7.01 (d, 2H, J=7 Hz), 6.69 (d, 2H, J=7 Hz), 4.99 (s, 2H), 3.57 (quint, 2H, J=7 Hz), 2.52 (t, 2H, J=8 Hz), 1.82 (quint, 2H, J=7 Hz), 1.45 (s, 6H), 1.12 (t, 3H, J=7 Hz); ¹³C NMR (DMSO-d₆) δ 175.8, 154.1, 154.0, 146.8, 135.6, 135.2, 133.5, 132.9, 129.7, 128.9, 128.3, 128.2, 127.0, 126.8, 126.7, 126.4, 119.2, 79.0, 48.7, 36.4, 34.0, 27.9, 25.7, 24.8, 14.9; IR (CHCl₃) 2940, 1693, 1509, 1469, 1156 cm⁻¹; Exact Mass Calcd. for C₂₈H₃₁N₃O₄: 474.2393. Found: 474.2393.

Example 130

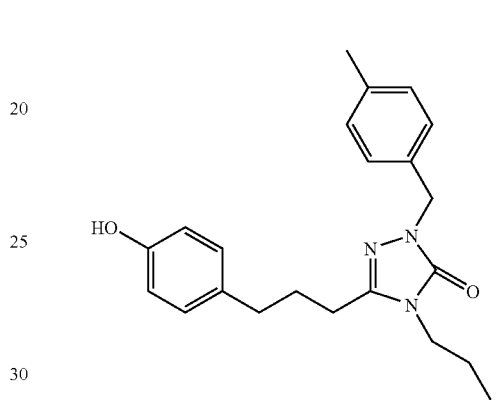

5-[3-(4-hydroxy-phenyl)-propyl]-2-(4-methyl-benzyl)-4-propyl-2,4-dihydro-[1,2,4]-triazol-3-one 1-[(4-Methoxyphenyl)butyryl]-2-(4-methylphenylmethyl)-4-propyl)semi-carbazide (0.312 g, 0.785 mmol) and excess pyridine hydrochloride were melted together with stirring at 180° C. for 1 h. After cooling to room temperature, the contents were diluted with ethyl acetate (25 mL) and 5 N HCl (25 mL). The organic layer was washed with additional 5 N HCl (25 mL) followed by sat'd aq. NaHCO₃ (2×25 mL). The organic layer was then washed with sat'd aq. NaCl (25 mL), dried (MgSO₄), filtered, and concentrated to afford the title compound as a yellow oil (0.201 g, 0.55 mmol, 70%). Spectral data in accord with previous example. Exact Mass Calc'd. for C₂₂H₂₈N₃O₃ (M+H)⁺: 366.2182. Found: 366.2192.

Example 131

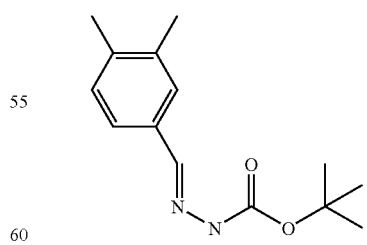

(3,4-dimethylphenyl)methylenehydrazinecarboxylic acid, 1,1-dimethylethyl ester

To a solution of t-butyl carbazate (5.06 g, 38.3 mmol) in ethyl acetate (15 mL) was added with stirring 3,4-dimethylbenzaldehyde (5.20 mL, 5.26 g, 39.2 mmol). Crystallization occurred and the resulting slurry was stirred at rt for 45 min. Hexanes (70 mL) was added and the slurry was cooled to 0° C. The slurry was stirred at 0° C. for 60 min, then filtered and rinsed with cold hexanes (20 mL), and dried in vacuo at 40° C. to afford the title compound as a solid (8.76 g, 92.1%): mp 167.7-168.6° C. $^1$H NMR (DMSO-$d_6$) δ 10.82 (s, 1H), 7.92 (s, 1H), 7.36 (s, 1H), 7.28 (d, 2H, J=3 Hz), 7.14 (d, 2H, J=3 Hz), 2.206 (s, 3H), 2.20 (s, 3H) 1.44 (s, 9H); $^{13}$C NMR (DMSO-$d_6$) δ 153.0, 144.1, 138.5, 137.3, 132.9, 130.5, 128.1, 124.8, 79.9, 28.8, 19.99, 19.97; IR (KBr mull) 3361, 3009, 2981, 2981, 1513, 1495 cm$^{-1}$. A portion was further purified by recrystallization from ethyl acetate for analysis. Anal. Calcd. for $C_{14}H_{20}N_2O_2$: C, 67.71; H, 8.12; N, 11.28. Found: C, 67.51; H, 8.07; N, 11.22.

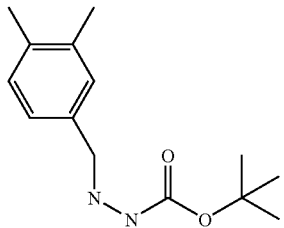

(3,4-dimethylbenzyl)hydrazinecarboxylic acid, 1,1-dimethylethyl ester (3,4-dimethylphenyl) methylenehydrazinecarboxilic acid, 1,1-dimethylethyl ester (7.02 g, 28.3 mmol) and 5% Pt/C (5.04 g) were slurried in THF (70 mL) and hydrogenated at 50 psi at rt for 4 hr. The slurry was then filtered through celite and concentrated in vacuo at 50° C. to afford the title compound as a clear oil (6.74 g, 95.2%): $^1$H NMR (DMSO-$d_6$, 20° C.) δ 8.20 (s, 1H), 7.06 (s, 1H), 7.01 (dd, 2H, J=8, 2 Hz ), 4.56 (s, 1H), 3.77 (s, 2H), 2.18 (s, 6H), 1.38 (s, 9H); $^{13}$C NMR (DMSO-$d_6$) δ 157.1, 136.5, 136.3, 135.2, 130.4, 129.8, 126.5, 78.9, 54.9, 28.9, 20.0, 19.7; IR (CHCl$_3$) 2982, 1712, 1453, 1369 cm$^{-1}$; Exact Mass Calcd. for $C_{14}H_{22}N_2O_2$: 251.1759. Found: 251.1757.

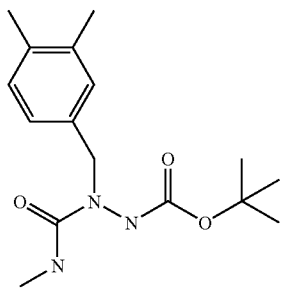

2-(Methylaminocarbonyl)-2-(3,4-dimethylphenylmethyl)hydrazine carboxylic acid, 1,1-dimethylethyl ester (3,4-Dimethylphenylmethyl)hydrazine carboxylic acid, 1,1-dimethylethyl ester (2.51 g, 10.0 mmol) was dissolved in isopropanol (25 mL). Methyl isocyanate (1.0 mL, 16.7 mmol) was added in one portion via syringe and the solution was allowed to stir at ambient temperature for 1 h. The solution was concentrated to afford the title compound as a white solid (3.30 g of 87% potency material by $^1$H-NMR, 2.86 g, 93%): mp 99.7-104.9° C.; $^1$H NMR (DMSO-$d_6$, 60° C.) δ 8.45 (s, 1H), 7.03 (d, 1H, J=8 Hz), 6.99 (s, 1H), 6.93 (d, 1H), 6.26 (s, 1H), 4.45 (s, 2H), 2.60 (d, 3H, J=7 Hz), 2.18 (s, 6H), 1.35 (s, 9H); $^{13}$C NMR (DMSO-$d_6$, 20° C.) δ 159.0, 155.0, 136.3, 135.7, 135.3, 130.3, 129.9, 126.6, 80.1, 50.8, 28.7, 27.7, 20.1, 19.7; IR (CHCl$_3$) 3466, 1681, 1528, 1247, 1155 cm$^{-1}$. A portion was recrystallized for elemental analysis: Anal. Calcd. for $C_{16}H_{25}N_3O_3$: C, 62.52.; H, 8.20; N, 13.67. Found: C, 62.87; H, 8.15; N, 13.59.

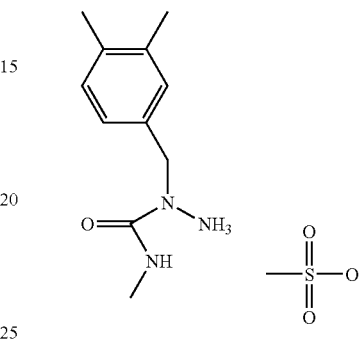

N-Methyl-1-(3,4-dimethylphenylmethyl)hydrazine carboxamide methanesulfonate 2-(Methylaminocarbonyl)-2-(3,4-dimethylphenylmethyl) hydrazine carboxylic acid, 1,1-dimethylethyl ester (2.52 g, 8.20 mmol) was dissolved in dichloromethane (25 mL). Methanesulfonic acid (717 μL, 11.04 mmol) was added in one portion and the solution was allowed to stir at rt for 4 h. An additional charge of methanesulfonic acid (132 μL, 2.0 mmol) was added and the solution stirred at rt for 12 h. The resulting slurry was cooled to 0° C., filtered, and the solids rinsed with cold dichloromethane. The solids were dried in vacuo at 40° C. overnight to afford a white solid (1.44 g). The filtrate was concentrated and purified by recrystallization (ethyl acetate) to afford an additional amount of white solid (0.73 g). The two crops were combined and homogenized to afford the title compound as a white solid (2.17 g, 87%): m.p. 124.3-125.6° C.; $^1$H NMR (DMSO-$d_6$) δ 9.4 (broad s, 3H), 7.45 (broad s, 1H), 7.10 (d, 1H, J=8 Hz), 7.05 (s, 1H), 7.00 (d, 1H, J=8 Hz), 4.61 (s, 2H), 2.67 (s, 3H), 2.36 (s, 3H), 2.19 (s, 6H); $^{13}$C NMR (DMSO-$d_6$) δ 158.2, 137.0, 136.7, 132.8, 130.4, 129.9, 126.2, 52.7, 40.4, 27.7, 20.2, 19.7; IR (CHCl$_3$) 3004, 2946, 1693, 1505, 1171 cm$^{-1}$; Anal. Calcd. for $C_{12}H_{21}N_3O_5$: C, 47.51.; H, 6.98; N, 13.85. Found: C, 47.30; H, 7.01; N, 13.51.

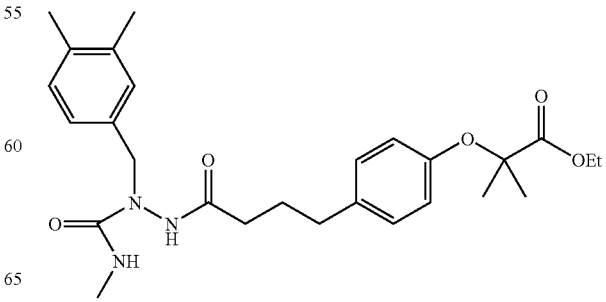

1-[4-[4-(1-Ethoxycarbonyl-1-methylethoxy)phenyl]butyryl]-2-(3,4-dimethylphenyl-methyl)-4-methylsemicarbazide 4-[4-(1-Ethoxycarbonyl-1-methyl-ethoxy)-phenyl]butyric acid (1.46 g, 4.96 mmol) was dissolved in ethyl acetate (10 mL). Oxalyl chloride (474 µL, 5.46 mmol) was added to this solution dropwise in the presence of a catalytic amount of N,N-dimethylformamide (30.6 µL, 0.39 mmol). Completion of acid chloride formation was verified by HPLC. This solution was then added dropwise to a suspension of N-Methyl-1-(3,4-dimethylphenylmethyl)hydrazine carboxamide methanesulfonate (1.50 g, 4.95 mmol) and pyridine (1.00 µL, 12.9 mmol) in ethyl acetate (15 mL) at 0° C. After stirring at 0° C. for 6 h, the solution was warmed to rt and washed with 1N HCl (2×20 mL), 5% aq. NaHCO$_3$ (2×20 mL) and sat'd aq. NaCl. The organic layer was dried (MgSO$_4$), filtered and concentrated to a yellow oil. The oil was purified by column chromatography (SiO$_2$, 9:1 ethyl acetate:hexanes), to afford the title compound as a clear oil (1.48 g, 62%): $^1$H NMR (DMSO-d$_6$, 60° C.) δ 9.42 (s, 1H), 6.97 (m, 5H), 6.71 (d, 2H, J=8 Hz), 6.23 (s, 1H), 4.46 (s, 2H), 4.15 (q, J=7 Hz), 2.59 (s, 3H), 2.43 (t, 2H, J=8 Hz ), 2.15 (s, 6H), 2.06 (t, 2H, J=8 Hz ), 1.70 (quint, 2H, J=7 Hz), 1.48 (s, 6H), 1.17 (t, 3H, J=7 Hz); $^{13}$C NMR (DMSO-d$_6$) δ 174.0, 172.0, 158.7, 153.8, 136.4, 136.0, 135.9, 135.4, 130.2, 129.9, 129.7, 126.5, 119.5, 79.2, 61.6, 50.6, 34.4, 33.5, 27.6, 27.2, 25.7, 20.0, 19.7, 14.6; IR (CHCl$_3$) 3009, 1669, 1509, 1142 cm$^{-1}$; Exact Mass Calcd. for C$_{27}$H$_{38}$N$_3$O$_5$: 484.2811. Found: 484.2822.

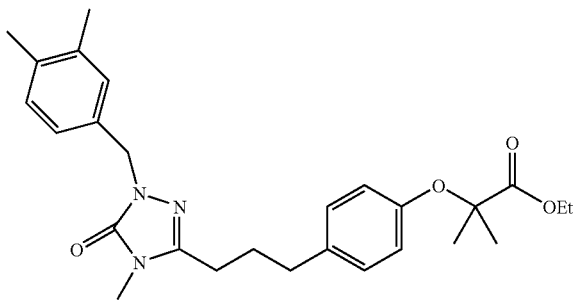

2-(4-{3-[1-(3,4-Dimethylphenylmethyl)-5-oxo-4,5-dihydro-1H-[1,2,4]triazol-3-yl]-propyl}-phenoxy)-2-methyl-propionic acid ethyl ester 1-[4-[4-(1-Ethoxycarbonyl-1-methylethoxy)phenyl]butyryl]-2-(3,4-dimethylphenylmethyl)-4-methylsemicarbazide (1.20 g, 2.47 mmol) was dissolved in ethyl acetate (10 mL). Camphorsulfonic acid (0.64 g, 2.72 mmol) was added in one portion and the solution was heated to reflux for 1 h. The solution was cooled to rt and washed with sat'd aq. NaHCO$_3$ (2×8 mL) followed by 1H HCl (2×8 mL ). The organic phase was dried (MgSO$_4$) and concentrated to afford the title compound as a clear, colorless oil (1.08 g, 94%). $^1$H NMR (DMSO-d$_6$) δ 7.04 (m, 3H), 7.03 (s, 1H), 6.93 (d, 1H, J=2 Hz), 6.68 (d, 2H, J=7 Hz), 4.72 (s, 2H), 4.13 (q, 2H, J=7 Hz), 3.08 (s, 3H), 2.53 (t, 2H, J=8 Hz), 2.47 (t, 2H, J=8 Hz), 1.80 (quint, 2H, J=7 Hz), 1.47 (s, 6H), 1.14 (t, 3H, J=7 Hz); $^{13}$C NMR (DMSO-d$_6$) δ 174.0, 154.1, 147.1, 136.8, 135.9, 135.6, 135.3, 130.1, 129.8, 129.4, 125.7, 119.5, 79.2, 61.6, 48.4, 34.1, 27.7, 27.6, 25.7, 25.0, 20.0, 19.7, 14.6; IR (CHCl$_3$) 2941, 1729, 1509, 1238, 1143 cm$^{-1}$; Anal. Calcd. for C$_{27}$H$_{35}$N$_3$O$_4$: C, 69.65; H, 7.58; N, 9.03. Found: C, 69.25; H, 7.47; N, 8.88.

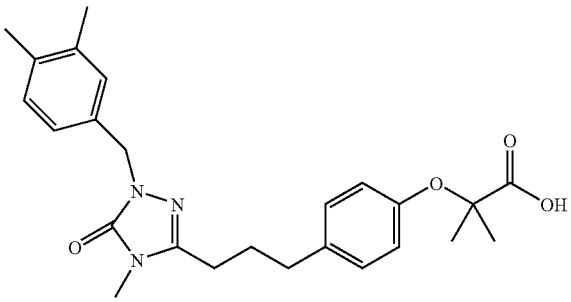

2-(4-{3-[1-(3,4-Dimethylphenylmethyl)-5-oxo-4,5-dihydro-1H-[1,2,4]triazol-3-yl]-propyl}-phenoxy)-2-methylpropionic acid 2-(4-{3-[1-(3,4-Dimethylphenylmethyl)-5-oxo-4,5-dihydro-1H-[1,2,4]triazol-3-yl]-propyl}-phenoxy)-2-methylpropionic acid ethyl ester (916 mg, 1.97 mmol) was dissolved in ethanol (10 mL) and 2N NaOH (3.0 mL, 6.0 mmol) was added in one portion. The solution was stirred at room temperature for one hour, then concentrated to a hazy colorless oil. This oil was partitioned between 1N HCl (10 mL) and ethyl acetate (10 mL). The aqueous layer was then reextracted with ethyl acetate (10 mL). Solids precipitated from this solution on stirring. The slurry was cooled to 0° C., filtered and dried in vacuo at 50° C. overnight to afford the title compound as a white solid (695 mg, 80%): mp 145.8-149.6° C.; $^1$H-NMR (DMSO-d$_6$) δ 12.98 (s, 1H), 7.05 (dd, 3H, J=8.5, 3.0 Hz), 7.00 (s, 1H), 6.93 (d, 1H, J=7.5 Hz), 6.73 (d, 2H, J=8.5 Hz), 4.73 (s, 2H), 2.52 (t, 2H, J=7.5 Hz), 2.47 (t, 2H, J=7.5 Hz), 2.14 (s, 6H), 1.80 (quint, 2H, J=7.5 Hz), 1.46 (s, 6H); $^{13}$C NMR (DMSO-d$_6$, 20° C.) δ 175.8, 154.1, 154.0, 147.1, 136.8, 135.9, 135.3, 135.2, 130.1, 129.7, 129.4, 125.7, 119.2, 78.9, 48.4, 34.1, 27.7, 27.6, 25.7, 25.1, 20.0, 19.7; IR (CHCl$_3$) 2936, 2490, 1730, 1658, 1510, 1148 cm$^{-1}$; Anal. Calcd. for C$_{25}$H$_{31}$N$_3$O$_4$: C, 68.63; H, 7.14; N, 9.60. Found: C, 68.23; H, 7.01; N, 9.44.

Example 132

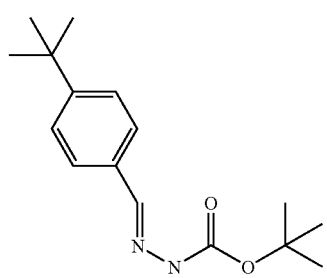

(4-t-Butyl)methylenehydrazinecarboxylic acid, 1,1-dimethylethyl ester

To a solution of t-butyl carbazate (5.02 g, 37.9 mmol) in ethyl acetate (15 mL) was added with stirring 4-t-butylbenzaldehyde (6.40 mL, 6.21 g, 37.9 mmol). Crystallization occurred and the resulting slurry was stirred at rt for 15 min. Hexanes (30 mL) was added and the slurry was cooled to 0° C. The slurry was stirred at 0° C. for 30 min, filtered and rinsed with cold hexanes (20 mL), then dried in vacuo at 40° C. to afford the title compound as a solid (9.27 g, 88.3%): mp 173.7-175.7° C. (dec.); $^1$H NMR (DMSO-$d_6$) δ 10.85 (s, 1H), 7.96 (s, 1H), 7.63 (s, 1H), 7.50 (d, 2H, J=3 Hz), 7.40 (d, 2H, J=3 Hz), 1.45 (s, 9H), 1.25 (s, 9H); $^{13}$C NMR (DMSO-$d_6$) δ 152.7, 143.8, 132.6, 127.0, 126.2, 80.0, 39.7, 35.2, 31.7, 28.8; IR (KBr mull) 3361, 3010, 2968, 1514, 1500 cm$^{-1}$; A portion was recrystallized (ethyl acetate) for analysis. Anal. Calcd. for $C_{16}H_{24}N_2O_2$: C, 69.53; H, 8.75; N, 10.13. Found: C, 69.20; H, 8.85; N, 10.09.

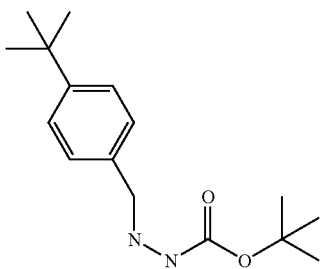

(4-t-Butylbenzyl)hydrazinecarboxylic acid, 1,1-dimethylethyl ester (4-t-Butylphenyl) methylenehydrazinecarboxilic acid, 1,1-dimethylethyl ester (7.05 g, 25.5 mmol) and 5% Pt/C (5.01 g) were slurried in THF (70 mL) and hydrogenated at 50 psig at rt for 3 hr. The slurry was then filtered through celite to remove the catalyst and concentrated in vacuo at 50° C. to afford the title compound as a clear oil (6.79 g, 95.6%): $^1$H NMR (bMSO-$d_6$, 60° C.) δ 7.30 (m, 2H), 7.23 (m, 2H), 4.44 (s, 1H), 3.82 (s, 1H), 1.38 (s, 9H), 1.27 (s, 9H); $^{13}$C NMR (DMSO-$d_6$) δ 157.1, 149.8, 136.3, 128.9, 125.5, 78.9, 54.7, 34.8, 31.9, 28.9; IR (CHCl$_3$) 3008, 2967, 2869, 1712 cm$^{-1}$; Anal. Calcd. for $C_{16}H_{26}N_2O_2$: C, 69.03; H, 9.41; N, 10.06. Found: C, 68.83; H, 9.21; N, 9.98.

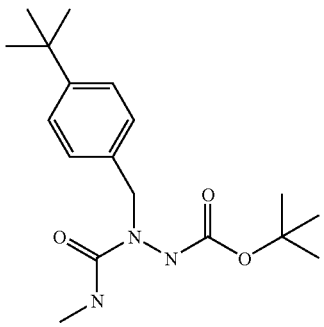

2-(Methylaminocarbonyl)-2-(4-t-butylphenylmethyl) hydrazine carboxylic acid, 1,1-dimethylethyl ester (4-t-Butylbenzyl) hydrazinecarboxilic acid, 1,1-dimethylethyl ester (2.54 g, 9.12 mmol) was dissolved in isopropanol (25 mL). Methyl isocyanate (0.83 g, 14.11 mmol) was added in one portion via syringe and the solution was allowed to stir at rt for 1 h. The solution was concentrated to afford the title compound as a waxy white solid (3.22 g of 89% potency material by $^1$H-NMR, 2.87 g, 93.7%): mp 124.1-128.6° C.; $^1$H NMR (DMSO-$d_6$, 60° C.) δ 8.54 (br s, 1H), 7.30 (d, 2H, J=2 Hz), 7.16 (d, 2H, J=2 Hz), 6.28 (s, 1H), 4.48 (s, 2H), 2.59 (d, 3H,

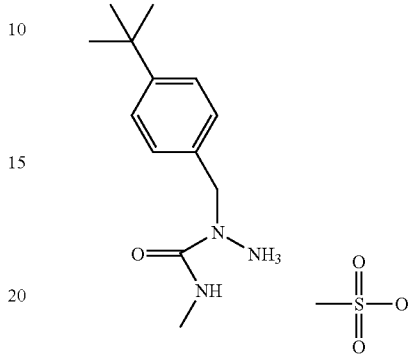

J=2 Hz), 1.31 (s, 9H), 1.26 (s, 9H); $^{13}$C NMR (DMSO-$d_6$, 60° C.) δ 159.1, 155.0, 149.9, 135.5, 128.9, 125.5, 80.1, 50.9, 34.8, 31.9, 28.7, 27.7; IR (CHCl$_3$) 3005, 2968, 2938, 1666 cm$^{-1}$. A portion of this material was recrystallized (toluene) for analysis. Anal. Calcd. for $C_{18}H_{29}N_3O_3$: C, 64.45; H, 8.71; N, 12.53. Found: C, 63.91; H, 8.51; N, 12.44.

N-Methyl-1-(4-t-butylphenylmethyl)hydrazine carboxamide methanesulfonate 3-(Methylaminocarbonyl)-2-(4-t-butylphenylmethyl)hydrazine carboxylic acid, 1,1-dimethylethyl ester (2.56 g, 7.90 mmol) was dissolved in dichloromethane (25 mL). Methanesulfonic acid (641 μL, 9.88 mmol) was added in one portion and the solution was stirred at rt overnight. The resulting slurry was cooled to 0° C., filtered, and the solids rinsed with cold dichloromethane. The solids were dried in vacuo at 40° C. to afford the title compound as a white solid (2.10 g, 80.1%): mp 96.8-97.4° C.; $^1$H NMR (DMSO-$d_6$) δ 9.7 (br s, 3H), 7.5 (br s, 1H), 7.39 (d, 2H, J=3 Hz), 7.20 (d, 2H, J=3 Hz), 4.65 (s, 2H), 2.67 (s, 3H), 2.35 (s, 3H), 1.26 (s, 9H); $^{13}$C NMR (DMSO-$d_6$) δ 158.2, 151.1, 132.7, 128.4, 126.1, 52.6, 40.4, 34.9, 31.8, 27.7; IR (KBr mull) 2967, 1690, 1550, 1188, 1076 cm$^{-1}$; Exact Mass Calcd. for $C_{13}H_{22}N_3O$: 236.1763. Found: 236.1758.

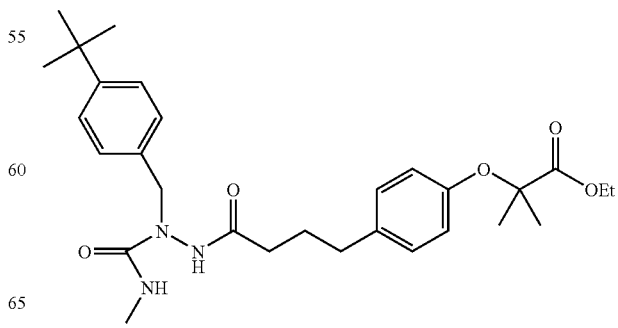

1-[4-[4-(1-Ethoxycarbonyl-1-methylethoxy)phenyl]butyryl]-2-(4-t-butylphenyl-methyl)-4-methylsemicarbazide 4-[4-(1-Ethoxycarbonyl-1-methyl-ethoxy)-phenyl]butyric acid (0.89 g, 3.02 mmol) was dissolved in ethyl acetate (10 mL). Oxalyl chloride (316 μL, 3.62 mmol) was added to this solution dropwise in the presence of a catalytic amount of N,N-dimethylformamide (17 μL, 0.24 mmol). Completion of acid chloride formation was verified by HPLC. The solution was then concentrated to remove excess oxalyl chloride and then redissolved in ethyl acetate (7 mL). This solution was then added dropwise to a suspension of N-Methyl-1-(4-t-butylphenylmethyl)hydrazine carboxamide methanesulfonate (1.02 g, 3.07 mmol) and pyridine (256 μL, 6.14 mmol) in ethyl acetate (10 mL) at 0° C. After stirring at 0° C. for 3 h, an additional charge of pyridine (256 μL, 6.14 mmol) was added and the solution was stirred at 0° C. for 1 h. The solution was warmed to rt and washed with 1N HCl (2×10 mL) and then with 5% aq. NaHCO₃ (2×10 mL). The organic layer was dried (MgSO₄), filtered and concentrated to an orange oil. Column chromatography (SiO₂, ethyl acetate) afforded the title compound as a clear oil (1.06 g, 68%): ¹H NMR (DMSO-d₆, 60° C.) δ 9.50 (s, 1H), 7.29 (d, 2H, J=8 Hz), 7.16 (d, 2H, J=8 Hz), 7.01 (d, 2H, J=8 Hz), 6.71 (d, 2H, J=8 Hz), 6.27 (br s, 1H), 4.52 (br s, 2H), 4.15 (q, J=7 Hz), 2.58 (d, 3H, J=4 Hz), 2.44 (t, 2H, J=7 Hz ), 2.07 (t, 2H, J=7 Hz ), 1.72 (quint, 2H, J=7 Hz), 1.48 (s, 6H), 1.25 (s, 9H), (1.17 (t, 3H, J=7 Hz); ¹³C NMR (DMSO-d₆) δ 174.0, 172.0, 158.7, 153.8, 149.9, 135.9, 129.7, 128.7, 125.6, 119.5, 79.2, 61.6, 50.8, 34.8, 34.4, 33.4, 31.8, 27.7, 27.1, 25.7, 14.6.; IR (CHCl₃) 3009, 2966, 1671, 1509, 1211 cm⁻¹; Anal. Calcd. for C₂₉H₄₁N₃O₅: C, 68.08; H, 8.08; N, 8.21. Found:,C, 67.70; H, 7.86; N, 8.11.

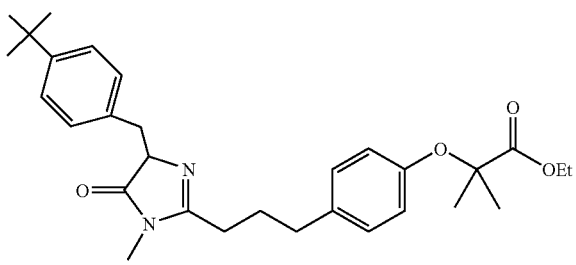

2-(4-{3-[1-(4-t-Butylphenylmethyl)-4-methyl-5-oxo-4,5-dihydro-1H-[1,2,4]triazol-3-yl]-propyl}-phenoxy)-2-methyl-propionic acid ethyl ester 1-[4-[4-(1-Ethoxycarbonyl-1-methylethoxy)phenyl]butyryl]-2-(4-t-butyl phenylmethyl)-4-methylsemicarbazide (0.93 g, 1.82 mmol) was dissolved in ethyl acetate (10 mL). Camphorsulfonic acid (0.46 g, 1.98 mmol) was added in one portion and the solution was heated to reflux and stirred for 1 h. The solution was cooled to rt and washed with sat'd aq. NaHCO₃ (2×8 mL), 1N HCl (2×8 mL) and sat'd aq. NaCl (8 mL)). The organic phase was dried (MgSO₄), filtered and concentrated to afford the title compound as clear, colorless oil (0.84 g, 93.6%): ¹H NMR (DMSO-d₆) δ 7.30 (d, 2H, J=8 Hz), 7.15 (d, 2H, J=8 Hz), 7.05 (d, 2H, J=8 Hz), 6.68 (d, 2H, J=8 Hz), 4.77 (s, 2H), 4.13 (q, 2H, J=7 Hz), 3.69 (s, 3H), 2.53 (t, 2H, J=8 Hz), 2.47 (t, 2H, J=8 Hz), 1.81 (quint, 2H, J=7 Hz), 1.47 (s, 6H), 1.22 (s, 9H), 1.14 (t, 3H, J=7 Hz); ¹³C NMR (DMSO-d₆) δ 174.0, 154.1, 153.8, 150.4, 147.1, 135.6, 135.0, 129.8, 128.0, 125.9, 119.5, 79.2, 61.6, 48.3, 34.9, 34.1, 31.8, 27.7, 27.6, 25.7, 25.1, 14.6; IR *(CHCl₃) 2967, 1695, 1509, 1475, 1232 cm⁻¹; Anal. Calcd. for C₂₉H₃₉N₃O₄: C, 70.56; H, 7.96; N, 8.51. Found: C, 70.28; H, 7.85; N, 8.43.

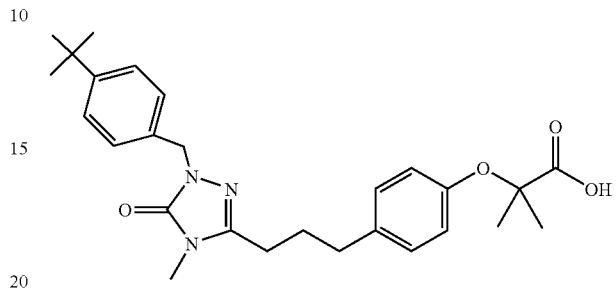

2-(4-{3-[1-(4-t-Butylbenzyl)-4-methyl-5-oxo-4,5-dihydro-1H-[1,2,4]triazol-3-yl]-propyl}-phenoxy)-2-methyl-propionic acid 2-(4-{3-[1-(4-t-Butylbenzyl)-4-methyl-5-oxo-4,5-dihydro-1H-[1,2,4]triazol-3-yl]-propyl}-phenoxy)-2-methyl-propionic acid ethyl ester (0.69 g, 1.39 mmol) was dissolved in ethanol (4 mL)), 1 N NaOH (4.75 mL) was added in one portion and the solution was stirred at ambient temperature overnight. The solution was concentrated to a hazy, colorless oil. This oil was partitioned between 1N HCl (5 mL) and ethyl acetate (5 mL). The aqueous layer was then reextracted with ethyl acetate (5 mL) and the organic layers combined, dried (MgSO₄), filtered and concentrated in vacuo at 50° C. to afford the title compound as a clear oil (0.56 g, 86%): ¹H NMR (DMSO-d₆) δ 12.9 (br s, 1H), 7.31 (d, 2H, J=6 Hz), 7.14 (d, 2H, J=8 Hz), 7.05 (d, 2H, J=7 Hz), 6.73 (d, 2H, J=2 Hz), 4.77 (s, 2H), 3.09 (s, 3H), 2.53 (t, 2H, J=8 Hz), 2.49 (t, 2H, J=8 Hz), 1.81 (quint, 2 H, J=7 Hz), 1.46 (s, 6H), 1.22 (s, 9H); ¹³C NMR (DMSO-d₆) δ 175.8, 154.14, 154.10, 150.5, 147.2, 135.2, 135.0, 129.7, 128.0, 125.9, 119.2, 79.0, 48.3, 34.9, 34.1, 31.8, 27.7, 27.6, 25.7, 25.1; IR (CHCl₃) 2966, 1695, 1509, 1235 cm⁻¹; Anal. Calcd. for C₂₇H35N₃O4: C, 69.65; H, 7.58; N, 9.02. Found: C, 69.30; H, 7.30; N, 8.96.

Example 133

2-Methyl-2-(4-{2-[5-oxo-4-propyl-1-(4-trifluoromethyl-phenyl)-4,5-dihydro-1H-[1,2,4]triazol-3-yl]-ethyl}-phenoxy-propionic acid

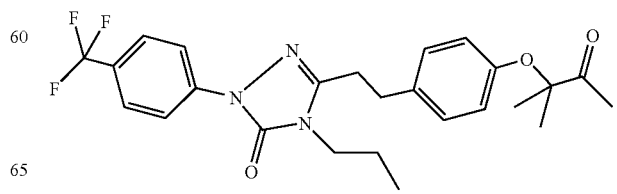

Step A: Preparation of 3-(4-Methoxy-phenyl)-N-propyl-propionamide

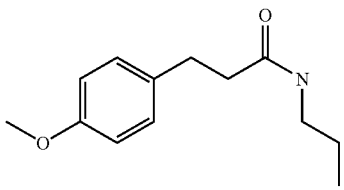

To a solution of 3-(4-methoxyphenyl)propionic acid (8.0 g, 44.4 mmol), propylamine hydrochloride (4.24 g, 44.4 mmol), 4-dimethylaminopyridine (0.65 g, 5.33 mmol) and triethylamine (6.9 mL, 48.96 mmol) in methylene chloride (70 mL) was added 1-[(3-dimethylamino)propyl]-3-ethyl-carbodiimide hydrochloride (10.21 g, 53.28 mmol). The reaction mixture was stirred overnight at ambient temperature followed by dilution with methylene chloride. The mixture was washed with 1N hydrochloric acid, 2N sodium hydroxide, water, brine and dried. Evaporation of the solvent yielded the pure product (10.36 g; 95.4%): $^1$HNMR (400 MHz, CDCl$_3$) δ 7.76 (brs, 1H), 7.10 (d, 2H, J=8.8 Hz), 6.79 (d, 2H, J=8.0 Hz), 3.68 (s, 3H), 2.95 (q, 2H, J=5.6 Hz). 2.71 (t, 2H, J=7.6 Hz), 2.28 (t, 2H, J=7.2 Hz), 1.34 (m, 2H), 0.77 (t, 3H, J=7.2 Hz); ESMS m/z (relative intensity) 222.2 (M+H$^+$, 100).

Step B: Preparation of 3-(4-Methoxyphenyl)-N-propyl-propionimidic acid methyl ester

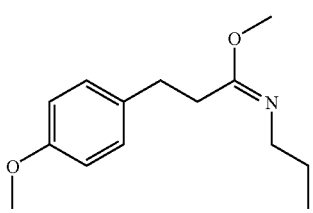

To a solution of 3-(4-Methoxy-phenyl)-N-propyl-propionamide (3.0 g, 13.57 mmol in methylene chloride (15 mL) was added trimethyloxonium tetrafluoroborate (2.0 g, 13.57 mmol) and the reaction mixture stirred overnight at ambient temperature. HPLC and TLC analysis indicated the presence of starting material. More trimethyloxonium tetrafluoroborate (0.25 g) was added and the reaction mixture was allowed to stir for 2.5 h and quenched with cold saturated aqueous potassium carbonate solution. The mixture was extracted ethyl acetate. The combined organic extracts were washed with water, brine, dried and evaporated to dryness to afford the pure product (3.0.g, 93.8%): $^1$HNMR (400 MHz, CDCl$_3$) δ 7.10 (d, 2H), 6.80 (d, 2H, J=8.4 Hz), 3.78 (s, 3H), 3.61 (s, 3H), 3.08 (t, 2H, J=7.6 Hz), 2.70 (m, 2H), 2.48 (m, 2H), 1.45 (m, 2H), 0.86 (t, 3H, J=7.6 Hz); ESMS m/z (relative intensity) 236.1 (M+H$^+$, 100).

Step C: Preparation of

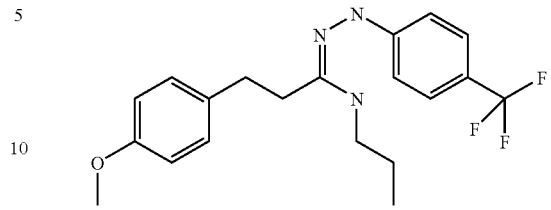

To a solution of 3-(4-Methoxyphenyl)-N-propyl-propionimidic acid methyl ester (3.0 g, 12.77 mmol) in methylene chloride (10 mL) was added 4-trifluoromethylphenylhydrazine (2.25 g, 12.77 mmol) in methylene chloride (10 mL) and the reaction mixture is stirred overnight at 45° C. HPLC and TLC analysis revealed the presence of considerable starting material. The reaction mixture was refluxed overnight with no appreciable change. The reaction solvent was evaporated and replaced with 1,2-dichloroethane (20 mL). The reaction mixture was stirred at 84° C. over 72 hr. The reaction mixture was quenched with water, extracted with ethyl acetate. The combined organic extracts were washed with water, brine, dried and evaporated to dryness to afford the crude product (5.3 g) which was carried on to the next step without further purification: ESMS m/z (relative intensity) 378.0 (M–H$^+$, 50).

Step D: Preparation of 5-[2-(4-Methoxyphenyl)ethyl]-4-propyl-2-(4-trifluoromethylphenyl)-2,4-dihydro-[1,2,4]triazol-3-one

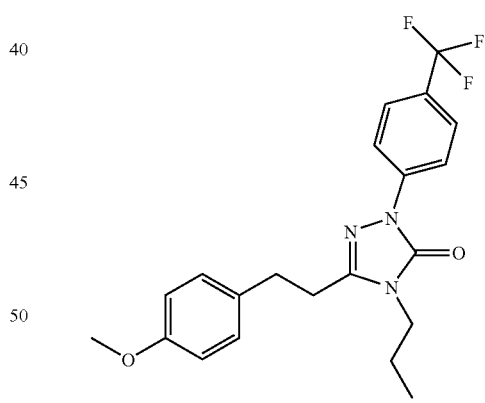

To a solution of the crude hydrazine intermediate from step C (5.3 g) in anhydrous THF (25 mL) was added carbonyldiimidazole (2.5 g, 15.38 mmol) and the reaction mixture is stirred overnight at ambient temperature. The solvent was evaporated and the residue was purified by flash chromatography on silica gel (gradient of ethyl acetate in hexanes) yielding the title compound (1.52 g,). $^1$HNMR (400 MHz, CDCl$_3$) δ 8.18 (d, 2H, J=8.0 Hz), 7.65 (d, 2H, J=8.0 Hz), 7.18 (d, 2H, J=7.8 Hz), 7.83 (d, 2H, 8.0 Hz), 3.80 (s, 3H), 3.55 (t, 2H, J=8.0 Hz), 3.08 (t, 2H, J=8.0 Hz), 2.82 (m, 2H), 1.65 (m, 2H), 0.96 (s, 3H); ESMS m/z (relative intensity) 406.2 (M+H$^+$, 100).

Step E: Preparation of 5-[2-(4-Hydroxyphenyl)ethyl]-4-propyl-2-(4-trifluoromethylphenyl)-2,4-dihydro-[1,2,4]triazol-3-one

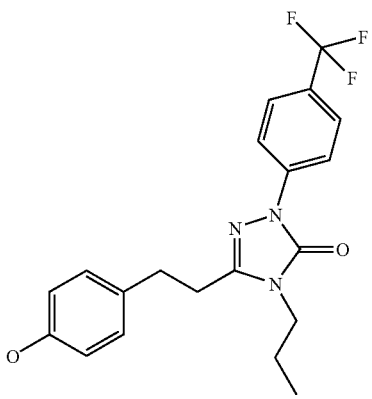

To a solution of 5-[2-(4-Methoxyphenyl)ethyl]-4-propyl-2-(4-trifluoromethylphenyl)-2,4-dihydro-[1,2,4triazol-3-one (1.52 g, 3.75 mmol) in methylene chloride (36 mL) at −78° C. was added boron tribromide (0.75 mL) and allowed to warm to ambient temperature. After 2 h, the reaction was quenched with water and extracted with ethyl acetate. The combined organic layers were washed with water, brine, dried and evaporated to dryness to yield the product (1.35 g, 92.5%). $^1$HNMR (400 MHz, CDCl$_3$) δ 8.13 (d, 2H, J=8.8 Hz), 7.81 (d, 2H, J=8.8 Hz), 7.09 (d, 2H, J=8.4 Hz), 6.66 (m, 2H), 3.56 (t, 2H), 2.89 (m, 4H), 1.58 (m, 2H), 0.84 (m, 3H); ESMS m/z (relative intensity) 392.2 (M+H$^+$, 100), 390.1 (M−H$^+$, 100).

Step F: Preparation of 2-Methyl-2-(4-{2-[5-oxo-4-propyl-1-(4-trifluoromethyl-phenyl)-4,5-dihydro-1H-[1,2,4]triazol-3-yl]-ethyl}-phenoxy)-propionic acid ethyl ester

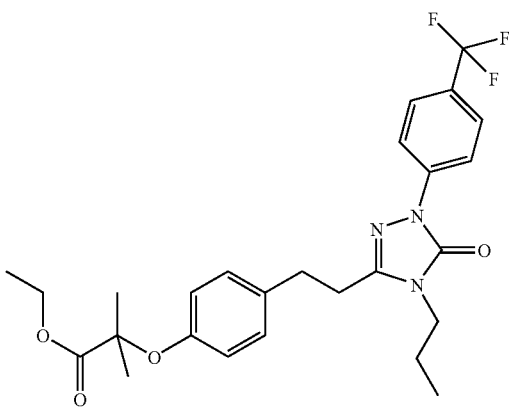

To a mixture of 5-[2-(4-Hydroxyphenyl)ethyl]-4-propyl-2-(4-trifluoromethylphenyl)-2,4-dihydro-[1,2,4]triazol-3-one (0.10 g, 0.26 mmol) and cesium carbonate (0.16 g, 0.49 mmol) in anhydrous DMF (2.5 mL) was added ethyl 2-bromoisobutyrate (81.1 mg, 60.6 □L, 0.42 mmol). The reaction mixture was heated to 75° C. overnight. More ethyl 2-bromoisobutyrate (30.3 □L) was added and the mixture was stirred at 110° C. overnight and ambient temperature over the weekend. The reaction mixture was quenched with water and extracted with ethyl acetate. The combined organic extracts were washed with 5% aqueous lithium chloride solution, water, brine, dried and evaporated. Chromatotron chromatography (gradient of ethyl acetate in hexanes) gave the pure compound (94 mg, 70.7%): $^1$HNMR (400 MHz, CDCl$_3$) δ 8.14 (m, 2H), 7.65 (m, 2 H,), 7.10 (m, 2H), 6.80 (m, 2H), 4.23 (m, 2H), 3.53 (m, 2 H), 3.05 (m, 2H), 2.83 (m, 2H), 1.70 (m, 2H), 1.57 (s, 6 H), 1.26 (m, 6H); ESMS m/z (relative intensity) 506.1 (M+H$^+$, 100).

Step G: 2-Methyl-2-(4-(2-[5-oxo-4-propyl-1-(4-trifluoromethyl-phenyl)-4,5-dihydro-1H-[1,2,4]triazol-3-yl]-ethyl}-phenoxy)-propionic acid

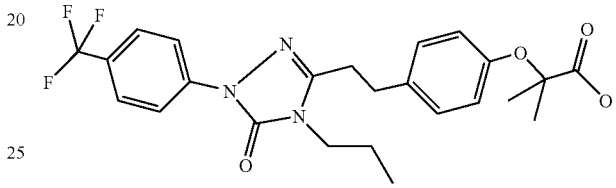

2-Methyl-2-(4-{2-[5-oxo-4-propyl-1-(4-trifluoromethyl-phenyl)-4,5-dihydro-1H-[1,2,4]triazol-3-yl]-ethyl}-phenoxy)-propionic acid ethyl ester (94 mg, 0.19 mmol) and a 2N solution of sodium hydroxide (2.3 mL) in ethanol (5 mL) was heated to 80° C. for 35 min. The solvent was evaporated, water added and the solution made acidic with concentrated hydrochloric acid (pH 0-1), extracted with ether. The combined organic extracts were washed with water, brine, dried and evaporated to dryness to afford the pure compound (82 mg, 92.3%): $^1$HNMR (400 MHz, CDCl$_3$) δ 8.06 (d, 2H, J=8.3 Hz), 7.59 (d, 2H, J=8.3 Hz), 7.09 (d, 2H, 6.4 Hz), 6.83 (d, 2H, J=8.3 Hz), 3.45 (t, 2H, J=7.4 Hz), 3.02 (d, 2 H, J=7.3 Hz), 2.79 (m, 2H), 1.60 (m, 2H), 1.52 (s, 6H), 0.87 (t, 3H, J=7.8 Hz); ESMS m/z (relative intensity) 476.1 (M−H$^+$, 50).

The following compounds were made in substantially similar method:

Example 134

(4-{2-[5-Oxo-4-propyl-1-(4-trifluoromethyl-phenyl)-4,5-dihydro-1H-[1,2,4]triazol-3-yl]-ethyl}-phenoxy)-acetic acid

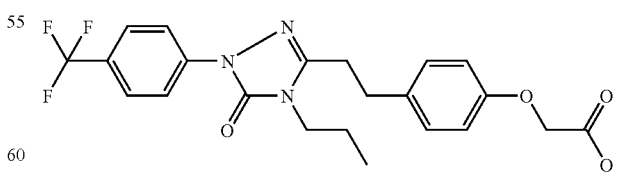

$^1$HNMR (400 MHz, CDCl$_3$) δ 8.08 (d, 2H, J=8.3 Hz), 7.60 (d, 2H, J=8.3 Hz), 7.12 (d, 2H, J=8.8 Hz), 6.82 (d, 2H, 8.8 Hz), 4.60 (s, 2H) 3.48 (t, 2H, J=7.4 Hz), 3.03 (d, 2 H, J=7.4 Hz), 2.80 (t, 2H, J=7.4 Hz), 1.60 (m, 2H), 0.88 (t, 3H, J=7.3 Hz); ESMS m/z (relative intensity) 450.2 (M+H$^+$, 80).

Example 135

2-Methyl-2-(4-{2-[5-oxo-4-propyl-1-(4-trifluoromethyl-phenyl)-4,5-dihydro-1H-[1,2,4]triazol-3-yl]-propyl}-phenoxy)-propionic acid

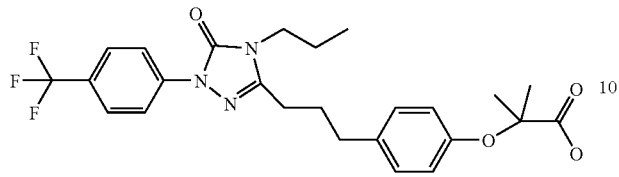

$^1$HNMR (400 MHz, CDCl$_3$) δ 8.12 (d, 2H, J=8.8 Hz), 7.80 (d, 2H, J=8.81 Hz), 7.12 (d, 2H, J=8.31 Hz), 6.74 (d, 2H, 8.8 Hz), 3.56 (m, 2H), 2.64 (m, 4H), 1.96 (m, 2H), 1.60 (m, 2H), 1.45 (s, 6H), 0.85 (t, 3H, J=7.33 Hz); ESMS m/z 492.15 (M+H$^+$).

Example 136

(4-{2-[5-Oxo-4-propyl-1-(4-trifluoromethyl-phenyl)-4,5-dihydro-1H-[1,2,4]triazol-3-yl]propyl}-phenoxy)-acetic acid

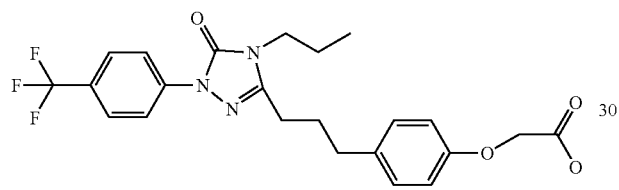

$^1$HNMR (400 MHz, CDCl$_3$) δ 8.12 (d, 2H, J=8.8 Hz), 7.80 (d, 2H, J=8.8 Hz), 7.14 (d, 2H, J=8.31 Hz), 6.82 (d, 2H, 8.32 Hz), 4.60 (s, 2H), 3.56 (t, 2H, J=7.33 Hz), 2.64 (m, 4H), 1.96 (m, 2H), 1.60 (m, 2H), 0.85 (t, 3H, J=7.34 Hz); ESMS m/z 464.14 (M+H$^+$).

Example 137

(4-{2-[4-[2-(2-Fluoro-phenyl)-ethyl]-5-oxo-1-(4-trifluoromethyl-phenyl)-4,5-dihydro-1H-[1,2,4]triazol-3-yl]-ethyl}-phenoxy)-acetic acid

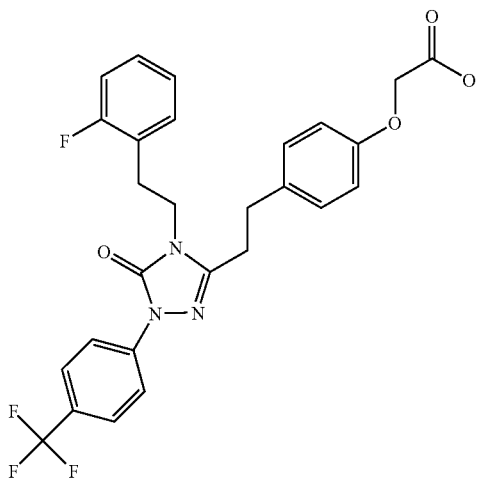

$^1$H NMR (DMSO-d$_6$, 400 MHz): δ 2.48-2.52 (m, 2H), 2.75-2.79 (m, 2H), 2.96 (m, 2H), 3.85 (m, 2H), 4.44 (s, 2H), 6.78 (d, J=7.82 Hz, 2H), 7.06-7.14 (m, 4H), 7.24-7.28 (m, 2H), 7.80 (d, J=8.32 Hz, 2H), 8.10 (d, J=8.32 Hz, 2H); MS (ES, m/z):C$_{27}$H$_{23}$F$_4$N$_3$O$_4$: 529.99(M$^+$+1), 528.01(M$^+$−1)

Example 138

2-(4-{2-[4-[2-(2-Fluoro-phenyl)-ethyl]-5-oxo-1-(4-trifluoromethyl-phenyl)-4,5-dihydro-1H-[1,2,4]triazol-3-yl]-ethyl}-phenoxy)-2-methyl-propionic acid

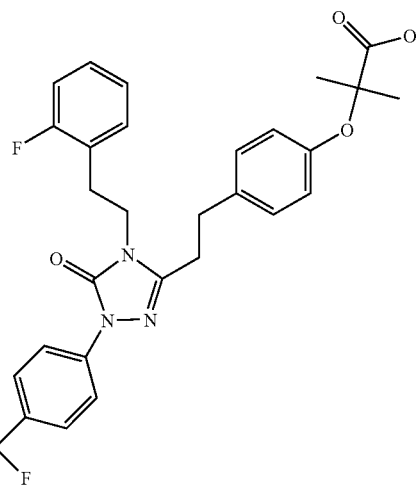

$^1$H NMR (DMSO-d$_6$, 400 MHz) δ 1.54 (s, 6H), 2.62 (t, J=7.33 Hz, 2H), 2.87 (t, J=7.34 Hz, 2H), 3.05 (m, 2H), 3.93 (m, 2H), 6.82 (d, J=8.32 Hz, 2H), 7.15-7.23 (m, 4H), 7.33-7.37 (m, 2H), 7.89 (d, J=8.32 Hz, 2H), 8.18 (d, J=8.31 Hz, 2H); MS (ES, m/z):C$_{29}$H$_{27}$F$_4$N$_3$O$_4$: 558.05(M$^+$+1), 556.07(M$^+$−1).

Example 139

(4-{3-[4-[2-(2-Fluoro-phenyl)-ethyl]-5-oxo-1-(4-trifluoromethyl-phenyl)-4,5-dihydro-1H-[1,2,4]triazol-3-yl]-propyl}-phenoxy)-acetic acid

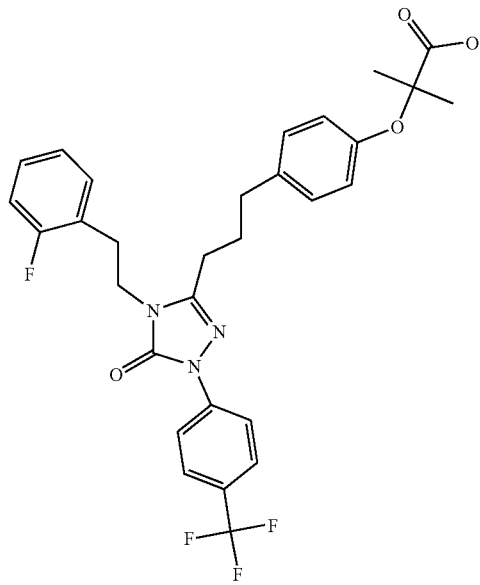

¹H NMR (DMSO-d₆, 400 MHz): δ 1.76-1.80 (m, 2H), 2.23 (t, J=7.82 Hz, 2H), 2.51 (t, J=7.34 Hz, 2H), 2.97 (t, J=6.85 Hz, 2H), 3.83 (t, J=6.85 Hz, 2H), 4.61 (s, 2H), 6.81 (d, J=8.80 Hz, 2H), 7.07-7.13 (m, 4H), 7.22-7.26 (m, 2H), 7.80 (d, J=8.80 Hz, 2H), 8.10 (d, J=8.82 Hz, 2H); MS (ES, m/z):C₂₈H₂₅F₄N₃O₄: 544.24(M⁺+1), 542.21(M⁺−1).

Example 140

2-(4-{3-[4-[2-(2-Fluoro-phenyl)-ethyl]-5-oxo-1-(4-trifluoromethyl-phenyl)-4,5-dihydro-1H-[1,2,4]triazol-3-yl]-propyl}-phenoxy)-2-methyl-propionic acid

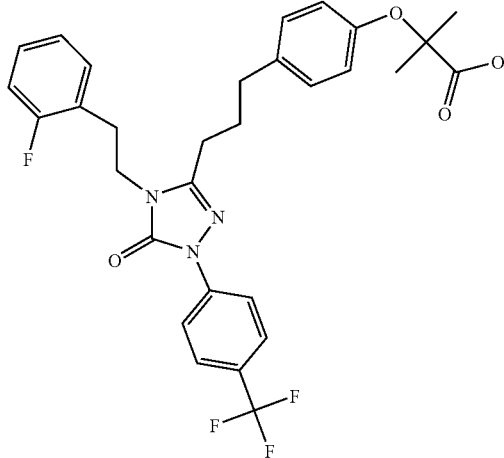

¹H NMR (DMSO-d₆, 400 MHz): δ 1.46 (s, 6H), 1.78 (m, 2H), 2.24(t, J=7.83 Hz, 2H), 2.51 (t, J=7.82 Hz, 2H), 2.97 (t, J=6.36 Hz, 2H), 3.83 (t, J=6.80 Hz, 2H), 6.74 (d, J=8.32 Hz, 2H), 7.05-7.11 (m, 4H), 7.24 (m, 2H), 7.79 (d, J=8.80 Hz, 2H), 8.10 (d, J=8.32 Hz, 2H); MS (ES, m/z):C₃₀H₂₉F₄N₃O₄: 572.20(M⁺+1), 570.30(M⁺−1)

Example 141

2-methyl-4-{2-[5-oxo-4-propyl-1-(4-trifluoromethyl-phenyl)-4,5-dihydro-1H-[1,2,4]triazol-3-yl]ethyl}-phenoxy)acetic acid

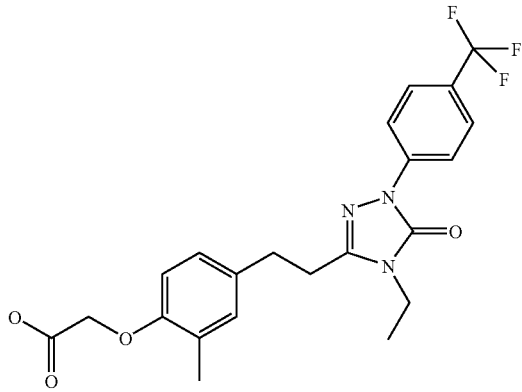

Step A: Preparation of (2-Iodo-4-{2-[5-oxo-4-propyl-1-(4-trifluoromethyl-phenyl)-4,5-dihydro-1H-[1,2,4]triazol-3-yl]-ethyl}-phenoxy)-acetic acid ethyl ester

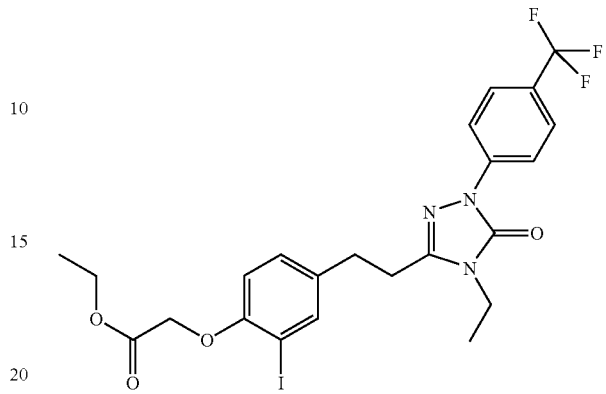

A mixture of (4-{2-[5-Oxo-4-propyl-1-(4-trifluoromethyl-phenyl)-4,5-dihydro-1H-[1,2,4]triazol-3-yl]-ethyl}-phenoxy)acetic acid ethyl ester (180 mg, 0.38 mmol), iodine (105 mg, 0.42 mmol), silver sulfate (131 mg, 0.42 mmol) and ethanol were stirred at room temperature. After 3.5 h, more iodine (86 mg) and silver sulfate (106 mg) were added and stirred for another 0.5 h. The reaction mixture was quenched with water and extracted with ethyl acetate. The combined organic extracts were washed with water, brine, dried and evaporated to dryness to afford the product (217 mg, 95%). ¹HMR (400 MHz, CDCl₃) δ 8.15 (d, 2H, J=8.4 Hz), 7.73 (s, 1H), 7.67 (d, 2H, J=8.4 Hz), 7.18 (m, 1H), 6.67 (d, 1H, J=8.0 Hz), 4.66 (s, 2H), 4.26 (q, 2H, J=7.6 Hz), 3.68 (t, 2H, J=7.3 Hz), 3.05 (t, 2H, J=7.4 Hz), 2.82 (t, 2H, J=7.3 Hz), 1.7 (m, 2H), 1.29 (t, 3H, J=7.6 Hz), 0.96 (t, 3H, J=7.6 Hz); ESMS m/z (relative intensity) 604.2 (M+H⁺, 100).

Step B: Preparation of 2-methyl-4-(2-[5-oxo-4-propyl-1-(4-trifluoromethyl-phenyl)-4,5-dihydro-1H-[1,2,4]triazol-3-yl]-ethyl}-phenoxy)acetic acid ethyl ester

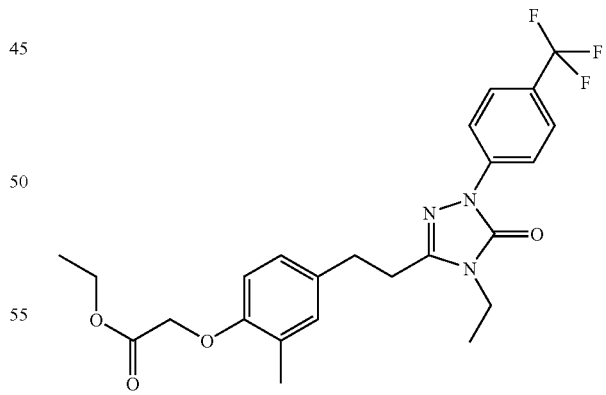

A mixture of 2-iodo-4-{2-[5-oxo-4-propyl-1-(4-trifluoromethyl-phenyl)-4,5-dihydro-1H-[1,2,4]triazol-3-yl]-ethyl}-phenoxy)acetic acid (182 mg, 0.3 mmol), methylboronic acid (53.9 mg, 0.9 mmol) and cesium fluoride (136.7 mg, 0.9 mmol) in dioxane (3 mL) was degassed and filled with nitrogen for three times, then [1,1'bis(diephenylphosphino)ferrocene]dichloropalladium(II), complex with dichloromethane (1:1) (36 mg, 0.04 mmol) was added and the reaction mixture was heated to 80° C. After 4h, reaction mixture was filtered through celite and evaporated. Flash chromatography on silica gel(gradient of ethyl acetate in hexanes) yielded the pure compound (73 mg, 49.3%): $^1$HNMR (400 MHz, CDCl$_3$) δ 8.16 (d, 2H, J=8.4 Hz), 7.66 (d, 2H, J=8.8 Hz), 7.05 (s, 1H), 7.00 (m, 1H), 6.64 (d, 1H, J=8.0 Hz), 4.62 (s, 2H), 4.25 (m, 2H), 3.56 (t, 2H, J=8.0 Hz), 3.02 (t, 2H, J=8.4 Hz), 2.83 (t, 2H, J=8.4 Hz), 2.29 (s, 3H), 1.7 (m, 2H), 1.29 (t, 3 H, J=6.8 Hz), 0.95 (t, 3H, J=7.2 Hz); ESMS m/z (relative intensity) 492.2 (M+H$^+$, 75).

Step C: Preparation of 2-methyl-4-{2-[5-oxo-4-propyl-1-(4-trifluoromethyl-phenyl)-4,5-dihydro-1H-[1,2,4]triazol-3-yl]-ethyl}-phenoxy)acetic acid

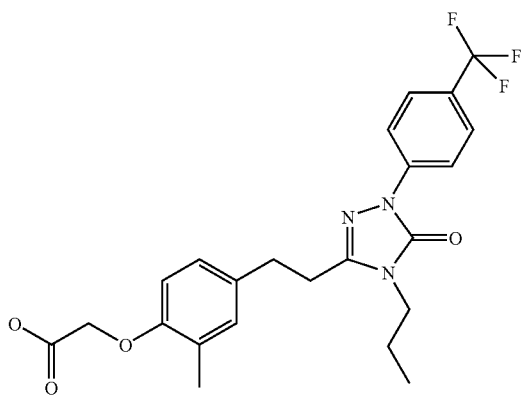

A mixture of 2-methyl-4-{2-[5-oxo-4-propyl-1-(4-trifluoromethyl-phenyl)-4,5-dihydro-1H-[1,2,4]triazol-3-yl]-ethyl}-phenoxy)acetic acid ethyl ester (70 mg, 0.14 mmol) and a 2N solution of sodium hydroxide (1.6 mL) in ethanol (3.3 mL) was heated to 75° C. for 45 min. The solvent was evaporated, water added and the solution made acidic with concentrated hydrochloric acid (pH 0-1), extracted with ether. The combined organic extracts were washed with water, brine, dried and evaporated to dryness to afford the pure compound (60 mg, 96.4%): $^1$HNMR (400 MHz, CDCl$_3$) δ 8.09 (d, 2 H, J=8.8 Hz), 7.60 (d, 2H, J=8.8 Hz), 6.99 (s, 1H), 6.94 (m, 1H), 6.60 (d, 1H, 8.4 Hz), 4.61 (s, 2H), 3.48 (t, 2H, J=8.0 Hz), 2.98 (t, 2H, J=8.4 Hz), 2.76 (t, 2 H, J=7.2 Hz), 2.21 (s. 3H), 1.62 (m, 2H), 0.88 (t, 3H, J=7.6 Hz); ESMS m/z (relative intensity) 464.2 (M+H$^+$, 40), 462.1 (M−H$^+$, 100).

The following compounds were made in a substantially similar method:

Example 142

2-Methyl-2-(2-methyl-4-{2-[5-oxo-4-propyl-1-(4-trifluoromethyl-phenyl)-4,5-dihydro-1H-[1,2,4]triazol-3-yl]-propyl}-phenoxy)-propionic acid

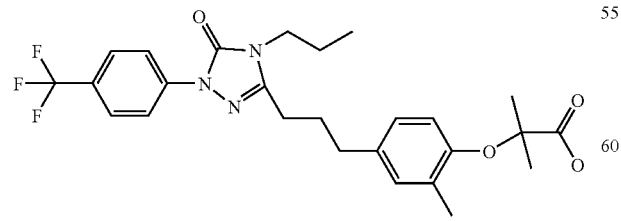

HNMR (400 MHz, CDCl$_3$) ☐ 8.15 (m, 2H), 7.80 (m, 2H), 6.99 (s, 1H), 6.94 (m, 1H), 6.62(m, 1H), 3.56 (m, 2H), 2.62 (m, 4H), 2.10 (s, 3H), 1.98 (m, 2H), 1.60 (m, 2H), 1.45 (s, 6H), 0.85 (m, 3H); ESMS m/z 506.3 (M+H$^+$)

Example 143

2-Methyl-2-(2-methyl-4-{2-[5-oxo-4-propyl-1-(4-trifluoromethyl-phenyl)-4,5-dihydro-1H-[1,2,4]triazol-3-yl]-ethyl}-phenoxy)-propionic acid

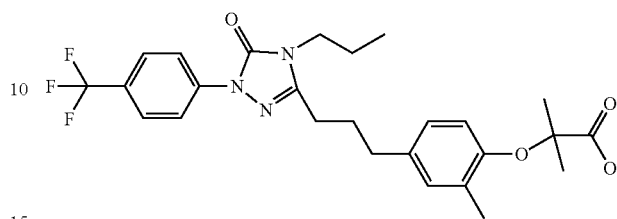

HNMR (400 MHz, CDCl$_3$) ☐ 8.13 (d, 2H, J=8.8 Hz), 7.82 (d, 2H, J=9.3 Hz), 7.1 (m, 1H), 7.0 (m, 1H), 6.62 (m, 1H), 3.58 (m, 2H), 2.91 (s, 4H), 2.12 (s, 3H), 1.59 (m, 2H), 1.46 (s, 6H), 0.85 (m, 3H); ESMS m/z 492.3 (M+H$^+$)

Example 144

2-Methyl-2-(2-vinyl-4-{2-[5-oxo-4-propyl-1-(4-trifluoromethyl-phenyl)-4,5-dihydro-1H-[1,2,4]triazol-3-yl]-ethyl}-phenoxy)-propionic acid

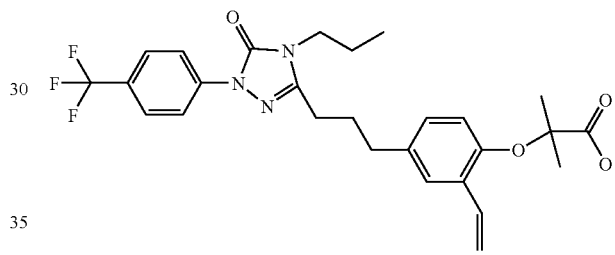

HNMR (400 MHz, CDCl$_3$) ☐ 8.13 (d, 2H, J=8.32 Hz), 7.81 (d, 2H, J=8.8 Hz), 7.51 (d, 1H, J=2.44 Hz), 7.13 (m, 1H), 6.96 (m, 1H), 6.69 (m, 1H), 5.78 (m, 1H), 5.23(m, 1H), 3.58 (t, 2H, J=7.34 Hz), 2.96 (m, 4H), 1.60 (m, 2H), 1.46 (s, 6H), 0.84 (t, 3H, J=7.3 Hz); ESMS m/z 504.03 (M+H$^+$)

Example 145

(2-Iodo-4-{2-[5-oxo-4-propyl-1-(4-trifluoromethyl-phenyl)-4,5-dihydro-1H-[1,2,4]triazol-3-yl]-ethyl}-phenoxy)acetic acid

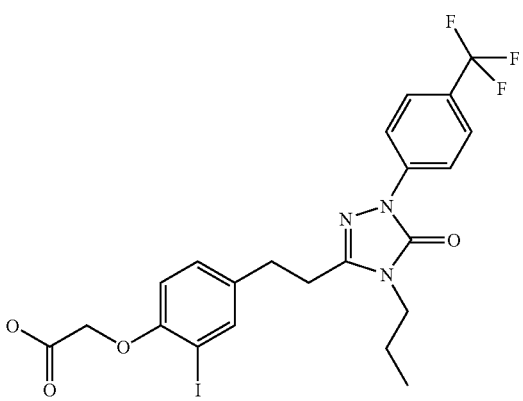

$^1$HNMR (400 MHz, CDCl$_3$) ☐ 8.08 (d, 2H, J=8.4 Hz), 7.69 (s, 1H), 7.61 (d, 2H, J=8.8 Hz), 7.11 (d, 1H, J=8.4 Hz), 6.65 (d, 1H, 8.0 Hz), 4.63 (s, 2H), 3.51 (t, 2H, J=7.6 Hz), 3.01 (t, 2H, J=7.6 Hz), 2.77 (t, 2H, J=7.2 Hz), 1.63 (m, 2H), 0.89 (t, 3H, J=7.2 Hz); ESMS m/z (relative intensity) 576.0 (M+H$^+$, 100), 574.0 (M−H$^+$, 100).

Example 146

(4-{2-[4-[2-(2-Fluoro-phenyl)-ethyl]-5-oxo-1-(4-trifluoromethyl-phenyl)-4,5-dihydro-1H-[1,2,4]triazol-3-yl]-ethyl}-2-methyl-phenoxy)-acetic acid

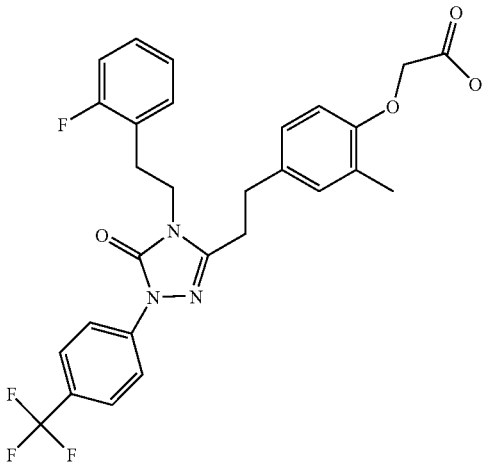

$^1$H NMR (DMSO-d$_6$, 400 MHz): δ 2.15 (s, 3H), 2.47-2.51 (m, 2H), 2.75 (t, J=7.34 Hz, 2H), 2.97 (t, J=6.36 Hz, 2H), 3.85 (t, J=6.36 Hz, 2H), 4.63 (s, 2H), 6.70 (d, J=8.32 Hz, 1H), 6.91-6.96 (m, 2H), 7.08-7.14 (m, 2H), 7.24-7.29 (m, 2H), 7.81 (d, J=8.31 Hz, 2H), 8.10 (d, J=8.31 Hz, 2H); MS (ES, m/z):C$_{28}$H$_{25}$F$_4$N$_3$O$_4$: 544.01(M$^+$+1), 542.05(M$^+$−1).

Example 147

2-(4-{2-[4-[2-(2-Fluoro-phenyl)-ethyl]-5-oxo-1-(4-trifluoromethyl-phenyl)-4,5-dihydro-1H-[1,2,4]triazol-3-yl]-ethyl}-2-methyl-phenoxy)-2-methyl-propionic acid

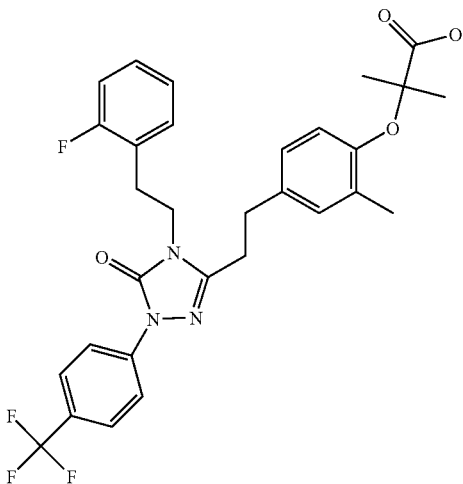

$^1$H NMR (DMSO-d$_6$, 400 MHz): δ 1.46 (s, 6H), 2.12 (s, 3H), 2.50-2.52 (m, 2H), 2.74 (t, J=7.83 Hz, 2H), 2.96 (t, J=6.85 Hz, 2H), 3.84 (t, J=6.85 Hz, 2H), 6.59 (d, J=7.83 Hz, 1H), 6.88 (d, J=8.31 Hz, 1H), 6.97 (s, 1H), 7.10-7.12 (m, 2H), 7.25-7.29 (m, 2H), 7.81 (d, J=8.30 Hz, 2H), 8.10 (d, J=8.30 Hz, 2H); MS (ES, m/z):C$_{30}$H$_{29}$F$_4$N$_3$O$_4$: 571.97(M$^+$+1), 570.00(M$^+$−1)

Example 148

(4-{3-[4-[2-(2-Fluoro-phenyl)-ethyl]-5-oxo-1-(4-trifluoromethyl-phenyl)-4,5-dihydro-1H-[1,2,4]triazol-3-yl]-propyl}-2-methyl-phenoxy)-acetic acid

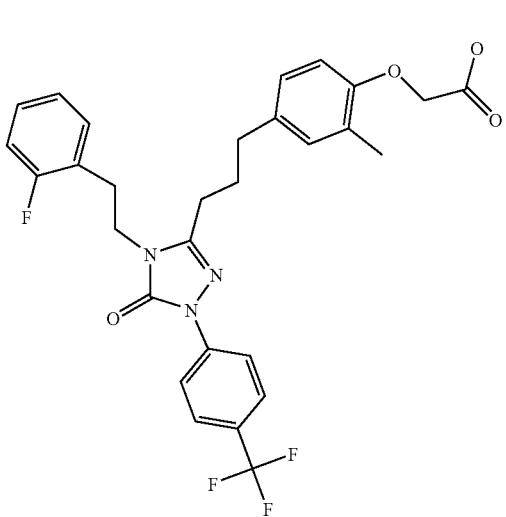

$^1$H NMR (DMSO-d$_6$, 400 MHz): δ 1.76-1.80 (m, 2H), 2.15 (s, 3H), 2.23 (t, J=7.82 Hz, 2H), 2.45-2.48 (m, 2H), 2.96 (t, J=6.36 Hz, 2H), 3.83 (t, J=6.85 Hz, 2H), 4.63 (s, 2H), 6.70 (d, J=8.32 Hz, 1H), 6.90 (d, J=7.83 Hz, 1H), 6.95 (s, 1H), 7.07-7.12 (m, 2H), 7.22 (m, 2H), 7.80 (d, J=8.80 Hz, 2H), 8.10 (d, J=8.32 Hz, 2H); MS (ES, m/z): C$_{29}$H$_{27}$F$_4$N$_3$O$_4$: 558.23 (M$^+$+1), 556.23 (M$^+$−1)

Example 149

2-(4-{3-[4-[2-(2-Fluoro-phenyl)-ethyl]-5-oxo-1-(4-trifluoromethyl-phenyl)-4,5-dihydro-1H-[1,2,4]triazol-3-yl]-propyl}-2-methyl-phenoxy)-2-methyl-propionic acid

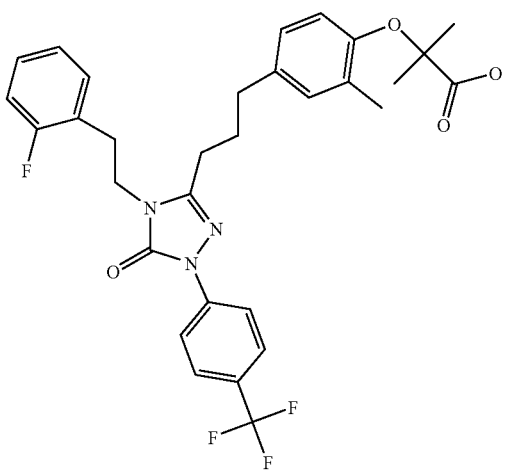

$^1$NMR (DMSO-d$_6$, 400 MHz): δ 1.46 (s, 6H), 1.76-1.80 (m, 2H), 2.11 (s, 3H), 2.23 (t, J=7.82 Hz, 2H), 2.45 (t, J=7.82

Hz, 2H), 2.96 (t, J=6.36 Hz, 2H), 3.83 (t, J=6.85 Hz, 2H), 6.60 (d, J=8.31 Hz, 1H), 6.86 (dd, J=8.31 Hz, J$_2$=1.96 Hz, 1H), 6.96 (d, J=1.96 Hz, 1H), 7.07-7.11 (m, 2H), 7.21-7.26 (m, 2H), 7.79 (d, J=8.80 Hz, 2H), 8.10 (d, J=8.80 Hz, 2H); MS (ES, m/z):C$_{31}$H$_{31}$F$_4$N$_3$O$_4$: 586.2 (M$^+$+1), 584.2(M$^+$-1).

Example 150

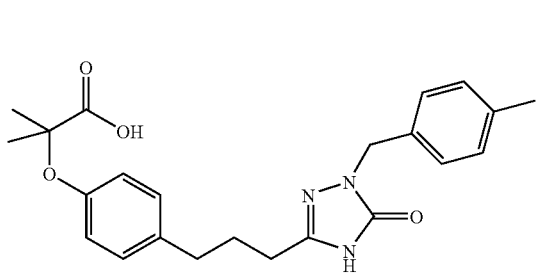

Preparation of Form IV Polymorph

Title compound (5.75 g) is combined with ethyl acetate (30 mL) and heated to ref lux as a slurry. Additional ethyl acetate (19 mL) is added and solution at reflux is obtained. The solution is cooled and crystallization occurs. The slurry is cooled to 0° C. and held at that temperature for 1 hr, then filtered and the filter cake rinsed with cold ethyl acetate. The crystals obtained are dried in vacuo at 60° C. overnight to afford the title compound as the desired form IV polymorph: 5.45 g, 94.5%. mp: 129.4-130.3° C.

| Form IV | | |
|---|---|---|
| Angle 2-Theta ° | d value Angstrom % | Intensity % |
| 6.863 | 12.87 | 4.7 |
| 7.933 | 11.135 | 25.7 |
| 13.225 | 6.689 | 49.9 |
| 13.746 | 6.437 | 12.5 |
| 15.023 | 5.893 | 1.2 |
| 15.97 | 5.545 | 33.9 |
| 16.669 | 5.314 | 4.3 |
| 17.005 | 5.21 | 3.1 |
| 17.327 | 5.114 | 23.1 |
| 17.925 | 4.944 | 12 |
| 19.598 | 4.526 | 30.5 |
| 20.132 | 4.407 | 2 |
| 20.453 | 4.339 | 3.2 |
| 20.764 | 4.274 | 100 |
| 21.714 | 4.089 | 2 |
| 21.954 | 4.045 | 2.2 |
| 22.736 | 3.908 | 2.4 |
| 24.055 | 3.697 | 32.5 |
| 24.538 | 3.625 | 3.2 |
| 24.803 | 3.587 | 5.5 |
| 25.498 | 3.491 | 5 |
| 26.667 | 3.34 | 7.4 |
| 27.83 | 3.203 | 3.4 |
| 28.333 | 3.147 | 1.6 |
| 28.739 | 3.104 | 6.5 |
| 29.503 | 3.025 | 0.8 |
| 30.193 | 2.9575 | 4.2 |
| 30.552 | 2.9236 | 1.4 |
| 30.894 | 2.8921 | 0.8 |
| 32.905 | 2.7197 | 1.1 |
| 33.296 | 2.6887 | 1 |
| 34.198 | 2.6198 | 2.7 |

Example 151

Preparation of

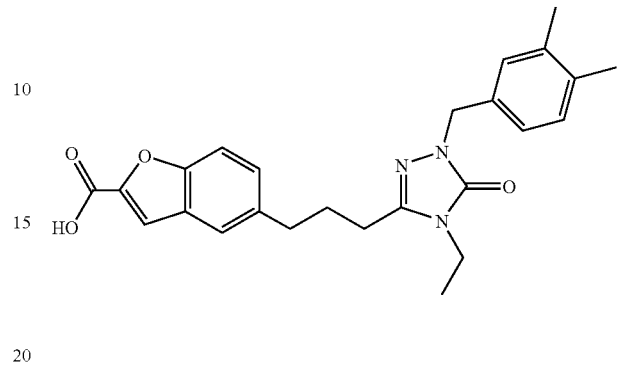

Step A: Preparation of

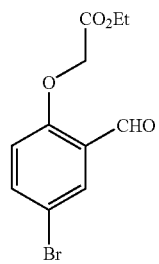

To a solution of 5-bromo salicylaldehyde (3.15 g, 15.6 mmol) in DMF (10 mL) at room temperature was added K$_2$CO$_3$ (5.0 g, 36.2 mmol) and ethyl bromoacetate (2.6 mL, 23.4 mmol). The mixture was stirred at room temperature for one hour. The mixture was diluted with diethyl ether (20 mL) and 1N HCl was added until pH 3-4. The organic layer was separated and washed with water and brine. The organic layer was dried over MgSO$_4$ and the solvent removed under reduced pressure to give the titled compound.

C$_{11}$H$_{11}$BrO$_4$. (MW: 287.11); MS:m/z (M$^+$+1) 288.1.

Step B: Preparation of

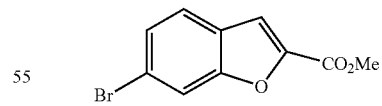

To a solution of MeONa (prepared from 88 mg of Na (3.8 mmol) in 10 mL of MeOH) was added a solution of the Step A product in methanol (1 mL) at room temperature. The mixture was refluxed for 10 minutes in a preheated bath at 80° C. Then, the reaction mixture was allowed to cool to room temperature and the titled compound precipitate from the solution as a white solid. The solid was filtered off and dry under vacuum.

C$_{10}$H$_7$BrO$_3$ (MW: 255.07); MS:m/z (M$^+$+1) 256.

Step C: Preparation of

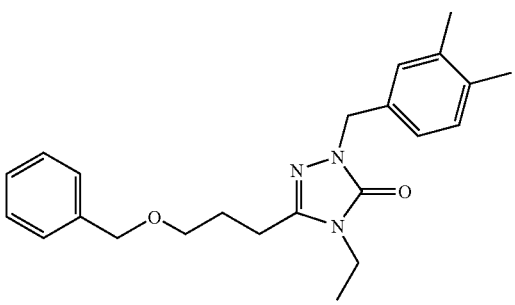

To a solution of the product prepared as in Example 38, Step D (11.3 g, 0.0436 mol) in methyl ethyl ketone (300 mL), was added 3,4-dimethylbenzyl chloride (16.0 mL, 0.1089 mol) followed by potassium carbonate powder (30.1 g, 0.1382 mol).The resulting mixture was stirred at 80-85° C. under a drying tube for 48 hours. The reaction mixture was cooled to room temperature and then partitioned between ethyl acetate (300 mL) and NH$_4$Cl saturated aqueous solution (300 mL). The aqueous layer was extracted with ethyl acetate (200 mL) and the combined organic phase dried over Na$_2$SO$_4$ and filtered. Evaporation of solvent gave a crude product, which was purified on a silica gel column eluting with 50% ethyl acetate in hexane to give the titled compound as colorless oil.

$C_{23}H_{29}N_3O_2$ (MW=379.51); MS: m/z (M$^+$+1)=380.2

Step D: Preparation of

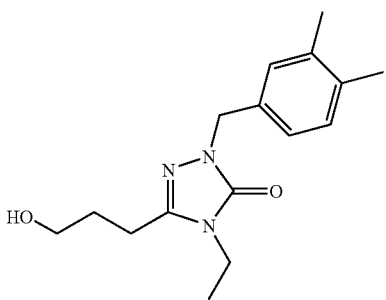

To a solution of the Step C product (16.0 g, 0.0421 mol) in ethanol (400 mL) at room temperature, palladium, 10% on activated carbon (4.2 g) was added. Mixture was stirred under hydrogen atmosphere (balloon) for 3 hours and then filtered through a plug of celite. Evaporation of the solvent gave the titled compound that was used in Step E without further purification.

$C_{16}H_{23}N_3O_2$ (MW=289.38); MS: m/z (M$^+$+1)=290.2

Step E: Preparation of

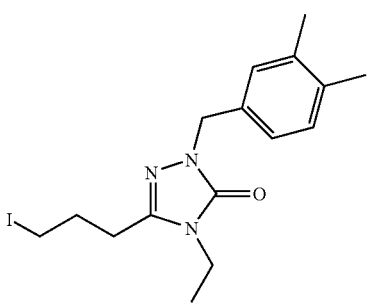

To a solution of triphenylphosphine (8.1 g, 31.0 mmol) and imidazole (2.1 g, 31.0 mmol) in a 3:1 mixture of Et$_2$O—CH$_3$CN (160 mL) at 0° C. under nitrogen atmosphere, iodine (7.8 g, 31.0 mmol) was added in small portions with vigorous stirring. The resulting mixture was warmed at room temperature and stirred for 30 minutes. Then, mixture was cooled to 0° C. and a solution of the Step D product (6.0 g, 20.7 mmol) in a 1:1 mixture of Et$_2$O—CH$_3$CN (40 mL) was added. Reaction was stirred at 0° C. for 15 min and at room temperature for 30 minutes and then poured onto 0.5N HCl (200 mL). The aqueous layer was extracted twice with a 1:1 mixture of Et$_2$O-hexanes (300 mL) and the combined organic phase dried over Na$_2$SO$_4$ and filtered. Evaporation of solvent gave a crude product, which was purified on a silica gel column eluting with 50% ethyl acetate in hexane to give the titled compound as yellow oil.

$C_{16}H_{22}IN_3O$ (MW=399.28); MS: m/z (M$^+$+1)=400.2

Step F: Preparation of

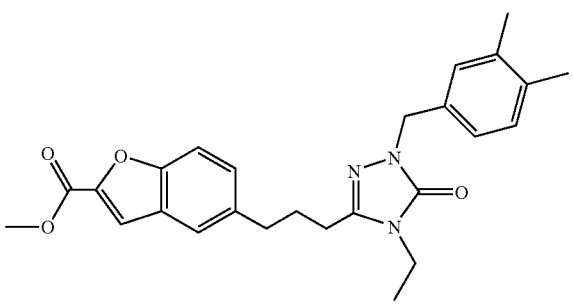

To a stirred slurry of zinc dust (0.968 g, 14.7 mmol) in anhydrous THF (5 mL) under nitrogen atmosphere at 60° C. was added 1,2-dibromoethane (63 μL, 0.7 mmol). After 15 minutes of vigorous stirring, the slurry was allowed to cool to room temperature and chlorotrimethylsilane (78 μL, 0.6 mmol) was added. Mixture was stirred for 30 minutes and then a solution of the Step E product (0.98 g, 2.46 mmol) in anhydrous THF (5 mL) was added dropwise. Mixture was reheated to 60° C. and then stirred for 10 minutes. A solution of the Step B (0.210 g, 0.82 mmol), Pd(dba)$_2$ (0.0237 g, 0.04 mmol) and tri-o-tolylphosphine (0.025 g, 0.082 mmol) in anhydrous THF (2.5 mL) was added and the resulting solution maintained at 60° C. for 2 h. Reaction was then cooled at room temperature and poured onto a 1:1 mixture of AcOEt and 0.5N HCl (40 mL). The layers were separated and the aqueous phase was extracted with ethyl acetate (20 mL). The combined organic layers were washed with 0.5N HCl (20 mL), dried over Na$_2$SO$_4$ and filtered. Evaporation of solvent gave a crude product, which was purified on a silica gel column eluting with 50% ethyl acetate in hexane to give the titled compound as colorless oil.

$C_{26}H_{29}N_3O_4$ (MW=447.54); MS: m/z (M$^+$+1)=448.2.

Step G: Preparation of

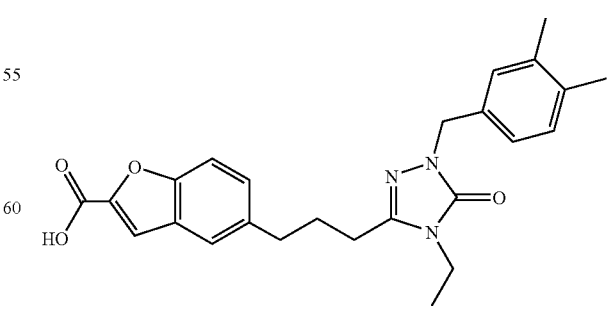

To a solution of Step F product (0.235 g, 0.52 mmol) in THF (10.5 mL) at room temperature a 1N solution of LiOH (4.2 mL, 4.2 mmol) was added. The mixture was stirred overnight, and then layers were separated. The aqueous layer was washed with diethyl ether (3×10 mL), and cooled to 0° C. After the pH was adjusted to 1-2 by addition of 1N HCl, the aqueous layer was extracted with AcOEt (2×20 mL). The combined organic layer was dried over $Na_2SO_4$, filtered and concentrated to dryness to give the titled compound.

$C_{25}H_{27}N_3O_4$ (MW=433.51); MS: m/z ($M^+$+1)=434.2.

Example 152

Preparation of

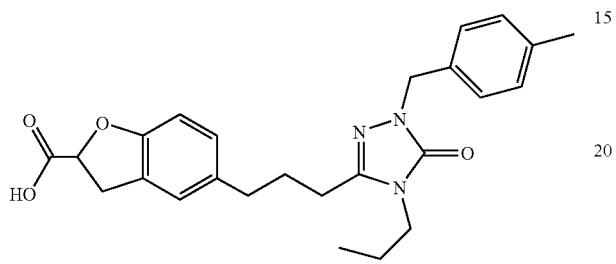

Step A: Preparation of

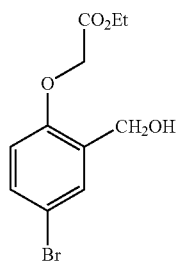

To a solution Step A Example 151 product (2.5 g, 8.7 mmol) in EtOH(10 mL) at 0° C. was added in one portion $NaBH_4$ (0.394 g, 10.4 mmol). The mixture was stirred for 90 min allowing the temperature to rise. Then acetone (1 mL) was added and the solvent was removed under vacuum. The oil obtained was disolved in $CH_2Cl_2$ (20 mL) and washed with Brine (20 mL). The layers were separated and the organic one was dried over $Na_2SO_4$ and filtered. Evaporation of solvent yielded the titled compound in pure form.

$C_{11}H_{11}BrO_4$. (MW: 289.11); MS:m/z ($M^+$+1) 290.1.

Step B: Preparation of

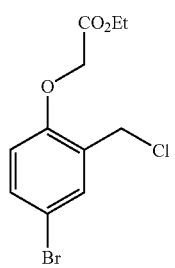

To a solution $SOCl_2$ (0.7 mL, 10.3 mmol) and Pyridine (3 drops) in $CH_2Cl_2$ (10 mL) at room temperature was added dropwise a solution of Step A product (2.5 g, 8.6 mmol) in $CH_2Cl_2$ (5 mL). The reaction mixture was heated at 50° C. for 2 h, then allowed to cool and washed with a saturated aqueous solution of $NaHCO_3$ (10 mL)). The layers were separated and the aqueous layer was extracted with $CH_2Cl_2$ (2×10 mL). The organics were joined, dried over $Na_2SO_4$ and filtered. Evaporation of solvent yielded the titled compound in pure form.

$C_{11}H_{12}BrClO_3$. (MW: 307.57); MS:m/z ($M^+$+1) 307.0.

Step C: Preparation of

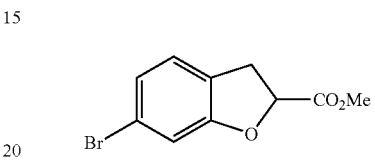

To a solution of Step B product (1.83 g, 5.9 mmol) in N-methyl-2-pyrrolidinone (6 mL) at 0° C. under $N_2$ atmosphere was added in one portion NaH (60% mineral oil, 0.283 g, 7 mmol). The reaction mixture was stirred at room temperature for a day, then some drops of MeOH were added. The mixture was diluted in AcOEt (20 mL) and HCl 10% (20 mL). The layers were separated and the organic layer was wased with HCl 10% (2×20 mL), and finally witn Brine (20 mL). The organic layer was dried over $Na_2SO_4$ and filtered. Evaporation of solvent yield the titled compound.

$C_{10}H_9BrO_3$ (MW: 257.09); MS:m/z ($M^+$+1) 257.0.

Step D: Preparation of

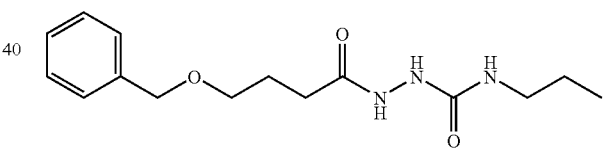

To a solution of the Example 38, Step B product (82.2 g, 0.423 mol) in THF (400 mL), was added a solution of propyl isocyanate (Aldrich, 47.6 mL, 0.508 mol) in THF (400 mL) dropwise and the mixture was stirred at room temperature for an hour. Evaporation of solvent gave the titled compound as an off-white powder that was used in step E without further purification.

$C_{15}H_{23}N_3O_3$ (MW=293.37); MS: m/z ($M^+$+1)=294.2

Step E: Preparation of

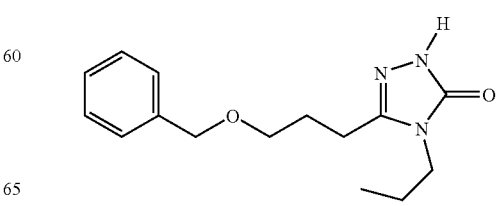

A suspension of the Step D product (124.0 g, 0.423 mol) in a solution of KOH (28.5 g, 0.508 mol) in water (570 mL) (1.2 eq of 5% KOH aqueous solution) was heated at 110° C. for 1 hour (as soon as the temperature is increased, suspension disappear). At that time, TLC showed no starting material remained and reaction was cooled to room temperature. Then, pH was adjusted to pH=6-7 by addition of 1N HCl, and extracted with AcOEt (3×500 mL). The combined organic layers were dried over $Na_2SO_4$, filtered and evaporated to give the titled compound as white solid.

$C_{15}H_{21}N_3O_2$ (MW=275.35); MS: m/z ($M^+$+1)=276.2

Step F: Preparation of

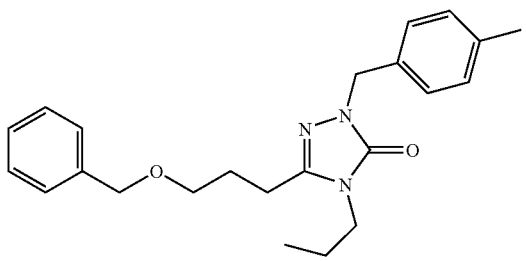

To a solution of the Step E product (11.5 g, 0.0418 mol) in methyl ethyl ketone (300 mL), was added 4-methylbenzyl bromide (11.6 g, 0.0616 mol) followed by potassium carbonate powder (28.9 g, 0.209 mol). The resulting mixture was stirred at 80-85° C. under a drying tube for 24 hours. The reaction mixture was cooled to room temperature and then partitioned between ethyl acetate (300 mL) and $NH_4Cl$ saturated aqueous solution (300 mL). The aqueous layer was extracted with ethyl acetate (200 mL) and the combined organic phase dried over $Na_2SO_4$ and filtered. Evaporation of solvent gave a crude product, which was purified on a silica gel column eluting with 50% ethyl acetate in hexane to give the titled compound as colorless oil.

$C_{23}H_{29}N_3O_2$ (MW=379.51); MS: m/z ($M^+$+1)=380.2

Step G: Preparation of

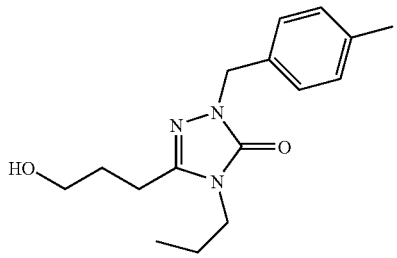

To a solution of the Step F product (10.0 g, 0.0263 mol) in ethanol (500 mL) at room temperature, palladium, 10% on activated carbon (2.6 g) was added. Mixture was stirred under hydrogen atmosphere (balloon) for 3 hours and then filtered through a plug of celite. Evaporation of the solvent gave the titled compound as white solid that was used in Step H without further purification.

$C_{16}H_{23}N_3O_2$ (MW=289.38); MS: m/z ($M^+$+1)=290.2

Step H: Preparation of

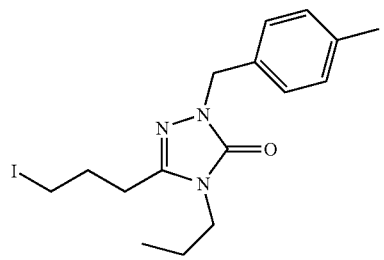

To a solution of triphenylphosphine (10.3 g, 39.4 mmol) and imidazole (2.7 g, 39.4 mmol) in a 3:1 mixture of $Et_2O$—$CH_3CN$ (200 mL) at 0° C. under nitrogen atmosphere, iodine (10.0 g, 39.4 mmol) was added in small portions with vigorous stirring. The resulting mixture was warmed at room temperature and stirred for 1 hour. Then, mixture was cooled to 0° C. and a solution of the Step G product (7.6 g, 26.3 mmol) in a 1:1 mixture of $Et_2O$—$CH_3CN$ (50 mL) was added. Reaction was stirred at 0° C. for 15 min and at room temperature for 1 hour and then poured onto 0.5N HCl (100 mL). The aqueous layer was extracted twice with a 1:1 mixture of $Et_2O$-hexanes (200 mL) and the combined organic phase dried over $Na_2SO_4$ and filtered. Evaporation of solvent gave a crude product, which was purified on a silica gel column eluting with 50% ethyl acetate in hexane to give the titled compound as yellow oil.

$C_{16}H_{22}IN_3O$ (MW=399.28); MS: m/z ($M^+$+1)=400.2

Step I: Preparation of

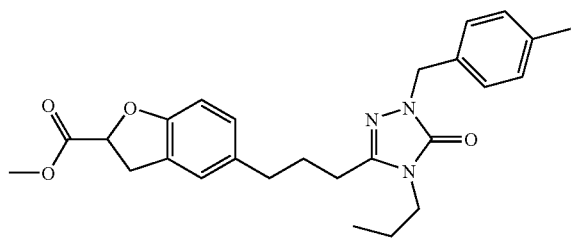

To a stirred slurry of zinc dust (0.411 g, 6.3 mmol) in anhydrous THF (1.5 mL) under nitrogen atmosphere at 60° C. was added 1,2-dibromoethane (27 µL, 0.31 mmol). After 15 minutes of vigorous stirring, the slurry was allowed to cool to room temperature and chlorotrimethylsilane (33 µL, 0.26 mmol) was added. Mixture was stirred for 30 minutes and then a solution of the Step H product (0.42 g, 1.05 mmol) in anhydrous THF (1.5 mL) was added dropwise. Mixture was reheated to 60° C. and then stirred for 10 minutes. A solution of Step C product (0.285 g, 1.05 mmol), $Pd(dba)_2$ (0.030 g, 0.052 mmol) and tri-o-tolylphosphine (0.032 g, 0.105 mmol) in anhydrous THF (2.5 mL) was added and the resulting solution maintained at 60° C. for 2 h. Reaction was then cooled at room temperature and poured onto a 1:1 mixture of AcOEt and 0.5N HCl (50 mL). The layers were separated and the aqueous phase was extracted with ethyl acetate (2×20 mL). The combined organic layers were washed with 0.5N HCl (25 mL), dried over $Na_2SO_4$ and filtered. Evaporation of solvent gave a crude product, which was purified on a silica gel column eluting with 50% ethyl acetate in hexane to give the titled compound as colorless oil.

$C_{26}H_{31}N_3O_4$ (MW=449.55); MS: m/z (M$^+$+1)=450.2.

Step J: Preparation of

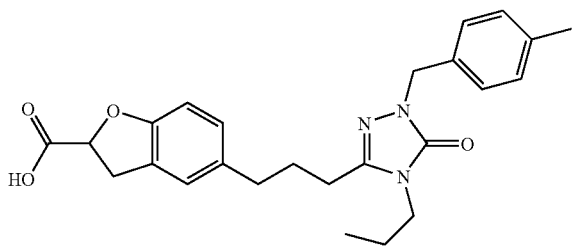

To a solution of Step I product (0.05 g, 0.11 mmol) in THF (2.5 mL) at room temperature a 1N solution of NaOH (2.5. mL, 2.5 mmol) was added. The mixture was stirred for two days and then layers were separated. The aqueous layer was washed with diethyl ether (4×5 mL), and cooled to 0° C. After the pH was adjusted to 1-2 by addition of 1N HCl, the aqueous layer was extracted with AcOEt (2×10 mL). The combined organic layer was dried over Na$_2$SO$_4$, filtered and concentrated to dryness to give the titled compound.

$C_{25}H_{29}N_3O_4$ (MW=435.53); MS: m/z (M$^+$+1)=435.2.

Example 153

Preparation of

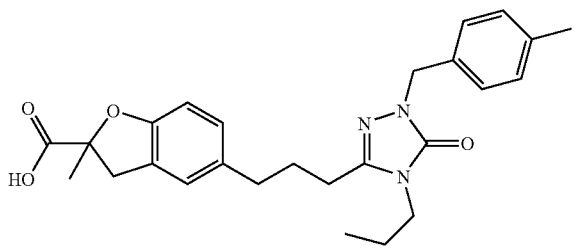

Step A: Preparation of

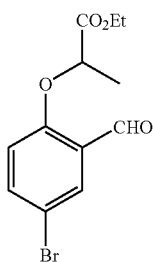

To a solution of 5-bromo salicylaldehyde (2.6 g, 13 mmol) in DMF (10 mL) at room temperature was added K$_2$CO$_3$ (5.5 g, 39 mmol) and ethyl 2-bromopropionate (2.6 mL, 19.5 mmol). The mixture was stirred at room temperature for two hours. The solid was filtered off and the filtrate was washed with 1N HCl (10 mL) and H$_2$O (10 mL). The organic layer was dried over Na$_2$SO$_4$ and filtered. Evaporation of solvent gave a solid which was suspended in hexane (30 mL) and filtered yielding the titled compound in pure form.

$C_{12}H_{13}BrO_4$. (MW: 301.14); MS:m/z (M$^+$+1) 302.2.

Step B: Preparation of

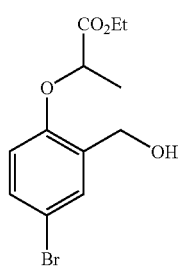

To a solution Step A product (1.5 g, 4.98 mmol) in EtOH(25 mL) at 0° C. was added in one portion NaBH$_4$ (0.206 g, 5.47 mmol). The mixture was stirred for 30 min allowing the temperature to rise. Then acetone (1 mL) was added and the solvent was removed under vacuum. The oil obtained was disolved in CH$_2$Cl$_2$ (20 mL) and washed with Brine (20 mL). The layers were separated and the organic one was dried over Na$_2$SO$_4$ and filtered. Evaporation of solvent yielded the titled compound in pure form.

$C_{12}H_{15}BrO_4$. (MW: 303.14); MS:m/z (M$^+$+1) 304.2.

Step C: Preparation of

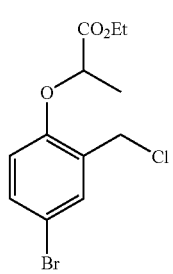

To a solution SOCl$_2$ (0.43 mL, 5.97 mmol) and Pyridine (2 drops) in CH$_2$Cl$_2$ (5 mL) at room temperature was added dropwise a solution of Step B product (1.3 g, 4.38 mmol) in CH$_2$Cl$_2$ (3 mL). The reaction mixture was heated at 50° C. for 90 min, then -allowed to cool and washed with a saturated aqueous solution of NaHCO$_3$ (10 mL). The layers were separated and the aqueous layer was extracted with CH$_2$Cl$_2$ (2×10 mL.). The organics were joined, dried over Na$_2$SO$_4$ and filtered. Evaporation of solvent yielded the titled compound in pure form.

$C_{12}H_{14}BrClO_3$. (MW: 321.60); MS:m/z (M$^+$+1) 321.0.

Step D: Preparation of

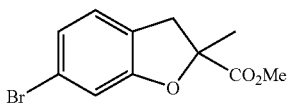

To a solution of Step C product (1.3 g, 4 mmol) in N-methyl-2-pyrrolidinone (4 mL) at 0° C. under $N_2$ atmosphere was added in one portion NaH (60% mineral oil, 0.194 g, 4.85 mmol). The reaction mixture was stirred at room temperature for a day, then some drops of MeOH were added. The mixture was diluted in AcOEt (20 mL) and HCl 10% (20 mL). The layers were separated and the organic layer was wased with HCl 10% (2×20 mL), and finally witn Brine (20 mL). The organic layer was dried over $Na_2SO_4$ and filtered. Evaporation of solvent yield the titled compound.

$C_{11}H_{11}BrO_3$ (MW: 271.11); MS:m/z ($M^++1$) 271.0.

Step E: Preparation of

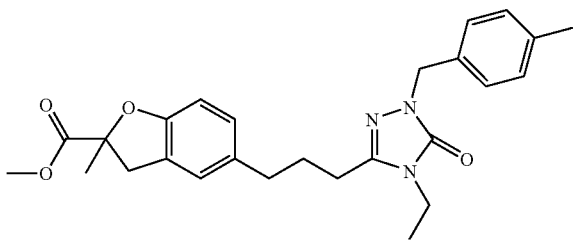

To a stirred slurry of zinc dust (0.411 g, 6.3 mmol) in anhydrous THF (1.5 mL) under nitrogen atmosphere at 60° C. was added 1,2-dibromoethane (27 □L, 0.31 mmol). After 15 minutes of vigorous stirring, the slurry was allowed to cool to room temperature and chlorotrimethylsilane (33 µL, 0.26 mmol) was added. Mixture was stirred for 30 minutes and then a solution of the Example 152, Step H product (0.42 g, 1.05 mmol) in anhydrous THF (1.5 mL) was added dropwise. Mixture was reheated to 60° C. and then stirred for 10 minutes. A solution of Step D product (0.271 g, 1.0 mmol), Pd(dba)$_2$ (0.030 g, 0.052 mmol) and tri-o-tolylphosphine (0.032 g, 0.105 mmol) in anhydrous THF (2.5 mL) was added and the resulting solution maintained at 60° C. for 2 h. Reaction was then cooled at room temperature and poured onto a 1:1 mixture of AcOEt and 0.5N HCl (50 mL). The layers were separated and the aqueous phase was extracted with ethyl acetate (2×20 mL). The combined organic layers were washed with 0.5N HCl (25 mL), dried over $Na_2SO_4$ and filtered. Evaporation of solvent gave a crude product, which was purified on a silica gel column eluting with 50% ethyl acetate in hexane to give the titled compound as colorless oil.

$C_{27}H_{33}N_3O_4$ (MW=463.58); MS: m/z ($M^++1$)=464.2.

Step F: Preparation of

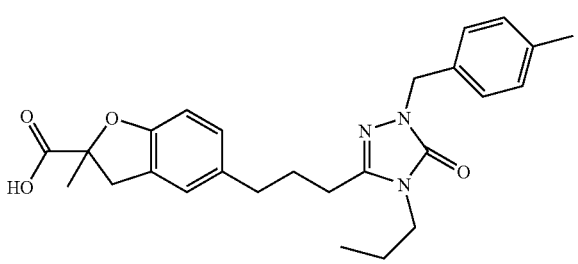

To a solution of Step D product (0.05 g, 0.10 mmol) in THF (2 mL) at room temperature a 1N solution of NaOH (2 mL, 2 mmol) was added. The mixture was stirred for three days, and then layers were separated. The aqueous layer was washed with diethyl ether (3×10 mL)), and cooled to 0° C. After the pH was adjusted to 1-2 by addition of 1N HCl, the aqueous layer was extracted with AcOEt (2×10 mL)). The combined organic layer was dried over $Na_2SO_4$, filtered and concentrated to dryness to give the titled compound.

$C_{26}H_{31}N_3O_4$ (MW=449.55); MS: m/z ($M^++1$)=450.2.

Example 154

Step A

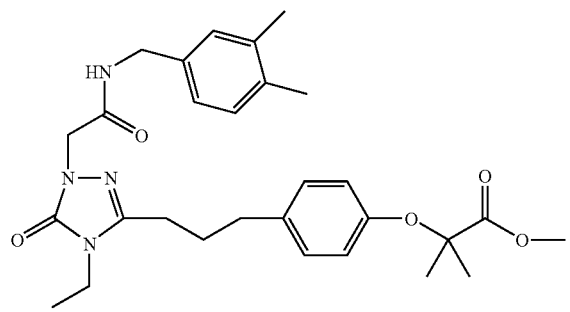

A THF solution of the acid described in Example 127, Step B (0.300 g, 0.0007 mol) was treated with EDC (0.212 g, 0.0011 mol) and HOAt (0.095 g, 0.0007 mol). An equivalent 3, 4 dimethyl benzyl amine (0.10 ml, 0.0007 mol) was added and the reaction was stirred overnight. The solvent was concentrated and the residue was redissolved in methylene chloride and extracted with water. Purification by flash chromatography (100% ethyl acetate) gave the desired amide.

$C_{29}H_{38}N_4O_5$ (MW=522.65); mass spectroscopy (MH$^+$)=523.3

Step B

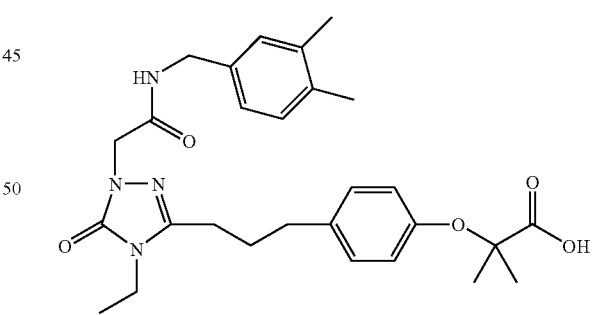

The amide from Step A (0.260 g, 0.0005 mol) was dissolved in dioxane (3 ml) and water (3 ml) then treated with LiOH (0.012 g, 0.0005 mol). The reaction was stirred for two hours. Water was added to the mixture and the layer was extracted with ether. The aqueous layer was acidified with 1N HCl and extracted with ethyl acetate. The organic layer was washed with brine, dried over $Na_2SO_4$ then concentrated to yield the desired product as a white foam.

$C_{28}H_{36}N_4O_5$ (MW=508.62); mass spectroscopy (MH$^+$)=509.4

Example 155

Step A

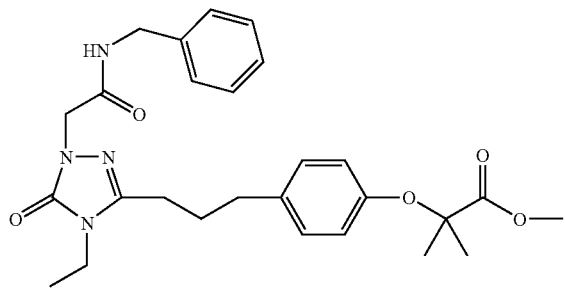

A THF solution of the acid described in Example 127, Step B (0.300 g, 0.0007 mol) was treated with EDC (0.212 g, 0.0011 mol) and HOAt (0.095 g, 0.0007 mol). An equivalent of benzyl amine (0.076 ml, 0.0007 mol) was added and the reaction was stirred overnight. The solvent was concentrated and the residue was redissolved in methylene chloride and extracted with water. Purification by flash chromatography (100% ethyl acetate) gave the desired amide. $C_{27}H_{34}N_4O_5$ (MW=494.60); mass spectroscopy (MH$^+$)=495.2

Step B

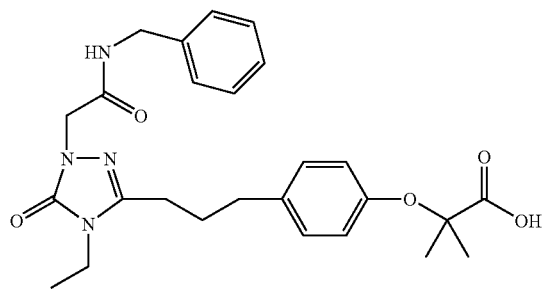

The amide from Step A (0.176 g, 0.00035 mol) was dissolved in dioxane (3 ml) and water (3 ml) then treated with LiOH (0.0085 g, 0.00035 mol). The reaction was stirred for two hours. Water was added to the mixture and the layer was extracted with ether. The aqueous layer was acidified with 1N HCl and extracted with ethyl acetate. The organic layer was washed with brine, dried over Na$_2$SO$_4$ then concentrated to yield the desired product as a white foam.

$C_{26}H_{32}N_4O_5$ (MW=480.57); mass spectroscopy (MH$^+$)=481.4

Example 156

Step A

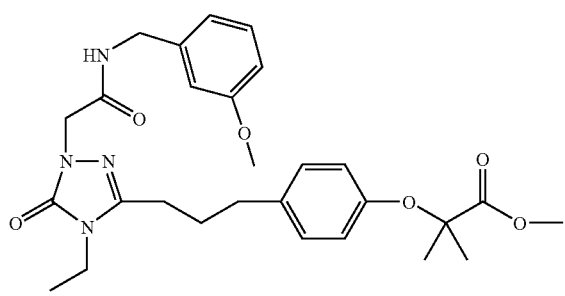

A THF solution of the acid described in Example 127, Step B (0.300 g, 0.0007 mol) was treated with EDC (0.212 g, 0.0011 mol) and HOAt (0.095 g, 0.0007 mol). An equivalent of 3-methoxy benzyl amine (0.090 ml, 0.0007 mol) was added and the reaction was stirred overnight. The solvent was concentrated and the residue was redissolved in methylene chloride and extracted with water. Purification by flash chromatography (100% ethyl acetate) gave the desired amide.

$C_{28}H_{36}N_4O_6$ (MW=524.62); mass spectroscopy (MH$^+$)=525.3

Step B

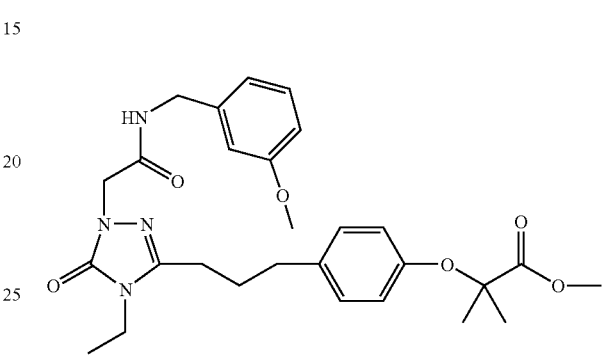

The amide from Step A (0.260 g, 0.00049 mol) was dissolved in dioxane (3 ml) and water (3 ml) then treated with LiOH (0.012 g, 0.00049 mol). The reaction was stirred for two hours. Water was added to the mixture and the layer was extracted with ether. The aqueous layer was acidified with 1N HCl and extracted with ethyl acetate. The organic layer was washed with brine, dried over Na$_2$SO$_4$ then concentrated to yield the desired product as a white foam.

$C_{27}H_{34}N_4O_6$ (MW=510.59); mass spectroscopy (MH$^+$)=511.3

Example 157

Step A

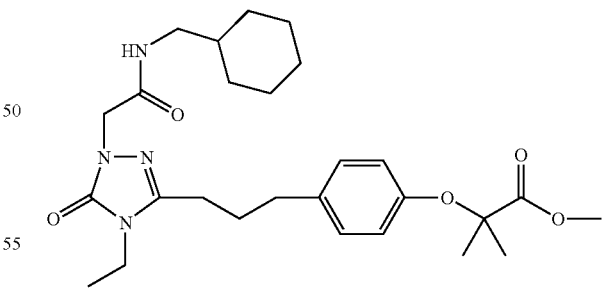

A THF solution of the acid described in Example 127, Step B (0.300 g, 0.0007 mol) was treated with EDC (0.212 g, 0.0011 mol) and HOAt (0.095 g, 0.0007 mol). An equivalent of 3-methoxy benzyl amine (0.091 ml, 0.0007 mol) was added and the reaction was stirred overnight. The solvent was concentrated and the residue was redissolved in methylene chloride and extracted with water. Purification by flash chromatography (100% ethyl acetate) gave the desired amide.

$C_{27}H_{40}N_4O_5$ (MW=500.6); mass spectroscopy (MH$^+$)= 501.4

Step B

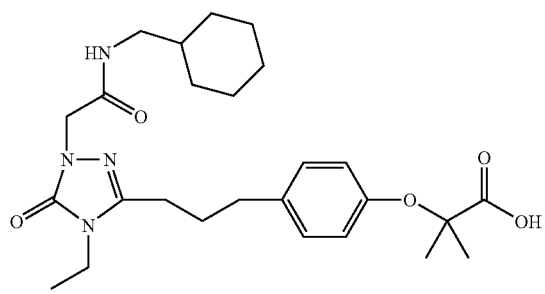

The amide from Step A (0.290 g, 0.00058 mol) was dissolved in dioxane (3 ml) and water (3 ml) then treated with LiOH (0.013 g, 0.00058 mol). The reaction was stirred for two hours. Water was added to the mixture and the layer was extracted with ether. The aqueous layer was acidified with 1N HCl and extracted with ethyl acetate. The organic layer was washed with brine, dried over $Na_2SO_4$ then concentrated to yield the desired product as a white solid.

$C_{26}H_{38}N_4O_5$ (MW=486.62); mass spectroscopy (MH$^+$)= 487.4

Biological Assays

Binding and Cotransfection Studies

The in vitro potency of compounds in modulating PPARα receptors were determined by the procedures detailed below. DNA-dependent binding (ABCD binding) was carried out using SPA technology with PPAR receptors. Tritium-labeled PPARα agonists were used as radioligands for generating displacement curves and $IC_{50}$ values with compounds of the invention. Cotransfection assays were carried out in CV-1 cells. The reporter plasmid contained an acylCoA oxidase (AOX) PPRE and TK promoter upstream of the luciferase reporter cDNA. Appropriate PPARs were constitutively expressed using plasmids containing the CMV promoter. For PPARα, interference by endogenous PPARγ in CV-1 cells was an issue. In order to eliminate such interference, a GAL4 chimeric system was used in which the DNA binding domain of the transfected PPAR was replaced by that of GAL4, and the GAL4 response element was utilized in place of the AOX PPRE. Cotransfection efficacy was determined relative to PPARα agonist reference molecules. Efficacies were determined by computer fit to a concentration-response curve, or in some cases at a single high concentration of agonist (10 μM).

These studies were carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention were compared with corresponding data for marketed compounds that act on huPPARα.

The binding and cotransfection efficacy values found, for compounds of the invention and compounds of this invention which are useful for modulating a PPAR alpha receptor, were ≦100 nM and ≧50%, respectively.

Evaluation of Triglyceride Reduction and HDL Cholesterol Elevation in HuapoAI Transgenic Mice Seventeen different series of studies were performed to evaluate the effect of compounds of the present invention upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) were acclimated in individual cages for two weeks with standard chow diet (Purina 5001) and water provided ad libitum. After the acclimation, mice and chow were weighed and assigned to test groups (n=5) with randomization by body weight. Mice were dosed daily by oral gavage for 8 days using a 29 gauge, 1½ inch curved feeding needle (Popper & Sons). The vehicle for the controls, test compounds and the positive control (fenofibrate 100 mg/kg) was 1% carboxymethylcellulose (w/v) with 0.25% tween 80 (w/v). All mice were dosed daily between 6 and 8 a.m. with a dosing volume of 0.2 ml. Prior to termination, animals and diets were weighed and body weight change and food consumption were calculated. Three hours after last dose, mice were euthanized with CO2 and blood was removed (0.5-1.0 ml) by cardiac puncture. After sacrifice, the liver, heart, and epididymal fat pad were, excised and weighed. Blood was permitted to clot and serum was separated from the blood by centrifugation.

Cholesterol and triglycerides were measured calorimetrically using commercially prepared reagents (for example, as available from Sigma #339-1000 and Roche #450061 for triglycerides and cholesterol, respectively). The procedures were modified from published work (McGowan M. W. et al., Clin Chem 29:538-542,1983; Allain C. C. et al., Clin Chem 20:470-475,1974. Commercially available standards for triglycerides and total cholesterol, respectively, commercial quality control plasma, and samples were measured in duplicate using 200 μl of reagent. An additional aliquot of sample, added to a well containing 200 μl water, provided a blank for each specimen. Plates were incubated at room temperature on a plate shaker and absorbance was read at 500 nm and 540 nm for total cholesterol and triglycerides, respectively. Values for the positive control were always within the expected range and the coefficient of variation for samples was below 10%. All samples from an experiment were assayed at the same time to minimize inter-assay variability.

Serum lipoproteins were separated and cholesterol quantitated-by fast protein liquid chromatography (FPLC) coupled to an in line detection system. Samples were applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol was monitored in the flow strem at 505 nm and the analog voltage from the monitor was converted to a digital signal for collection and analysis. The change in voltage corresponding to change in cholesterol concentration was plotted vs time and the area under the curve corresponding to the elution of very low density lipoprotein (VLDL), low density lipoprotein (LDL) and high density lipoprotein (HDL) was calculated using Perkin Elmer Turbochrome software. The results of these studies are provided in the following tables for triglyceride and HDL cholesterol levels. Note that the superscripted numbers in the following tables refer to the study numbers. Further, the values, determined in each study, for triglyceride levels in the control mice and for HDL cholesterol levels in fenofibrate-treated mice are also provided in the following tables.

Triglyceride Serum Levels in Mice Dosed with a Compound of the Invention was Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention was compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of five different compounds of the present invention and the PPAR gamma agonist rosiglitazone (BRL49653) or the PPAR alpha agonist fenofibrate, and the control, to male db/db mice, were studied.

Five week old male diabetic (db/db) mice [for example, C57BlKs/j-m+/+Lepr(db), Jackson Laboratory, Bar Harbor, Me] or lean littermates were housed 6 per cage with food and water available at all times. After an acclimation period of 2 weeks, animals were individually identified by ear notches, weighed, and bled via the tail vein for determination of initial glucose levels. Blood was collected (100 µl) from unfasted animals by wrapping each mouse in a towel, cutting the tip of the tail with a scalpel, and milking blood from the tail into a heparinized capillary tube. Sample was discharged into a heparinized microtainer with gel separator and retained on ice. Plasma was obtained after centrifugation at 4° C. and glucose measured immediately. Remaining plasma was frozen until the completion of the experiment, when glucose and triglycerides were assayed in all samples. Animals were grouped based on initial glucose levels and body weights. Beginning the following morning, mice were dosed daily by oral gavage for 7 days. Treatments were test compounds (30 mg/kg), a positive control agent (30 mg/kg) or vehicle [1% carboxymethylcellulose (w/v)/0.25% Tween80 (w/v); 0.3 ml/mouse]. On day 7, mice were weighed and bled (tail vein) 3 hours after dosing. Twenty-four hours after the $7^{th}$ dose (i.e., day 8), animals were bled again (tail vein). Samples obtained from conscious animals on days 0, 7 and 8 were assayed for glucose. After the 24 hour bleed, animals were weighed and dosed for the final time. Three hours after dosing on day 8, animals were anesthetized by inhalation of isoflurane and blood obtained via cardiac puncture (0.5-0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed.

Glucose was measured calorimetrically using commercially purchased reagents. According to the manufacturers, the procedures were modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays were further modified in our laboratory for use in a 96 well format. The commercially available standard for glucose, commercially available quality control plasma, and samples (2 or 5 µl/well) were measured in duplicate using 200 µl of reagent. An additional aliquot of sample, pipetted to a third well and diluted in 200 µl water, provided a blank for each specimen. Plates were incubated at room temperature for 18 minutes for glucose on a plate shaker (DPC Micormix 5) and absorbance read at 500 nm on a plate reader. Sample absorbances were compared to a standard curve (100-800 for glucose). Values for the quality control sample were always within the expected range and the coefficient of variation for samples was below 10%. All samples from an experiment were assayed at the same time to minimize inter-assay variability.

The results of the study, suggest compounds of the present invention that significantly reduced db/db mouse plasma glucose levels while resulting in body weight gains that were less than those observed for rosiglitazone.

Evaluation of the Effects of Compounds of the Present Invention upon $A^y$ Mice Body Weight, Fat Mass, Glucose and Insulin Levels Female $A^y$ Mice Female $A^y$ mice were singly housed, maintained under standardized conditions (22° C., 12 h light:dark cycle), and provided free access to food and water throughout the duration of the study. At twenty weeks of age the mice were randomly assigned to vehicle control and treated groups based on body weight and body fat content as assessed by DEXA scanning (N=6). Mice were then dosed via oral gavage with either vehicle or a Compound of this invention (50 mg/kg), one hour after the initiation of the light cycle (for example, about 7 A.M.) for 18 days. Body weights were measured daily throughout the study. On day 14 mice were maintained in individual metabolic chambers for indirect calorimetry assessment of energy expenditure and fuel utilization. On day 18 mice were again subjected to DEXA scanning for post treatment measurement of body composition.

The results of p.o. dosing of compound for 18 days on body weight, fat mass, and lean mass were evaluated and suggest which compounds of this invention can be especially useful for maintaining desirable weight and/or promoting desired lean to fat mass.

Indirect calorimetry measurements revealed a significant reduction in respiratory quotient (RQ) in treated animals during the dark cycle [0.864±0.013 (Control) vs. 0.803±0.007 (Treated); p<0.001]. This reduction in RQ is indicative of an increased utilization of fat during the animals' active (dark) cycle. Additionally, treated animals displayed significantly higher rates of energy expenditure than control animals (17.40±0.49 vs. 13.62±0.26 kcal/kg/hr, respectively).

Male KK/A$^y$ Mice

Male KK/A$^y$ mice were singly housed, maintained under standardized conditions (22° C., 12 h light:dark cycle), and provided free access to food and water throughout the duration of the study. At twenty-two weeks of age the mice were randomly assigned to vehicle control and treated groups based on plasma glucose levels. Mice were then dosed via oral gavage with either vehicle or a Compound of this invention (30 mg/kg) one hour after the initiation of the light cycle (7 A.M.) for 14 days. Plasma glucose, triglyceride, and insulin levels were assessed on day 14.

The results of p.o. dosing of compound for 14 days on plasma glucose, triglycerides, and insulin are evaluated to identify compounds of this invention which may be especially desired.

Method to Elucidate the LDL-cholesterol Total-cholesterol and Triglyceride Lowering Effect of Compound 5 (8)

Male Syrian hamsters (Harlan Sprague Dawley) weighing 80-120 g were placed on a high-fat cholesterol-rich diet for two to three weeks prior to use. Feed and water were provided ad libitum throughout the course of the experiment. Under these conditions, hamsters became hypercholesterolemic showing plasma cholesterol levels between 180-280 mg/dl. (Hamsters fed with normal chow had a total plasma cholesterol level between 100-150 mg/dl.) Hamsters with high plasma cholesterol (180 mg/dl and above) were randomized into treatment groups based on their total cholesterol level using the GroupOptimizeV211. xls program.

A Compound of this invention was dissolved in an aqueous vehicle (containing CMC with Tween 80) such that each hamster received once a day approx. 1 ml of the solution by garvage at doses 3 and 30 mg/kg body weight. Fenofibrate (Sigma Chemical, prepared as a suspension in the same vehicle) was given as a known alpha-agonist control at a dose of 200 mg/kg, and the blank control was vehicle alone. Dosing was performed daily in the early morning for 14 days.

Quantification of Plasma Lipids:

On the last day of the test, hamsters were bled (400 ul) from the suborbital sinus while under isoflurane anesthesia 2 h after dosing. Blood samples were collected into heparinized microfuge tubes chilled in ice bath. Plasma samples were separated from the blood cells by brief centrifugation. Total cholesterol and triglycerides were determined by means of enzymatic assays carried out automatically in the Monarch equipment (Instrumentation Laboratory) following the manufacturer's precedure. Plasma lipoproteins (VLDL, LDL and HDL) were resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids were accomplished by postcolumn incubation of the effluent with a Cholesterol/HP reagent (for example, Roche Lab System; infused at 0.12 ml/min) in a knitted reaction coil maintained at 37° C. The intensity of the color formed was proportional to the cholesterol concentration and was measured photometrically at 505 nm.

The effect of administration of a Compound of this invention for 14 days is studied for the percent reduction in LDL level with reference to the vehicle group. The LDL-lowering efficacy for certain compounds of this invention is markedly more potent than that of fenofibrate. Compounds of this invention that decrease LDL greater than or equal to 30% (thirty percent) compared to vehicle can be especially desired.

The total-cholesterol and triglyceride lowering effects of a Compound of this invention was also studied. The data for reduction in total cholesterol and triglyceride levels after treatment with a compound of this invention for 14 days was compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention was part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that was stored at −70° C. prior to fibrinogen assay.

Quantification of Rat Plasma Fibrinogen:

Rat plasma fibrinogen levels were quantified by using a commercial assay system consists of a coagulation instrument following the manufacturer's protocol. In essence, 100 ul of plasma was sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitored the clotting time, a function of fibrinogen concentration quantified with reference to standard samples.

Results:

Compounds of this invention are capable of lowering fibrinogen level in vivo. Compounds that lower fibrinogen level greater than vehicle can be especially desired.

Cholesterol and triglyceride lowering effects of compounds of this invention were also produced in Zucker rats.

Method to Elucidate the Anti-Body Weight Gain and Anti-Appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight were acclimated for 1 week prior to treatment. Rats were on normal chow and water was provided ad libitum throughout the course of the experiment.

α-agonists were dissolved in an aqueous vehicle such that each rat received once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle were controls. Dosing was performed daily in the early morning for 14 days. Over the course of the experiment, body weight and food consumption were monitored.

Using this assay, compounds of this invention were found to result in significant weight reduction.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound represented by the following structural Formula I:

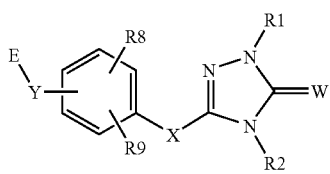

and pharmaceutically acceptable salts, solvates and hydrates thereof, wherein:
(a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, C3-C6 cycloalkylaryl-$C_{0-2}$-alkyl, and —$CH_2$—C(O)—R17-R18, wherein R17 is O or NH and R18 is optionally substituted benzyl;
(b) W is O;
(c) R2 is H or a substituted or unsubstituted group selected from the group consisting of $C_1$-$C_6$ alkyl, $C_1$-$C_6$ allyl, aryl-$C_{0-4}$-alkyl, heteroaryl-$C_{0-4}$-alkyl, sulfonamide, amide, OR10 and $C_3$-$C_6$ cycloalkyl;
(d) X is an optionally substituted $C_2$ $C_5$ alkylene linker;
(e) Y is O, S, or NH; and

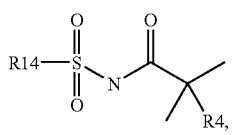

(f) E is selected from the group consisting of A, C(R3)(R4)A,

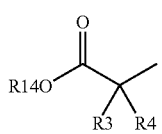

$(CH_2)_n$ COOR19 wherein the $(CH_2)_n$ COOR19 moiety is substituted or unsubstituted with from one to three substituents each independently selected from the group consisting of $C_1$-$C_5$ alkyl, $C_1$-$C_5$ alkoxy, $C_1$-$C_5$ haloalkyl, $C_1$-$C_5$ haloalkoxy, nitro, cyano, CHO, hydroxyl, $C_1$-$C_4$ alkanoic acid phenyl, aryloxy, $SO_2R7$, SR7, benzyloxy, alkylcarboxamido, and COOH, wherein R7 is alkyl or haloalkyl,
wherein
(i) n is 0, 1, 2 or 3,
(ii) A is a moiety selected from the group consisting of carboxyl, $C_1$-$C_3$alkylnitrile, carboxamide, substituted or unsubstituted sulfonamide, substituted or unsubstituted acylsulfonamide and substituted or unsubstituted tetrazole;
(iii) R3 is H, saturated or unsaturated $C_1$-$C_5$ alkyl, $C_1$-$C_5$ alkoxy, and
(iv) R4 is H, halo, a substituted or unsubstituted group selected from $C_1$-$C_5$ alkyl, $C_1$-$C_5$ alkoxy, $C_3$-$C_6$ cycloalkyl, aryl $C_0$-$C_4$ alkyl and phenyl, or R3 and R4 are combined to form a $C_3$-$C_4$ cycloalkyl;
(v) R19 is selected from the group consisting of hydrogen, optionally substituted arylmethyl and optionally substituted $C_1$-$C_4$alkyl;
(vi) R14 is selected from the group consisting of $CF_3$, substituted or unsubstituted phenyl, substituted or unsubstituted aryl-$C_0$-$C_4$ alkyl, and $C_1$-$C_6$ alkyl;
(g) R8 is independently selected from the group consisting of hydrogen, $C_1$-$C_4$ alkyl, $C_1$-$C_4$ alkylenyl, and halo;
(h) R9 is independently selected from the group consisting of hydrogen, $C_1$-$C_4$ alkyl, $C_1$-$C_4$ alkylenyl, halo, substituted or unsubstituted aryl, substituted or unsubstituted aryl-C-$C_4$ alkyl, substituted or unsubstituted heteroaryl, $C_1$-$C_6$ allyl, and OR10; and R10 is independently selected from the group consisting of hydrogen and $C_1$-$C_4$ alkyl.

2. A compound as claimed by claim 1-wherein E is A.
3. A compound as claimed by claim 2 wherein A is COOH.
4. A compound as claimed by claim 1, wherein Y is O.
5. A compound as claimed by claim 1, wherein E is a group of the formula:

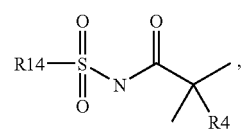

wherein R14 is selected from the group consisting of $CF_3$, substituted or unsubstituted phenyl, substituted or unsubstituted aryl-$C_{0-4}$-alkyl, and $C_{1-6}$-alkyl.

6. A compound as claimed by claim 1, wherein E is a group of the formula:

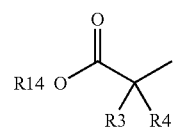

wherein R14 is selected from the group consisting of $CF_3$, substituted or unsubstituted phenyl, substituted or unsubstituted aryl-$C_{0-4}$-alkyl, and $C_{1-6}$-alkyl.

7. A compound as claimed by claim 1 wherein X is propylene.

8. A compound which is Propanoic Acid, 2-[4-[3-[2,5-dihydro-1-[(4-methylphenyl)methyl]-5-oxo-1H-1,2,4-triazol-3-yl]propyl]phenoxy]-2-methyl-.

9. A compound of claim 8 which is Crystalline Propanoic Acid,2-[4-[3-[2,5-dihydro-1-[(4-methylphenyl)methyl]-5-oxo-1H-1,2,4-triazol-3-yl]propyl]phenoxy]-2-methyl- having an X-ray diffraction pattern comprising at least the following peaks: 13.2 +/−0.2, 15.9 +/−0.2, 20.7 +/−0.2, and 24.1 +/−0.2 in 2θ when obtained from a copper radiation source.

10. A compound as claimed by claim 1 that is represented by the following structural formula:

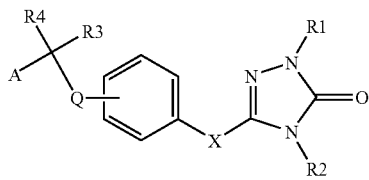

and pharmaceutically acceptable salts, solvates and hydrates thereof, wherein:
  (a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and —CH$_2$—C(O)—R17-R18, wherein R17 is O or NH and R18 is optionally substituted benzyl;
  (b) R2 is H or a substituted or unsubstituted group selected from $C_1$-$C_6$ alkyl, $C_3$-$C_6$ cycloalkyl and heteroaryl;
  (c) X is a $C_2$-$C_5$ alkylene linker;
  (d) Q is O or S;
  (e) A is a moiety selected from the group consisting of carboxyl, $C_1$-$C_3$ alkylnitrile, carboxamide, substituted or unsubstituted sulfonamide, substituted or unsubstituted acylsulfonamide and substituted or unsubstituted tetrazole;
  (f) R3 is H, saturated or unsaturated $C_1$-$C_5$ alkyl, $C_1$-$C_5$ alkoxy; and
  (g) R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl.

11. A compound as claimed by claim 10 wherein A is COOH.

12. A compound as claimed by claim 11 wherein R3 is methyl.

13. A compound as claimed by claim 12 wherein R4 is methyl.

14. A compound as claimed by claim 1 that is represented by the following structural formula:

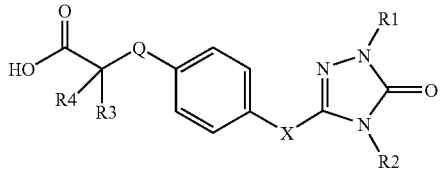

and pharmaceutically acceptable salts, solvates and hydrates thereof, wherein:
  (a) R1 is selected from the group consisting of hydrogen, substituted or unsubstituted group selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and —CH$_2$—C(O)—R17-R18, wherein R17 is O or NH and R18 is optionally substituted benzyl;
  (b) R2 is H or a substituted or unsubstituted group selected from $C_1$-$C_6$ alkyl, $C_3$-$C_6$ cycloalkyl and heteroaryl;
  (c) X is an optionally substituted $C_2$-$C_5$ alkylene linker;
  (d) Q is O or S;
  (e) R3 is H, saturated or unsaturated $C_1$-$C_5$ alkyl, $C_1$-$C_5$ alkoxy; and
  (f) R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl.

15. A compound as claimed by any one of claims 1, 10, or 14 wherein R1 selected from the group consisting of a substituted or unsubstituted $C_1$-$C_8$ alkyl, aryl-$C_{0-4}$-alkyl, heteroaryl-$C_{0-4}$-alkyl, and $C_3$-$C_6$ cycloalkylaryl-$C_{0-2}$-alkyl.

16. A compound as claimed by claim 15 wherein R1 is substituted aryl.

17. A compound as claimed by claim 1 that is represented by the following structural formula:

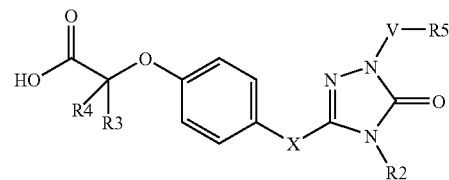

and pharmaceutically acceptable salts, solvates and hydrates thereof, wherein:
  (a) R2 is H or a substituted or unsubstituted group selected from $C_1$-$C_6$ alkyl, $C_3$-$C_6$ cycloalkyl and heteroaryl;
  (b) X is an optionally substituted $C_2$-$C_5$ alkylene linker;
  (c) R3 is H, saturated or unsaturated $C_1$-$C_5$ alkyl, $C_1$-$C_5$ alkoxy;
  (d) R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl;
  (e) V is a bond or a unsubstituted or substituted C1-C3 alkylene group; and
  (f) R5 is substituted or unsubstituted group selected from aryl, heteroaryl and cycloalkyl groups.

18. A compound as claimed by claim 1 that is represented by the following structural formula:

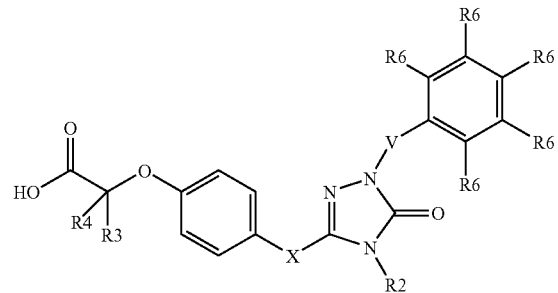

and pharmaceutically acceptable salts, solvates and hydrates thereof, wherein:
  (a) R2 is H or a substituted or unsubstituted group selected from $C_1$-$C_6$ alkyl, $C_3$-$C_6$ cycloalkyl and heteroaryl;
  (b) X is an optionally substituted $C_2$-$C_5$ alkylene linker;
  (c) R3 is H, saturated or unsaturated $C_1$-$C_5$ alkyl, $C_1$-$C_5$ alkoxy;
  (d) R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl;

(e) V is a bond or a unsubstituted or substituted C1-C3 alkylene group; and
(f) R6 is H, OH, C1-C5 alkyl, alkoxy, halo, haloalkyl, haloalkoxy, nitro, phenyl, aryloxy, SO2R7, SR7, cyano, benzyloxy, phenoxy, alkylcarboxamido or COOH wherein R7 is an alkyl or a haloalkyl.

19. A compound of claim 18 wherein V is methylene.

20. A compound as claimed by claim 18 wherein X is propylene.

21. A compound as claimed by claim 20 wherein R3 is methyl.

22. A compound as claimed by claim 21 wherein R4 is methyl.

23. A compound as claimed by claim 1 that is represented by the following structural formula:

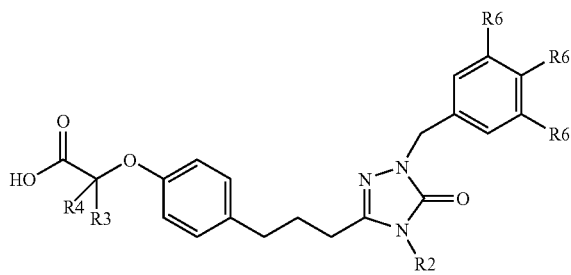

and pharmaceutically acceptable salts, solvates and hydrates thereof, wherein:
(a) R2 is H or a substituted or unsubstituted group selected from $C_1$-$C_6$ alkyl, $C_3$-$C_6$ cycloalkyl and heteroaryl;
(b) R3 is H, saturated or unsaturated $C_1$-$C_5$ alkyl, $C_1$-$C_5$ alkoxy;
(c) R4 is H, halo, a substituted or unsubstituted group selected from $C_1$-$C_5$ alkyl, $C_1$-$C_5$ alkoxy, $C_3$-$C_6$ cycloalkyl and phenyl, or R3 and R4 are combined to form a $C_3$-$C_4$ cycloalkyl; and
(d) R6 is independently selected from the group consisting of H, OH, C1-C5 alkyl, alkoxy, halo, haloalkyl, haloalkoxy, nitro, phenyl, aryloxy, SO2R7, SR7, cyano, benzyloxy, phenoxy, alkylcarboxamido or COOH wherein R7 is an alkyl or a haloalkyl.

24. A compound as claimed by claim 1, that is represented by the following structure:

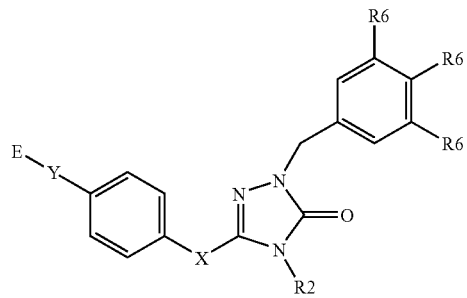

wherein R6 is independently selected from the group consisting of H, OH, $C_1$-$C_5$ alkyl, alkoxy, halo, haloalkyl, haloalkoxy, nitro, phenyl, aryloxy, SO2R7, SR7, cyano, benzyloxy, phenoxy, alkylcarboxamido or COOH wherein R7 is an alkyl or a haloalkyl.

25. A compound as claimed by any one of claims 1 or 24 wherein there are two R6 substituents independently selected from the group consisting of hydrogen, $C_1$-$C_5$ alkyl, Cl, F, $OCH_3$, $CF_3$, and $SCF_3$.

26. A compound as claimed by claim 25 wherein EY is

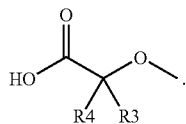

27. A compound as claimed by claim 1 wherein said compound is radiolabeled.

28. A compound as claimed by claim 27 wherein said compound is tritiated.

29. A pharmaceutical composition, comprising a pharmaceutically acceptable carrier and at least one compound as claimed by any one of claims 1 or 8.

30. A method of treating diabetes mellitus in a mammal, comprising the step of administering to the mammal a therapeutically effective amount of at least one compound of claim 1.

31. The method of claim 30 wherein the compound lowers blood glucose levels.

32. A method of treating Syndrome X in a mammal, comprising the step of administering to the mammal a therapeutically effective amount of at least one compound of claim 1.

33. The method of claim 32 wherein the compound lowers blood glucose levels.

34. The method of claim 32, wherein the compound lowers serum concentration of triglycerides in the mammal.

35. The method of claim 32, wherein the compound lowers serum concentration of low density lipoproteins in the mammal.

36. The method of claim 32, wherein the compound increases serum concentration of high density lipoproteins in a mammal.

37. A compound as claimed by claim 1, wherein E is C(R3)(R4)A, which is unsubstituted or substituted with a group selected from the group consisting of $(CH_2)_n$ COOH, $C_1$-$C_6$ alkyl, $C_1$-$C_6$ allyl, aryl-$C_{0-4}$-alkyl, thio-$C_{1-4}$-alkyl, thioaryl, $C_{1-4}$alkoxyaryl, $C_{1-4}$alkoxy $C_{1-4}$alkyl, aminoaryl, and amino $C_{1-4}$alkyl.

* * * * *